United States Patent
Kirschberg et al.

(10) Patent No.: US 10,800,767 B2
(45) Date of Patent: Oct. 13, 2020

(54) THYROID HORMONE RECEPTOR BETA AGONIST COMPOUNDS

(71) Applicant: Terns, Inc., San Mateo, CA (US)

(72) Inventors: Thorsten A. Kirschberg, San Carlos, CA (US); Randall Halcomb, Foster City, CA (US); Yingzi Xu, Palo Alto, CA (US); F. Anthony Romero, Redwood City, CA (US)

(73) Assignee: Terns, Inc., Foster City, CA (US)

( * ) Notice: Subject to any disclaimer, the term of this patent is extended or adjusted under 35 U.S.C. 154(b) by 0 days.

(21) Appl. No.: 16/549,979

(22) Filed: Aug. 23, 2019

(65) Prior Publication Data

US 2020/0062742 A1  Feb. 27, 2020

Related U.S. Application Data

(60) Provisional application No. 62/867,117, filed on Jun. 26, 2019, provisional application No. 62/722,312, filed on Aug. 24, 2018.

(51) Int. Cl.
C07D 413/12  (2006.01)

(52) U.S. Cl.
CPC .................. *C07D 413/12* (2013.01)

(58) Field of Classification Search
CPC .................................................. C07D 413/12
See application file for complete search history.

(56) References Cited

U.S. PATENT DOCUMENTS

2005/0085541 A1  4/2005  Shiohara et al.
2009/0247539 A1  10/2009  Bell et al.

FOREIGN PATENT DOCUMENTS

| WO | WO-2007/009913 A1 | 1/2007 |
| WO | WO-2019144835 A1 | 8/2019 |
| WO | WO-2019240938 A1 | 12/2019 |
| WO | WO-2020073974 A1 | 4/2020 |

OTHER PUBLICATIONS

Hill, S. R. Jr., S. et al. (1960). "The Metabolic Effects of the Acetic and Propionic Acid Analogs of Thyroxine and Triiodothyronine," J Clin. Invest. (39):523-533.
International Search Report and Written Opinion of the International Searching Authority dated Nov. 21, 2019, for PCT Patent Application No. PCT/US19/47968, 13 pages.
Klein, I. et al. (Oct. 9, 2007). "Cardiovascular Involvement in General Medical Conditions, Thyroid Disease and the Heart," Circulation 116(15):1725-1735.
Sinha, R. A. et al. (May 2018, e-pub. Feb. 23, 2018). "Direct Effects of Thyroid Hormones on Hepatic Lipid Metabolism," Nat. Rev. Endocrinology 14(5):259-269.

*Primary Examiner* — Paul V Ward
(74) *Attorney, Agent, or Firm* — Morrison & Foerster LLP

(57) ABSTRACT

Provided herein are compounds, preferably thyroid hormone receptor beta (THR beta) agonist compounds, compositions thereof, and methods of their preparation, and methods of agonizing THR beta and methods for treating disorders mediated by THR beta.

21 Claims, No Drawings

THYROID HORMONE RECEPTOR BETA AGONIST COMPOUNDS

CROSS-REFERENCE TO RELATED APPLICATIONS

This application claims priority to U.S. Provisional Application No. 62/722,312, filed Aug. 24, 2018, and U.S. Provisional Application No. 62/867,117, filed Jun. 26, 2019, the disclosures of each of which are hereby incorporated by reference in their entireties for all purposes.

FIELD OF THE INVENTION

This invention relates to compounds, preferably thyroid hormone receptor beta (THR beta) agonist compounds, compositions thereof, and methods of their preparation, and methods of agonizing THR beta and methods for treating disorders mediated by THR beta.

STATE OF THE ART

The beneficial effects arising from treating hyperthyroid or hypothyroid patients with T3/T4 endogenous ligands or early analogs of these endogenous ligands have been described in the literature (Richardson Hill Jr., S. et al. *J. Clin. Invest.* 1960, 39, 523-533). These early studies, as well as similar follow-up studies, established the heart as a major organ for the manifestation of side effects of both hyperthyroidism and hypothyroidism (Klein, I. et al. *Circulation*, 2007, 1725-1735). In particular, tachycardia, hypertrophism, atrial dysrhythmias, and atrial fibrillation are serious concerns. In addition, increased bone turn-over leading to decreased bone mineral density has also been noted. Negative effects at both sites, heart and bone, have been linked to the agonism of the THR alpha isoform, whereas the beneficial effects of THR agonism in the liver are largely linked to the THR beta isoform (Sinha, R. A. et al. *Nat. Rev. Endocrinology* 2018, 14, 259-269).

Diseases or disorders associated with THR beta include non-alcoholic steatohepatitis (NASH), non-alcoholic fatty liver disease (NAFLD), metabolic syndrome, dyslipidemia, hypertriglyceridemia, and hypercholesterolemia. There is a need for thyroid hormone analogs, such as those that are THR beta agonists, and preferably those that avoid the undesirable effects of hyperthyroidism and hypothyroidism, and maintain the beneficial effects of thyroid hormones, e.g., for the treatment for patients with non-alcoholic steatohepatitis (NASH). In particular, there is a need to develop new thyroid hormone analogs that are selective agonists for THR beta, and preferably those that avoid the undesirable effects associated with agonism of THR alpha, and maintain the beneficial effects of thyroid hormones, e.g., for the treatment for patients with non-alcoholic steatohepatitis (NASH), non-alcoholic fatty liver disease (NAFLD), metabolic syndrome, dyslipidemia, hypertriglyceridemia, or hypercholesterolemia.

SUMMARY

In one aspect, provided herein is a compound of formula (I):

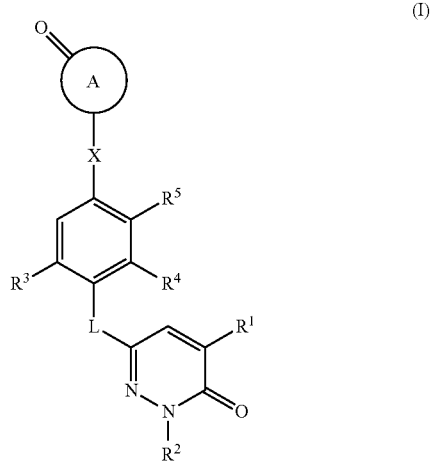

or a pharmaceutically acceptable salt thereof, wherein:

ring A together with the carbonyl (keto) group within the ring form a 5 membered heterocycle containing 1-3 ring heteroatoms selected from the group consisting of N, O, and S, wherein the heterocycle is optionally substituted with 1-2 $C_1$-$C_3$ alkyl or $C_3$-$C_4$ cycloalkyl groups, and wherein the carbonyl (keto) group is not adjacent to the atom attached to X;

$R^1$ is $C_1$-$C_4$ alkyl optionally substituted with 1-5 halo or hydroxyl groups, $C_3$-$C_5$ cycloalkyl, $CON(R^{10})_2$, or $NR^{10}COR^{10}$;

$R^2$ is H or $C_1$-$C_3$ alkyl;

L is O, $CH_2$, S, SO, $SO_2$, CO, CHF, $CF_2$, $C(R^{11})CN$, $CHR^{11}$, or $C(R^{11})R^{11}$;

$R^3$ and $R^4$ are independently Cl, Br, methyl, or ethyl;

$R^5$ is H, halo, $C_1$-$C_4$ alkyl, or $C_3$-$C_4$ cycloalkyl;

or $R^5$ together with $R^4$ and the intervening atoms form a 5-7 membered cycloalkyl or a 5-7 membered heterocycle containing 1-2 ring heteroatoms;

X is absent, O, $NR^{12}$, $C(O)NR^{12}$, $NR^{12}C(O)$, $CR^{12}R^{12}$, $OCR^{12}R^{12}$, $CR^{12}R^{12}O$, $NR^{12}CR^{12}R^{12}$, $CR^{12}R^{12}NR^{12}$, $SO_2NR^{12}$, or $NR^{12}SO_2$;

each $R^{10}$ is independently $C_1$-$C_3$ alkyl or H;

each $R^{11}$ is independently $C_1$-$C_2$ alkyl optionally substituted with 1-5 halo, or two $R^{11}$ groups together with the carbon atom to which they are attached form a cyclopropyl or cyclobutyl ring; and each $R^{12}$ is independently H or methyl.

In some embodiments, the compound is of formula (IIA) or (IIB):

(IIA)

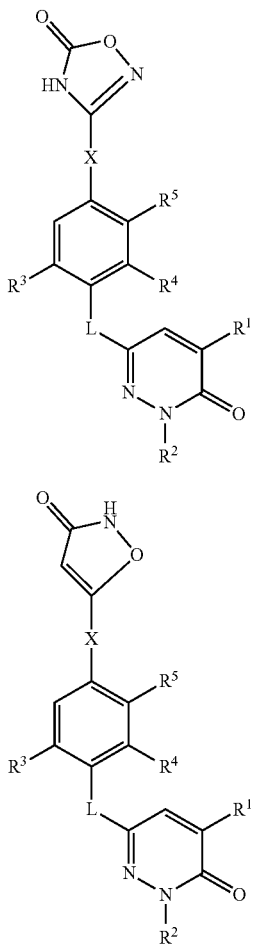

(IIB)

wherein $R^1$, $R^2$, $R^3$, $R^4$, $R^5$, X, and L are as defined for the compound of formula (I).

In some embodiments, the compound is of formula (VD):

(VD)

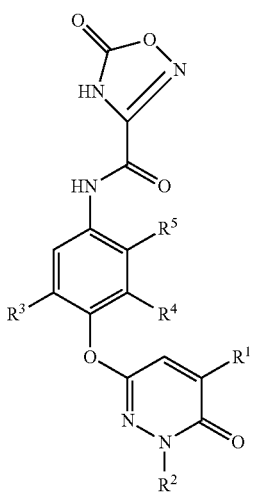

wherein $R^1$, $R^2$, $R^3$, $R^4$, and $R^5$ are as defined in claim 1.

In some embodiments, $R^1$ is $C_1$-$C_4$ alkyl optionally substituted with 1-2 halo or hydroxyl groups, or $C_3$-$C_5$ cycloalkyl. In some embodiments, $R^1$ is isopropyl, t-butyl, HO—CH(CH$_3$)—, HO—CH(CH$_2$CH$_3$)—, HO—C(CH$_3$)$_2$—, HO—CH$_2$CH(CH$_3$)—, cyclopropyl, or

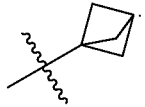

In some embodiments, $R^2$ is H or —CH$_3$.
In some embodiments, $R^3$ is chloro or —CH$_3$.
In some embodiments, $R^4$ is chloro or —CH$_3$; or $R^5$ together with $R^4$ and the intervening atoms form a 5-6 membered cycloalkyl. In some embodiments, $R^5$ together with $R^4$ and the intervening atoms form cyclopentyl. In some embodiments, $R^5$ is H or fluoro.

In some embodiments, X is a bond. In some embodiments, X is $NR^{12}C(O)$, $OCR^{12}R^{12}$, or $NR^{12}CR^{12}R^{12}$; and each $R^{12}$ is independently H or methyl. In some embodiments, X is —OCH$_2$—, —NHCH$_2$—, —NHC(O)—, —N(CH$_3$)CH$_2$—, or —N(H)CH(CH$_3$)—.

In some embodiments, L is O, CH$_2$, SO$_2$, CO, $CHR^{11}$, or $C(R^{11})R^{11}$; and each $R^{11}$ is independently methyl or ethyl. In some embodiments, L is O, CH$_2$, SO$_2$, or CO.

In some embodiments, provided herein is a compound selected from the compounds in Table 1, or a pharmaceutically acceptable salt thereof.

In one aspect, provided herein is a pharmaceutical composition comprising a compound provided herein and at least one pharmaceutically acceptable excipient.

In one aspect, provided herein is a method of agonizing thyroid hormone receptor beta (THR beta) comprising contacting either an effective amount of a compound provided herein, or an effective amount of a pharmaceutical composition provided herein, with the THR beta.

In one aspect, provided herein is a method of treating a disorder which is mediated by THR beta in a patient, comprising administering to the patient a therapeutically effective amount of a compound provided herein, or a therapeutically effective amount of a composition provided herein. In some embodiments, the disorder is non-alcoholic steatohepatitis (NASH).

DETAILED DESCRIPTION

Definitions

As used herein, the following definitions shall apply unless otherwise indicated. Further, if any term or symbol used herein is not defined as set forth below, it shall have its ordinary meaning in the art.

"Comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of, e.g., other ingredients and substantial method steps recited. Embodiments defined by each of these transition terms are within the scope of this invention.

"Effective amount" or dose of a compound or a composition refers to that amount of the compound or the composition that results in an intended result as desired based on the disclosure herein. Effective amounts can be determined by standard pharmaceutical procedures in cell cultures or experimental animals, e.g., and without limitation, by determining the $LD_{50}$ (the dose lethal to 50% of the population) and the $ED_{50}$ (the dose therapeutically effective in 50% of the population).

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Patient" refers to mammals and includes humans and non-human mammals. Examples of patients include, but are not limited to mice, rats, hamsters, guinea pigs, pigs, rabbits, cats, dogs, goats, sheep, cows, and humans. In some embodiments, patient refers to a human.

"Pharmaceutically acceptable" refers to safe and non-toxic, preferably for in vivo, more preferably, for human administration.

"Pharmaceutically acceptable salt" refers to a salt that is pharmaceutically acceptable. A compound described herein may be administered as a pharmaceutically acceptable salt.

"Prodrug" refers to a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug may have, relative to the active drug, altered metabolic stability or transport characteristics, fewer side effects or lower toxicity, or improved flavor (for example, see the reference Nogrady, 1985, Medicinal Chemistry A Biochemical Approach, Oxford University Press, New York, pages 388-392, incorporated herein by reference). A prodrug may be synthesized using reactants other than employing the corresponding drug. For illustration and without limitation, prodrugs include, carboxy esters, linear and cyclic phosphate esters and phosphoramide and phosphoramidates, carbamates, preferably phenolic carbamates (i.e., carbamates where the hydroxy group is part of an aryl or heteroaryl moiety, where the aryl and heteroaryl may be optionally substituted), and the likes.

"Salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary and non-limiting cations useful in pharmaceutically acceptable salts include Na, K, Rb, Cs, $NH_4$, Ca, Ba, imidazolium, and ammonium cations based on naturally occurring amino acids. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisulfate, mono-, di-, and tribasic phosphate, mesylate, tosylate, and the likes.

"Therapeutically effective amount" or dose of a compound or a composition refers to that amount of the compound or the composition that results in reduction or inhibition of symptoms or a prolongation of survival in a patient. The results may require multiple doses of the compound or the composition.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease. As used herein, "treatment" or "treating" is an approach for obtaining beneficial or desired results including clinical results. For purposes of this invention, beneficial or desired results include, but are not limited to, one or more of the following: decreasing one more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delay or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a patient. Also encompassed by "treatment" is a reduction of pathological consequence of the disease or disorder. The methods of the invention contemplate any one or more of these aspects of treatment.

An "isotopomer" of a compound is a compound in which one or more atoms of the compound have been replaced with isotopes of those same atoms. For example, where H has been replaced by D or T, or $^{12}C$ has been replaced by $^{11}C$ or $^{14}N$ has been replaced by $^{15}N$. For example, and without limitation, replacement of with D can in some instances lead to reduced rates of metabolism and therefore longer half-lives. Replacement of H with T can provide radioligands potentially useful in binding studies. Replacement of $^{12}C$ with the short-lived isotope $^{11}C$ can provide ligands useful in Positron Emission Tomography (PET) scanning. Replacement of $^{14}$N with $^{15}$N provides compounds that can be detected/monitored by $^{15}$N NMR spectroscopy. For example, an isotopomer of a compound containing —CH$_2$CH$_3$ is that compound but containing —CD$_2$CD$_3$ instead of the —CH$_2$CH$_3$.

Unless a specific isotope of an element is indicated in a formula, the disclosure includes all isotopologues of the compounds disclosed herein, such as, for example, deuterated derivatives of the compounds (where H can be $^2$H, i.e., D). Isotopologues can have isotopic replacements at any or at all locations in a structure, or can have atoms present in natural abundance at any or all locations in a structure.

"Stereoisomer" or "stereoisomers" refer to compounds that differ in the stereogenicity of the constituent atoms such as, without limitation, in the chirality of one or more stereocenters or related to the cis or trans configuration of a carbon-carbon or carbon-nitrogen double bond. Stereoisomers include enantiomers and diastereomers.

"Tautomer" refers to alternate forms of a compound that differ in the position of a proton, such as enol-keto and imine-enamine tautomers, or the tautomeric forms ofheteroaryl groups containing a ring atom attached to both a ring —NH— moiety and a ring=N— moiety such as pyrazoles, imidazoles, benzimidazoles, triazoles, and tetrazoles.

"Alkyl" refers to monovalent saturated aliphatic hydrocarbyl groups having from 1 to 12 carbon atoms, preferably from 1 to 10 carbon atoms, and more preferably from 1 to 6 carbon atoms. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—). C$_x$ alkyl refers to an alkyl group having x number of carbon atoms.

"Alkenyl" refers to straight or branched monovalent hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers. C$_x$ alkenyl refers to an alkenyl group having x number of carbon atoms.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH$_2$C≡CH). C$_x$ alkynyl refers to an alkynyl group having x number of carbon atoms.

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_{03}$H, substituted sulfonyl, sulfonyloxy, sulfonylamino, thioacyl, thiol, alkylthio, and substituted alkylthio, wherein said substituents are defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, sulfonylamino, thioacyl, thiol, alkylthio, and substituted alkylthio, wherein said substituents are defined herein and with the proviso that any hydroxy or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, sulfonylamino, thioacyl, thiol, alkylthio, and substituted alkylthio, wherein said substituents are defined herein and with the proviso that any hydroxyl or thiol substitution is not attached to an acetylenic carbon atom.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluromethyl, fluoromethyl and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —$NR^{30}C(O)$alkyl, —$NR^{30}C(O)$ substituted alkyl, —$NR^{30}C(O)$cycloalkyl, —$NR^{30}C(O)$substituted cycloalkyl, —N $R^{30}C(O)$alkenyl, —$NR^{30}C(O)$substituted alkenyl, alkoxy, substituted alkoxy-$NR^{30}C(O)$alkynyl, —$NR^{30}C(O)$substituted alkynyl, —$NR^{30}C(O)$aryl, —$NR^{30}C(O)$substituted aryl, —$NR^{30}C(O)$heteroaryl, —$NR^{30}C(O)$substituted heteroaryl, —$NR^{30}C(O)$heterocyclic, and —$NR^{30}C(O)$substituted heterocyclic wherein $R^{30}$ is hydrogen, alkyl, substituted alkyl, aryl, substituted aryl, heteroaryl, substituted heteroaryl, cycloalkyl, or substituted cycloalkyl; and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{31}R^{32}$ where $R^{31}$ and $R^{32}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, substituted heterocyclic, arylamino, substituted arylamino, heteroarylamino, substituted heteroarylamino, cycloalkylamino, substituted cycloalkylamino, heterocycloalkylamino, substituted heterocyclylamino, sulfonylamino, and substituted sulfonyl and wherein $R^{31}$ and $R^{32}$ are optionally joined, together with the nitrogen bound thereto to form a heterocyclic or substituted heterocyclic group, provided that $R^{31}$ and $R^{32}$ are both not hydrogen, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic, and substituted heterocyclic are as defined herein. When $R^{31}$ is hydrogen and $R^{32}$ is alkyl, the substituted amino group is sometimes referred to herein as alkylamino. When $R^{31}$ and $R^{32}$ are alkyl, the substituted amino group is sometimes referred to herein as dialkylamino. When referring to a monosubstituted amino, it is meant that either $R^{31}$ or $R^{32}$ is hydrogen but not both. When referring to a disubstituted amino, it is meant that neither $R^{31}$ nor $R^{32}$ are hydrogen.

"Aminocarbonyl" refers to the group —$C(O)NR^{33}R^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —$C(S)NR^{33}R^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —$NR^{30}C(O)NR^{33}R^{34}$ where $R^{30}$ is hydrogen, alkyl, substituted alkyl, aryl, substituted aryl, heteroaryl, substituted heteroaryl, cycloalkyl, or substituted cycloalkyl, and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —$NR^{30}C(S)NR^{33}R^{34}$ where $R^{30}$ is hydrogen, alkyl, substituted alkyl, aryl, substituted aryl, heteroaryl, substituted heteroaryl, cycloalkyl, or substituted cycloalkyl, and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—$C(O)NR^{33}R^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —SO$_2$NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—SO$_2$NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{30}$—SO$_2$NR$^{33}$R$^{34}$ where $R^{30}$ is hydrogen, alkyl, substituted alkyl, aryl, substituted aryl, heteroaryl, substituted heteroaryl, cycloalkyl, or substituted cycloalkyl, and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{35}$)NR$^{33}$R$^{34}$ where $R^{33}$, $R^{34}$, and $R^{35}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl (Ph)) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, sulfonylamino, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Arylamino" refers to the group —NR$^{37}$(aryl), where aryl is as defined herein and $R^{37}$ is hydrogen, alkyl, or substituted alkyl.

"Substituted arylamino" refers to the group —NR$^{37}$(substituted aryl), where $R^{37}$ is hydrogen, alkyl, or substituted alkyl where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR$^{30}$—C(O)O-alkyl, —NR$^{30}$—C(O)O-substituted alkyl, —NR$^{30}$—C(O)O-alkenyl, —NR$^{30}$—C(O)O-substituted alkenyl, —NR$^{30}$—C(O)O-alkynyl, —NR$^{30}$—C(O)O-substituted alkynyl, —NR$^{30}$—C(O)O-aryl, —NR$^{30}$—C(O)O-substituted aryl, —NR$^{30}$—C(O)O-cycloalkyl, —NR$^{30}$—C(O)O-substituted cycloalkyl, —NR$^{30}$—C(O)O-heteroaryl, —NR$^{30}$—C(O)O-substituted heteroaryl, —NR$^{30}$—C(O)O-heterocyclic, and —NR$^{30}$—C(O)O-substituted heterocyclic wherein R$^{30}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" refers to the group —C≡N.

"Cycloalkyl" refers to saturated or unsaturated but non-aromatic cyclic alkyl groups of from 3 to 10 carbon atoms, preferably from 3 to 8 carbon atoms, and more preferably from 3 to 6 carbon atoms, having single or multiple cyclic rings including fused, bridged, and spiro ring systems. $C_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylamino" refers to the group —NR$^{37}$(cycloalkyl) where R$^{37}$ is hydrogen, alkyl, or substituted alkyl.

"Substituted cycloalkylamino" refers to the group —NR$^{37}$(substituted cycloalkyl) where R$^{37}$ is hydrogen, alkyl, or substituted alkyl and substituted cycloalkyl is as defined herein.

"Cycloalkylthio" refers to —S-cycloalkyl.

"Substituted cycloalkylthio" refers to —S-(substituted cycloalkyl).

"Guanidino" refers to the group —NHC(=NH)NH$_2$.

"Substituted guanidino" refers to —NR$^{36}$C(=NR$^{36}$)N(R$^{36}$)$_2$ where each R$^{36}$ is independently selected from the group consisting of hydrogen, alkyl, substituted alkyl, aryl, substituted aryl, heteroaryl, substituted heteroaryl, heterocyclic, and substituted heterocyclic and two R$^{36}$ groups attached to a common guanidino nitrogen atom are optionally joined together with the nitrogen bound thereto to form a heterocyclic or substituted heterocyclic group, provided that at least one R$^{36}$ is not hydrogen, and wherein said substituents are as defined herein.

"Halo" or "halogen" refers to fluoro, chloro, bromo and iodo and preferably is fluoro or chloro.

"Hydroxy" or "hydroxyl" refers to the group —OH.

"Heteroalkylene" refers to an alkylene group wherein one or more carbons is replaced with —O—, —S—, SO$_2$, —NR$^Q$—,

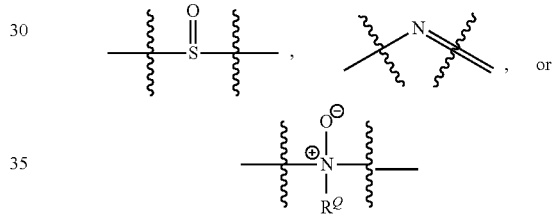

moieties where R$^Q$ is H or C$_1$-C$_6$ alkyl. "Substituted heteroalkylene" refers to heteroalkynylene groups having from 1 to 3 substituents, and preferably 1 to 2 substituents, selected from the substituents disclosed for substituted alkylene.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, thiophenyl, and furanyl. Other preferred heteroaryls include 9 or 10 membered heteroaryls, such as indolyl, quinolinyl, quinolonyl, isoquinolinyl, and isoquinolonyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heteroarylamino" refers to the group —NR$^{37}$(heteroaryl) where R$^{37}$ is hydrogen, alkyl, or substituted alkyl.

"Substituted heteroarylamino" refers to the group —NR$^{37}$(substituted heteroaryl), where R$^{37}$ is hydrogen, alkyl, or substituted alkyl and substituted heteroaryl is defined as herein.

"Heterocycle" or "heterocyclic" or "heterocycloalkyl" or "heterocyclyl" refers to a saturated or partially saturated, but not aromatic, group having from 1 to 10 ring carbon atoms, preferably from 1 to 8 carbon atoms, and more preferably from 1 to 6 carbon atoms, and from 1 to 4 ring heteroatoms, preferably from 1 to 3 heteroatoms, and more preferably from 1 to 2 heteroatoms selected from the group consisting of nitrogen, sulfur, or oxygen. C$_x$ heterocycloalkyl refers to a heterocycloalkyl group having x number of ring atoms including the ring heteroatoms. Heterocycle encompasses single ring or multiple condensed rings, including fused bridged and spiro ring systems. In fused ring systems, one or more of the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Heterocyclylene" refers to a divalent saturated or partially saturated, but not aromatic, group having from 1 to 10 ring carbon atoms and from 1 to 4 ring heteroatoms selected from the group consisting of nitrogen, sulfur, or oxygen. "Substituted heterocyclylene" refers to heterocyclylene groups that are substituted with from 1 to 5 or preferably 1 to 3 of the same substituents as defined for substituted cycloalkyl "Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

"Heterocyclylamino" refers to the group —NR$^{37}$(heterocyclyl) where R$^{37}$ is hydrogen, alkyl, or substituted alkyl.

"Substituted heterocyclylamino" refers to the group —NR$^{37}$(substituted heterocyclyl), where R$^{37}$ is hydrogen, alkyl, or substituted alkyl and substituted heterocyclyl is defined as herein.

Examples of heterocyclyl and heteroaryl include, but are not limited to, azetidinyl, pyrrolyl, imidazolyl, pyrazolyl, pyridyl, pyrazyl, pyrimidyl, pyridazyl, indolizyl, isoindolyl, indolyl, dihydroindolyl, indazolyl, purinyl, quinolizinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, isoxazolyl, phenoxazinyl, phenothiazinyl, imidazolidinyl, imidazolinyl, piperidinyl, piperazinyl, indolinyl, phthalimidyl, 1,2,3,4-tetrahydroisoquinolinyl, 4,5,6,7-tetrahydrobenzo[b]thiophenyl, thiazolyl, thiazolidinyl, thiophenyl, benzo[b]thiophenyl, morpholinyl, thiomorpholinyl (also referred to as thiamorpholinyl), 1,1-dioxothiomorpholinyl, piperidinyl, pyrrolidinyl, and tetrahydrofuranyl.

"Nitro" refers to the group —NO$_2$.

"Oxo" refers to the atom (=O) or (O).

"Spiro ring systems" refers to bicyclic ring systems that have a single ring carbon atom common to both rings.

"Sulfinyl" refers to the divalent group —S(O)— or —S(=O)—.

"Sulfonyl" refers to the divalent group —S(O)$_2$— or —S(=O)$_2$—.

"Substituted sulfonyl" refers to the group —SO$_2$-alkyl, —SO$_2$-substituted alkyl, —SO$_2$—OH, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—. Preferred substituted alkyl groups on the substituted alkyl-SO$_2$— include halogenated alkyl groups and particularly halogenated methyl groups such as trifluoromethyl, difluromethyl, fluoromethyl and the like.

"Substituted sulfinyl" refers to the group —SO-alkyl, —SO-substituted alkyl, —SO-alkenyl, —SO-substituted alkenyl, —SO-cycloalkyl, —SO-substituted cycloalkyl, —SO-aryl, —SO-substituted aryl, —SO-heteroaryl, —SO-substituted heteroaryl, —SO-heterocyclic, —SO-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfinyl includes groups such as methyl-SO—, phenyl-SO—, and 4-methylphenyl-SO—. Preferred substituted alkyl groups on the substituted alkyl-SO— include halogenated alkyl groups and particularly halogenated methyl groups such as trifluoromethyl, difluromethyl, fluoromethyl and the like.

"Sulfonyloxy" or "substituted sulfonyloxy" refers to the group —OSO$_2$-alkyl, —OSO$_2$-substituted alkyl, —OSO$_2$—OH, —OSO$_2$-alkenyl, —OSO$_2$-substituted alkenyl, —OSO$_2$-cycloalkyl, —OSO$_2$-substituted cycloalkyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the group —NR$^{37}$(substituted sulfonyl) where R$^{37}$ is hydrogen, alkyl, or substituted alkyl and substituted sulfonyl is as defined here.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Mercapto" or "thiol" refers to the group —SH.

"Formyl" refers to the group —C(O)H.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein. Preferred substituted alkyl groups on —S-(substituted alkyl) include halogenated alkyl groups and particularly halogenated methyl groups such as trifluoromethyl, difluromethyl, fluoromethyl and the like.

"Vinyl" refers to unsaturated hydrocarbon radical —CH=CH$_2$, derived from ethylene.

The terms "optional" or "optionally" as used throughout the specification means that the subsequently described event or circumstance may but need not occur, and that the description includes instances where the event or circumstance occurs and instances in which it does not. For example, "the nitrogen atom is optionally oxidized to provide for the N-oxide (N→O) moiety" means that the nitrogen atom may but need not be oxidized, and the description includes situations where the nitrogen atom is not oxidized and situations where the nitrogen atom is oxidized.

The term "optionally substituted" refers to a substituted or unsubstituted group. The substituted group may be substituted with one or more substituents, such as e.g., 1, 2, 3, 4 or 5 substituents. Preferably, the substituents are selected from the functional groups provided herein. In certain more preferred embodiments, the substituents are selected from oxo, halo, —CN, NO$_2$, —CO$_2$R$^{100}$, —OR$^{100}$, —SR$^{100}$, —SOR$^{100}$, —SO$_2$R$^{100}$, —NR$^{101}$R$^{102}$, —CONR$^{101}$R$^{102}$, —SO$_2$NR$^{101}$R$^{102}$, C$_1$-C$_6$ alkyl, C$_1$-C$_6$ alkoxy, —CR$^{100}$=C(R$^{100}$)$_2$, —CCR$^{100}$, C$_3$-C$_{10}$ cycloalkyl, C$_4$-C$_{10}$ heterocyclyl, C$_6$-C$_{14}$ aryl and C$_5$-C$_{12}$ heteroaryl, wherein each R$^{100}$ independently is hydrogen or C$_1$-C$_8$ alkyl; C$_3$-C$_{12}$ cycloalkyl; C$_4$-C$_{10}$ heterocyclyl; C$_6$-C$_{14}$ aryl; or C$_2$-C$_{12}$ heteroaryl; wherein each alkyl, cycloalkyl, heterocyclyl, aryl, or heteroaryl is optionally substituted with 1-3 halo, 1-3 C$_1$-C$_6$ alkyl, 1-3 C$_1$-C$_6$ haloalkyl or 1-3 C$_1$-C$_6$ alkoxy groups. More preferably, the substituents are selected from the group consisting of chloro, fluoro, —OCH$_3$, methyl, ethyl, isopropyl, cyclopropyl, —OCF$_3$, —CF$_3$ and —OCHF$_2$.

R$^{101}$ and R$^{102}$ independently are hydrogen; C$_1$-C$_8$ alkyl, optionally substituted with —CO$_2$H or an ester thereof, C$_1$-C$_6$ alkoxy, oxo, —CR$^{103}$=C(R$^{103}$)$_2$, —CCR, C$_3$-C$_{10}$ cycloalkyl, C$_3$-C$_{10}$ heterocyclyl, C$_6$-C$_{14}$ aryl, or C$_2$-C$_{12}$ heteroaryl, wherein each R$^{103}$ independently is hydrogen or C$_1$-C$_8$ alkyl; C$_3$-C$_{12}$ cycloalkyl; C$_4$-C$_{10}$ heterocyclyl; C$_6$-C$_{14}$ aryl; or C$_2$-C$_{12}$heteroaryl; wherein each cycloalkyl, heterocyclyl, aryl, or heteroaryl is optionally substituted with 1-3 alkyl groups or 1-3 halo groups, or R$^{101}$ and R$^{102}$ together with the nitrogen atom they are attached to form a 5-7 membered heterocycle.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

It is understood that the above definitions are not intended to include impermissible substitution patterns (e.g., methyl substituted with 4 fluoro groups). Such impermissible substitution patterns are well known to the skilled artisan.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

Compounds

In one aspect, provided herein is a compound of formula (I):

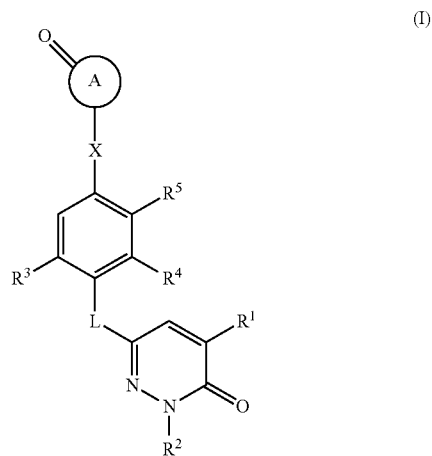

or a tautomer or an N-oxide thereof, or an isotopomer of each thereof, or a prodrug of each of the above, or a stereoisomer of the aforesaid, or a pharmaceutically acceptable salt of each of the foregoing, or a solvate of each of the preceding, wherein:

ring A together with the carbonyl (keto) group within the ring form a 5 membered heterocycle containing 1-3 ring heteroatoms selected from the group consisting of N, O, and S, wherein the heterocycle is optionally substituted with 1-2 substituents selected from the group consisting of C$_1$-C$_3$ alkyl and C$_3$-C$_4$ cycloalkyl, and wherein the carbonyl (keto) group is not adjacent to the atom attached to X;

R$^1$ is C$_1$-C$_4$ alkyl; C$_1$-C$_4$ alkyl optionally substituted with 1-5 halo, preferably fluoro, or hydroxyl groups; C$_3$-C$_5$ cycloalkyl, CON(R$^{10}$)$_2$, or NR$^{10}$COR$^{10}$, wherein each R$^{10}$ is independently C$_1$-C$_3$ alkyl or H;

R$^2$ is H or C$_1$-C$_3$ alkyl;

L is O, CH$_2$, S, SO, SO$_2$, CO, CHF, CF$_2$, C(R$^{11}$)CN such as C(Me)CN, CHR$^{11}$, or C(R$^1$)R$^{11}$, wherein each R$^{11}$ is C$_1$-C$_2$ alkyl optionally substituted with 1-5 halo, preferably fluoro, or the 2 R¹¹ groups together with the carbon atom they are attached to form a cyclopropyl or cyclobutyl ring;

each of $R^3$ and $R^4$ is independently Cl, Br, Me, or ethyl;

$R^5$ is H, halo, $C_1$-$C_4$ alkyl preferably $CH_3$, or $C_3$-$C_4$ cycloalkyl, or $R^5$ together with $R^4$ and the intervening atoms form a 5-7 membered cycloalkyl or a 5-7 membered heterocycle containing 1-2 ring heteroatoms; and X is absent (i.e., X is a bond), or is O, $NR^{12}$, $C(O)NR^{12}$, $NR^{12}C(O)$, $CR^{12}R^{12}$, $OCR^{12}R^{12}$, $CR^{12}R^{12}O$, $NR^{12}CR^{12}R^{12}$, $CR^{12}R^{12}NR^{12}$, $SO_2NR^{12}$, or $NR^{12}SO_2$, wherein each $R^{12}$ is independently H or methyl.

In some embodiments, the compound of formula (I) is a pharmaceutically acceptable salt thereof.

In one embodiment, the compound of formula (I) is a compound of formula (IIA):

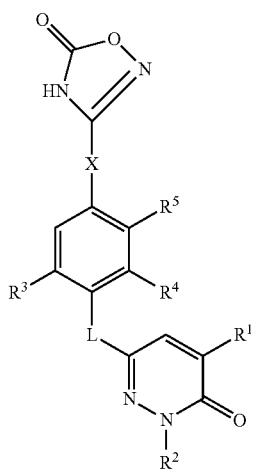

(IIA)

wherein the variables are defined as in formula (I).

In one embodiment, the compound of formula (I) is a compound of formula (IIB):

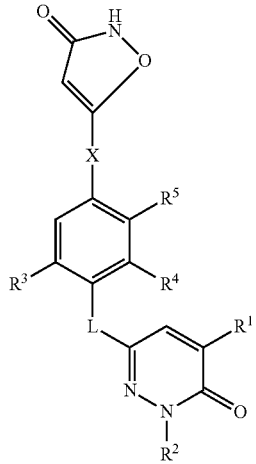

(IIB)

wherein the variables are defined as in formula (I).

In one embodiment, the compound of formula (I) is a compound of formula (IIIA).

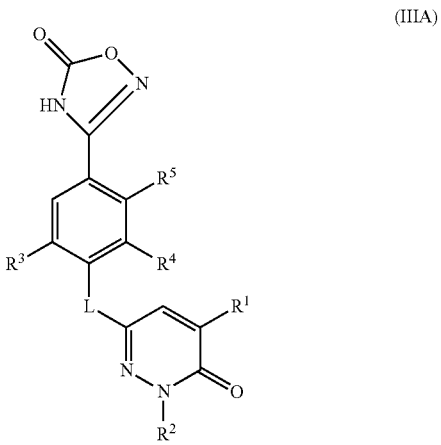

(IIIA)

wherein the variables are defined as in formula (I).

In one embodiment, the compound of formula (I) is a compound of formula (IIIB):

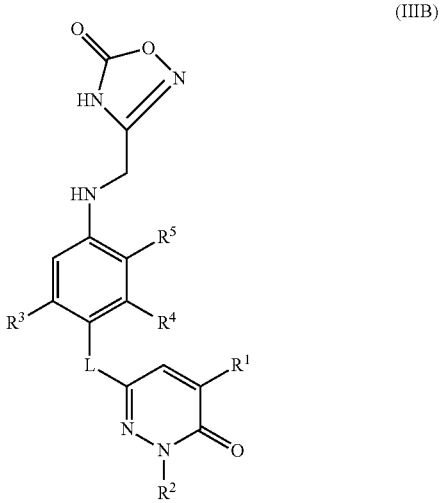

(IIIB)

wherein the variables are defined as in formula (I).

In one embodiment, the compound of formula (I) is a compound of formula (IIIC):

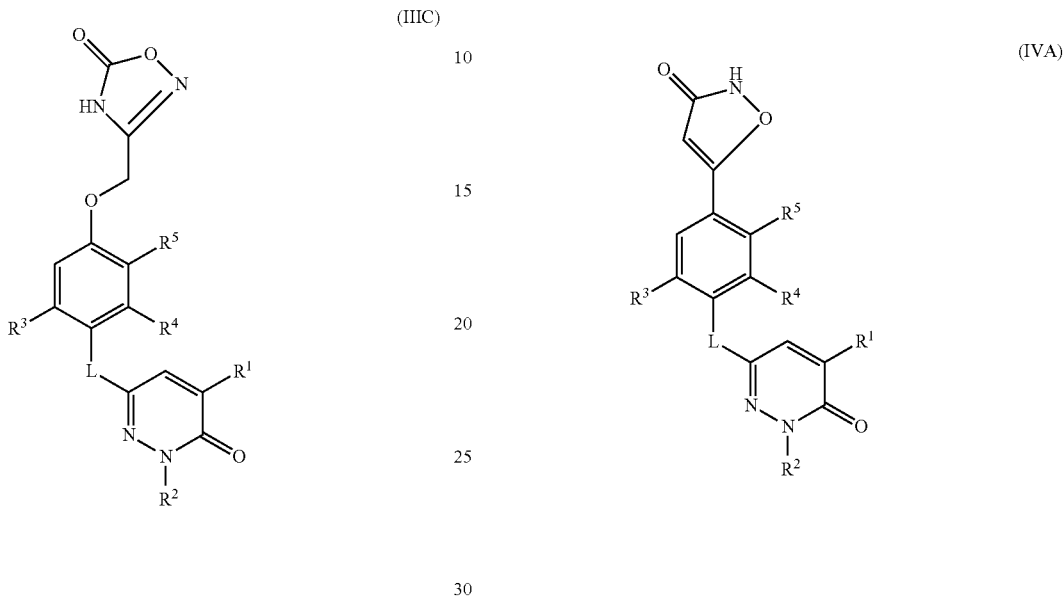

(IIIC)

wherein the variables are defined as in formula (I).

In one embodiment, the compound of formula (I) is a compound of formula (IIID):

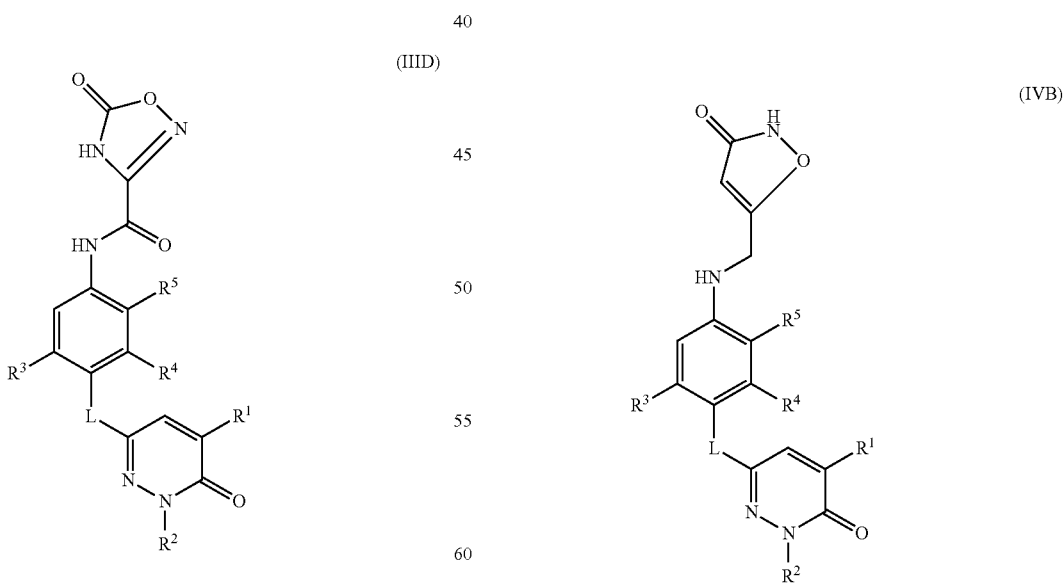

(IIID)

wherein the variables are defined as in formula (I).

In one embodiment, the compound of formula (I) is a compound of formula (IVA):

(IVA)

wherein the variables are defined as in formula (I).

In one embodiment, the compound of formula (I) is a compound of formula (IVB):

(IVB)

wherein the variables are defined as in formula (I).

In one embodiment, the compound of formula (I) is a compound of formula (IVC):

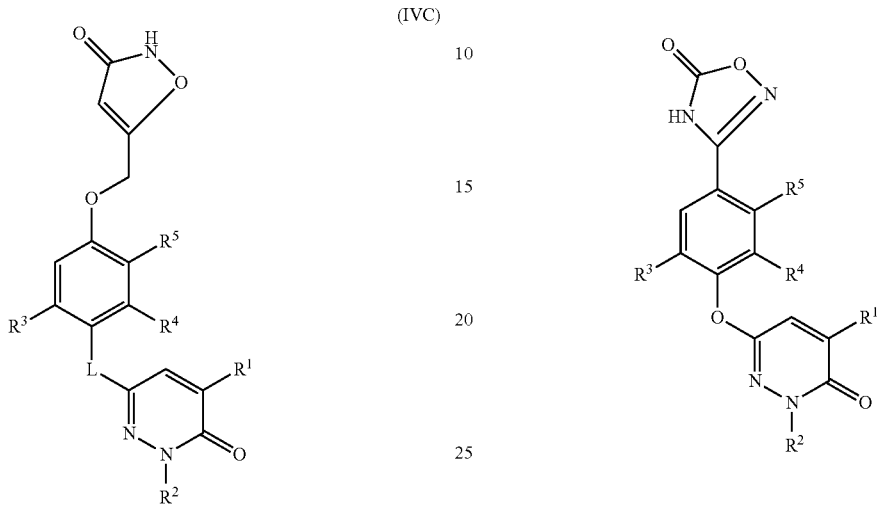

wherein the variables are defined as in formula (I).

In one embodiment, the compound of formula (I) is a compound of formula (IVD):

(IVD)

wherein the variables are defined as in formula (I).

In one embodiment, the compound of formula (I) is a compound of formula (VA):

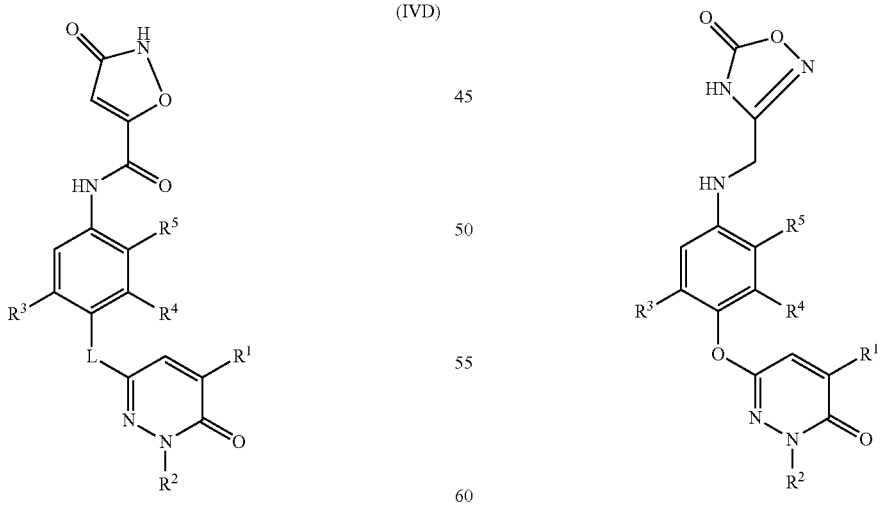

wherein the variables are defined as in formula (I).

In one embodiment, the compound of formula (I) is a compound of formula (VB):

(VB)

wherein the variables are defined as in formula (I).

In one embodiment, the compound of formula (I) is a compound of formula (VC):

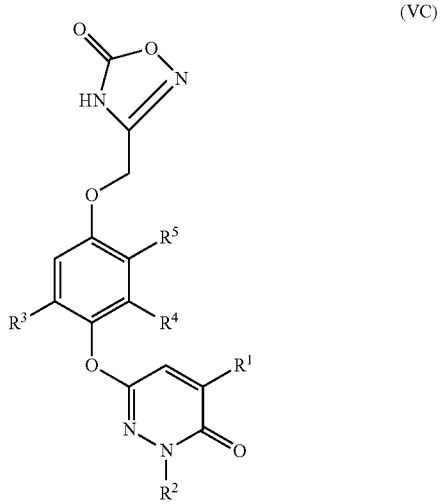

(VC)

wherein the variables are defined as in formula (I).

In one embodiment, the compound of formula (I) is a compound of formula (VD):

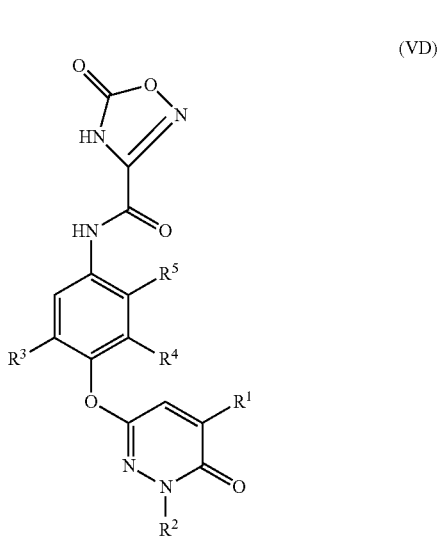

(VD)

wherein the variables are defined as in formula (I).

In one embodiment, the compound of formula (I) is a compound of formula (VIA):

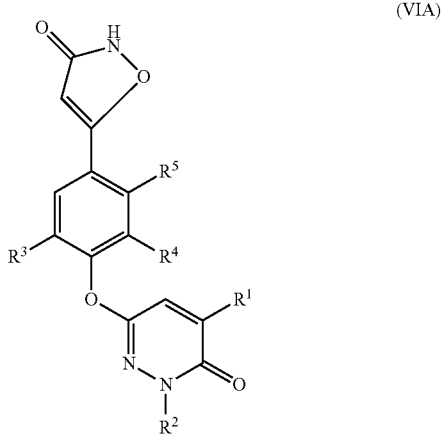

(VIA)

wherein the variables are defined as in formula (I).

In one embodiment, the compound of formula (I) is a compound of formula (VIB):

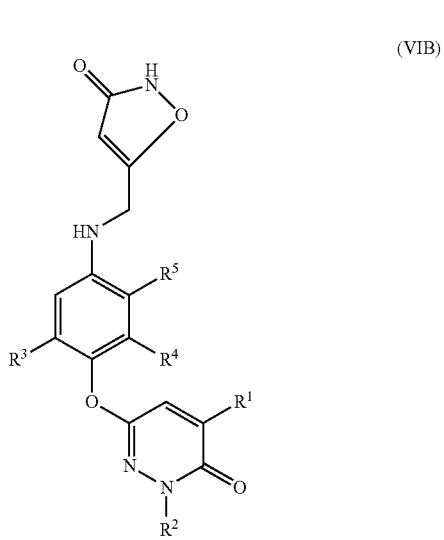

(VIB)

wherein the variables are defined as in formula (I).

In one embodiment, the compound of formula (I) is a compound of formula (VIC):

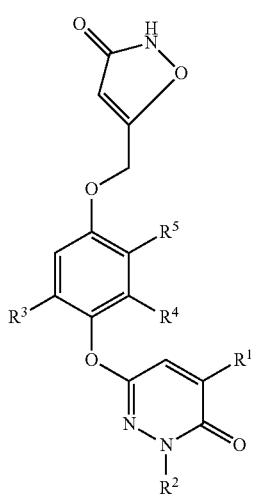

(VIC)

wherein the variables are defined as in formula (I).

In one embodiment, the compound of formula (I) is a compound of formula (VID):

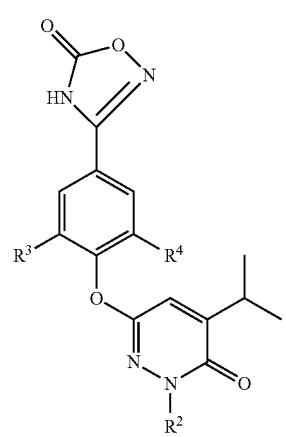

(VID)

wherein the variables are defined as in formula (I).

In one embodiment, the compound of formula (I) is a compound of formula (VIIA).

(VIIA)

wherein $R^2$ is H or methyl, and the variables are defined as in formula (I).

In one embodiment, the compound of formula (I) is a compound of formula (VIIB):

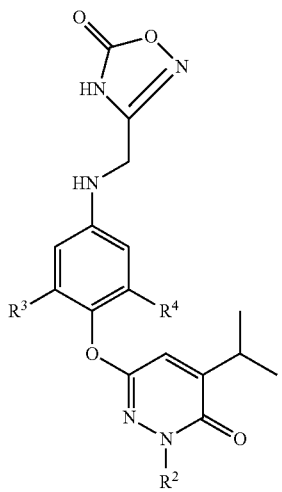

(VIIB)

wherein $R^2$ is H or methyl, and the variables are defined as in formula (I).

In one embodiment, the compound of formula (I) is a compound of formula (VIIC):

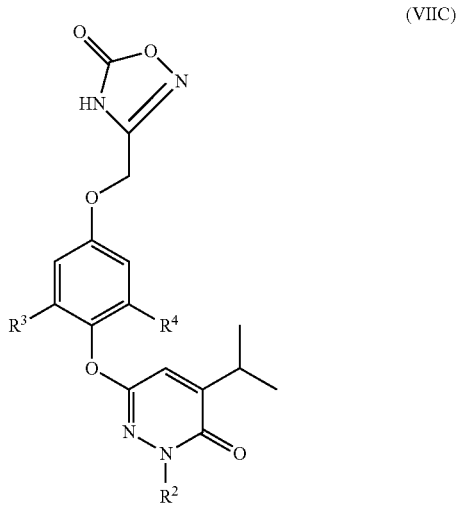

(VIIC)

wherein R² is H or methyl, and the variables are defined as in formula (I).

In one embodiment, the compound of formula (I) is a compound of formula (VIID):

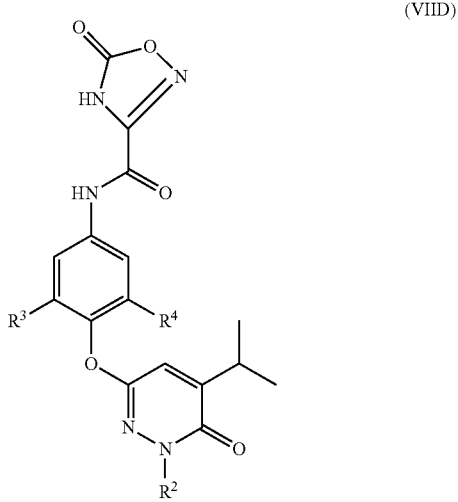

(VIID)

wherein R² is H or methyl, and the variables are defined as in formula (I).

In one embodiment, the compound of formula (I) is a compound of formula (VIIIA):

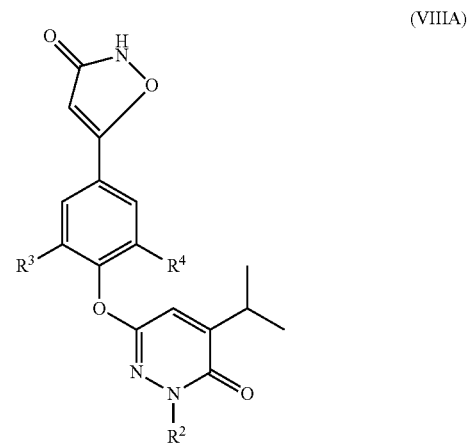

(VIIIA)

wherein R² is H or methyl, and the variables are defined as in formula (I).

In one embodiment, the compound of formula (I) is a compound of formula (VIIIB):

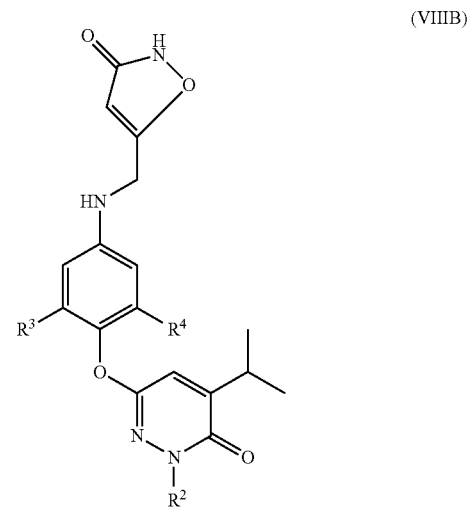

(VIIIB)

wherein R² is H or methyl, and the variables are defined as in formula (I).

In one embodiment, the compound of formula (I) is a compound of formula (VIIIC):

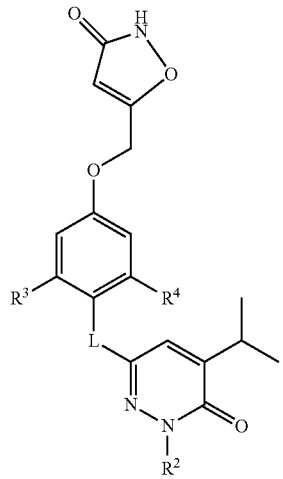

(VIIIC)

wherein R² is H or methyl, and the variables are defined as in formula (I).

In one embodiment, the compound of formula (I) is a compound of formula (VIIID):

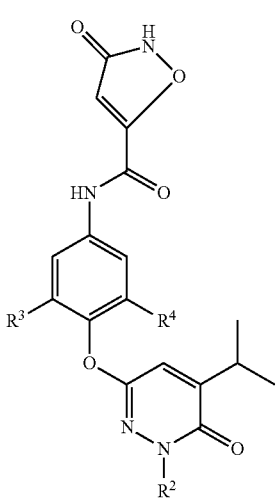

(VIIID)

wherein R² is H or methyl, and the variables are defined as in formula (I).

In one embodiment, the compound of formula (I) is a compound of formula (IXA), (IXB), (IXC), (IXD), (IXE), or (IXF):

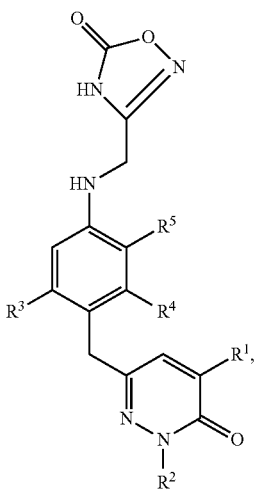

(IXA)

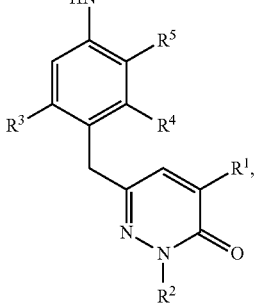

(IXB)

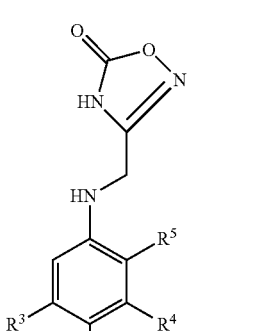

(IXC)

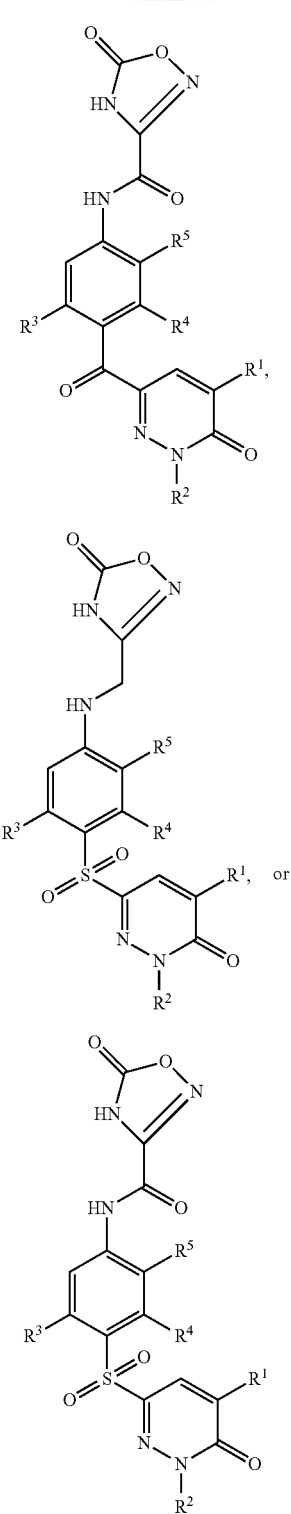

wherein the variables are defined as in formula (I). In some embodiments, the compound is of formula (IXA). In some embodiments, the compound is of formula (IXB). In some embodiments, the compound is of formula (IXC). In some embodiments, the compound is of formula (IXD). In some embodiments, the compound is of formula (IXE). In some embodiments, the compound is of formula (IXF).

In one embodiment, ring A together with the carbonyl (keto) group within the ring form a 5 membered heterocycle containing 1-3 ring heteroatoms selected from the group consisting of N, O, and S, and wherein the keto group is not adjacent to the atom attached to X. In one embodiment, ring A together with the carbonyl (keto) group within the ring form a 5 membered heterocycle containing 1-3 ring heteroatoms selected from the group consisting of N, O, and S, wherein the heterocycle is substituted with 1-2 $C_1$-$C_3$ alkyl or $C_3$-$C_4$ cycloalkyl, and wherein the keto group is not adjacent to the atom attached to X. In one embodiment, the 5 membered heterocycle contains 1-3 ring heteroatoms selected from the group consisting of N and O. In some embodiments, ring A together with the carbonyl (keto) group within the ring is

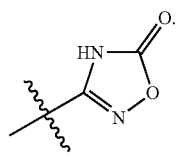 [SMILES: *c1noc(=O)[nH]1]

In some embodiments, ring A together with the carbonyl (keto) group within the ring is

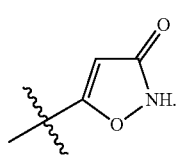

In one embodiment, $R^1$ is $C_1$-$C_4$ alkyl. In some embodiments, $R^1$ is methyl, ethyl, n-propyl, isopropyl, n-butyl, or t-butyl. In some embodiments, $R^1$ is $C_3$-$C_4$ alkyl. In one embodiment, $R^1$ is isopropyl. In some embodiments, $R^1$ is t-butyl. In one embodiment, $R^1$ is $C_1$-$C_4$ alkyl optionally substituted with 1-5 halo, preferably fluoro. In some embodiments, $R^1$ is $C_1$-$C_4$ alkyl optionally substituted with 1-2 halo, such as fluoro or chloro. In one embodiment, $R^1$ is $C_1$-$C_4$ alkyl optionally substituted with 1-5 halo or hydroxyl groups. In some embodiments, $R^1$ is $C_2$-$C_4$ alkyl optionally substituted with 1-5 halo or hydroxyl groups. In some embodiments, $R^1$ is $C_1$-$C_4$ alkyl optionally substituted with 1-2 halo or hydroxyl groups. In one embodiment, $R^1$ is $C_1$-$C_4$ alkyl optionally substituted with 1-5 hydroxyl groups. In some embodiments, $R^1$ is $C_1$-$C_4$ alkyl optionally substituted with 1-2 hydroxyl groups. In some embodiments, $R^1$ is $C_1$-$C_4$ alkyl substituted with 1 hydroxyl group. In some embodiments, $R^1$ is $C_1$-$C_4$ alkyl optionally substituted with 1-2 halo or hydroxyl groups. In some embodiments, $R^1$ is HO—CH($CH_3$)—. In some embodiments, $R^1$ is HO—CH($CH_2CH_3$)—. In some embodiments, $R^1$ is HO—C($CH_3$)$_2$—. In some embodiments, $R^1$ is HO—$CH_2$CH($CH_3$)—. In one embodiment, $R^1$ is $C_3$-$C_5$ cycloalkyl. In some embodiments, $R^1$ is a monocyclic $C_3$-$C_5$ cycloalkyl. In some embodiments, $R^1$ is cyclopropyl, cyclobutyl, or cyclopentyl. In some embodiments, $R^1$ is cyclopropyl. In some embodiments, $R^1$ is a fused bicyclic $C_3$-$C_5$ cycloalkyl. In some embodiments, $R^1$ is a bridged bicyclic $C_3$-$C_5$ cycloalkyl. In some embodiments, $R^1$ is

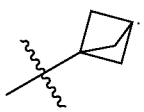

In one embodiment, $R^1$ is $CON(R^{10})_2$. In one embodiment, $R^1$ is $NR^{10}COR^{10}$.

In one embodiment, each $R^{10}$ is independently $C_1$-$C_3$ alkyl. In some embodiments, each $R^{10}$ is independently methyl, ethyl, n-propyl, or isopropyl. In some embodiments, each $R^{10}$ is methyl. In one embodiment, each $R^{10}$ is H. In some embodiments, one $R^{10}$ is H and the other $R^{10}$ is $C_1$-$C_3$ alkyl. In some embodiments, one $R^{10}$ is H and the other $R^{10}$ is methyl.

In one embodiment, $R^2$ is H. In one embodiment, $R^2$ is $C_1$-$C_3$ alkyl. In some embodiments, $R^2$ is methyl, ethyl, n-propyl, or isopropyl. In some embodiments, $R^2$ is methyl. In some embodiments, $R^2$ is H or —$CH_3$.

In one embodiment, L is O. In one embodiment, L is $CH_2$. In one embodiment, L is S. In one embodiment, L is SO. In one embodiment, L is $SO_2$. In one embodiment, L is CO. In one embodiment, L is CHF. In one embodiment, L is $CF_2$. In one embodiment, L is $C(R^{11})CN$. In one embodiment, L is C(Me)CN. In one embodiment, L is $CHR^{11}$ or $C(R^{11})R^{11}$, wherein each $R^{11}$ is independently $C_1$-$C_2$ alkyl optionally substituted with 1-5 halo, preferably fluoro, or the 2 $R^{11}$ groups together with the carbon atom they are attached to form a cyclopropyl or cyclobutyl ring. In one embodiment, L is $CHR^{11}$. In one embodiment, L is $C(R^{11})R^{11}$. In one embodiment, each $R^{11}$ independently is $C_1$-$C_2$ alkyl, i.e., is methyl or ethyl. In one embodiment, each $R^{11}$ independently is $C_1$-$C_2$ alkyl substituted with 1-5 halo, preferably fluoro. In one embodiment, the 2 $R^{11}$ groups together with the carbon atom they are attached to form a cyclopropyl or cyclobutyl ring. In some embodiments, L is O, $CH_2$, $SO_2$, CO, $CHR^{11}$, or $C(R^{11})R^{11}$, and each $R^{11}$ is independently methyl or ethyl. In some embodiments, L is O, $CH_2$, $SO_2$, or CO.

In one embodiment, $R^3$ is $C_1$. In one embodiment, $R^3$ is Br. In one embodiment, $R^3$ is Me. In one embodiment, $R^3$ is ethyl. In some embodiments, $R^3$ is $C_1$ or —$CH_3$. In one embodiment, $R^4$ is $C_1$. In one embodiment, $R^4$ is Br. In one embodiment, $R^4$ is Me. In one embodiment, $R^4$ is ethyl. In one embodiment, $R^3$ and $R^4$ are each $C_1$. In some embodiments, $R^3$ and $R^4$ are each methyl. In some embodiments, $R^3$ is $C_1$ and $R^4$ is methyl. In some embodiments, $R^3$ is methyl and $R^4$ is $C_1$.

In one embodiment, $R^5$ is H. In one embodiment, $R^5$ is halo. In some embodiments, $R^5$ is fluoro, chloro, or bromo. In some embodiments, $R^5$ is fluoro. In one embodiment, $R^5$ is $C_1$-$C_4$ alkyl. In some embodiments, $R^5$ is $C_1$-$C_3$ alkyl. In some embodiments, $R^5$ is methyl, ethyl, n-propyl, or isopropyl. In one embodiment, $R^5$ is $CH_3$. In some embodiments, $R^5$ is H or —$CH_3$. In one embodiment, $R^5$ is $C_3$-$C_4$ cycloalkyl. In some embodiments, $R^5$ is cyclopropyl. In some embodiments, $R^5$ is cyclobutyl. In one embodiment, $R^4$ together with $R^5$ and the intervening atoms form a 5-7 membered cycloalkyl. In some embodiments, $R^4$ together with $R^5$ and the intervening atoms form cyclopentyl or cyclohexyl. In one embodiment, $R^4$ together with $R^5$ and the intervening atoms form cyclopentyl. In one embodiment, $R^4$ together with $R^5$ and the intervening atoms form a 5-7 membered heterocycle containing 1-2 ring heteroatoms. Preferred heteroatoms include one or more of N, O, and S.

In one embodiment, X is absent (i.e., X is a bond). In one embodiment, X is O. In one embodiment, X is $NR^{12}$. In one embodiment, X is $C(O)NR^{12}$. In one embodiment, X is $NR^{12}C(O)$. In one embodiment, X is $NR^{12}SO_2$. In one embodiment, X is $SO_2NR^{12}$. In one embodiment, X is $NR^{12}C(O)$. In one embodiment, X is $CR^{12}R^{12}$. In one embodiment, X is $OCR^{12}R^{12}$. In one embodiment, X is $CR^{12}R^{12}O$. In one embodiment, X is $CR^{12}R^{12}NH$. In one embodiment, X is $NR^{12}CR^{12}R^{12}$. In some embodiments, X is $NR^{12}C(O)$, $OCR^{12}R^{12}$, or $NR^{12}CR^{12}R^{12}$, and each $R^{12}$ is independently H or methyl. In some embodiments, X is $N(CH_3)CH_2$. In one embodiment, X is $CR^{12}R^{12}NR^{12}$. In one embodiment, X is NH. In one embodiment, X is $CH_2$. In one embodiment, X is $OCH_2$. In one embodiment, X is $CH_2O$. In one embodiment, X is $NHCH_2$. In one embodiment, X is $CH_2NH$. In one embodiment, X is NHC(O). In one embodiment, X is C(O)NH. In one embodiment, X is $SO_2NH$. In one embodiment, X is $NHSO_2$. In some embodiments, X is $OCH_2$, $NHCH_2$, NHC(O), $N(CH_3)CH_2$, or $N(H)CH(CH_3)$. In one embodiment, $R^{12}$ is H. In one embodiment, $R^{12}$ is methyl. In some embodiments, all $R^{12}$ groups in a given moiety, such as $OCR^{12}R^{12}$, are H. In some embodiments, all $R^{12}$ groups in a given moiety, such as $OCR^{12}R^{12}$, are methyl. In some embodiments, the $R^{12}$ groups in a given moiety, such as $OCR^{12}R^{12}$, are a combination of H and methyl.

In one aspect, provided is a compound of formula (I) wherein the compound has any one or more of the following features:

(I) ring A together with the carbonyl group within the ring is:

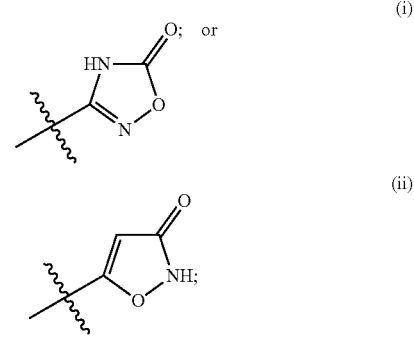

(II) $R^1$ is:
  (iii) $C_1$-$C_4$ alkyl optionally substituted with 1-5 halo or hydroxyl groups; or
  (iv) $C_3$-$C_5$ cycloalkyl;
(III) $R^2$ is H or $C_1$-$C_3$ alkyl;
(IV) $R^3$ is $C_1$ or methyl;
(V) $R^4$ is $C_1$ or methyl;
(VI) $R^5$ is H, halo, or $C_1$-$C_4$ alkyl;
(VII) $R^5$ together with $R^4$ and the intervening atoms form a 5-7 membered cycloalkyl or a 5-7 membered heterocycle containing 1-2 ring heteroatoms;
(VIII) X is:
  (v) a bond; or
  (vi) $NR^{12}C(O)$, $OCR^{12}R^{12}$, or $NR^{12}CR^{12}R^{12}$, wherein each $R^{12}$ is independently H or methyl; and
(IX) L is O, $CH_2$, $SO_2$, or CO.

In one variation, (I) applies. In one variation, (II) applies. In one variation, (III) applies. In one variation, (IV) applies. In one variation, (V) applies. In one variation, (VI) applies. In one variation, (VII) applies. In one variation, (VIII) applies. In one variation, (IX) applies. In one aspect of this variation, (I), (II), (III), (IV), (V), (VI), (VIII), and (IX)

apply. In another aspect of this variation, (I), (II), (III), (IV), (VII), (VIII), and (IX) apply. In one variation, (i), (iii), and (vi) apply. In one variation, (ii), (iii), and (v) apply. In one variation, (i), (iii), and (vi) apply. In one variation, (i), (iv), and (vi) apply. In one variation, (i), (iii), (VII), and (vi) apply.

In some embodiments, the compound of formula (I) is an agonist of THR beta. In some embodiments, the compound of formula (I) is an agonist of THR beta and is selective over THR alpha. In some embodiments, the compound of formula (I) has at least 2-fold selectivity for THR beta over THR alpha. In some embodiments, the compound of formula (I) has at least 5-fold selectivity for THR beta over THR alpha. In some embodiments, the compound of formula (I) has at least 10-fold selectivity for THR beta over THR alpha. In some embodiments, the compound of formula (I) has at least 20-fold selectivity for THR beta over THR alpha. In some embodiments, the compound of formula (I) has at least 50-fold selectivity for THR beta over THR alpha. In some embodiments, the compound of formula (I) has at least 75-fold selectivity for THR beta over THR alpha. In some embodiments, the compound of formula (I) has at least 100-fold selectivity for THR beta over THR alpha. In some embodiments, the compound of formula (I) has at least 2-, 3-, 4-, 5-, 6-, 7-, 8-, 9-, 10-, 15-, 20-, 25-, 30-, 35-, 40-, 45-, 50-, 55-, 60-, 65-, 70-, 75-, 80-, 85-, 90-, 95-, or 100-fold selectivity for THR beta over THR alpha. In any such embodiment, in one aspect selectivity is assessed via a biochemical assay, such as the TR-FRET assay described in Example B1.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to the ring A moiety of formula (I) may be combined with every description, variation, embodiment or aspect of $R^1$, $R^2$, $R^3$, $R^4$, $R^5$, $R^{10}$, $R^{11}$, $R^{12}$, X, and L the same as if each and every combination were specifically and individually listed. It is also understood that all descriptions, variations, embodiments or aspects of formula (I), where applicable, apply equally to other formulae detailed herein, and are equally described, the same as if each and every description, variation, embodiment or aspect were separately and individually listed for all formulae. For example, all descriptions, variations, embodiments or aspects of formula (I), where applicable, apply equally to any of formulae as detailed herein, such as formulae (IIA), (IIB), (IIIA)-(IIID), (IVA)-(IVD), (VA)-(VD), (VIA)-(VID), (VIIA)-(VIID), (VIIIA)-(VIIID), and (IXA)-(IXF), and are equally described, the same as if each and every description, variation, embodiment or aspect were separately and individually listed for all formulae.

In some embodiments, provided is a compound selected from the compounds in Table 1, or pharmaceutically acceptable salt thereof. Although certain compounds described in the present disclosure, including in Table 1, are presented as specific stereoisomers and/or in a non-stereochemical form, it is understood that any or all stereochemical forms, including any enantiomeric or diastereomeric forms, and any tautomers or other forms of any of the compounds of the present disclosure, including in Table 1, are herein described.

In one embodiment, provided herein is a compound selected from those tabulated below in Table 1:

TABLE 1

| Example | Structure |
|---|---|
| 1 | 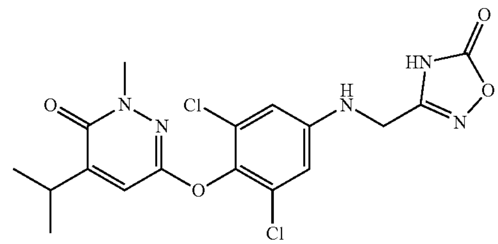 [SMILES: CC(C)c1cc(Oc2c(Cl)cc(NCc3noc(=O)[nH]3)cc2Cl)nn(C)c1=O] |
| 2 | 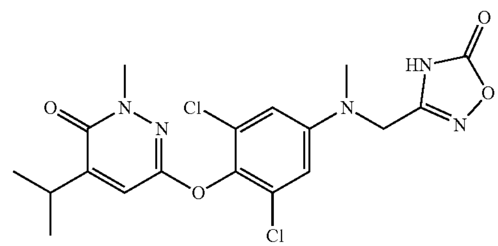 [SMILES: CC(C)c1cc(Oc2c(Cl)cc(N(C)Cc3noc(=O)[nH]3)cc2Cl)nn(C)c1=O] |
| 3 | 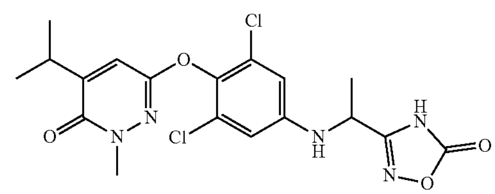 [SMILES: CC(C)c1cc(Oc2c(Cl)cc(NC(C)c3noc(=O)[nH]3)cc2Cl)nn(C)c1=O] |
| 4 | 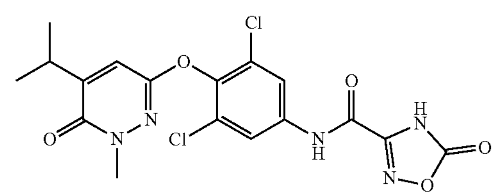 [SMILES: CC(C)c1cc(Oc2c(Cl)cc(NC(=O)c3noc(=O)[nH]3)cc2Cl)nn(C)c1=O] |
| 5 | 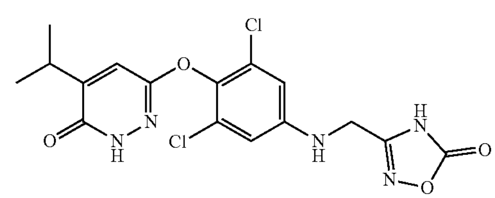 [SMILES: CC(C)c1cc(Oc2c(Cl)cc(NCc3noc(=O)[nH]3)cc2Cl)n[nH]c1=O] |
| 6 | 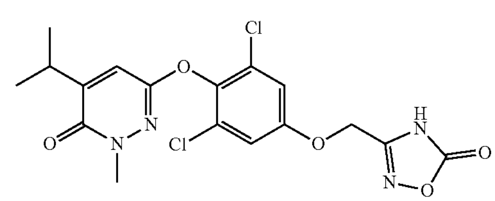 [SMILES: CC(C)c1cc(Oc2c(Cl)cc(OCc3noc(=O)[nH]3)cc2Cl)nn(C)c1=O] |
| 7 | 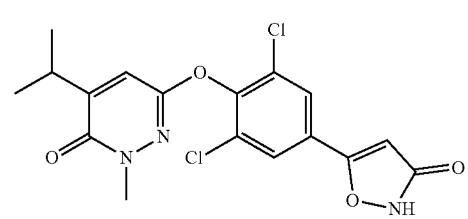 [SMILES: CC(C)c1cc(Oc2c(Cl)cc(-c3cc(=O)[nH]o3)cc2Cl)nn(C)c1=O] |

TABLE 1-continued

| Example | Structure |
|---|---|
| 8 | 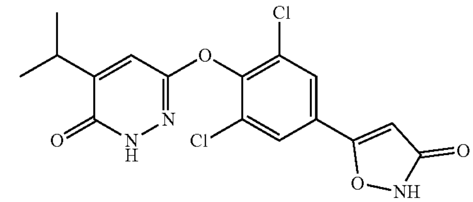 [SMILES: CC(C)c1cc(Oc2c(Cl)cc(-c3cc(=O)[nH]o3)cc2Cl)n[nH]c1=O] |
| 9 | 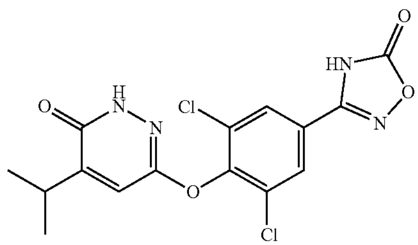 [SMILES: CC(C)c1cc(Oc2c(Cl)cc(-c3noc(=O)[nH]3)cc2Cl)n[nH]c1=O] |
| 10 | 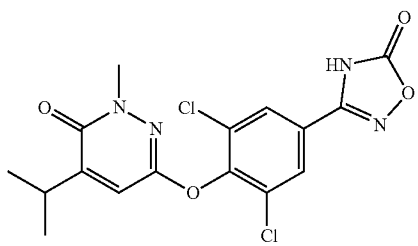 [SMILES: CC(C)c1cc(Oc2c(Cl)cc(-c3noc(=O)[nH]3)cc2Cl)nn(C)c1=O] |
| 11 | 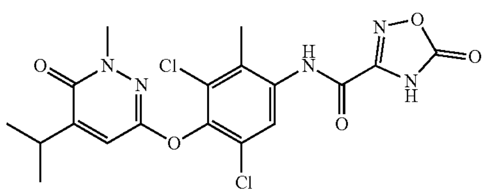 [SMILES: Cc1c(NC(=O)c2noc(=O)[nH]2)cc(Cl)c(Oc2cc(C(C)C)c(=O)n(C)n2)c1Cl] |
| 12 | 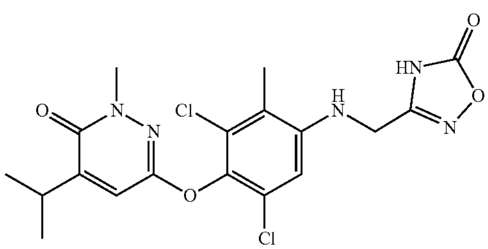 [SMILES: Cc1c(NCc2noc(=O)[nH]2)cc(Cl)c(Oc2cc(C(C)C)c(=O)n(C)n2)c1Cl] |
| 13 | 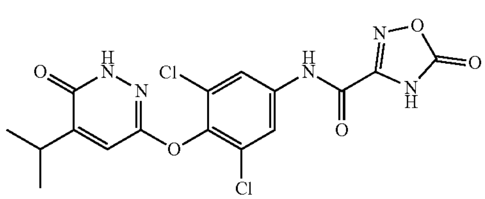 [SMILES: CC(C)c1cc(Oc2c(Cl)cc(NC(=O)c3noc(=O)[nH]3)cc2Cl)n[nH]c1=O] |
| 14 | 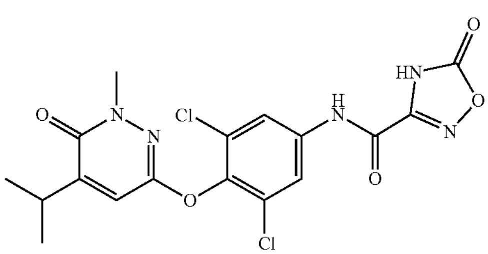 [SMILES: CC(C)c1cc(Oc2c(Cl)cc(NC(=O)c3noc(=O)[nH]3)cc2Cl)nn(C)c1=O] |
| 15 | |
| 16 | |
| 17 | |
| 18 | |
| 19 | |
| 20 | |

TABLE 1-continued

| Example | Structure |
|---------|-----------|
| 21 | 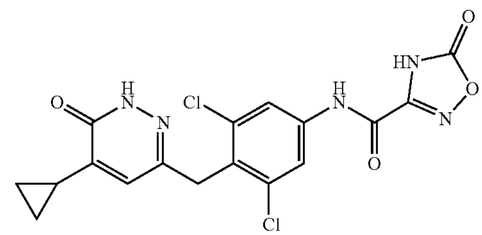 [SMILES: O=C(Nc1cc(Cl)c(Cc2cc(C3CC3)c(=O)[nH]n2)c(Cl)c1)c1noc(=O)[nH]1] |
| 22 | 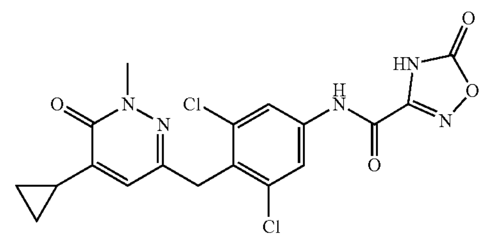 [SMILES: Cn1nc(Cc2c(Cl)cc(NC(=O)c3noc(=O)[nH]3)cc2Cl)cc(C2CC2)c1=O] |
| 23 | 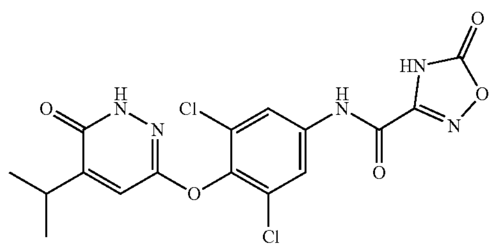 [SMILES: CC(C)c1cc(Oc2c(Cl)cc(NC(=O)c3noc(=O)[nH]3)cc2Cl)n[nH]c1=O] |
| 24 | 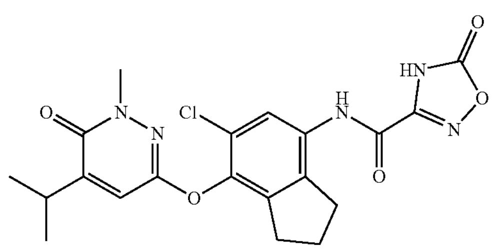 [SMILES: CC(C)c1cc(Oc2c(Cl)cc(NC(=O)c3noc(=O)[nH]3)c3c2CCC3)nn(C)c1=O] |
| 25 | 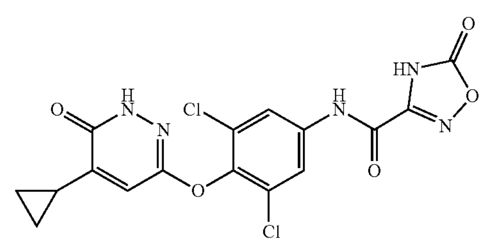 |
| 26 | 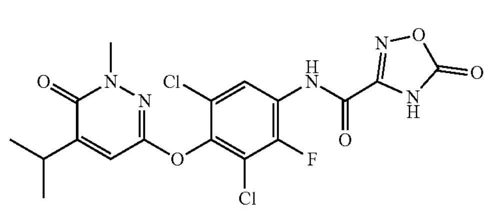 [SMILES: CC(C)c1cc(Oc2c(Cl)cc(NC(=O)c3noc(=O)[nH]3)c(F)c2Cl)nn(C)c1=O] |
| 27 | |
| 28 | |
| 29 | |
| 30 | |
| 31 | |
| 32 | |

TABLE 1-continued

| Example | Structure |
|---------|-----------|
| 33 | 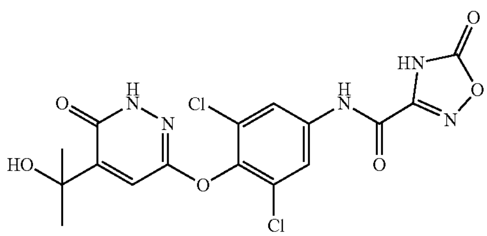 [SMILES: CC(C)(O)c1cc(Oc2c(Cl)cc(NC(=O)c3noc(=O)[nH]3)cc2Cl)n[nH]c1=O] |
| 34 | 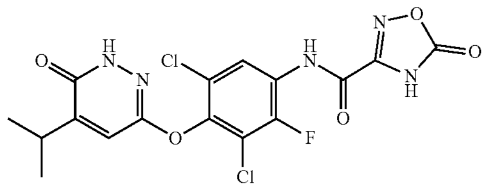 |
| 35 | 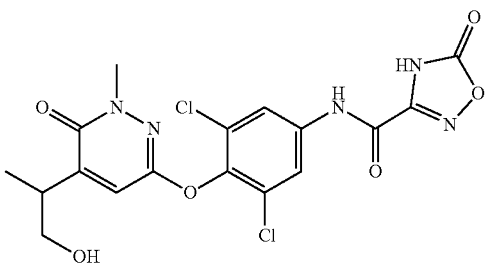 [SMILES: CC(CO)c1cc(Oc2c(Cl)cc(NC(=O)c3noc(=O)[nH]3)cc2Cl)nn(C)c1=O] |
| 36 | 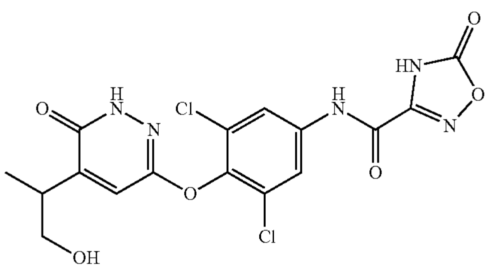 [SMILES: CC(CO)c1cc(Oc2c(Cl)cc(NC(=O)c3noc(=O)[nH]3)cc2Cl)n[nH]c1=O] |
| 37 | | or a tautomer or an N-oxide thereof, or an isotopomer of each thereof, or a prodrug of each of the above, or a stereoisomer of the aforesaid, or a pharmaceutically acceptable salt of each of the foregoing, or a solvate of each of the preceding.

In some embodiments, provided herein is a compound selected from those listed in Table 1 or a pharmaceutically acceptable salt thereof.

The invention also includes all salts, such as pharmaceutically acceptable salts, of compounds referred to herein. The invention also includes any or all of the stereochemical forms, including any enantiomeric or diastereomeric forms, and any tautomers or other forms, such as N-oxides, solvates, prodrugs, or isotopomers, of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

Methods of Synthesis

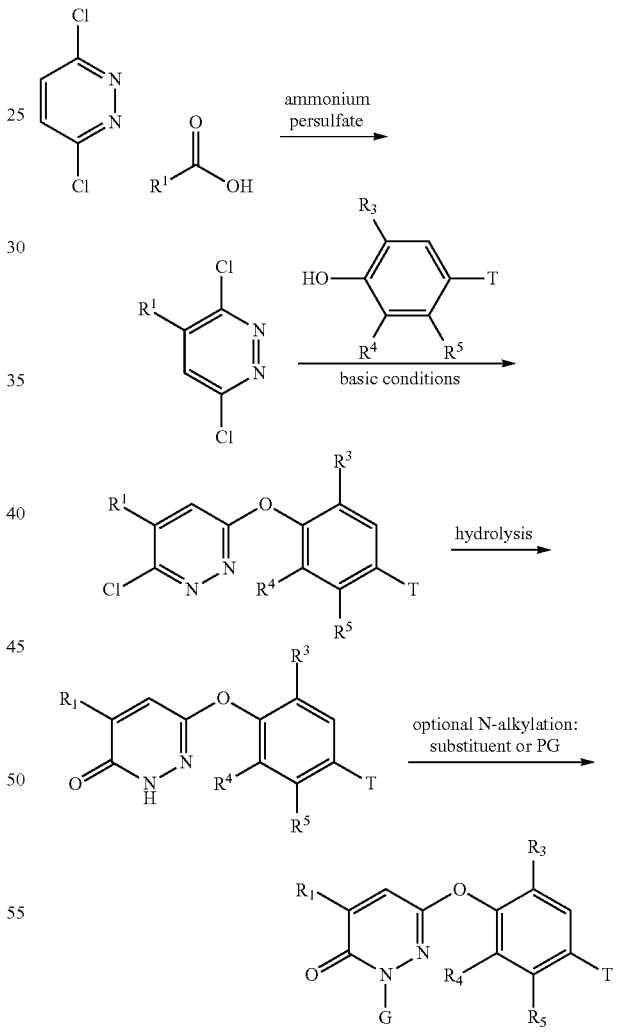

Scheme 1: General synthesis of biaryl-ether core

T = Br, CN, $NH_2$ wherein $R^1$, $R^3$, $R^4$, and $R^5$ are as defined for the compound of formula (I); T is Br, CN, or $NH_2$; and PG and G are suitable protecting groups.

The biaryl-ether core of the compounds disclosed herein can be prepared as outlined in Scheme 1. Reaction of 3,6-dichloropyridazine and compounds of general formula R$^1$—CO$_2$H with ammonium persulfate provides R$^1$-substituted dichloropyridazine compounds, which can then be reacted with phenol derivatives, hydrolyzed, and optionally N-protected to provide the desired intermediate compounds.

Scheme 1': Alternative pyridazine synthesis

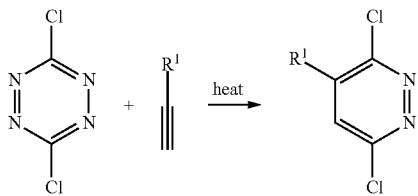

wherein R$^1$ is as defined for the compound of formula (I).

Scheme 1' provides an alternative synthesis of the pyridazines used for the preparation of compounds of formula (I) disclosed herein. Reaction of 3,6-dichloro-1,2,4,5-tetrazine with R$^1$-substituted acetylenes affords R$^1$-substituted dichloropyridazine compounds.

Scheme 1a: Arriving at G = alkyl and T = NH$_2$

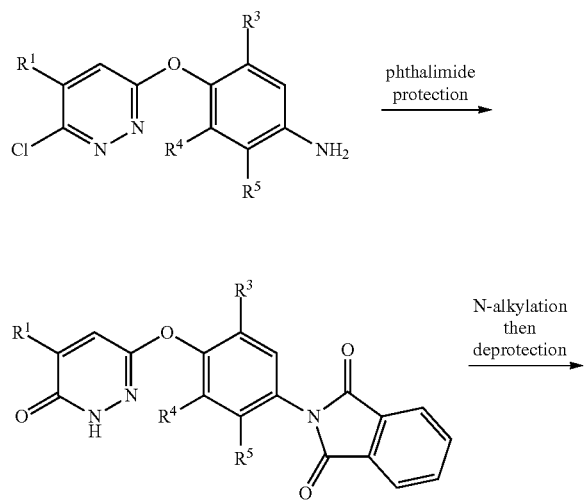

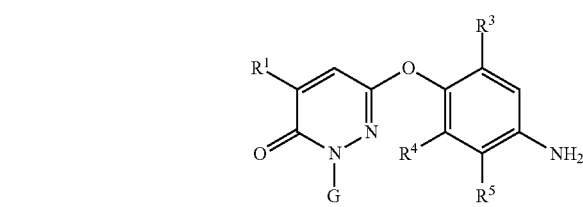

wherein R$^1$, R$^3$, R$^4$, and R$^5$ are as defined for the compound of formula (I); and G is a suitable protecting group.

Scheme 1a outlines a synthesis wherein G is an alkyl group and T is NH$_2$. Compounds having the biaryl-ether core with an amine moiety can undergo phthalimide protection, N-alkylation, and subsequent deprotection to provide the desired intermediate compounds.

Scheme 2:

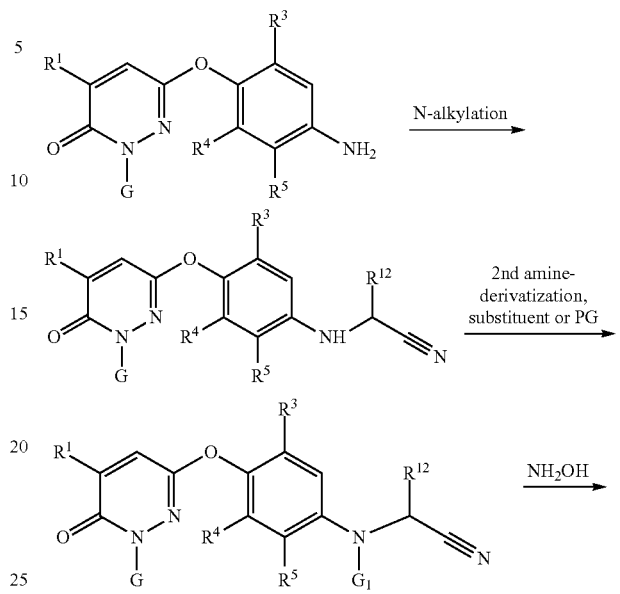

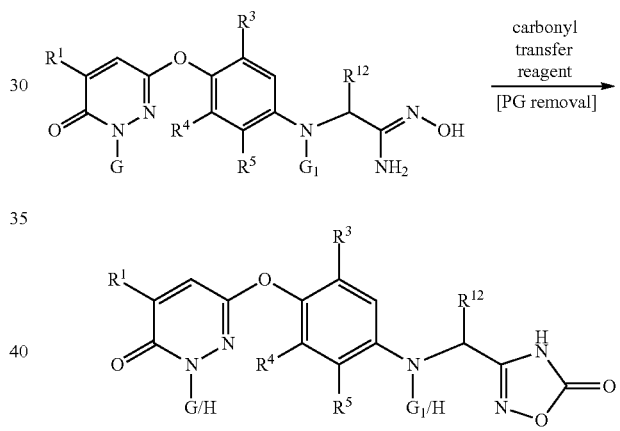

wherein R$^1$, R$^3$, R$^4$, R$^5$, and R$^{12}$ are as defined for the compound of formula (I); and PG, G, and G$_1$ are suitable protecting groups.

Scheme 2 outlines the synthesis of certain compounds of formula (I) disclosed herein. Compounds having the biaryl-ether core with an amine moiety, for example as provided in Scheme 1a, can undergo N-alkylation and second amine derivatization, followed by reaction with NH$_2$OH, treatment with a carbonyl transfer reagent, and optional deprotection to afford the desired compounds.

Scheme 2a:

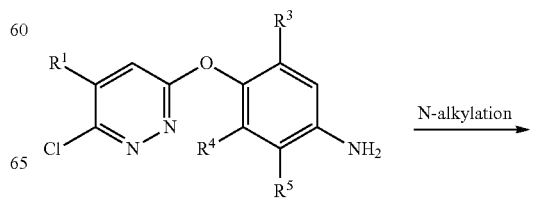

-continued

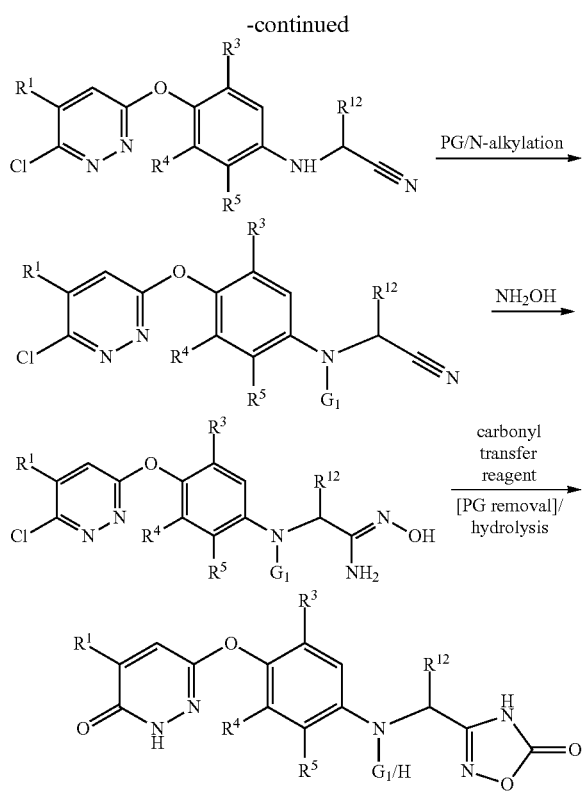

wherein $R^1$, $R^3$, $R^4$, $R^5$, and $R^{12}$ are as defined for the compound of formula (I); and PG and $G_i$ are suitable protecting groups.

Scheme 2a outlines an alternative synthesis of certain compounds of formula (I) disclosed herein. Compounds having the biaryl-ether core with an amine moiety can undergo N-alkylation, protection of the amine group, reaction with $NH_2OH$, treatment with a carbonyl transfer reagent, and optional deprotection or hydrolysis to afford the desired compounds.

Scheme 3:

wherein $R^1$, $R^3$, $R^4$, $R^5$, and ring A are as defined for the compound of formula (I); and G and $G_i$ are suitable protecting groups.

Scheme 3 shows the synthesis of certain compounds of formula (I). Reaction of biaryl-ether derivatives containing an amine moiety with carboxylic acid derivatives of ring A provides amide bond formation to form the desired compounds.

Scheme 4:

wherein $R^1$, $R^3$, $R^4$, $R^5$, and $R^{12}$ are as defined for the compound of formula (I); and G and PG are suitable protecting groups.

Scheme 4 shows the synthesis of certain compounds of formula (I). Palladium-mediated hydroxylation of biaryl-ether derivatives containing a bromo group, followed by O-alkylation, reaction with $NH_2OH$, treatment with a carbonyl transfer reagent, and optional deprotection or hydrolysis provides the desired compounds.

Scheme 5:

-continued

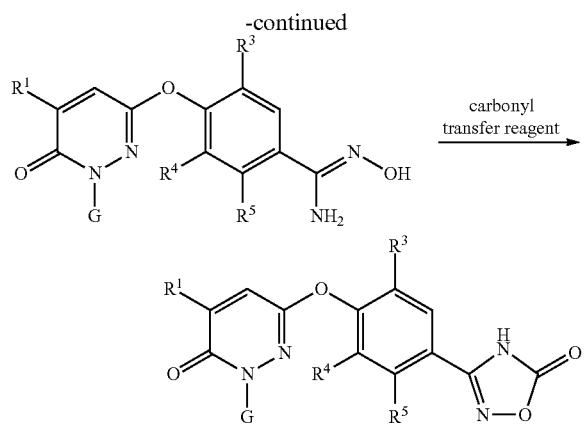

wherein $R^1$, $R^3$, $R^4$, and $R^5$ are as defined for the compound of formula (I); and G is a suitable protecting group.

Scheme 5 shows the synthesis of certain compounds of formula (I). Treatment of biaryl-ether derivatives containing a cyano group with $NH_2OH$, followed by treatment with a carbonyl transfer reagent provides the desired compounds.

Scheme 6:

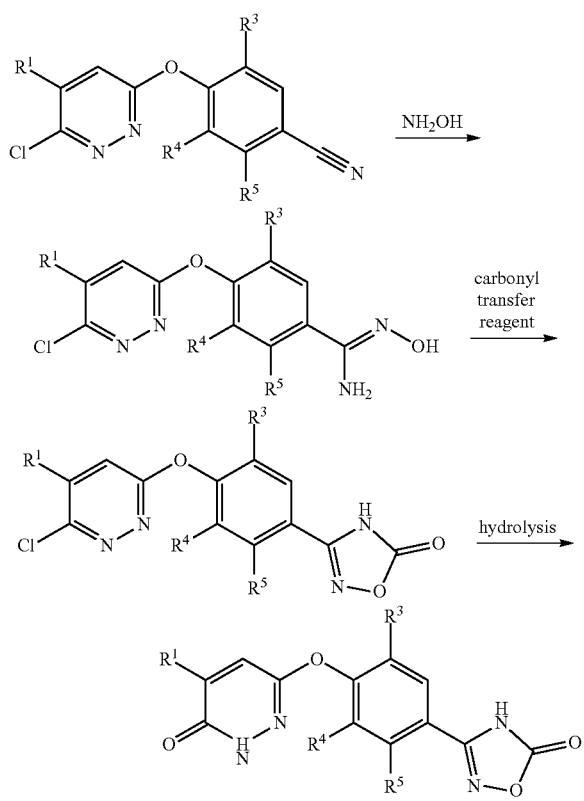

wherein $R^1$, $R^3$, $R^4$, and $R^5$ are as defined for the compound of formula (I).

Scheme 6 shows the synthesis of certain compounds of formula (I). Treatment of biaryl-ether derivatives containing a cyano group with $NH_2OH$, followed by treatment with a carbonyl transfer reagent and hydrolysis provides the desired compounds.

Scheme 7:

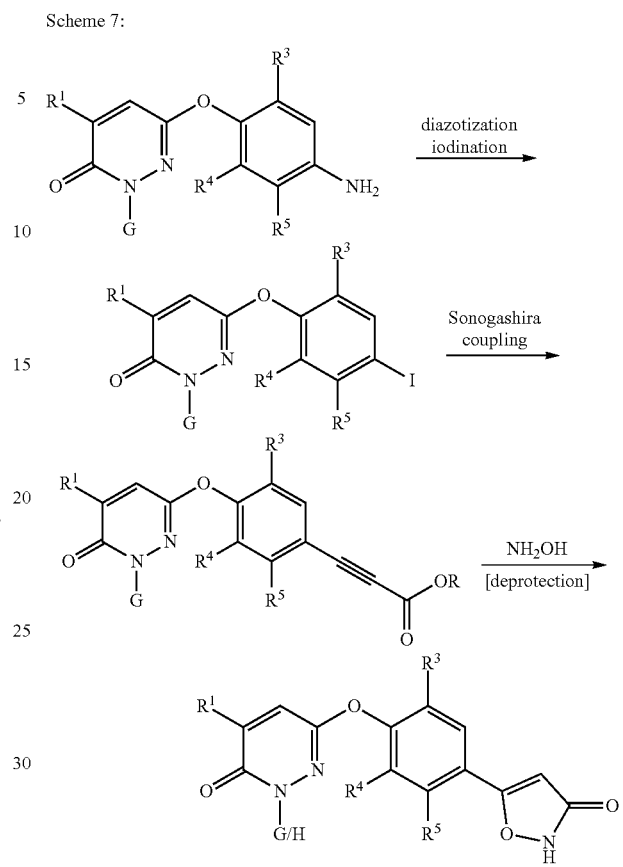

wherein $R^1$, $R^3$, $R^4$, and $R^5$ are as defined for the compound of formula (I); and G is a suitable protecting group.

Scheme 7 shows the synthesis of certain compounds of formula (I). Diazotization/iodination of biaryl-ether derivatives containing an amino group, followed by Sonogashira coupling, reaction with $NH_2OH$, and subsequent optional deprotection provides the desired compounds.

Synthesis of certain compounds provided herein are schematically illustrated above, and provided in the Examples section below. The variables listed in the schemes above are as defined for the compound of formula (I) or any variation, embodiments, or aspect thereof. Synthesis of other compounds provided herein will be apparent to the skilled artisan based on the guidance provided herein and based on synthetic methods well known to the skilled artisan.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization, and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

It is understood that the synthetic process disclosed here may be modified to arrive at various compounds of the invention by selection of appropriate reagents and starting materials. It is also understood that where protection of certain active or incompatible groups (e.g., an amine or a carboxylic acid) is required, the formulae in e.g., the scheme(s) provided here intend and include compounds where such active or incompatible groups are in appropriate protected forms. For a general description of protecting groups and their use, see P.G.M. Wuts and T.W. Greene, Greene's Protective Groups in Organic Synthesis 4$^{th}$ edition, Wiley-Interscience, New York, 2006.

Pharmaceutical Compositions and Formulations

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In one variation, "substantially pure" intends a composition that contains no more than 35% impurity, wherein the impurity denotes a compound other than the compound comprising the majority of the composition or a salt thereof. For example, a composition of a substantially pure compound selected from a compound of Table 1 intends a composition that contains no more than 35% impurity, wherein the impurity denotes a compound other than the compound or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 15% or preferably no more than 10% or more preferably no more than 5% or even more preferably no more than 3% and most preferably no more than 1% impurity, which impurity may be the compound in a different stereochemical form. For instance, and without limitation, a composition of substantially pure (S) compound means that the composition contains no more than 15% or no more than 10% or no more than 5% or no more than 3% or no more than 1% of the (R) form of the compound.

In one variation, the compounds herein are synthetic compounds prepared for administration to an individual such as a human. In another variation, compositions are provided containing a compound in substantially pure form. In another variation, the invention embraces pharmaceutical compositions comprising a compound detailed herein and a pharmaceutically acceptable carrier or excipient. In another variation, methods of administering a compound are provided. The purified forms, pharmaceutical compositions and methods of administering the compounds are suitable for any compound or form thereof detailed herein.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington: The Science and Practice of Pharmacy*, Lippincott Williams & Wilkins, 21st ed. (2005), which is incorporated herein by reference.

Compounds as described herein may be administered to individuals (e.g., a human) in a form of generally accepted oral compositions, such as tablets, coated tablets, and gel capsules in a hard or in soft shell, emulsions or suspensions.

Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid polyols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described.

Compositions comprising a compound provided herein are also described. In one variation, the composition comprises a compound and a pharmaceutically acceptable carrier or excipient. In another variation, a composition of substantially pure compound is provided.

Methods of Use/Treatments

Compounds and compositions detailed herein, such as a pharmaceutical composition containing a compound of any formula provided herein, or a pharmaceutically acceptable salt thereof, and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

In one aspect, provided herein is a method of agonizing thyroid hormone receptor beta (THR beta) comprising contacting either an effective amount of a compound provided herein, or an effective amount of a pharmaceutical composition provided herein, with the THR beta.

In one aspect, provided herein is a method of treating a disorder, which is mediated by THR beta, in a patient, comprising administering to the patient in need thereof a therapeutically effective amount of a compound provided herein, or a therapeutically effective amount of a composition provided herein.

Methods of treating a disorder mediated by THR beta, including without limitation non-alcoholic fatty liver disease, non-alcoholic steatohepatitis, and symptoms and manifestations of each thereof are well known to the skilled artisan and can be adapted to treating such a disorder with a compound or composition provided herein.

In one aspect, provided herein is a method of agonizing thyroid hormone receptor beta (THR beta) comprising contacting either an effective amount of a compound provided herein, or a salt thereof, such as a pharmaceutically acceptable salt thereof, or an effective amount of a pharmaceutical composition provided herein, with the THR beta. In one aspect, provided herein is a method of selectively agonizing THR beta over THR alpha comprising contacting either an effective amount of a compound provided herein, or a pharmaceutically acceptable salt thereof, or an effective amount of a pharmaceutical composition provided herein, with the THR beta. In one such aspect, the method selectively agonizes THR beta over THR alpha by at least 2-, 3-, 4-, 5-, 6-, 7-, 8-, 9-, 10-, 15-, 20-, 25-, 30-, 35-, 40-, 45-, 50-, 55-, 60-, 65-, 70-, 75-, 80-, 85-, 90-, 95-, or 100-fold. In any such embodiment, in one aspect selectivity is assessed via a biochemical assay, such as the TR-FRET assay described in Example B1.

In one aspect, provided herein is a method of treating a disease or disorder that is mediated by THR beta in a patient in need thereof, comprising administering to the patient a therapeutically effective amount of a compound provided herein, or a therapeutically effective amount of a composition provided herein. In one aspect, the disease or disorder is a liver disease or disorder. In one aspect, provided herein is a method of treating a disease or disorder of the liver associated with sub-optimal THR beta agonism in a patient in need thereof, comprising administering to the patient a compound of formula (I), or a pharmaceutically acceptable salt thereof, wherein the compound selectively agonizes THR beta over THR alpha.

In one aspect, provided herein is a method of treating non-alcoholic fatty liver disease in a patient in need thereof, comprising administering to the patient a therapeutically effective amount of a compound provided herein, or a therapeutically effective amount of a composition provided herein. In one aspect, provided herein is a method of treating non-alcoholic steatohepatitis (NASH) in a patient in need thereof, comprising administering to the patient a therapeutically effective amount of a compound provided herein, or a therapeutically effective amount of a composition provided herein. In one aspect, provided herein is a method of treating metabolic syndrome in a patient in need thereof, comprising administering to the patient a therapeutically effective amount of a compound provided herein, or a therapeutically effective amount of a composition provided herein. In one aspect, provided herein is a method of treating dyslipidemia in a patient in need thereof, comprising administering to the patient a therapeutically effective amount of a compound provided herein, or a therapeutically effective amount of a composition provided herein. In one aspect, provided herein is a method of treating hypertriglyceridemia in a patient in need thereof, comprising administering to the patient a therapeutically effective amount of a compound provided herein, or a therapeutically effective amount of a composition provided herein. In one aspect, provided herein is a method of treating hypercholesterolemia in a patient in need thereof, comprising administering to the patient a therapeutically effective amount of a compound provided herein, or a therapeutically effective amount of a composition provided herein.

In any of the embodiments described herein, a patient having a disease or disorder associated with THR beta agonism may include, but is not limited to, a patient with an underlying hypothyroid disorder.

In another aspect is provided a method of delaying the onset and/or development of a disease or disorder that is mediated by THR beta in a patient (such as a human) who is at risk for developing the disease or disorder. It is appreciated that delayed development may encompass prevention in the event the individual does not develop the disease or disorder. An individual at risk of developing a disease or disorder that is mediated by THR beta in one aspect has one or more risk factors for developing the disease or disorder, such as age, increased waist circumference, high body to mass index or the presence of an associated comorbidity.

In one aspect, provided herein is a method of delaying the onset and/or development of non-alcoholic fatty liver disease in a patient in need thereof, comprising administering to the patient a therapeutically effective amount of a compound provided herein, or a therapeutically effective amount of a composition provided herein. In one aspect, provided herein is a method of delaying the onset and/or development of non-alcoholic steatohepatitis (NASH) in a patient in need thereof, comprising administering to the patient a therapeutically effective amount of a compound provided herein, or a therapeutically effective amount of a composition provided herein. In one aspect, provided herein is a method of delaying the onset and/or development of metabolic syndrome in a patient in need thereof, comprising administering to the patient a therapeutically effective amount of a compound provided herein, or a therapeutically effective amount of a composition provided herein. In one aspect, provided herein is a method of delaying the onset and/or development of dyslipidemia in a patient in need thereof, comprising administering to the patient a therapeutically effective amount of a compound provided herein, or a therapeutically effective amount of a composition provided herein. In one aspect, provided herein is a method of delaying the onset and/or development of hypertriglyceridemia in a patient in need thereof, comprising administering to the patient a therapeutically effective amount of a compound provided herein, or a therapeutically effective amount of a composition provided herein. In one aspect, provided herein is a method of delaying the onset and/or development of hypercholesterolemia in a patient in need thereof, comprising administering to the patient a therapeutically effective amount of a compound provided herein, or a therapeutically effective amount of a composition provided herein.

In one aspect, provided herein is a compound of formula (I) or any variation thereof, or a pharmaceutically acceptable salt thereof, for use in therapy. In some embodiments, provided herein is a compound of formula (I) or any variation thereof, or a pharmaceutically acceptable salt thereof or pharmaceutical composition comprising such compound or a pharmaceutically acceptable salt thereof, for use in the treatment of non-alcoholic fatty liver disease. In some embodiments, provided herein is a compound of formula (I) or any variation thereof, or a pharmaceutically acceptable salt thereof or pharmaceutical composition comprising such compound or a pharmaceutically acceptable salt thereof, for use in the treatment of non-alcoholic steatohepatitis (NASH). In some embodiments, provided is a compound of formula (I) or any variation thereof, or a pharmaceutically acceptable salt thereof, or a pharmaceutical composition comprising such compound or a pharmaceutically acceptable salt thereof, for use in the treatment of metabolic syndrome. In some embodiments, provided is a compound of formula (I) or any variation thereof, or a pharmaceutically acceptable salt thereof, or a pharmaceutical composition comprising such compound or a pharmaceutically acceptable salt thereof, for use in the treatment of dyslipidemia. In some embodiments, provided is a compound of formula (I) or any variation thereof, or a pharmaceutically acceptable salt thereof, or a pharmaceutical composition comprising such compound or a pharmaceutically acceptable salt thereof, for use in the treatment of hypertriglyceridemia. In some embodiments, provided is a compound of formula (I) or any variation thereof, or a pharmaceutically acceptable salt thereof, or a pharmaceutical composition comprising such compound or a pharmaceutically acceptable salt thereof, for use in the treatment of hypercholesterolemia.

In another embodiment, provided herein is a compound of formula (I) or any variation thereof, or a pharmaceutically acceptable salt thereof, for use in the manufacture of a medicament for the treatment of non-alcoholic fatty liver disease. In another embodiment, provided herein is a compound of formula (I) or any variation thereof, or a pharmaceutically acceptable salt thereof, for use in the manufacture of a medicament for the treatment of non-alcoholic steatohepatitis (NASH). In another embodiment, provided herein is a compound of formula (I) or any variation thereof, or a pharmaceutically acceptable salt thereof, for use in the manufacture of a medicament for the treatment of metabolic syndrome. In some embodiments, the medicament is for the treatment of dyslipidemia. In some embodiments, the medicament is for the treatment of hypertriglyceridemia. In some embodiments, the medicament is for the treatment of dyslipidemia. In some embodiments, the medicament is for the treatment of hypercholesterolemia.

In some embodiments, the individual is a mammal. In some embodiments, the individual is a primate, dog, cat, rabbit, or rodent. In some embodiments, the individual is a primate. In some embodiments, the individual is a human. In some embodiments, the human is at least about or is about any of 18, 21, 30, 50, 60, 65, 70, 75, 80, or 85 years old. In some embodiments, the human is a child. In some embodiments, the human is less than about or about any of 21, 18, 15, 10, 5, 4, 3, 2, or 1 years old.

Dosing and Method of Administration

The dose of a compound described herein, or a stereoisomer, tautomer, solvate, or salt thereof, administered to an individual (such as a human) may vary with the particular compound or salt thereof, the method of administration, and the particular disease or disorder, such as non-alcoholic fatty liver disease, non-alcoholic steatohepatitis (NASH), metabolic syndrome, hypertriglyceridemia, dyslipidemia, or hypercholesterolemia, being treated. In some embodiments, the amount of the compound, or a stereoisomer, tautomer, solvate, or salt thereof, is a therapeutically effective amount.

The compounds provided herein or a salt thereof may be administered to an individual via various routes, including, e.g., intravenous, intramuscular, subcutaneous, oral, and transdermal.

The effective amount of the compound may in one aspect be a dose of between about 0.01 and about 100 mg/kg. Effective amounts or doses of the compounds of the present disclosure may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein, or a stereoisomer, tautomer, solvate, or salt thereof, and a pharmaceutically acceptable excipient.

A compound or composition provided herein may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

Articles of Manufacture and Kits

The present disclosure further provides articles of manufacture comprising a compound described herein or a salt thereof, a composition described herein, or one or more unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the present disclosure, which comprises one or more compounds described herein or a composition comprising a compound described herein. The kits may employ any of the compounds disclosed herein. In one variation, the kit employs a compound described herein or pharmaceutically acceptable salt thereof. The kits may be used for any one or more of the uses described herein, and, accordingly, may contain instructions for the treatment of any disease or described herein, for example for the treatment of non-alcoholic steatohepatitis (NASH).

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to an individual.

EXEMPLARY EMBODIMENTS

The present disclosure is further described by the following embodiments. The features of each of the embodiments are combinable with any of the other embodiments where appropriate and practical.

Embodiment 1

A compound of formula (I-a):

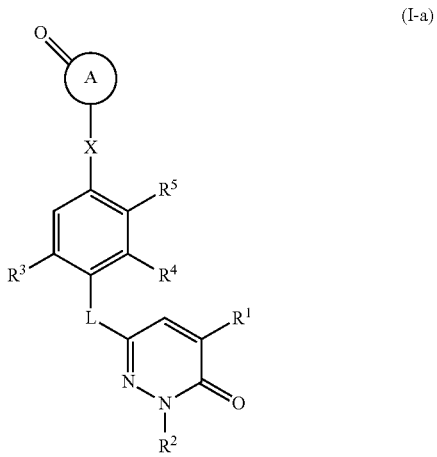

or a tautomer or an N-oxide thereof, or an isotopomer of each thereof, or a prodrug of each of the above, or a stereoisomer of the aforesaid, or a pharmaceutically acceptable salt of each of the foregoing, or a solvate of each of the preceding, wherein:

ring A together with the carbonyl (keto) group within the ring form a 5 membered heterocycle containing 1-3 ring heteroatoms selected from N, O, and S, wherein the heterocycle is optionally substituted with 1-2 $C_1$-$C_3$ alkyl or $C_3$-$C_4$ cycloalkyl, and wherein the carbonyl (keto) group is not adjacent to the atom attached to X;

$R^1$ is $C_1$-$C_4$ alkyl; $C_1$-$C_4$ alkyl optionally substituted with 1-5 halo, preferably fluoro; $C_3$-$C_5$ cycloalkyl, $CON(R^{10})_2$, or $NR^{10}COR^{10}$, wherein each $R^{10}$ independently is $C_1$-$C_3$ alkyl or H;

$R^2$ is H or $C_1$-$C_3$ alkyl;

L is O, $CH_2$, S, SO, $SO_2$, CO, CHF, $CF_2$, $C(R^{11})CN$, $CHR^{11}$, or $C(R^{11})R^{11}$, wherein each $R^{11}$ is $C_1$-$C_2$ alkyl optionally substituted with 1-5 halo, preferably fluoro, or the 2 $R^{11}$ groups together with the carbon atom they are attached to form a cyclopropyl or cyclobutyl ring;

each of $R^3$ and $R^4$ is independently Cl, Br, Me, or ethyl;

$R^5$ is H, halo, $C_1$-$C_4$ alkyl, or $C_3$-$C_4$ cycloalkyl, or $R^5$ together with $R^4$ and the intervening atoms form a 5-7 membered cycloalkyl or a 5-7 membered heterocycle containing 1-2 ring heteroatoms;

X is absent (i.e., X is a bond), or is O, $NR^{12}$, $C(O)NR^{12}$, $NR^{12}C(O)$, $CR^{12}R^{12}$, $OCR^{12}R^{12}$, $CR^{12}R^{12}O$, $NR^{12}CR^{12}R^{12}$, $CR^{12}R^{12}NR^{12}$, $SO_2NR^{12}$, $NR^{12}SO_2$ wherein each $R^{12}$ independently is H or methyl.

Embodiment 2

The compound of embodiment 1 of formula (IIA), (IIB), (IIIA), (IIIB), (IIIC), (IVA), (IVB), (IVC), (IVA), (VB), (VC), (VIA), (VIB), or (VIC):

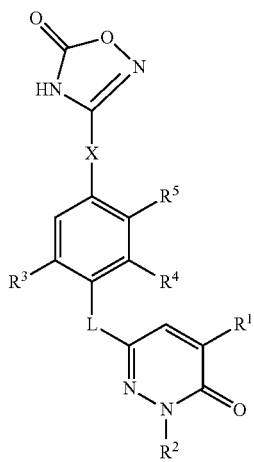 (IIA)
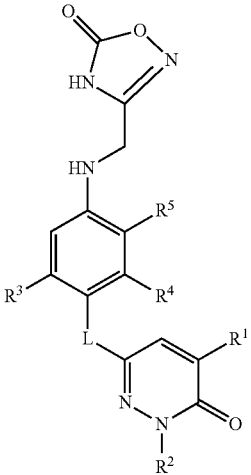 (IIIB)
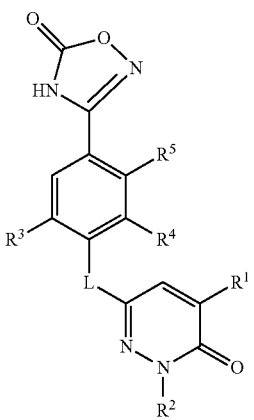 (IIB)
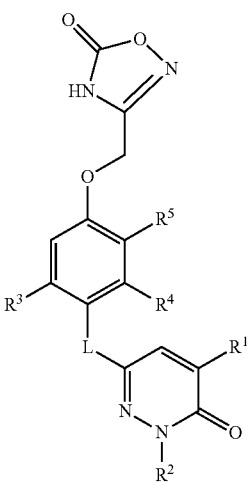 (IIIC)
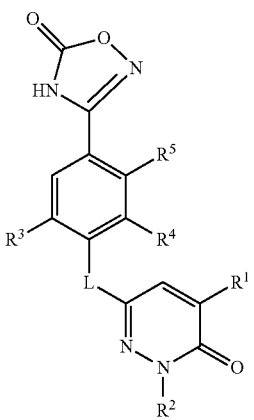 (IIIA)
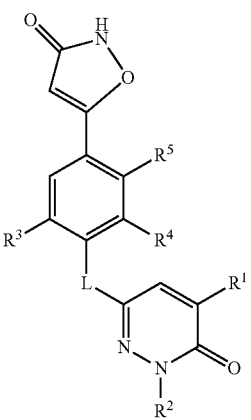 (IVA)

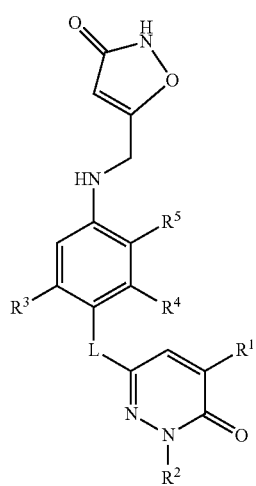
(IVB)
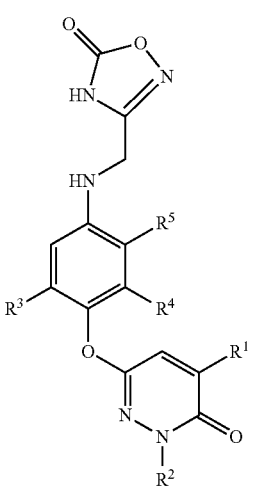
(VB)
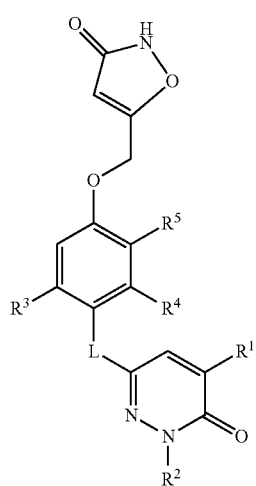
(IVC)
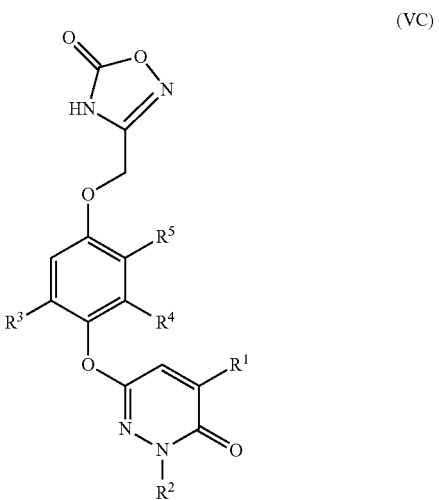
(VC)
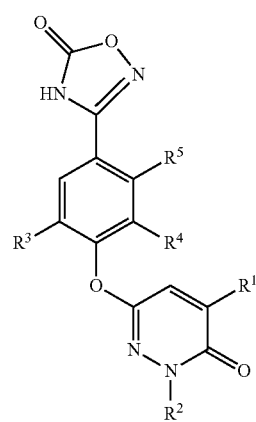
(VA)
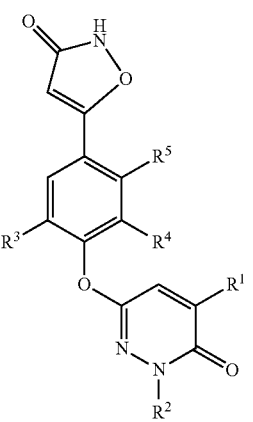
(VIA)

63
-continued
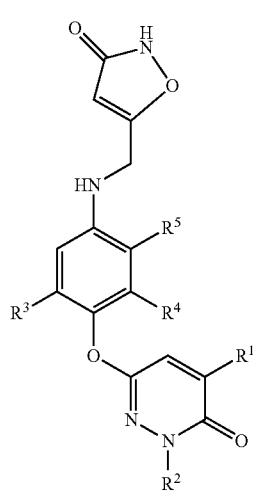
(VIB)
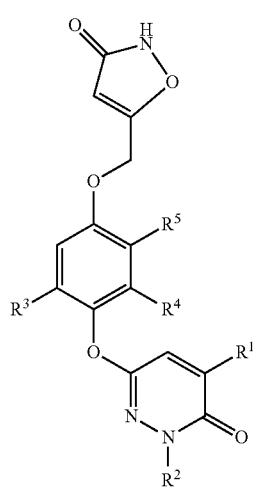
(VIC)
wherein the variables are defined as in embodiment 1.
Embodiment 3
The compound of embodiment 1, of formula (VIIA), (VIIB), (VIIC), (VIIIA), (VIIIB), or (VIIIC):
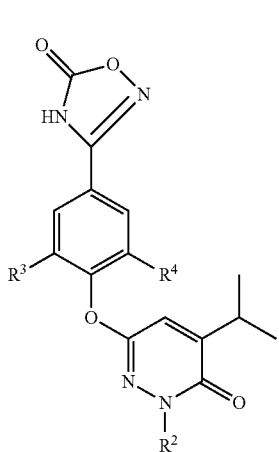
(VIIA)
64
-continued
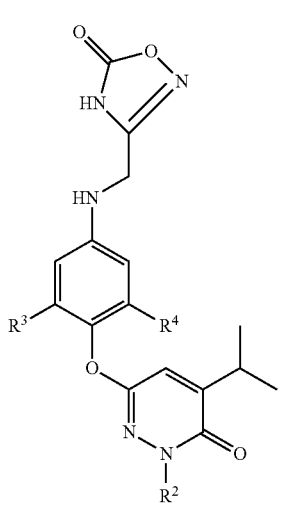
(VIIB)
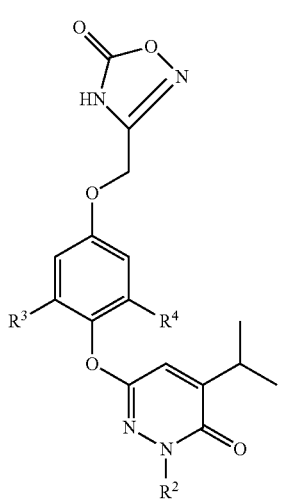
(VIIC)
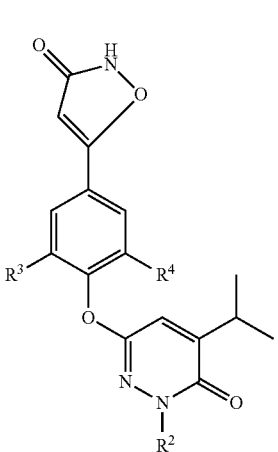
(VIIIA)

-continued

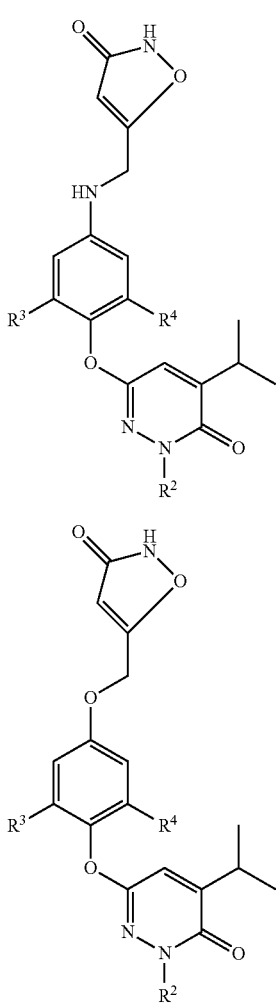

(VIIIB)

(VIIIC)

wherein $R^2$ is H or methyl, and the remaining variables are defined as in embodiment 1.

Embodiment 4

The compound of embodiment 1, wherein $R^1$ is isopropyl.

Embodiment 5

The compound of embodiment 1, wherein $R^2$ is H.

Embodiment 6

The compound of embodiment 1, wherein $R^3$ is chloro.

Embodiment 7

The compound of embodiment 1, wherein $R^4$ is chloro.

Embodiment 8

The compound of embodiment 1, wherein $R^5$ is hydrogen.

Embodiment 9

The compound of embodiment 1, wherein X is a bond.

Embodiment 10

The compound of embodiment 1, wherein X is $CHR^{11}$, $OCHR^{11}$, $NR^{11}CHR^{11}$, $NR^{11}CH_2$, $CHR^{11}NH$, $CHR^{11}NR^{11}$, $NHCR^{11}R^{11}$, $C(O)NR^{12}$, $NR^{12}C(O)$, $SO_2NR^{12}$, or $NR^{12}SO_2$, wherein $R^{12}$ is defined as in embodiment 1.

Embodiment 11

The compound of embodiment 1, wherein X is NH, $CH_2$, $OCH_2$, $CH_2O$, $NHCH_2$, $CH_2NH$, $C(O)NH$, $NHC(O)$, $SO_2NH$, or $NHSO_2$.

Embodiment 12

The compound of embodiment 1, wherein —X— is —NH—$CH_2$—, —NHC(O)— or —O—$CH_2$—.

Embodiment 13

The compound of embodiment 1, wherein -L- is O.

Embodiment 14

A compound selected from those tabulated in Table 1.

Embodiment 15

A pharmaceutical composition comprising a compound of embodiment 1 and at least one pharmaceutically acceptable excipient.

Embodiment 16

A method of agonizing thyroid hormone receptor beta (THR beta) comprising contacting either an effective amount of a compound of embodiment 1, or an effective amount of the composition of embodiment 15, with the THR beta.

Embodiment 17

A method of treating a disorder, which is mediated by THR beta, in a patient, comprising administering to the patient a therapeutically effective amount of a compound of embodiment 1, or a therapeutically effective amount of the composition of embodiment 15.

Embodiment 18

A compound of formula (I):

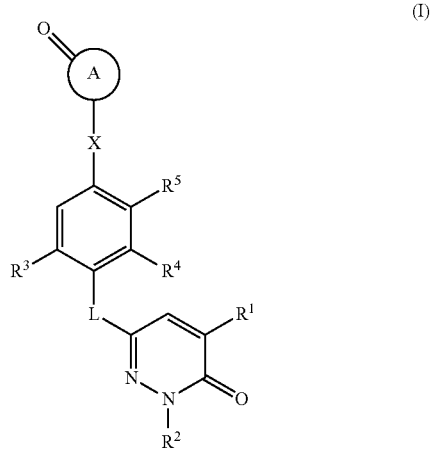

(I)

or a pharmaceutically acceptable salt thereof, wherein:

ring A together with the carbonyl (keto) group within the ring form a 5 membered heterocycle containing 1-3 ring heteroatoms selected from the group consisting of N, O, and S, wherein the heterocycle is optionally substituted with 1-2 $C_1$-$C_3$ alkyl or $C_3$-$C_4$ cycloalkyl groups, and wherein the carbonyl (keto) group is not adjacent to the atom attached to X;

$R^1$ is $C_1$-$C_4$ alkyl optionally substituted with 1-5 halo or hydroxyl groups, $C_3$-$C_5$ cycloalkyl, $CON(R^{10})_2$, or $NR^{10}COR^{10}$;

$R^2$ is H or $C_1$-$C_3$ alkyl;

L is O, $CH_2$, S, SO, $SO_2$, CO, CHF, $CF_2$, $C(R^{11})CN$, $CHR^{11}$, or $C(R^{11})R^{11}$;

$R^3$ and $R^4$ are independently Cl, Br, methyl, or ethyl;

$R^5$ is H, halo, $C_1$-$C_4$ alkyl, or $C_3$-$C_4$ cycloalkyl;

or $R^5$ together with $R^4$ and the intervening atoms form a 5-7 membered cycloalkyl or a 5-7 membered heterocycle containing 1-2 ring heteroatoms;

X is absent, O, $NR^{12}$, $C(O)NR^{12}$, $NR^{12}C(O)$, $CR^{12}R^{12}$, $OCR^{12}R^{12}$, $CR^{12}R^{12}O$, $NR^{12}CR^{12}R^{12}$, $CR^{12}R^{12}NR^{12}$, $SO_2NR^{12}$, or $NR^{12}SO_2$;

each $R^{10}$ is independently $C_1$-$C_3$ alkyl or H;

each $R^{11}$ is independently $C_1$-$C_2$ alkyl optionally substituted with 1-5 halo, or two $R^{11}$ groups together with the carbon atom to which they are attached form a cyclopropyl or cyclobutyl ring; and each $R^{12}$ is independently H or methyl.

Embodiment 19

The compound of embodiment 18, or a pharmaceutically acceptable salt thereof, which is of formula (IIA) or (IIB):

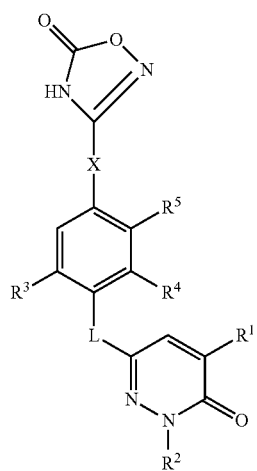

(IIA)

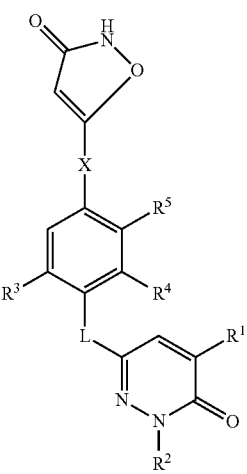

(IIB)

wherein $R^1$, $R^2$, $R^3$, $R^4$, $R^5$, X, and L are as defined in embodiment 18.

Embodiment 20

The compound of embodiment 18 or 19, or a pharmaceutically acceptable salt thereof, which is of formula (VD):

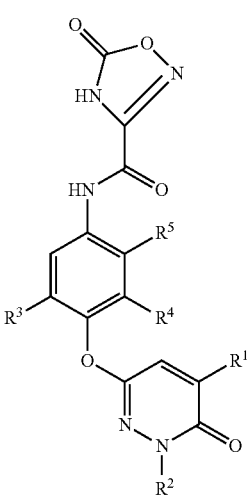

(VD)

wherein $R^1$, $R^2$, $R^3$, $R^4$, and $R^5$ are as defined in embodiment 18.

Embodiment 21

The compound of any one of embodiments 18-20, or a pharmaceutically acceptable salt thereof, wherein:
$R^1$ is $C_1$-$C_4$ alkyl optionally substituted with 1-2 halo or hydroxyl groups, or $C_3$-$C_5$ cycloalkyl.

Embodiment 22

The compound of embodiment 21, or a pharmaceutically acceptable salt thereof, wherein:
$R^1$ is isopropyl, t-butyl, HO—CH($CH_3$)—, HO—CH($CH_2CH_3$)—, HO—C($CH_3$)$_2$—, HO—$CH_2$CH($CH_3$)—, cyclopropyl, or

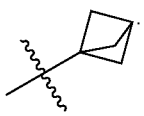

Embodiment 23

The compound of any one of embodiments 18-22, or a pharmaceutically acceptable salt thereof, wherein:
$R^2$ is H or —$CH_3$.

Embodiment 24

The compound of any one of embodiments 18-23, or a pharmaceutically acceptable salt thereof, wherein:
$R^3$ is chloro or —$CH_3$.

Embodiment 25

The compound of any one of embodiments 18-24, or a pharmaceutically acceptable salt thereof, wherein:
$R^4$ is chloro or —$CH_3$;
or $R^5$ together with $R^4$ and the intervening atoms form a 5-6 membered cycloalkyl.

Embodiment 26

The compound of embodiment 25, or a pharmaceutically acceptable salt thereof, wherein:
$R^5$ together with $R^4$ and the intervening atoms form cyclopentyl.

Embodiment 27

The compound of any one of embodiments 18-25, or a pharmaceutically acceptable salt thereof, wherein:
$R^5$ is H or fluoro.

Embodiment 28

The compound of any one of embodiments 18, 19, and 21-27, or a pharmaceutically acceptable salt thereof, wherein:
X is a bond.

Embodiment 29

The compound of any one of embodiments 18-27, or a pharmaceutically acceptable salt thereof, wherein:
X is $NR^{12}C(O)$, $OCR^{12}R^{12}$, or $NR^{12}CR^{12}R^{12}$; and each $R^{12}$ is independently H or methyl.

Embodiment 30

The compound of embodiment 29, or a pharmaceutically acceptable salt thereof, wherein:
X is —$OCH_2$—, —$NHCH_2$—, —NHC(O)—, —N($CH_3$)$CH_2$—, or —N(H)CH($CH_3$)—.

Embodiment 31

The compound of any one of embodiments 18-30, or a pharmaceutically acceptable salt thereof, wherein:
L is O, $CH_2$, $SO_2$, CO, $CHR^{11}$, or $C(R^{11})R^{11}$; and each $R^{11}$ is independently methyl or ethyl.

Embodiment 32

The compound of embodiment 31, or a pharmaceutically acceptable salt thereof, wherein:
L is O, $CH_2$, $SO_2$, or CO.

Embodiment 33

A compound of formula (I-a):

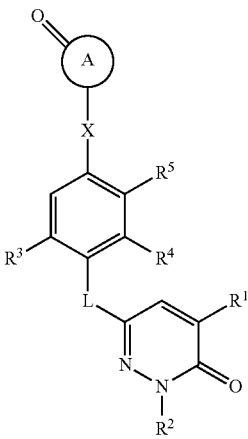

(I-a)

or a tautomer or an N-oxide thereof, or an isotopomer of each thereof, or a prodrug of each of the above, or a stereoisomer of the aforesaid, or a pharmaceutically acceptable salt of each of the foregoing, or a solvate of each of the preceding, wherein:

ring A together with the carbonyl (keto) group within the ring form a 5 membered heterocycle containing 1-3 ring heteroatoms selected from the group consisting of N, O, and S, wherein the heterocycle is optionally substituted with 1-2 $C_1$-$C_3$ alkyl or $C_3$-$C_4$ cycloalkyl, and wherein the carbonyl (keto) group is not adjacent to the atom attached to X;

$R^1$ is $C_1$-$C_4$ alkyl; $C_1$-$C_4$ alkyl optionally substituted with 1-5 halo; $C_3$-$C_5$ cycloalkyl, $CON(R^{10})_2$, or $NR^{10}COR^{10}$, wherein each $R^{10}$ is independently $C_1$-$C_3$ alkyl or H;

$R^2$ is H or $C_1$-$C_3$ alkyl;

L is O, $CH_2$, S, SO, $SO_2$, CO, CHF, $CF_2$, $C(R^{11})CN$, $CHR^{11}$, or $C(R^{11})R^{11}$, wherein each $R^{11}$ is $C_1$-$C_2$ alkyl optionally substituted with 1-5 halo, or the 2 $R^{11}$ groups together with the carbon atom they are attached to form a cyclopropyl or cyclobutyl ring;

each of $R^3$ and $R^4$ is independently Cl, Br, methyl, or ethyl;

$R^5$ is H, halo, $C_1$-$C_4$ alkyl, or $C_3$-$C_4$ cycloalkyl, or $R^5$ together with $R^4$ and the intervening atoms form a 5-7 membered cycloalkyl or a 5-7 membered heterocycle containing 1-2 ring heteroatoms;

X is absent, or is O, $NR^{12}$, $C(O)NR^{12}$, $NR^{12}C(O)$, $CR^{12}R^{12}$, $OCR^{12}R^{12}$, $CR^{12}R^{12}O$, $NR^{12}CR^{12}R^{12}$, $CR^{12}R^{12}NR^{12}$, $SO_2NR^{12}$, or $NR^{12}SO_2$, wherein each $R^{12}$ is independently H or methyl.

Embodiment 34

A compound selected from the compounds in Table 1, or a pharmaceutically acceptable salt thereof.

Embodiment 35

A pharmaceutical composition comprising the compound of any one of embodiments 18-34, or a pharmaceutically acceptable salt thereof, and at least one pharmaceutically acceptable excipient.

Embodiment 36

A method of agonizing thyroid hormone receptor beta (THR beta) comprising contacting either an effective amount of the compound of any one of embodiments 18-34, or a pharmaceutically acceptable salt thereof, or an effective amount of the pharmaceutical composition of embodiment 35, with the THR beta.

Embodiment 37

A method of treating a disorder which is mediated by THR beta in a patient in need thereof, comprising administering to the patient a therapeutically effective amount of the compound of any one of embodiments 18-34, or a pharmaceutically acceptable salt thereof, or a therapeutically effective amount of the pharmaceutical composition of embodiment 35.

Embodiment 38

The method of embodiment 37, wherein the disorder is non-alcoholic steatohepatitis (NASH).

EXAMPLES

It is understood that the present disclosure has been made only by way of example, and that numerous changes in the combination and arrangement of parts can be resorted to by those skilled in the art without departing from the spirit and scope of present disclosure.

The chemical reactions in the Examples described can be readily adapted to prepare a number of other compounds disclosed herein, and alternative methods for preparing the compounds of this disclosure are deemed to be within the scope of this disclosure. For example, the synthesis of non-exemplified compounds according to the present disclosure can be successfully performed by modifications apparent to those skilled in the art, e.g., by appropriately protecting interfering groups, by utilizing other suitable reagents known in the art other than those described, or by making routine modifications of reaction conditions, reagents, and starting materials. Alternatively, other reactions disclosed herein or known in the art will be recognized as having applicability for preparing other compounds of the present disclosure.

The following abbreviations may be relevant for the application.

Abbreviations

Ac: acetyl
ACN: acetonitrile
Boc: tertiarybutyloxycarbonyl
Bu: butyl
DBA: dibenzylideneacetone
DMAP: dimethylaminopyridine
DMF: dimethylformamide
DMF-DMA: dimethylformamide dimethylacetal
DMSO: dimethylsulfoxide
DSC: disuccinimidylcarbonate
Et: ethyl
Me: methyl
Pr: propyl
Py or Pyr: pyridine
rt: room temperature
SEMCl: 2-(Trimethylsilyl)ethoxymethyl chloride
SFC: supercritical fluid chromatography
TEA: triethylamine
THF: tetrahydrofuran
TFA: trifluoroacetic acid
t-Bu Xphos: 2-Di-tert-butylphosphino-2',4',6'-triisopropyl-biphenyl

SYNTHETIC EXAMPLES

Scheme A: 6-(4-amino-2,6-dichlorophenoxy)-4-isopropyl-2-methylpyridizan-3(2H)-one (Compound 1e)

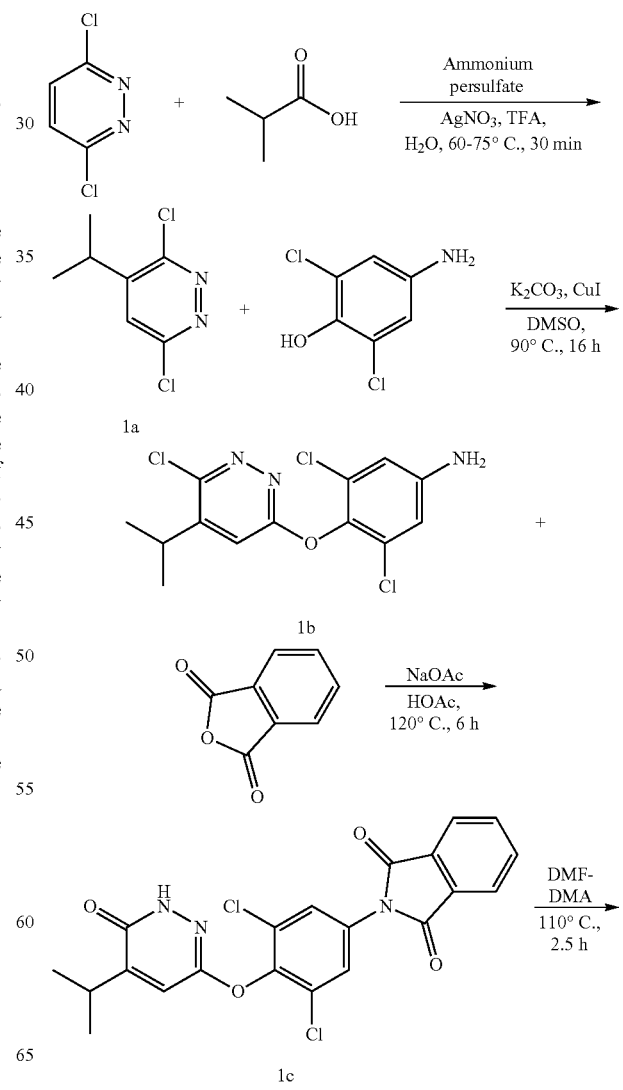

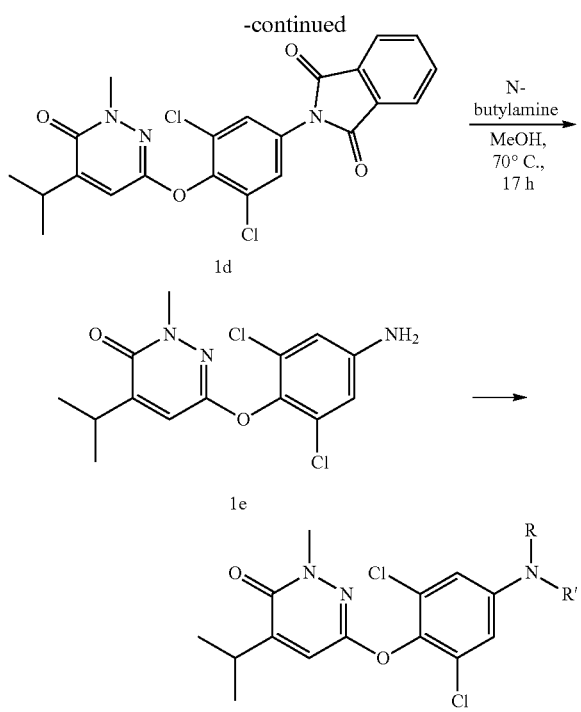

Example 1: R = H, R' = Cy1
Example 2: R = Me, R' = Cy1
Example 3: R = H, R' = Cy2; P1 & P2
Example 4: R = H, R' = Cy3

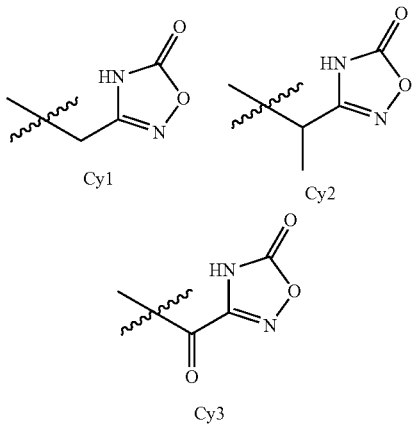

3,6-dichloro-4-isopropylpyridazine (1a)

Sulfuric acid (19.75 g, 201.37 mmol, 10.73 mL) was added to a mixture of 3,6-dichloropyridazine (10 g, 67.12 mmol), 2-methylpropanoic acid (6.21 g, 70.48 mmol, 6.54 mL) and AgNO3 (5.70 g, 33.56 mmol, 5.64 mL) in H$_2$O (200 mL) at 60° C. Then a solution of ammonium persulphate (45.95 g, 201.37 mmol) in H$_2$O (100 mL) was added by drop-wise to the mixture at 75° C., the resulting mixture was stirred at 75° C. for 30 min. TLC showed the reaction was completed. after cooling the mixture was adjusted to pH=9~10 with NH$_3$.H$_2$O, the mixture was extracted with ethyl acetate (200 mL*2), the organic phases were washed with brine (100 mL), dried over Na$_2$SO$_4$, filtered and concentrated to give 1a. The product was used directly in next step. MS mass calculated for [M+1]$^+$ (C$_7$H$_8$Cl$_2$N$_2$) requires m/z 191.1, LCMS found m/z 191.1; $^1$H NMR (400 MHZ, CDCl$_3$) δ 7.38 (s, 1H), 3.24-3.31 (m, 1H), 1.31 (d, J=6.8 HZ, 6H).

3,5-dichloro-4-((6-chloro-5-isopropylpyridazin-3-yl)oxy)aniline (1b)

To a solution of 4-amino-2,6-dichlorophenol (3 g, 16.85 mmol) and 3,6-dichloro-4-isopropylpyridazine (1a) (3.22 g, 16.85 mmol) in DMSO (30 mL) was added K$_2$CO$_3$ (9.32 g, 67.41 mmol) and CuI (1.93 g, 10.11 mmol). Then the mixture was degassed and purged with N$_2$ for 3 times, and stirred at 90° C. for 16 hours under N$_2$ atmosphere. TLC and LCMS showed the starting material was consumed completely and desired MS was detected. The mixture was concentrated in vacuum. The residue was partitioned between ethyl acetate (1000 mL*2) and H$_2$O (500 mL). The combined organic phase was washed with brine (50 mL*3), dried with anhydrous Na$_2$SO$_4$, filtered and concentrated in vacuum. The residue was purified by column chromatography (SiO$_2$, petroleum ether/ethyl acetate=10:1 to 3:1, according TLC) to give 1b. MS mass calculated for [M+1]$^+$ (C$_{13}$H$_{12}$Cl$_3$N$_3$O) requires m/z 332.0, LCMS found m/z 332.0; $^1$H NMR (400 MHZ, DMSO) δ 7.66 (s, 1H), 6.67-6.76 (m, 2H), 5.67 (s, 2H), 3.11-3.21 (m, 1H), 1.28 (d, J=6.85 HZ, 6H).

2-(3,5-dichloro-4-((5-isopropyl-6-oxo-1,6-dihydropyridazin-3-yl)oxy)phenyl)isoindoline-1,3-dione (1c)

To a mixture of 3,5-dichloro-4-((6-chloro-5-isopropylpyridazin-3-yl)oxy)aniline (1b) (2.6 g, 7.82 mmol) and isobenzofuran-1,3-dione (1.16 g, 7.82 mmol) in HOAc (5 mL) was added NaOAc (3.21 g, 39.08 mmol). The mixture was stirred at 120° C. for 6 hours. LCMS showed the starting material was consumed completely and desired MS was detected. The reaction mixture was concentrated under reduced pressure to remove AcOH. The solid was dissolved in water and the pH was adjusted to 9 with saturate NaHCO$_3$ solution (10 mL). Then the mixture was partitioned with ethyl acetate (30 mL*2) and H$_2$O (30 mL). The combined organic phase was washed with brine (10 mL*3), dried with anhydrous Na$_2$SO$_4$, filtered and concentrated in vacuum. The solid was diluted in ethyl acetate (10 mL), and then petroleum ether (50 mL) was added in the mixture by portions. The mixture was filtered to collect solid. The solid was dried to give 1c. MS mass calculated for [M+1]$^+$ (C$_{21}$H$_{15}$Cl$_2$N$_3$O$_4$) requires m/z 444.0, LCMS found m/z 444.1; $^1$H NMR (400 MHZ, DMSO) δ 12.21 (s, 1H), 7.98-8.06 (m, 2H), 7.90-7.97 (m, 2H), 7.78-7.83 (m, 2H), 7.46 (s, 1H), 3.03-3.10 (m, 1H), 1.20 (d, J=6.85 HZ, 6H).

2-(3,5-dichloro-4-((5-isopropyl-1-methyl-6-oxo-1,6-dihydropyridazin-3-yl)oxy)phenyl)isoindoline-1,3-dione (1d)

A solution of 2-(3,5-dichloro-4-((5-isopropyl-6-oxo-1,6-dihydropyridazin-3-yl)oxy)phenyl)iso-indoline-1,3-dione (1c) (500 mg, 1.13 mmol) in DMF-DMA (4 mL) was stirred at 110° C. for 2.5 hours. TLC showed the starting material was consumed completely and two new spots formed. The mixture was concentrated in vacuum. The residue was partitioned between Ethyl acetate (10 mL*2) and H$_2$O (3 mL). The combined organic phase was washed with brine (5 mL*3), dried with anhydrous Na$_2$SO$_4$, filtered and concentrated in vacuum to give 1d. The product was used directly in next step without further purification.

6-(4-amino-2,6-dichlorophenoxy)-4-isopropyl-2-methylpyridazin-3(2H),-one (1e)

A mixture of 2-(3,5-dichloro-4-((5-isopropyl-1-methyl-6-oxo-1,6-dihydropyridazin-3-yl)oxy)phenyl)isoindoline-1,3-dione (1d) (700 mg, 1.53 mmol) and butan-1-amine (335.13 mg, 4.58 mmol) in MeOH (10 mL) was stirred at 70° C. for 1 hour. TLC (Petroleum ether:Ethyl acetate=1:1, P1:$R_f$=0.6) and LCMS showed the starting material was consumed completely and desired MS was detected. The mixture was concentrated in vacuum to give a residue. The residue was purified by preparative TLC (petroleum ether:ethyl acetate=1:1, P1:$R_f$=0.6) to give 1e. MS mass calculated for [M+1]$^+$ ($C_{14}H_{15}Cl_2N_3O_2$) requires m/z 328.1, LCMS found m/z 328.2; $^1$H NMR (400 MHZ, CD$_3$OD) δ 7.22 (s, 1H) 6.70 (s, 1H) 3.52 (s, 3H) 3.17 (dt, J=13.81, 7.13 Hz, 1H) 1.43 (s, 2H) 1.25 (d, J=6.58 Hz, 6H).

Example 1: 3-(((3,5-dichloro-4-((5-isopropyl-1-methyl-6-oxo-1,6-dihydropyridazin-3-yl)oxy)phenyl)amino)methyl)-1,2,4-oxadiazol-5(4H)-one

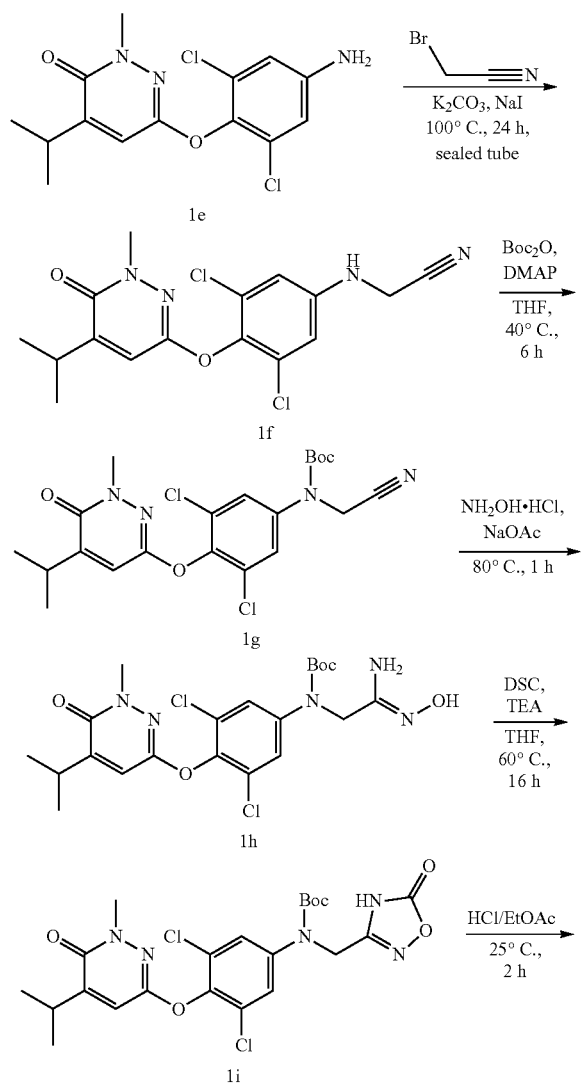

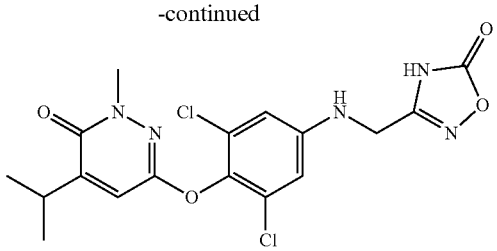

Example 1

2-((3,5-dichloro-4-((5-isopropyl-1-methyl-6-oxo-1,6-dihydropyridazin-3-yl)oxy)phenyl)amino)-acetonitrile (1f)

To a solution of 6-(4-amino-2,6-dichlorophenoxy)-4-isopropyl-2-methylpyridazin-3(2H)-one (1e) (240 mg, 731.28 umol) in ACN (4 mL) was added 2-bromoacetonitrile (438.58 mg, 3.66 mmol, 243.65 uL), NaI (219.23 mg, 1.46 mmol) and K$_2$CO$_3$ (202.13 mg, 1.46 mmol). Then the mixture was sealed in tube, and stirred at 100° C. for 16 hours. LCMS showed the starting material was consumed completely and desired MS was detected. The suspension was filtered through a pad of Celite and the pad cake was washed with EtOAc (5 mL*3). The combined filtrates were concentrated to dryness to give a residue. The residue was purified by preparative TLC (petroleum ether:ethyl acetate=1:1, P1:$R_f$=0.5) to give 1f as a yellow oil. MS mass calculated for [M+1]$^+$ ($C_{16}H_{16}Cl_2N_4O_2$) requires m/z 367.1, LCMS found m/z 366.8; $^1$H NMR (400 MHZ, CDCl$_3$) δ 7.04 (s, 1H), 6.72 (s, 2H), 4.13 (d, J=6.85 HZ, 2H), 3.54 (s, 3H), 3.21-3.28 (m, 1H), 1.26 (d, J=6.85 HZ, 5H).

Tert-butyl (cyanomethyl)(3,5-dichloro-4-((5-isopropyl-1-methyl-6-oxo-1,6-dihydropyridazin-3-yl)oxy)-phenyl)carbamate (1g)

To a solution 2-((3,5-dichloro-4-((5-isopropyl-1-methyl-6-oxo-1,6-dihydropyri-dazin-3-yl)oxy)phenyl)amino)acetonitrile (1f) (210 mg, 571.85 umol) in THF (3 mL) was added Boc$_2$O (374.41 mg, 1.72 mmol, 394.12 uL) and DMAP (69.86 mg, 571.85 umol). The mixture was stirred at 40° C. for 3 hours. TLC (Petroleum ether:Ethyl acetate=1:1, P1:$R_f$=0.9) and LCMS showed the starting material was consumed completely and desired MS was detected. The mixture was partitioned between ethyl acetate (10 mL*2) and H$_2$O (3 mL) twice. The combined organic phase was washed with brine (5 mL*3), dried with anhydrous Na$_2$SO$_4$, filtered and concentrated in vacuum to give a residue. The residue was purified by prep-TLC (SiO$_2$, petroleum ether:ethyl acetate=3:1, P1:$R_f$=0.5) to give 1g. MS mass calculated for [M+1]$^+$ ($C_{21}H_{24}Cl_2N_4O_4$) requires m/z 467.1, LCMS found m/z 467.0; $^1$H NMR (400 MHZ, CDCl$_3$) δ 7.45 (s, 2H), 4.61 (s, 2H), 3.43 (s, 3H), 3.13 (dt, J=13.8, 6.8 HZ, 1H), 1.45 (s, 9H), 1.22 (d, J=6.8 HZ, 6H).

(Z)-tert-butyl (2-amino-2-(hydroxyimino)ethyl)(3,5-dichloro-4-((5-isopropyl-1-methyl-6-oxo-1,6-dihydropyridazin-3-yl)oxy)phenyl)carbamate (1h)

To a solution of tert-butyl (cyanomethyl)(3,5-dichloro-4-((5-isopropyl-1-methyl-6-oxo-1,6-dihydropyridazin-3-yl)oxy)phenyl)carbamate (1g) (250 mg, 534.94 umol) in DMF (3 mL) was added NH$_2$OH.HCl (297.39 mg, 4.28 mmol) and NaOAc (351.06 mg, 4.28 mmol). The mixture was stirred at 80° C. for 1 hour. LCMS showed the starting material was consumed completely and desired MS was detected. The reaction mixture was concentrated under reduced pressure to remove DMF. The residue was partitioned between ethyl acetate (10 mL*2) and H₂O (3 mL). The combined organic phase was washed with brine (5 mL*3), dried with anhydrous Na₂SO₄, filtered and concentrated in vacuum to give 1h (260 mg, crude) as a yellow solid. The product was used directly for the next step without further purification. MS mass calculated for [M+1]⁺ ($C_{21}H_{27}Cl_2N_5O_5$) requires m/z 500.1, LCMS found m/z 500.1.

tert-butyl (3,5-dichloro-4-((5-isopropyl-1-methyl-6-oxo-1,6-dihydropyridazin-3-yl)oxy)phenyl)((5-oxo-4,5-dihydro-1,2,4-oxadiazol-3-yl)methyl)carbamate (1i)

To a solution of (Z/E)-tert-butyl (2-amino-2-(hydroxyimino)ethyl)(3,5-dichloro-4-((5-isopropyl-1-methyl-6-oxo-1,6-dihydropyridazin-3-yl)oxy)phenyl)-carbamate (1h) (260 mg, 519.61 umol) in THF (3 mL) was added DSC (173.04 mg, 675.49 umol, 1.3 eq) and TEA (105.16 mg, 1.04 mmol, 144.65 uL). The mixture was stirred at 60° C. for 16 hours. TLC (Dichloromethane:Methanol=10:1, P1:$R_f$=0.3) and LCMS showed the starting material was consumed completely and desired MS was detected. The mixture was partitioned between ethyl acetate (10 mL*2) and H₂O (3 mL). The combined organic phase was washed with brine (5 mL*3), dried with anhydrous Na₂SO₄, filtered and concentrated in vacuum to give a residue. The residue was purified by prep-TLC (SiO₂, DCM:MeOH=10:1, P1:$R_f$=0.3) to give 1i. MS mass calculated for [M+1]⁺ ($C_{22}H_{25}Cl_2N_5O_6$) requires m/z 526.1, LCMS found m/z 526.2; ¹H NMR (400 MHZ, CD₃OD) δ 7.54 (s, 2H), 7.32 (s, 1H), 4.77 (s, 2H), 3.48 (s, 3H), 3.18 (dt, J=13.6, 6.84 HZ, 1H), 1.46 (s, 9H), 1.27 (d, J=6.8 HZ, 6H).

3-(((3,5-dichloro-4-((5-isopropyl-1-methyl-6-oxo-1,6-dihydropyridazin-3-yl)oxy)phenyl)amino)methyl)-1,2,4-oxadiazol-5(4H),-one (Example 1)

To a solution of tert-butyl (3,5-dichloro-4-((5-isopropyl-1-methyl-6-oxo-1,6-dihydropyridazin-3-yl)oxy)phenyl)((5-oxo-4,5-dihydro-1,2,4-oxadiazol-3-yl)methyl)carbamate (1i) (170 mg, 322.97 umol) in HCl/EtOAc (2 mL) was stirred at 25° C. for 2 hours. LCMS and HPLC showed the starting material was consumed completely and desired MS was detected. The mixture was diluted with water (0.5 mL) and the pH was adjusted to 8 with NaHCO₃ (5 mL). Then the mixture was partitioned with Ethyl acetate 10 mL twice. The combined organic phase was washed with brine (5 mL*3), dried with anhydrous Na₂SO₄, filtered and concentrated in vacuum to give a residue. The residue was purified by Prep-HPLC (FA) column: Luna C18 100*30 5 u; mobile phase: [water (0.2% FA)-ACN]; B %: 25%-60%, 12 min] to give Example 1. MS mass calculated for [M+1]⁺ ($C_{17}H_{17}Cl_2N_5O_4$) requires m/z 426.1, LCMS found m/z 426.0; ¹H NMR (400 MHZ, CD₃OD) δ 7.23 (s, 1H), 6.76 (s, 2H), 4.88 (s, 139H), 4.28 (s, 2H), 3.50 (s, 3H), 3.12-3.21 (m, 1H), 1.25 (d, J=7.06 HZ, 6H).

Example 2: 3-(((3,5-dichloro-4-((5-isopropyl-1-methyl-6-oxo-1,6-dihydropyridazin-3-yl)oxy)phenyl)(methyl)amino)methyl)-1,2,4-oxadiazol-5(4H)-one

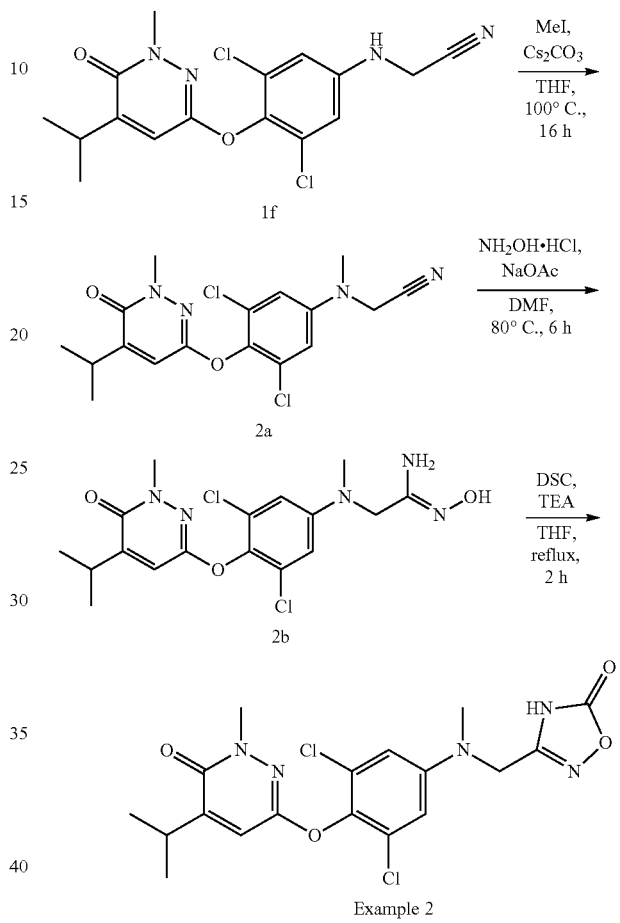

Example 2

2-((3, 5-dichloro-4-((5-isopropyl-1-methyl-6-oxo-1,6-dihydropyridazin-3-yl)oxy)phenyl)(methyl)amino)acetonitrile (2a)

To a solution of 2-((3,5-dichloro-4-((5-isopropyl-1-methyl-6-oxo-1,6-dihydropyridazin-3-yl)oxy)phenyl)amino)acetonitrile (1f) (50 mg, 136.15 umol) in THF (2 mL) was added Cs₂CO₃ (66.54 mg, 204.23 umol) and MeI (193.26 mg, 1.36 mmol, 84.76 uL). The mixture was stirred at 100° C. for 16 hours under sealed tube. TLC and LCMS showed ~30% of Reactant 1f was remained and the desired MS was detected. The suspension was filtered through a pad of Celite and the pad cake was washed with EtOAc (5 mL*3). The combined filtrates were concentrated to dryness to give a residue. The residue was purified by prep-TLC (SiO₂, petroleum ether:ethyl acetate=1:1, according TLC) to give the 2a. MS mass calculated for [M+1]⁺ ($C_{17}H_{18}Cl_2N_4O_2$) requires m/z 381.1, LCMS found m/z 381.0. ¹H NMR (400 MHZ, CDCl3) δ 7.03 (d, J=0.7 HZ, 1H), 6.82 (s, 2H), 4.19 (s, 2H), 3.54 (s, 3H), 3.28-3.20 (m, 1H), 3.05 (s, 3H), 1.27-1.25 (m, 6H).

(Z)-2-((3,5-dichloro-4-((5-isopropyl-1-methyl-6-oxo-1,6-dihydropyridazin-3-yl)oxy)phenyl)(methyl)-amino)-N'-hydroxyacetimidamide (2b)

To a solution of 2-((3,5-dichloro-4-((5-isopropyl-1-methyl-6-oxo-1,6-dihydropyridazin-3-yl)oxy)phenyl)(methyl)amino)acetonitrile (2a) (52 mg, 136.39 umol) in DMF (2 mL) was added NH$_2$OH·HCl (75.82 mg, 1.09 mmol) and NaOAc (89.51 mg, 1.09 mmol). The mixture was stirred at 80° C. for 6 hours. TLC showed reactant 2a was consumed completely, LCMS showed one main peak with desired MS. The suspension was filtered through a pad of Celite and the pad cake was washed with EtOAc (5 mL*3). The combined filtrates were washed with brine (10 mL), dried over anhydrous Na$_2$SO$_4$, filtered and concentrated under reduced pressure to give a residue. The residue was purified by prep-TLC (SiO$_2$, DCM:MeOH=10:1, according TLC) to give 2b. MS mass calculated for [M+1]$^+$ (C$_{17}$H$_{21}$Cl$_2$N$_5$O$_3$) requires m/z 414.1, LCMS found m/z 414.1.

3-(((3,5-dichloro-4-((5-isopropyl-1-methyl-6-oxo-1,6-dihydropyridazin-3-yl)oxy)phenyl)(methyl)amino)methyl)-1,2,4-oxadiazol-5(4H)-one (Example 2)

To a solution of (Z/E)-2-((3,5-dichloro-4-((5-isopropyl-1-methyl-6-oxo-1,6-dihydropyridazin-3-yl)oxy)phenyl)(methyl)amino)-N'-hydroxyacetimidamide (2b) (30 mg, 65.17 umol) in THF (2 mL) was added DSC (21.70 mg, 84.72 umol) and TEA (33.97 mg, 335.75 umol, 46.73 uL). The mixture was stirred at 80° C. for 2 hours. TLC and LCMS showed 2b was consumed completely and desired MS was detected. The reaction mixture was concentrated under reduced pressure to give a residue. The residue was checked by HPLC and then purified by prep-HPLC (column: Waters Atlantis T3 150*30*5 um; mobile phase: [water (0.225% FA)-ACN]; B %: 40%-70%, 13 min) to give Example 2. MS mass calculated for [M+1]$^+$ (C$_{18}$H$_{19}$Cl$_2$N$_5$O$_4$) requires m/z 440.1, LCMS found m/z 0.440.1. $^1$H NMR (400 MHZ, CD$_3$OD) δ 7.24 (s, 1H), 6.92 (s, 2H), 4.48 (s, 2H), 3.49 (s, 3H), 3.17 (td, J=7.2, 13.9 HZ, 1H), 3.05 (s, 3H), 1.26 (d, J=6.8 HZ, 6H).

Example 3: P1 and P2: 3-(1-((3,5-dichloro-4-((5-isopropyl-1-methyl-6-oxo-1,6-dihydropyridazin-3-yl)oxy)phenyl)amino)ethyl)-1,2,4-oxadiazol-5(4H)-one

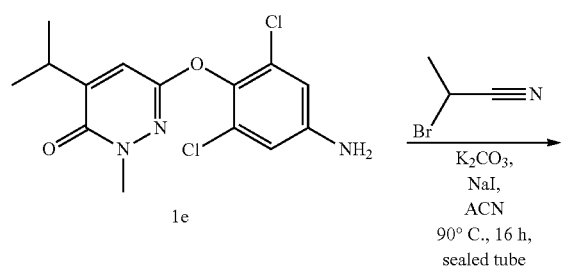

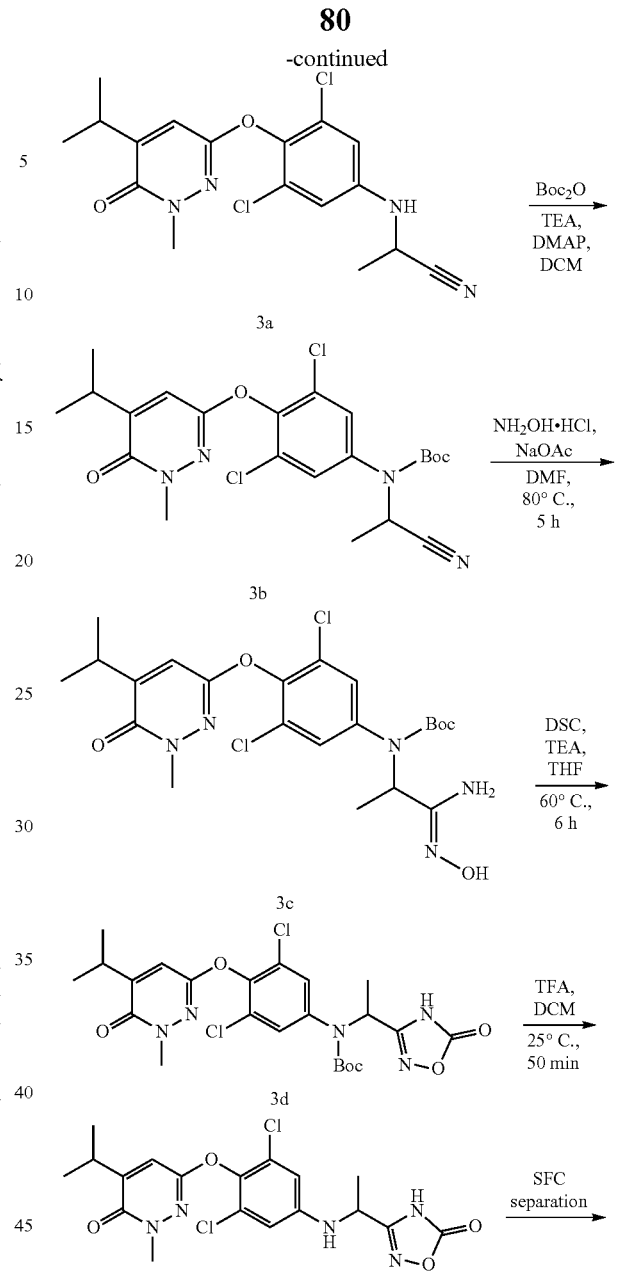

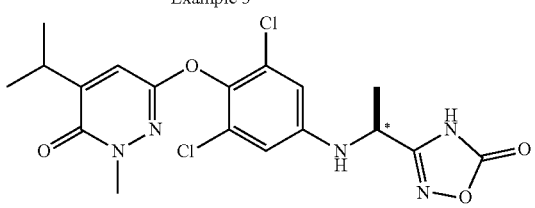

Example 3-P1

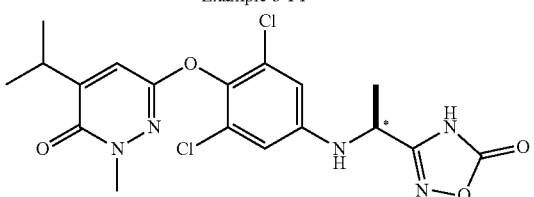

Example 3-P2

2-((3,5-dichloro-4-((5-isopropyl-1-methyl-6-oxo-1,6-dihydropyridazin-3-yl)oxy)phenyl)amino) propanenitrile (3a)

A mixture of 6-(4-amino-2,6-dichlorophenoxy)-4-isopropyl-2-methylpyridazin-3(2H)-one (1e) (0.2 g, 609.40 umol, 1 eq), $K_2CO_3$ (168.44 mg, 1.22 mmo), NaI (182.69 mg, 1.22 mmol) and 2-bromopropanenitrile (816.44 mg, 6.09 mmol) in $CH_3CN$ (5 mL) was added to a seal tube and heated to 90° C. for 16 hours. LCMS showed desired MS and STM of 1e, the mixture was filtered and washed with ethyl acetate (10 mL*2). The combined filtrates was washed with brine (20 mL), and the organic phase was concentrated to give 3a (0.25 g, crude), the crude product was used for the next step directly. MS mass calculated for $[M+1]^+$ ($C_{17}H_{18}Cl_2N_4O_2$) requires m/z 381.1, LCMS found m/z 381.0.

Tert-butyl (1-cyanoethyl)(3,5-dichloro-4-((5-isopropyl-1-methyl-6-oxo-1,6-dihydropyridazin-3-yl)oxy)phenyl)carbamate (3b)

A mixture of 2-((3,5-dichloro-4-((5-isopropyl-1-methyl-6-oxo-1,6-dihydropyridazin-3-yl)oxy)phenyl)amino) propanenitrile (3a) (0.25 g, 655.73 umol), $Boc_2O$ (429.33 mg, 1.97 mmol, 451.93 uL) and DMAP (80.11 mg, 655.73 umol) in THF (5 mL) was heated to 50° C. for 1 hour. LCMS showed desired MS, and TLC showed new spot. The mixture was concentrated, and the residue was purified by prep-TLC (petroleum ether:ethyl acetate=3:1) to give 3b. MS mass calculated for $[M+1]^+$ ($C_{22}H_{26}Cl_2N_4O_4$) requires m/z 481.1, LCMS found m/z 481.3; $^1$H NMR (400 MHz, $CDCl_3$) δ 7.31 (s, 2H), 7.07 (s, 1H), 3.51 (s, 3H), 3.30-3.23 (m, 1H), 3.20 (q, J=7.0 Hz, 1H), 2.03 (s, 3H), 1.75 (d, J=7.0 Hz, 3H), 1.57 (s, 4H), 1.51-1.43 (m, 9H), 1.28 (d, J=6.8 Hz, 6H).

(Z/E)-tert-butyl (1-amino-1-(hydroxyimino)propan-2-yl)(3,5-dichloro-4-((5-isopropyl-1-methyl-6-oxo-1,6-dihydropyridazin-3-yl)oxy)phenyl)carbamate (3c)

A mixture of tert-butyl (1-cyanoethyl)(3,5-dichloro-4-((5-isopropyl-1-methyl-6-oxo-1,6-dihydropyridazin-3-yl)oxy)phenyl)carbamate (3b) (80 mg, 166.19 umol), $NH_2OH \cdot HCl$ (92.39 mg, 1.33 mmol) and NaOAc (109.07 mg, 1.33 mmol) in DMF (3 mL) was heated to 80° C. for 5 hours. LCMS showed desired MS, TLC (Petroleum ether:Ethyl acetate=1:1, $R_f$=0.47) showed new point, the mixture was filtered and washed with ethyl acetate (10 mL*2), the filtrate was washed with brine (10 mL*2), the organic phase was dried over $Na_2SO_4$, filtered and concentrated, the residue was purified by prep-TLC (petroleum ether:ethyl acetate=1:1) to give 3c. MS mass calculated for $[M+1]^+$ ($C_{22}H_{29}Cl_2N_5O_5$) requires m/z 514.2, LCMS found m/z 514.0;

Tert-butyl (3,5-dichloro-4-((5-isopropyl-1-methyl-6-oxo-1,6-dihydropyridazin-3-yl)oxy)phenyl)(1-(5-oxo-4,5-dihydro-1,2,4-oxadiazol-3-yl)ethyl)carbamate (3d)

A mixture of (Z/E)-tert-butyl (1-amino-1-(hydroxyimino) propan-2-yl)(3,5-dichloro-4-((5-isopropyl-1-methyl-6-oxo-1,6-dihydropyridazin-3-yl)oxy)phenyl)carbamate (3c) (39 mg, 75.82 umol), DSC (25.25 mg, 98.56 umol) and TEA (15.34 mg, 151.63 umol, 21.11 uL) in THF (4 mL) was heated to 60° C. for 2 hours. Then the mixture was heated to reflux for another 4 hours. TLC (Petroleum ether:Ethyl acetate=1:1, $R_f$=0) showed the reaction was completed, and the mixture was concentrated to give 3d (70 mg, crude), which was used for the next step directly. MS mass calculated for $[M+1]^+$ ($C_{23}H_{27}Cl_2N_5O_6$) requires m/z 540.1, LCMS found m/z 540.2;

3-(1-((3,5-dichloro-4-((5-isopropyl-1-methyl-6-oxo-1,6-dihydropyridazin-3-yl)oxy)phenyl)amino)ethyl)-1,2,4-oxadiazol-5(4H)-one (Example 3)

To a solution of tert-butyl (3,5-dichloro-4-((5-isopropyl-1-methyl-6-oxo-1,6-dihydropyridazin-3-yl)oxy)phenyl)(1-(5-oxo-4,5-dihydro-1,2,4-oxadiazol-3-yl)ethyl)carbamate (3d) (70 mg, 129.53 umol) in DCM (2 mL) was added TFA (0.5 mL), and the mixture was stirred at 25° C. for 50 min. LCMS showed the reaction was completed, and desired MS was detected. Then the mixture was concentrated in vacuum. The residue was purified by prep-HPLC (FA) (column: Waters Atlantis T3 150*30*5 um; mobile phase: [water (0.225% FA)-ACN]; B %: 40%-80%, 13 min) to give 3-(1-((3,5-dichloro-4-((5-isopropyl-1-methyl-6-oxo-1,6-dihydropyridazin-3-yl)oxy)phenyl)amino)ethyl)-1,2,4-oxadiazol-5(4H)-one Example 3. MS mass calculated for $[M+1]^+$ ($C_{18}H_{19}Cl_2N_5O_4$) requires m/z 440.0, LCMS found m/z 440.1; $^1$H NMR (400 MHz, $CD_3OD$) δ 7.25 (d, J=0.8 Hz, 1H), 6.78 (s, 2H), 4.55 (q, J=6.8 Hz, 1H), 3.52 (s, 3H), 3.23-3.13 (m, 1H), 1.60 (d, J=6.8 Hz, 3H), 1.27 (d, J=7.0 Hz, 6H).

Sfc Separation:
3-(1-((3,5-dichloro-4-((5-isopropyl-1-methyl-6-oxo-1,6-dihydropyridazin-3-yl)oxy)phenyl)amino)ethyl)-1,2,4-oxadiazol-5(4H)-one (Example 3) (17.17 mg, 39.00 umol, 1 eq) was separated by SFC ([Monitoring] Instrument: Thar SFC80 preparative SFC; Column: Chiralpak AS-H, 250*30 mm i.d. 10 u; Mobile phase: A for $CO_2$ and B for MeOH (0.1% ammonia); Gradient: B %=40%; Flow rate:70 g/min; Wavelength:220 nm; Column temperature: 40° C.; System back pressure: 100 bar) to give Example-P1; MS mass calculated for $[M+1]^+$ ($C_{18}H_{19}Cl_2N_5O_4$) requires m/z 440.1, LCMS found m/z 440.0; $^1$H NMR (400 MHz, $CD_3OD$) δ 7.23 (d, J=0.8 Hz, 1H), 6.75 (s, 2H), 4.48 (q, J=6.8 Hz, 1H), 3.51 (s, 3H), 3.17 (td, J=6.6, 13.6 Hz, 1H), 1.58 (d, J=6.8 Hz, 3H), 1.26 (d, J=7.2 Hz, 6H) and Example-P2; MS mass calculated for $[M+1]^+$ ($C_{18}H_{19}Cl_2N_5O_4$) requires m/z 440.1, LCMS found m/z 440.0; $^1$H NMR (400 MHz, $CD_3OD$) δ 7.23 (s, 1H), 6.75 (s, 2H), 4.48 (q, J=6.8 Hz, 1H), 3.51 (s, 3H), 3.17 (quin, J=6.8 Hz, 1H), 1.58 (d, J=6.8 Hz, 3H), 1.26 (d, J=6.8 Hz, 6H).

Example 4: N-(3,5-dichloro-4-((5-isopropyl-1-methyl-6-oxo-1,6-dihydropyridazin-3-yl)oxy)phenyl)-5-oxo-4,5-dihydro-1,2,4-oxadiazole-3-carboxamide

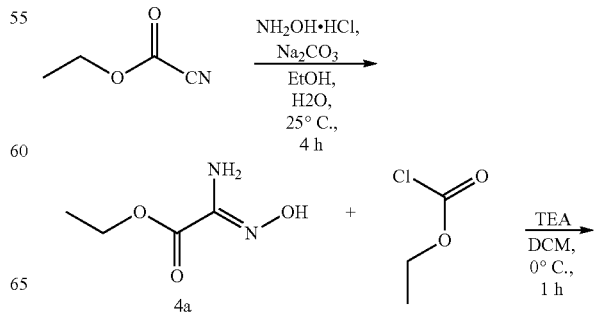

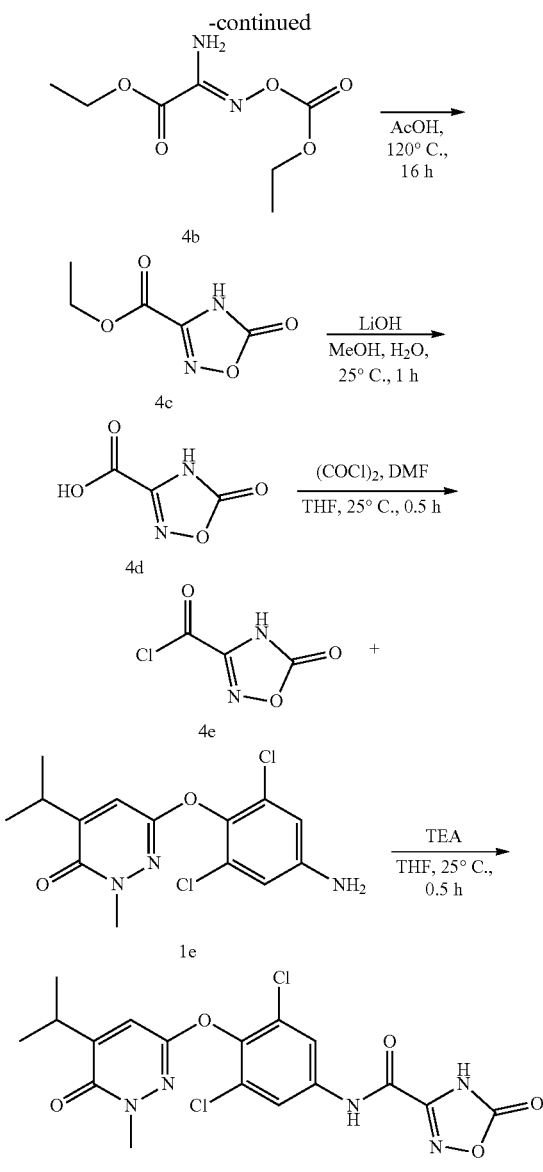

Example 4

(Z/E)-ethyl 2-amino-2-(hydroxyimino)acetate (4a)

To a solution of ethyl carbonocyanidate (2.5 g, 25.23 mmol, 2.48 mL) in EtOH (25 mL) was added NH$_2$OH.HCl (2.63 g, 37.85 mmol) and Na$_2$CO$_3$ (2.67 g, 25.23 mmol). The mixture was stirred at 25° C. for 2 hours. TLC showed the reaction was completed. LCMS showed one main peak with desired MS. The reaction mixture was concentrated under reduced pressure to remove EtOH. The residue was diluted with H$_2$O (5 mL) and extracted with etOAc (20 mL*5). The combined organic layers was washed with brine (5 mL), dried over anhydrous Na$_2$SO$_4$, filtered and concentrated under reduced pressure to give a residue. The residue was purified by re-crystallization from MTBE:petroleum ether=1:1 (20 mL) at 70° C. to give 4a. MS mass calculated for [M+1]$^+$ (C$_4$H$_8$N$_2$O$_3$) requires m/z 133.1, LCMS found m/z 133.1; $^1$H NMR (400 MHz, CDCl$_3$) δ 8.90 (br s, 1H), 5.12 (br s, 2H), 4.34 (q, J=7.1 Hz, 2H), 1.36 (t, J=7.2 Hz, 3H)

(Z)-ethyl 2-amino-2-(((ethoxycarbonyl)oxy)imino) acetate (4b)

To a solution of (Z/E)-ethyl 2-amino-2-(hydroxyimino)acetate (4a) (1 g, 7.57 mmol) in DCM (5 mL) was added TEA (2.30 g, 22.71 mmol, 3.16 mL) and ethyl carbonochloridate (903.56 mg, 8.33 mmol, 792.59 uL). The mixture was stirred at 0° C. for 1 hour. TLC indicated 5a was consumed completely and one new spot formed. The reaction was clean according to TLC. The reaction mixture was concentrated under reduce pressure to give 4b (1.34 g, crude). $^1$H NMR (400 MHz, CDCl$_3$) δ 5.44 (br s, 2H), 4.40 (q, J=7.2 Hz, 2H), 4.34 (q, J=7.2 Hz, 2H), 1.42-1.38 (m, 3H), 1.38-1.34 (m, 3H).

Ethyl 5-oxo-4,5-dihydro-1,2,4-oxadiazole-3-carboxylate (4c)

A solution of (Z/E)-ethyl 2-amino-2-(((ethoxycarbonyl)oxy)imino)acetate (4b) (1.34 g, 6.56 mmol) in AcOH (5 mL) was degassed and purged with N$_2$ for 3 times, and then the mixture was stirred at 120° C. for 10 hours under N$_2$ atmosphere. LCMS showed 4b was consumed completely and one main peak with the desired MS was detected. The reaction mixture was concentrated under reduced pressure to remove AcOH and then to give the 4c (1.03 g, crude). The crude product was used in next step without further purification. MS mass calculated for [M−1]$^−$ (C$_5$H$_6$N$_2$O$_4$) requires m/z 157.0, LCMS found m/z 157.0.

5-oxo-4,5-dihydro-1,2,4-oxadiazole-3-carboxylic acid (4d)

To a solution of ethyl 5-oxo-4,5-dihydro-1,2,4-oxadiazole-3-carboxylate (4c) (200 mg, 1.26 mmol, 1 eq) in MeOH (1 mL) and H$_2$O (0.2 mL) was added LiOH (36.35 mg, 1.52 mmol, 1.2 eq). The mixture was stirred at 25° C. for 1 hour. TLC showed reactant 4 was consumed completely and one new spot was formed. The reaction mixture was concentrated under reduce pressure to give a residue. The residue was diluted with HCl (1M, 5 mL) to adjust the pH=4-6 and then extracted with EtOAc (5 mL*4). The combined organic layers were washed with brine (5 mL), dried over anhydrous Na$_2$SO$_4$, filtered and concentrated under reduced pressure to give 4d (114 mg, crude). The crude product was used in next step without further purification. MS mass calculated for [M+1]$^+$ (C$_5$H$_6$N$_2$O$_4$) requires m/z 159.0, LCMS found no m/z; $^1$H NMR (400 MHz, DMSO) δ 4.35 (q, J=7.0 Hz, 2H), 1.28 (t, J=7.0 Hz, 3H).

5-oxo-4,5-dihydro-1,2,4-oxadiazole-3-carbonyl chloride (4e)

To a solution of 5-oxo-4,5-dihydro-1,2,4-oxadiazole-3-carboxylic acid (4d) (110 mg, 845.77 umol) in THF (3 mL) was added (COCl)$_2$ (128.82 mg, 1.01 mmol, 88.84 uL) and DMF (6.18 mg, 84.58 umol, 6.51 uL). The mixture was stirred at 25° C. for 1 hour. A few drops of reaction mixture were quenched with MeOH for monitoring. TLC indicated 4d was consumed completely and one new spot formed, the mixture was concentrated under reduced pressure to give 4e (155 mg, crude). The crude product was used in next step without further purification.

N-(3,5-dichloro-4-((5-isopropyl-1-methyl-6-oxo-1,6-dihydropyridazin-3-yl)oxy)phenyl)-5-oxo-4,5-dihydro-1,2,4-oxadiazole-3-carboxamide (Example 4)

To a solution of 6-(4-amino-2,6-dichlorophenoxy)-4-isopropyl-2-methylpyridazin-3(2H)-one (1e) (20 mg, 60.94 umol) in THF (3 mL) was added TEA (18.50 mg, 182.82 umol, 25.45 uL) and 5-oxo-4,5-dihydro-1,2,4-oxadiazole-3-carbonyl chloride (4e) (13.57 mg, 91.41 umol). The mixture was stirred at 25° C. for 0.5 hour. LCMS showed 1e was consumed completely and desired MS was detected. The reaction mixture was quenched by addition MeOH (1 mL) at 25° C., and then concentrated under reduced pressure to give a residue. The residue was checked by HPLC and purified by Prep-HPLC (column: Xtimate C18 150*25 mm*5 um; mobile phase: [water (10 mM NH$_4$HCO$_3$)-ACN]; B %: 30%-55%, 10 min) to give Example 4. MS mass calculated for [M+1]$^+$ (C$_{17}$H$_{15}$Cl$_2$N$_5$O$_5$) requires m/z 440.0, LCMS found m/z 440.0. $^1$H NMR (400 MHz, CD$_3$OD) δ 7.93 (s, 2H), 7.31 (s, 1H), 3.51 (s, 3H), 3.19 (quind, J=7.0, 13.8 Hz, 1H), 1.27 (d, J=6.8 Hz, 6H).

Example 5: 3-(((3,5-dichloro-4-((5-isopropyl-6-oxo-1,6-dihydropyridazin-3-yl)oxy)phenyl)amino)methyl)-1,2,4-oxadiazol-5(4H)-one

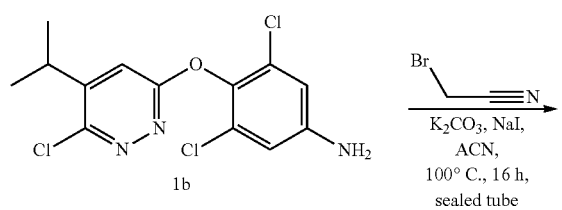

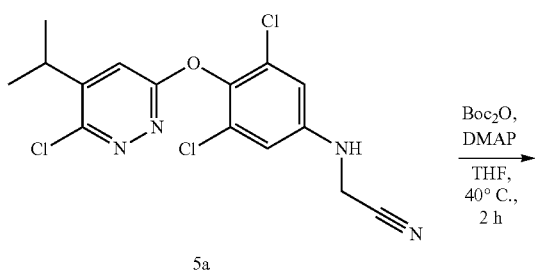

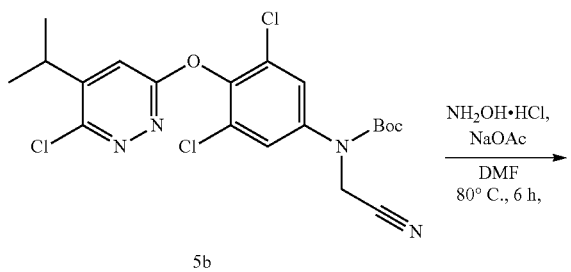

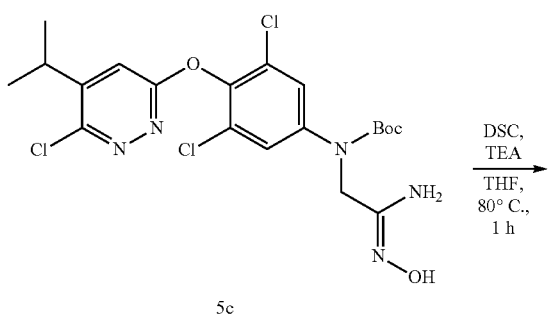

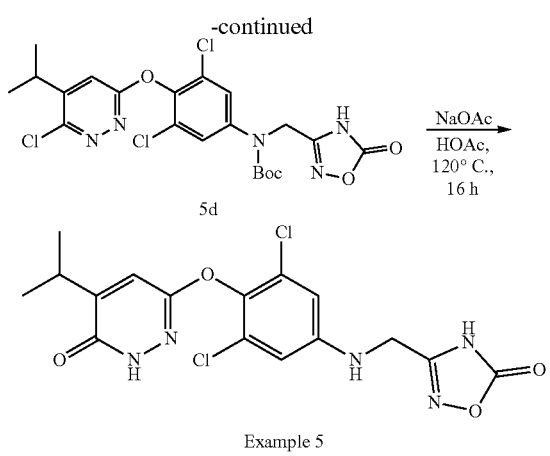

Example 5

2-((3,5-dichloro-4-((6-chloro-5-isopropylpyridazin-3-yl)oxy)phenyl)amino)acetonitrile (5a)

To a solution of 3,5-dichloro-4-((6-chloro-5-isopropylpyridazin-3-yl)oxy)aniline (1b) (180 mg, 432.94 umol) and 2-bromoacetonitrile (259.65 mg, 2.16 mmol, 144.25 uL) in ACN (2 mL) was added K$_2$CO$_3$ (119.67 mg, 865.87 umol) and NaI (129.79 mg, 865.87 umol). The mixture was stirred at 100° C. for 16 hours under sealed tube. LCMS showed reactant 1 b was consumed completely and desired MS was detected. The reaction mixture was concentrated under reduce pressure to give a residue. The residue was purified by prep-TLC (SiO$_2$, petroleum ether:ethyl acetate=1:1, according TLC) to give 4a. MS mass calculated for [M+1]$^+$ (C$_{15}$H$_{13}$Cl$_3$N$_4$O) requires m/z 371.0, LCMS found m/z 0.371.0. $^1$H NMR (400 MHz, CD$_3$Cl) δ 7.25 (s, 1H), 6.66 (s, 2H), 4.83-4.77 (m, 1H), 4.05 (d, J=6.4 Hz, 2H), 3.29 (td, J=6.8, 13.6 Hz, 1H), 1.37 (d, J=6.8 Hz, 6H).

Tert-butyl (cyanomethyl)(3,5-dichloro-4-((6-chloro-5-isopropylpyridazin-3-yl)oxy)phenyl)carbamate (5b)

To a solution of 2-((3,5-dichloro-4-((6-chloro-5-isopropylpyridazin-3-yl)oxy)phenyl)amino)acetonitrile (5a) (172 mg, 379.50 umol) in THF (10 mL) was added DMAP (51.00 mg, 417.45 umol) and Boc$_2$O (248.48 mg, 1.14 mmol, 261.55 uL). The mixture was stirred at 40° C. for 2 hours. TLC indicated Reactant 5a was consumed completely and one new spot formed. The reaction mixture was concentrated under reduced pressure to give a residue. The residue was purified by prep-TLC (SiO$_2$, petroleum ether:ethyl acetate=1:1, according TLC) to give 5b. MS mass calculated for [M+1]$^+$ (C$_{20}$H$_{21}$Cl$_3$N$_4$O$_3$) requires m/z 471.1, LCMS found m/z 471.1. $^1$H NMR (400 MHz, CD$_3$Cl) δ 7.38 (s, 2H), 7.24 (s, 1H), 4.48 (s, 2H), 3.29 (td, J=6.7, 13.6 Hz, 1H), 1.53 (s, 9H), 1.37 (d, J=6.8 Hz, 6H).

(Z/E)-tert-butyl (2-amino-2-(hydroxyimino)ethyl)(3,5-dichloro-4-((6-chloro-5-isopropylpyridazin-3-yl)oxy)phenyl)carbamate (5c)

To a solution of tert-butyl (cyanomethyl)(3,5-dichloro-4-((6-chloro-5-isopropylpyridazin-3-yl)oxy)phenyl)carbamate (5b) (145 mg, 307.36 umol) in DMF (2 mL) was added NH$_2$OH.HCl (170.87 mg, 2.46 mmol) and NaOAc (201.70 mg, 2.46 mmol). The mixture was stirred at 80° C. for 6 hours. TLC showed reactant 5b was consumed completely. LCMS showed one main peak with desired MS. The suspension was filtered through a pad of Celite and the pad cake was washed with EtOAc (5 ml*3). The combined filtrates were washed with brine (10 mL), dried over anhydrous Na$_2$SO$_4$, filtered and concentrated under reduce pressure to give a residue. The residue was purified by prep-TLC (SiO$_2$, petroleum ether:ethyl acetate=1:1, according TLC) to give 5c. MS mass calculated for [M+1]$^+$ (C$_{20}$H$_{24}$Cl$_3$N$_5$O$_4$) requires m/z 504.1, LCMS found m/z 504.1. $^1$H NMR (400 MHz, CD$_3$C$_1$) δ 7.37 (s, 2H), 7.21 (s, 1H), 5.11 (br s, 2H), 4.23 (s, 2H), 3.28 (td, J=7.0, 13.8 Hz, 1H), 2.09 (s, 1H), 1.49 (s, 9H), 1.36 (d, J=6.8 Hz, 6H).

Tert-butyl (3,5-dichloro-4-((6-chloro-5-isopropylpyridazin-3-yl)oxy)phenyl)((5-oxo-4,5-dihydro-1,2,4-oxadiazol-3-yl)methyl)carbamate (5d)

To a solution of (Z/E)-tert-butyl (2-amino-2-(hydroxyimino)ethyl)(3,5-dichloro-4-((6-chloro-5-isopropylpyridazin-3-yl)oxy)phenyl)carbamate (5c) (50 mg, 89.15 umol) in THF (2 mL) was added DSC (29.69 mg, 115.89 umol) and TEA (33.97 mg, 335.75 umol, 46.73 uL). The mixture was stirred at 80° C. for 1 hour. LCMS showed 5c was consumed completely and desired MS was detected. The reaction mixture was concentrated under reduced pressure to give a residue. The residue was purified by prep-TLC (dichloromethane:methanol=10:1, according TLC) to give 5d. MS mass calculated for [M+1]$^+$ (C$_{21}$H$_{22}$Cl$_3$N$_5$O$_5$) requires m/z 530.1, LCMS found m/z 530.1.

3-(((3,5-dichloro-4-((5-isopropyl-6-oxo-1,6-dihydropyridazin-3-yl)oxy)phenyl)amino)methyl)-1,2,4-oxadiazol-5(4H)-one (Example 5)

To a solution of (tert-butyl (3,5-dichloro-4-((6-chloro-5-isopropylpyridazin-3-yl)oxy)phenyl)((5-oxo-4,5-dihydro-1,2,4-oxadiazol-3-yl)methyl)carbamate) 5d (68 mg, 115.30 umol) in AcOH (3 mL) was added NaOAc (75.66 mg, 922.40 umol). The mixture was stirred at 110° C. for 3 hours. LCMS showed reactant 5d was consumed and desired MS was detected. The reaction mixture was concentrated under reduced pressure to remove AcOH and then to give a residue. The residue was checked by HPLC and purified by Prep-HPLC (column: Waters Xbridge Prep OBD C18 150*30 5 u; mobile phase: [water (0.225% FA)-ACN]; B %: 30%-65%, 13 min) to give Example 5. MS mass calculated for [M+1]$^+$ (C$_{16}$H$_{15}$Cl$_2$N$_5$O$_4$) requires m/z 412.0, LCMS found m/z 412.0. $^1$H NMR (400 MHz, DMSO) δ 12.11 (s, 1H), 7.31 (s, 1H), 6.79 (s, 2H), 6.66 (br t, J=6.0 Hz, 1H), 4.27 (d, J=6.2 Hz, 2H), 3.02 (td, J=7.0, 13.6 Hz, 1H), 1.17 (d, J=6.8 Hz, 6H).

Example 6: 3-((3,5-dichloro-4-((5-isopropyl-1-methyl-6-oxo-1,6-dihydropyridazin-3-yl)oxy)phenoxy)methyl)-1,2,4-oxadiazol-5(4H)-one

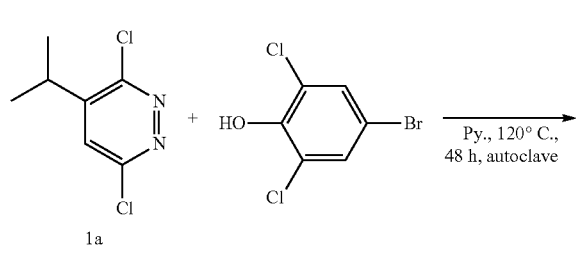

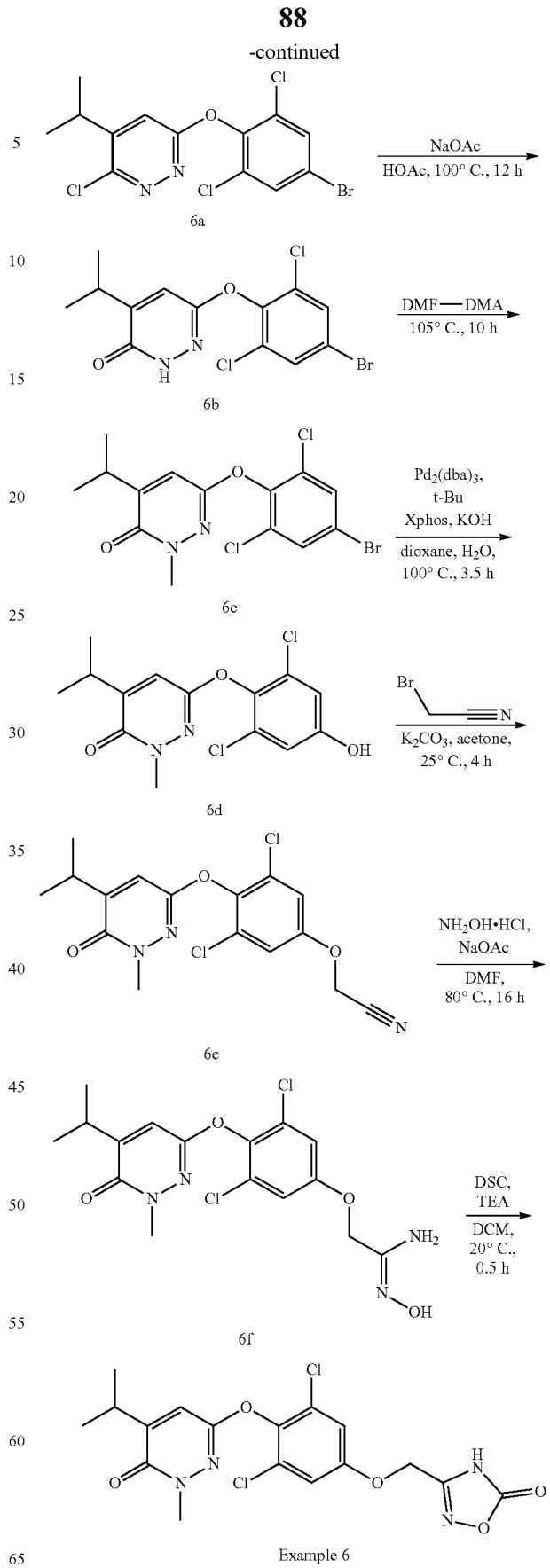

6-(4-bromo-2,6-dichlorophenoxy)-3-chloro-4-isopropylpyridazine (6a)

A mixture of 4-bromo-2,6-dichloro-phenol (3.04 g, 12.56 mmol) and 3,6-dichloro-4-isopropyl-pyridazine (1a) (2 g, 10.47 mmol) in pyridine (10 mL) was stirred at 130° C. for 48 hours in a 100 mL of autoclave. LCMS showed the starting material of 1a was consumed completely and the desired MS was found. The mixture was diluted with Tol. (30 mL) and concentrated in vacuum. The residue was partitioned between ethyl acetate (30 mL*2) and H$_2$O (10 mL). The combined organic phase was washed with brine (10 mL*3), dried with anhydrous Na$_2$SO$_4$, filtered and concentrated in vacuum. The residue was purified by column chromatography (SiO$_2$, petroleum ether:ethyl acetate=1:0 to 100:1) to give 6a. MS mass calculated for [M+1]$^+$ (C$_{13}$H$_{10}$BrCl$_3$N$_2$O) requires m/z 394.9, LCMS found m/z 394.9. $^1$H NMR (400 MHz, DMSO) δ ppm 7.98-8.04 (m, 1H) 7.92-7.97 (m, 1H) 7.84 (s, 1H) 3.11-3.29 (m, 1H) 1.23-1.47 (m, 6H).

6-(4-bromo-2,6-dichlorophenoxy)-4-isopropylpyridazin-3(2H)-one (6b)

A mixture of 6-(4-bromo-2,6-dichlorophenoxy)-3-chloro-4-isopropyl-pyridazine (6a) (1 g, 2.52 mmol) and NaOAc (827.59 mg, 10.09 mmol) in AcOH (10 mL) was stirred at 120° C. for 18 hours. LCMS showed the starting material was consumed completely and the desired MS was found. The mixture was concentrated in vacuum. The solid was dissolved in water and the pH was adjusted to 9 with saturated NaHCO$_3$(2 mL). Then the mixture was extracted with Ethyl acetate (10 mL*2). The combined organic phase was washed with brine (5 mL*3), dried with anhydrous Na$_2$SO$_4$, filtered and concentrated in vacuum to give 6b. The product was used directly for the next step without further purification. [M+1]$^+$ (C$_{13}$H$_{11}$BrCl$_2$N$_2$O$_2$) requires m/z 376.9, LCMS found m/z 376.9. $^1$H NMR (400 MHz, DMSO) δ ppm 12.22 (br s, 1H) 7.91-8.02 (m, 2H) 7.39 (s, 1H) 2.97-3.11 (m, 1H) 2.87-2.95 (m, 1H) 1.29 (d, J=6.72 Hz, 1H) 1.15-1.23 (m, 6H).

6-(4-bromo-2,6-dichlorophenoxy)-4-isopropyl-2-methylpyridazin-3(2H)-one (6c)

A mixture of 3-(4-bromo-2,6-dichloro-phenoxy)-5-isopropyl-1H-pyridazin-6-one (6b) (500 mg, 1.32 mmol) in DMF-DMA (22.42 g, 188.19 mmol, 25.00 mL) was stirred at 105° C. for 16 hours. LCMS showed the starting material was consumed completely and desired MS was detected. The mixture was concentrated in vacuum. The residue was partitioned between ethyl acetate (10 mL*2) and H$_2$O (3 mL). The combined organic phase was washed with brine (5 mL*3), dried with anhydrous Na$_2$SO$_4$, filtered and concentrated in vacuum. The residue was purified by column chromatography (SiO$_2$, petroleum ether/ethyl acetate=1:0 to 30:1) to give 6c. [M+1]$^+$ (C$_{14}$H$_{13}$BrCl$_2$N$_2$O$_2$) requires m/z 391.0, LCMS found m/z 391.0. $^1$H NMR (400 MHz, DMSO) δ ppm 7.96 (s, 2H) 7.41 (s, 1H) 3.32 (s, 1H) 3.08 (dt, J=13.67, 6.84 Hz, 1H) 2.50 (br d, J=3.53 Hz, 8H) 1.18 (d, J=7.06 Hz, 5H) 1.23 (br s, 1H).

6-(2,6-dichloro-4-hydroxyphenoxy)-4-isopropyl-2-methylpyridazin-3(2H)-one (6d)

A mixture of 6-(4-bromo-2,6-dichlorophenoxy)-4-isopropyl-2-methylpyridazin-3(2H)-one (6c) (170 mg, 433.59 umol), KOH (31.63 mg, 563.67 umol), t-Bu Xphos (27.62 mg, 65.04 umol) and Pd$_2$(dba)$_3$ (39.70 mg, 43.36 umol) in dioxane (8 mL) and H$_2$O (8 mL) was degassed and purged with N$_2$ for 3 times, and then the mixture was stirred at 100° C. for 3.5 hours under N$_2$ atmosphere. TLC showed 6c was consumed completely, and LCMS detected the desired MS. The suspension was filtered through a pad of Celite and the pad cake was washed with EtOAc (5 mL*3). The combined filtrates were concentrated to give a residue. The residue was purified by prep-TLC (SiO$_2$, ethyl acetate:petroleum ether=1:1, according TLC) to give 6d. MS mass calculated for [M+1]$^+$ (C$_{14}$H$_{14}$Cl$_2$N$_2$O$_3$) requires m/z 329.0, MS found m/z 329.0. 1H NMR (400 MHz, CDCl$_3$) δ 7.06 (s, 1H), 6.93 (s, 2H), 6.45 (br s, 1H), 3.55 (s, 3H), 3.25 (td, J=6.8, 13.6 Hz, 1H), 1.27 (d, J=6.8 Hz, 6H).

2-(3,5-dichloro-4-((5-isopropyl-1-methyl-6-oxo-1,6-dihydropyridazin-3-yl)oxy)phenoxy)acetonitrile (6e)

To a solution of 6-(2,6-dichloro-4-hydroxyphenoxy)-4-isopropyl-2-methylpyridazin-3(2H)-one (6d) (40 mg, 121.51 umol) in acetone (2 mL) was added K$_2$CO$_3$ (50.38 mg, 364.54 umol) and 2-bromoacetonitrile (21.86 mg, 182.27 umol, 12.15 uL). The mixture was stirred at 20° C. for 2 hours. TLC showed 6d was consumed completely and one new spot was formed. The suspension was filtered through a pad of Celite and the pad cake was washed with EtOH (5 mL*3). The combined filtrates were concentrated to dryness to give a residue. The residue was purified by prep-TLC (SiO$_2$, ethyl acetate:petroleum ether=1:1) to give 6e as a yellow solid. MS mass calculated for [M+1]$^+$ (C$_{16}$H$_{15}$Cl$_2$N$_3$O$_3$) requires m/z 368.0, MS found m/z 368.0. $^1$H NMR (400 MHz, CDCl$_3$) δ 7.04 (s, 3H), 4.80 (s, 2H), 3.53 (s, 3H), 3.25 (td, J=6.8, 13.4 Hz, 1H), 1.27 (d, J=6.8 Hz, 6H).

(Z/E)-2-(3,5-dichloro-4-((5-isopropyl-1-methyl-6-oxo-1,6-dihydropyridazin-3-yl)oxy)phenoxy)-N'-hydroxyacetimidamide (6f)

To a solution of 2-(3,5-dichloro-4-((5-isopropyl-1-methyl-6-oxo-1,6-dihydropyridazin-3-yl)oxy)phenoxy)acetonitrile (6e) (38 mg, 103.20 umol) in DMF (2 mL) was added NH$_2$OH.HCl (57.37 mg, 825.61 umol) and NaOAc (67.72 mg, 825.61 umol). The mixture was stirred at 80° C. for 6 hours. TLC showed 6e was consumed completely, and LCMS showed one main peak with desired MS. The reaction mixture was concentrated under reduced pressure to remove DMF. The residue was diluted with brine (5 mL) and extracted with EtOAc (5 mL*3). The combined organic layers were dried over anhydrous Na$_2$SO$_4$, filtered and concentrated under reduced pressure to give 6f (66.3 mg, crude). The product was used into the next step without further purification. MS mass calculated for [M+1]$^+$ (C$_{16}$H$_{18}$Cl$_2$N$_4$O$_4$) requires m/z 401.0, LCMS found m/z 401.2.

3-((3,5-dichloro-4-((5-isopropyl-1-methyl-6-oxo-1,6-dihydropyridazin-3-yl)oxy)phenoxy)methyl)-1,2,4-oxadiazol-5(4H)-one (Example 6)

To a solution of (Z/E)-2-(3,5-dichloro-4-((5-isopropyl-1-methyl-6-oxo-1,6-dihydropyridazin-3-yl)oxy)phenoxy)-N'-hydroxyacetimidamide (6f) (66.3 mg, 132.19 umol) in THF (2 mL) was added DSC (44.02 mg, 171.85 umol) and TEA (26.75 mg, 264.38 umol, 36.80 uL). The mixture was stirred at 60° C. for 4 hours. LCMS showed 6f was consumed completely and desired MS was detected. The reaction mixture was concentrated under reduced pressure to give a residue. The residue was purified by prep-HPLC (column: Waters Xbridge Prep OBD C18 150*30 5 u; mobile phase: [water(0.04% $NH_3H_2O$)-ACN]; B %: 5%-35%, 10 min) to give Example 6. MS mass calculated for $[M+1]^+$ ($C_{17}H_{16}Cl_2N_4O_5$) requires m/z 427.1, LCMS found m/z 427.1. $^1$H NMR (400 MHz, $CD_3OD$) δ 7.30 (s, 1H), 7.24 (s, 2H), 5.10 (s, 2H), 3.49 (s, 3H), 3.19 (quind, J=7.0, 13.8 Hz, 1H), 1.27 (d, J=6.8 Hz, 6H).

Example 7: 5-(3,5-dichloro-4-((5-isopropyl-1-methyl-6-oxo-1,6-dihydropyridazin-3-yl)oxy)phenyl)isoxazol-3(2H)-one

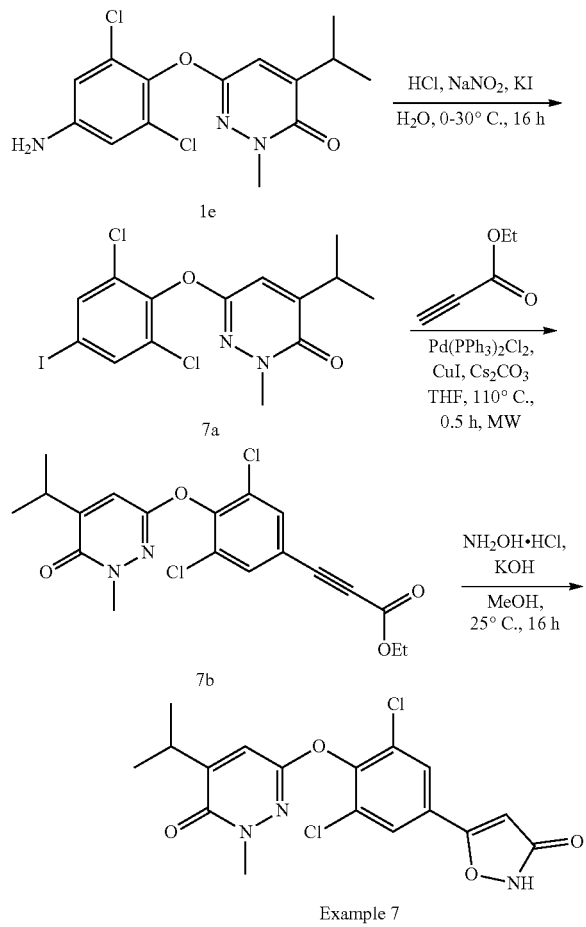

6-(2,6-dichloro-4-iodophenoxy)-4-isopropyl-2-methylpyridazin-3(2H)-one (7a)

To a solution of 6-(4-amino-2,6-dichlorophenoxy)-4-isopropyl-2-methylpyridazin-3(2H)-one (1e) (50 mg, 152.35 umol) in HCl (5 M, 304.70 uL) was added $NaNO_2$ (12.61 mg, 182.82 umol) at 0° C. Then the mixture was stirred for 0.5 hour at 0° C. Then a solution of KI (50.58 mg, 304.70 umol) in $H_2O$ (1.5 mL) was added in the mixture, and the mixture was stirred at 20° C. for another 16 hours. TLC indicated Reactant 1e was consumed completely. LCMS showed Reactant 1e was consumed completely and one main peak with the desired MS was formed. The reaction mixture was extracted with EtOAc (5 mL*4). The combined organic layers were washed with brine (5 mL), dried over $Na_2SO_4$, filtered and concentrated under reduced pressure to give a residue. The residue was purified by prep-TLC ($SiO_2$, petroleum ether:ethyl acetate=1:1, product $R_f$=0.80, according TLC) to give 7a. MS mass calculated for $[M+1]^+$ ($C_{14}H_{12}Cl_2N_2O_2$) requires m/z 438.9, LCMS found m/z 438.9. $^1$H NMR (400 MHz, $CDCl_3$) δ 7.71 (s, 2H), 7.04 (s, 1H), 3.52 (s, 3H), 3.25 (td, J=7.0, 13.4 Hz, 1H), 1.26 (d, J=6.8 Hz, 6H).

Ethyl 3-(3,5-dichloro-4-((5-isopropyl-1-methyl-6-oxo-1,6-dihydropyridazin-3-yl)oxy)phenyl)propiolate (7b)

A mixture of 6-(2,6-dichloro-4-iodophenoxy)-4-isopropyl-2-methylpyridazin-3(2H)-one (7a) (25 mg, 56.94 umol), ethyl propiolate (12.29 mg, 125.26 umol), $Pd(PPh_3)_2Cl_2$ (4.00 mg, 5.69 umol), CuI (2.17 mg, 11.39 umol) and $Cs_2CO_3$ (37.10 mg, 113.88 umol) in THF (5 mL) was degassed and purged with $N_2$ for 3 times. Then the mixture was stirred at 110° C. for 0.5 hour under microwave. TLC indicated Reactant 7a was consumed completely and many spots formed. The suspension was filtered through a pad of Celite and the pad cake was washed with EtOAc (5 mL*3). The combined filtrates were concentrated to give a residue. The residue was purified by prep-TLC ($SiO_2$, petroleum ether:ethyl acetate=3:1, according TLC) to give 7b. MS mass calculated for $[M+1]^+$ ($C_{19}H_{18}Cl_2N_2O_4$) requires m/z 409.1, LCMS found m/z 409.1. $^1$H NMR (400 MHz, $CDCl_3$) δ 7.61 (s, 2H), 7.06 (s, 1H), 4.32 (q, J=7.0 Hz, 2H), 3.51 (s, 3H), 3.25 (quind, J=6.8, 13.8 Hz, 1H), 1.37 (t, J=7.2 Hz, 3H), 1.27 (d, J=6.8 Hz, 6H).

5-(3,5-dichloro-4-((5-isopropyl-1-methyl-6-oxo-1,6-dihydropyridazin-3-yl)oxy)phenyl)isoxazol-3(2H)-one (Example 7)

To a solution of ethyl 3-(3,5-dichloro-4-((5-isopropyl-1-methyl-6-oxo-1,6-dihydropyridazin-3-yl)oxy)phenyl)propiolate (7b) (27 mg, 48.56 umol) in MeOH (3 mL) was added $NH_2OH \cdot HCl$ (13.50 mg, 194.22 umol) and KOH (16.35 mg, 291.33 umol). The mixture was stirred at 25° C. for 16 hours. TLC showed reactant 7b was consumed completely. The reaction mixture was concentrated under reduced pressure to remove MeOH. The residue was diluted with $H_2O$ (5 mL) and extracted with EtOAc (5 mL*3). The combined organic layers were washed with brine (5 mL), dried over anhydrous $Na_2SO_4$, filtered and concentrated under reduced pressure to give a residue. The residue was checked by HPLC and purified by prep-HPLC (column: Waters Xbridge Prep OBD C18 150*30 5 u; mobile phase: [water (0.04% $NH_3H_2O$)-ACN]; B %: 5%-35%, 10 min) to give Example 7. MS mass calculated for $[M+1]^+$ ($C_{17}H_{15}Cl_2N_3O_4$) requires m/z 396.0, LCMS found m/z 396.0. $^1$H NMR (400 MHz, $CDCl_3$) δ 7.76 (s, 2H), 7.08 (s, 1H), 6.25 (s, 1H), 3.52 (s, 3H), 3.31-3.22 (m, 1H), 1.28 (d, J=6.8 Hz, 6H).

Example 8: 5-(3,5-dichloro-4-((5-isopropyl-6-oxo-1,6-dihydropyridazin-3-yl)oxy)phenyl)isoxazol-3(2H)-one

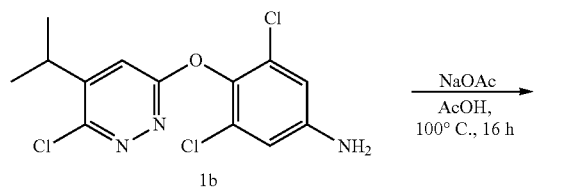
1b

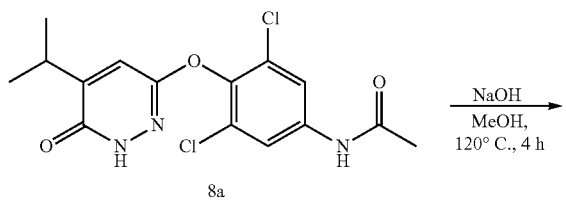
8a

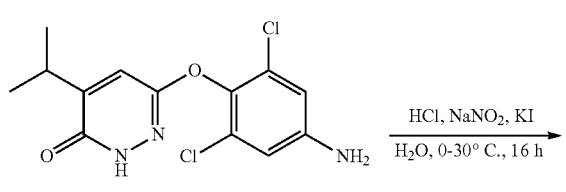
8b

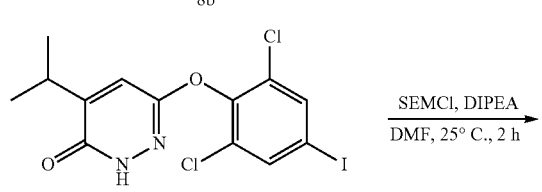
8c

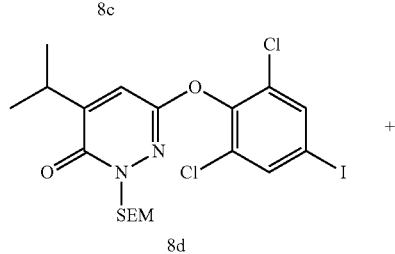
8d

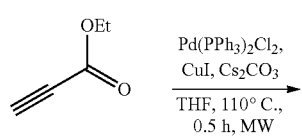

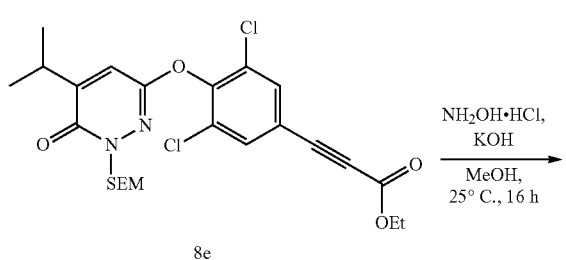
8e

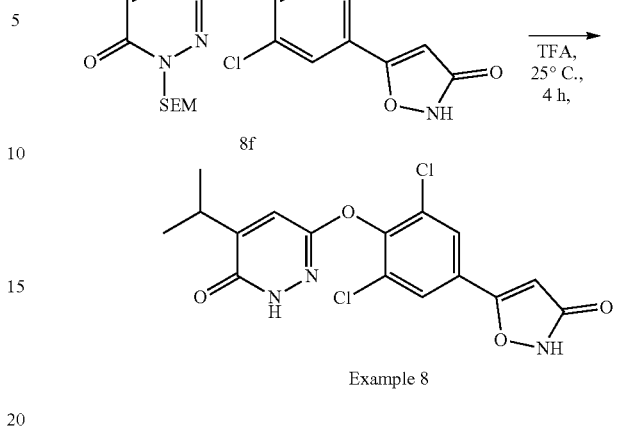
8f

Example 8

N-(3,5-dichloro-4-((5-isopropyl-6-oxo-1,6-dihydropyridazin-3-yl)oxy)phenyl)acetamide (8a)

To a solution of 3,5-dichloro-4-((6-chloro-5-isopropylpyridazin-3-yl)oxy)aniline (1b) (1 g, 3.01 mmol) in AcOH (10 mL) was added NaOAc (863.18 mg, 10.52 mmol). The mixture was stirred at 100° C. for 16 hours. LCMS showed one main peak with the desired MS. The reaction mixture was concentrated under reduced pressure to remove AcOH. The residue was diluted with water (20 mL) and added 1N NaOH to adjusted pH=9-10. The suspension was extracted with EtOAc (10 mL*4), the combined organic layers were dried over anhydrous $Na_2SO_4$, filtered and concentrated under reduced pressure to give 8a (1.55 g, crude). The product was used into the next step which without further purification. MS mass calculated for $[M+1]^+$ ($C_{15}H_{15}Cl_2N_3O_3$) requires m/z 356.1, LCMS found m/z 356.1.

6-(4-amino-2,6-dichlorophenoxy)-4-isopropylpyridazin-3(2H)-one (8b)

To a solution of N-(3,5-dichloro-4-((5-isopropyl-6-oxo-1,6-dihydropyridazin-3-yl)oxy)phenyl)acetamide (8a) (1.55 g, 3.48 mmol) in MeOH (20 mL) was added aqueous of NaOH (1 M, 21.26 mL). The mixture was stirred at 120° C. for 4 hours. LCMS showed one main peak with the desired MS. The reaction mixture was concentrated under reduced pressure to remove MeOH. The residue was diluted with water (20 mL) and extracted with EtOAc (10 mL*4). The combined organic layers were dried over anhydrous $Na_2SO_4$, filtered and concentrated under reduce pressure to give a residue. The residue was purified by column chromatography ($SiO_2$, petroleum ether/ethyl acetate=5:1 to 1:5, according TLC) to give 8b. MS mass calculated for $[M+1]^+$ ($C_{13}H_{13}Cl_2N_3O_2$) requires m/z 314.0, LCMS found m/z 314.0. $^1$H NMR (400 MHz, DMSO) δ 12.11 (s, 1H), 7.25 (s, 1H), 6.64 (s, 2H), 5.60 (s, 2H), 3.07-2.94 (m, 1H), 1.19-1.12 (m, 7H).

6-(2,6-dichloro-4-iodophenoxy)-4-isopropylpyridazin-3(2H)-one (8c)

To a solution of 6-(4-amino-2,6-dichlorophenoxy)-4-isopropylpyridazin-3(2H)-one (8b) (250 mg, 795.76 umol) in HCl (967.11 mg, 7.96 mmol, 948.14 uL, 30% purity) was added NaNO$_2$ (65.89 mg, 954.91 umol) at 0° C., the mixture was stirred for 0.5 hour. Then to the mixture was added a solution of KI (264.19 mg, 1.59 mmol) in H$_2$O (5 mL). Then the mixture was stirred at 20° C. for another 16 hours. LCMS showed one main peak with the desired MS. The reaction mixture was extracted with EtOAc (10 mL*4). The combined organic layers were washed, dried over Na$_2$SO$_4$, filtered and concentrated under reduced pressure to give a residue. The residue was purified by prep-TLC (SiO$_2$, petroleum ether:ethyl acetate=3:1, product R$_f$=0.60, according TLC) to give 8c. MS mass calculated for [M+1]$^+$ (C$_{13}$H$_{11}$Cl$_2$IN$_2$O$_2$) requires m/z 424.9, LCMS found m/z 424.9. $^1$H NMR (400 MHz, CDCl$_3$) δ 10.50-10.29 (m, 1H), 7.75-7.69 (m, 2H), 7.13-7.08 (m, 1H), 3.30-3.14 (m, 1H), 1.28-1.25 (m, 6H).

6-(2,6-dichloro-4-iodophenoxy)-4-isopropyl-2-((2-(trimethylsilyl)ethoxy)methyl)pyridazin-3(2H)-one (8d)

To a mixture of 6-(2,6-dichloro-4-iodophenoxy)-4-isopropylpyridazin-3(2H)-one (8c) (50 mg, 117.63 umol), DIPEA (30.41 mg, 235.27 umol, 40.98 uL) in DMF (4 mL) was added 2-(chloromethoxy)ethyl-trimethyl-silane (58.84 mg, 352.90 umol, 62.46 uL). The mixture was degassed and purged with N$_2$ for 3 times, the mixture was stirred at 25° C. for 2 hours under N$_2$ atmosphere. TLC indicated 8c was consumed completely. LCMS showed one main peak with the desired MS. The reaction mixture was quenched by addition water (5 mL), and then extracted with EtOAc (6 mL*3). The combined organic layers were concentrated under reduce pressure to give a residue. The residue was purified by prep-TLC (SiO$_2$, petroleum ether:ethyl acetate=5:1, according TLC) to give 8d. MS mass calculated for [M+1]$^+$ (C$_{19}$H$_{25}$Cl$_2$IN$_2$O$_3$Si) requires m/z 555.0, LCMS found m/z 555.0. $^1$H NMR (400 MHz, CD$_3$OD) δ 7.78-7.61 (m, 2H), 7.13-7.00 (m, 1H), 5.28-5.16 (m, 2H), 3.58-3.50 (m, 2H), 3.32-3.18 (m, 1H), 1.31-1.23 (m, 6H), 0.91-0.83 (m, 2H), 0.01-0.11 (m, 9H).

Ethyl 3-(3,5-dichloro-4-((5-isopropyl-6-oxo-1-((2-(trimethylsilyl)ethoxy)methyl)-1,6-dihydropyridazin-3-yl)oxy)phenyl)propiolate (8e)

A mixture of 6-(2,6-dichloro-4-iodophenoxy)-4-isopropyl-2-((2-(trimethylsilyl)ethoxy)methyl)pyridazin-3(2H)-one (8d) (18 mg, 32.41 umol), ethyl propiolate (7.00 mg, 71.31 umol, 7.00 uL), Pd(PPh$_3$)$_2$C$_{12}$ (2.28 mg, 3.24 umol), CuI (1.23 mg, 6.48 umol) and Cs$_2$CO$_3$ (21.12 mg, 64.83 umol) in THF (4 mL) was degassed and purged with N$_2$ for 3 times, and then the mixture was stirred at 110° C. for 0.5 hour under microwave. TLC indicated 8d was consumed completely and many spots formed. LCMS showed one main peak with the desired MS was formed. The suspension was filtered through a pad of Celite and the pad cake was washed with EtOAc (5 mL*3). The combined filtrates were concentrated to dryness to give a residue. The residue was purified by prep-TLC (SiO$_2$, petroleum ether:ethyl acetate=8:1, according TLC) to give 8e. MS mass calculated for [M+1]$^+$ (C$_{24}$H$_{30}$Cl$_2$N$_2$O$_5$Si) requires m/z 525.1, LCMS found m/z 525.1. $^1$H NMR (400 MHz, CD$_3$OD) δ 7.61-7.57 (m, 2H), 7.08-7.06 (m, 1H), 5.19-5.17 (m, 2H), 4.35-4.28 (m, 2H), 3.57-3.50 (m, 2H), 3.31-3.19 (m, 1H), 1.38-1.34 (m, 3H), 1.28-1.25 (m, 6H), 0.89-0.84 (m, 2H), −0.03-0.06 (m, 9H).

5-(3,5-dichloro-4-((5-isopropyl-6-oxo-1-((2-(trimethylsilyl)ethoxy)methyl)-1,6-dihydropyridazin-3-yl)oxy)phenyl)isoxazol-3(2H)-one (8f)

To a solution of Ethyl 3-(3,5-dichloro-4-((5-isopropyl-6-oxo-1-((2-(trimethylsilyl)ethoxy)methyl)-1,6-dihydropyridazin-3-yl)oxy)phenyl)propiolate (8e) (5 mg, 9.51 umol) in MeOH (2 mL) was added NH$_2$OH.HCl (2.64 mg, 38.06 umol) and KOH (3.20 mg, 57.09 umol). The mixture was stirred at 25° C. for 5 hours. TLC indicated 8e was consumed completely. LCMS showed one main peak with the desired MS was formed. The reaction mixture was concentrated under reduced pressure to remove MeOH. The residue was diluted with H$_2$O (5 mL) and extracted with EtOAc (5 mL*3). The combined organic layers were washed with brine (5 mL), dried over anhydrous Na$_2$SO$_4$, filtered and concentrated under reduce pressure to give a residue. The residue was purified by prep-TLC (SiO$_2$, petroleum ether:ethyl acetate=3:2, according TLC) to give 8f. MS mass calculated for [M+1]$^+$ (C$_{22}$H$_{27}$Cl$_2$N$_3$O$_5$Si) requires m/z 512.1, LCMS found m/z 512.1. $^1$H NMR (400 MHz, CD$_3$OD) δ 7.78-7.73 (m, 2H), 7.12-7.08 (m, 1H), 6.29-6.24 (m, 1H), 5.23-5.20 (m, 2H), 3.59-3.52 (m, 2H), 3.33-3.22 (m, 1H), 1.30-1.27 (m, 6H), 0.90-0.85 (m, 2H), −0.05-0.10 (m, 9H).

5-(3,5-dichloro-4-((5-isopropyl-6-oxo-1,6-dihydropyridazin-3-yl)oxy)phenyl)isoxazol-3(2H)-one (Example 8)

A solution of 5-(3,5-dichloro-4-((5-isopropyl-6-oxo-1-((2-(trimethylsilyl)ethoxy)methyl)-1,6-dihydropyridazin-3-yl)oxy)phenyl)isoxazol-3(2H)-one (8f) (4 mg, 7.81 umol) in TFA (2 mL) was stirred at 25° C. for 4 hours. LCMS showed 8f was consumed completely and the desired MS was detected. Then the mixture was concentrated in vacuum. The residue was checked by HPLC and purified by prep-HPLC (column: Luna C18 100*30 5 u; mobile phase: [water (0.2% FA)-ACN]; B %: 30%-60%, 12 min) to give Example 8. MS mass calculated for [M+1]$^+$ (C$_{16}$H$_{13}$Cl$_2$N$_3$O$_4$) requires m/z 382.0, LCMS found m/z 382.0. $^1$H NMR (400 MHz, CD$_3$OD) δ 7.91-7.86 (m, 2H), 7.37-7.35 (m, 1H), 6.48-6.46 (m, 1H), 3.20-3.14 (m, 1H), 1.33-1.24 (m, 6H).

Example 9: 3-[3,5-dichloro-4-[(5-isopropyl-6-oxo-1H-pyridazin-3-yl)oxy]phenyl]-4H-1,2,4-oxadiazol-5-one

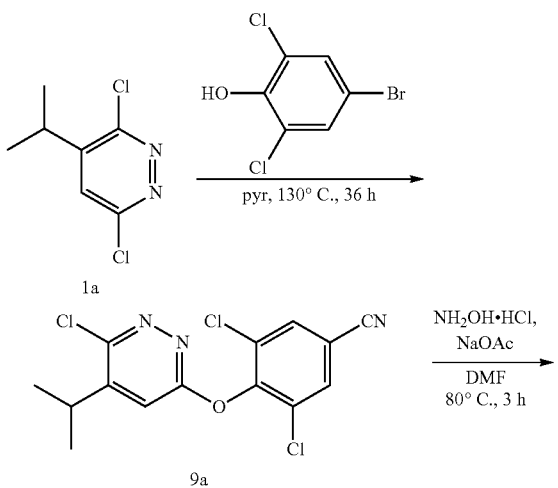

3-(3,5-dichloro-4-((6-chloro-5-isopropylpyridazin-3-yl)oxy)phenyl)-1,2,4-oxadiazol-5(4H),-one (9c)

To a solution of (Z/E)-3,5-dichloro-4-((6-chloro-5-isopropylpyridazin-3-yl)oxy)-N'-hydroxybenzimidamide (9b) (60 mg, 159.73 umol) in THF (3 mL) was added DSC (53.19 mg, 207.65 umol) and TEA (32.33 mg, 319.46 umol, 44.46 uL). The mixture was stirred at 60° C. for 16 hours. LCMS showed the starting material was consumed completely and desired MS was detected. The mixture was concentrated in vacuum to give 9c (60 mg, crude). The product was used directly for the next step without further purification. MS mass calculated for [M+1]$^+$ ($C_{15}H_{11}Cl_3N_4O_3$) requires m/z 401.0, LCMS found m/z 401.0.

3-(3,5-dichloro-4-((5-isopropyl-6-oxo-1,6-dihydropyridazin-3-yl)oxy)phenyl)-1,2,4-oxadiazol-5(4H),-one (Example 9)

To a solution of 3-(3,5-dichloro-4-((6-chloro-5-isopropylpyridazin-3-yl)oxy)phenyl)-1,2,4-oxadiazol-5(4H),-one (9c) (60 mg, 149.39 umol) in HOAc (3 mL) was added NaOAc (49.02 mg, 597.56 umol). The mixture was stirred at 120° C. for 16 hours. LCMS showed the starting material was consumed completely and desired MS was detected. The mixture was concentrated in vacuum to give a residue. The residue was purified by Prep-HPLC (column: Waters Atlantis T3 150*30*5 um; mobile phase: [water (0.225% FA)-ACN]; B %: 35%-75%, 13 min) to give Example 9. MS mass calculated for [M+1]$^+$ ($C_{15}H_{12}Cl_2N_4O_4$) requires m/z 383.0, LCMS found m/z 383.0; $^1$H NMR (400 MHZ, CD$_3$OD) δ 7.93 (s, 2H), 7.38 (d, J=0.8 HZ, 1H), 3.17 (spt, J=6.8 HZ, 1H), 1.29 (d, J=6.8 HZ, 6H).

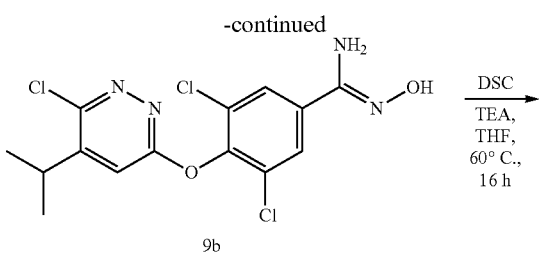

9b

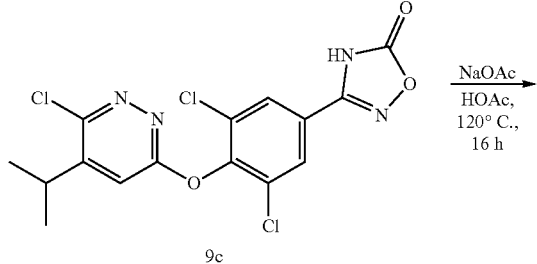

9c

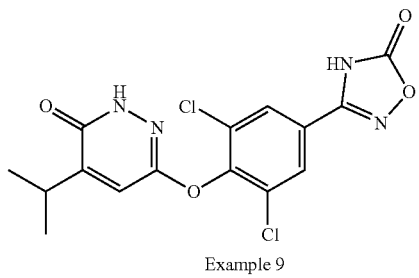

Example 9

3,5-dichloro-4-(6-chloro-5-isopropyl-pyridazin-3-yl)oxy-benzonitrile (9a)

A mixture of 3,5-dichloro-4-hydroxy-benzonitrile (1a) (100 mg, 531.88 umol) and 3,6-dichloro-4-isopropyl-pyridazine (101.62 mg, 531.88 umol) in Py (3 mL) was stirred at 130° C. for 36 hours. LCMS showed 1a was consumed completely and desired MS was detected. The mixture was diluted with Tol. (5 mL*3) and concentrated in vacuum to give a residue. The residue was purified by preparative TLC (petroleum ether:ethyl acetate=5:1) to give 9a. MS mass calculated for [M+1]$^+$ ($C_{14}H_{10}Cl_3N_3O$) requires m/z 342.0, LCMS found m/z 342.1; $^1$HNMR (400 MHZ, CD$_3$OD) δ 8.02 (s, 2H), 7.67 (s, 1H), 3.47-3.50 (m, 1H), 3.32-3.39 (m, 1H), 1.37 (d, J=6.84 HZ, 6H).

(Z/E)-3,5-dichloro-4-((6-chloro-5-isopropylpyridazin-3-yl)oxy)-N'-hydroxybenzimidamide (9b)

To a solution of 3,5-dichloro-4-(6-chloro-5-isopropyl-pyridazin-3-yl)oxy-benzonitrile (9a) (60 mg, 175.13 umol) in DMF (2 mL) was added NH$_2$OH.HCl (97.36 mg, 1.40 mmol) and NaOAc (114.93 mg, 1.40 mmol). The mixture was stirred at 80° C. for 1 hour. LCMS showed the starting material was consumed completely and desired MS was detected. The reaction mixture was concentrated under reduced pressure to remove DMF. The residue was partitioned between ethyl acetate (10 mL*2) and H$_2$O (3 mL). The combined organic phase was washed with brine (5 mL*3), dried with anhydrous Na$_2$SO$_4$, filtered and concentrated in vacuum to give a residue. The residue was purified by preparative TLC (petroleum ether:ethyl acetate=5:1) to give 9b. MS mass calculated for [M+1]$^+$ ($C_{14}H_{13}Cl_3N_4O_2$) requires m/z 375.0, LCMS found m/z 375.0.

Example 10: 3-(3,5-dichloro-4-((5-isopropyl-1-methyl-6-oxo-1,6-dihydropyridazin-3-yl)oxy)phenyl)-1,2,4-oxadiazol-5(4H),-one

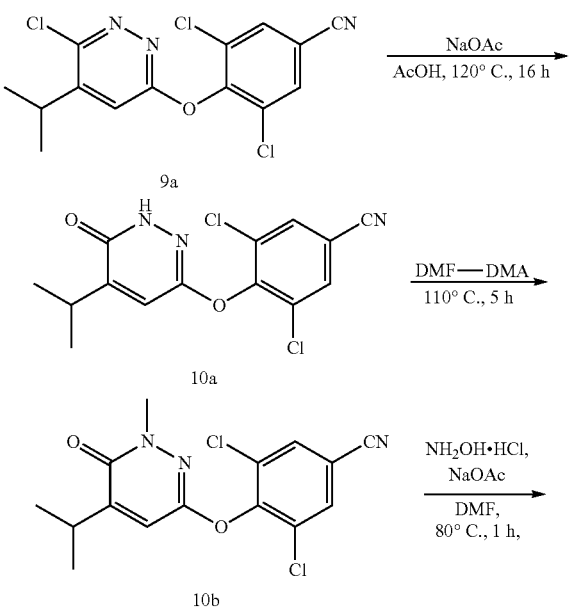

9a

10a

10b

-continued

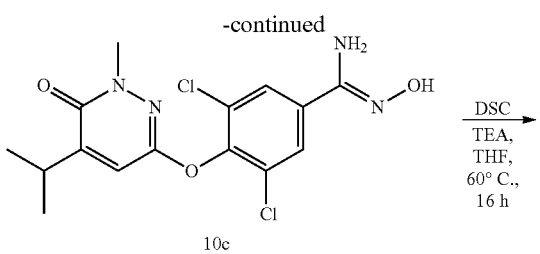

10c

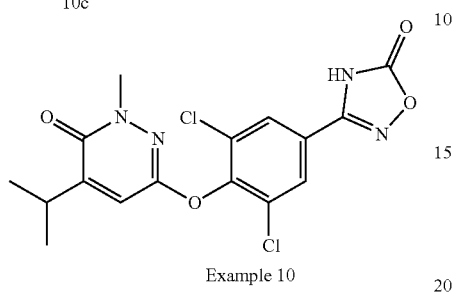

Example 10

3,5-dichloro-4-((5-isopropyl-6-oxo-1,6-dihydro-pyridazin-3-yl)oxy)benzonitrile (10a)

To a solution of 3,5-dichloro-4-((6-chloro-5-isopropylpyridazin-3-yl)oxy)benzonitrile (9a) (40 mg, 116.75 umol) in HOAc (4 mL) was added NaOAc (38.31 mg, 467.01 umol). The mixture was stirred at 120° C. for 16 hours. LCMS showed the starting material was consumed completely and the desired MS was found. The mixture was concentrated in vacuum. The solid was dissolved in water and the pH was adjusted to 9 with NaHCO$_3$(4 mL). Then the mixture was partitioned with ethyl acetate 10 mL twice. The combined organic phase was washed with brine (5 mL*3), dried with anhydrous Na$_2$SO$_4$, filtered and concentrated in vacuum to give 10a (34 mg, crude). MS mass calculated for [M+1]$^+$ (C$_{14}$H$_{11}$Cl$_2$N$_3$O$_2$) requires m/z 324.0, LCMS found m/z 324.2; $^1$H NMR (400 MHZ, DMSO) δ 12.28 (s, 1H), 8.27-8.35 (m, 2H), 7.44 (s, 1H), 3.27-3.44 (m, 25H), 2.98-3.10 (m, 1H), 1.15-1.23 (m, 6H).

3,5-dichloro-4-((5-isopropyl-1-methyl-6-oxo-1,6-dihydropyridazin-3-yl)oxy)benzonitrile (10b)

A mixture of 3,5-dichloro-4-((5-isopropyl-6-oxo-1,6-dihydropyridazin-3-yl)oxy)benzonitrile (10a) (34 mg, 104.89 umol) in DMF-DMA (2 mL) was stirred at 110° C. for 5 hours under reflux. LCMS showed the starting material was consumed completely and desired MS was detected. The mixture was concentrated in vacuum. The residue was partitioned between ethyl acetate (10 mL) and H$_2$O (3 mL) twice. The combined organic phase was washed with brine (5 mL*3), dried with anhydrous Na$_2$SO$_4$, filtered and concentrated in vacuum to give a residue. The residue was purified by preparative TLC (petroleum ether:ethyl acetate=5:1) to give 10b. MS mass calculated for [M+1]$^+$ (C$_{15}$H$_{13}$Cl$_2$N$_3$O$_2$) requires m/z 338.0, LCMS found m/z 338.0; $^1$H NMR (400 MHZ, CD$_3$OD) δ 8.00 (s, 2H), 7.38 (s, 1H), 3.48 (s, 3H), 3.14-3.25 (m, 1H), 1.28 (d, J=6.85 HZ, 6H).

(Z)-3,5-dichloro-N'-hydroxy-4-((5-isopropyl-1-methyl-6-oxo-1,6-dihydropyridazin-3-yl)oxy)benzimidamide (10c)

To a solution of 3,5-dichloro-4-((5-isopropyl-1-methyl-6-oxo-1,6-dihydropyridazin-3-yl)oxy)benzonitrile (10b) (25 mg, 73.92 umol) in DMF (2 mL) was added NH$_2$OH.HCl (41.10 mg, 591.39 umol) and NaOAc (48.51 mg, 591.39 umol). The mixture was stirred at 80° C. for 1 hour. LCMS showed 10b was consumed completely and desired MS was detected. The reaction mixture was concentrated under reduced pressure to remove DMF. The residue was partitioned between ethyl acetate (10 mL) and H$_2$O (3 mL). The combined organic phase was washed with brine (5 mL*3), dried with anhydrous Na$_2$SO$_4$, filtered and concentrated in vacuum to give 10c (25 mg, crude). The product was used directly for the next step without further purification. MS mass calculated for [M+1]$^+$ (C$_{15}$H$_{16}$Cl$_2$N$_4$O$_3$) requires m/z 371.1, LCMS found m/z 371.2.

3-(3,5-dichloro-4-((5-isopropyl-1-methyl-6-oxo-1,6-dihydropyridazin-3-yl)oxy)phenyl)-1,2,4-oxadiazol-5(4H),-one (Example 10)

To a solution of (Z)-3,5-dichloro-N'-hydroxy-4-((5-isopropyl-1-methyl-6-oxo-1,6-dihydropyridazin-3yl)oxy)benzimidamide (10c) (25 mg, 67.35 umol) in THF (3 mL) was added DSC (22.43 mg, 87.55 umol) and TEA (13.63 mg, 134.69 umol, 18.75 uL). The mixture was stirred at 60° C. for 16 hours. LCMS showed the starting material was consumed completely and desired MS was detected. The mixture was concentrated in vacuum to give a residue. The residue was purified by Prep-HPLC (column: Waters Atlantis T3 150*30*5 um; mobile phase: [water (0.225% FA)-ACN]; B %: 30%-70%, 13 min) to give Example 10. MS mass calculated for [M+1]$^+$ (C$_{16}$H$_{14}$Cl$_2$N$_4$O$_4$) requires m/z 397.0, LCMS found m/z 397.0; $^1$H NMR (400 MHZ, CD$_3$OD) δ 7.92-7.98 (m, 2H), 7.37 (d, J=0.73 HZ, 1H), 3.48 (s, 3H), 3.12-3.26 (m, 1H), 1.28 (d, J=6.85 HZ, 6H).

Scheme B: 6-(4-amino-2,6-dichloro-3-methylphenoxy)-4-isopropyl-2-methylpyridazin-3(2H)-one (Compound 11d)

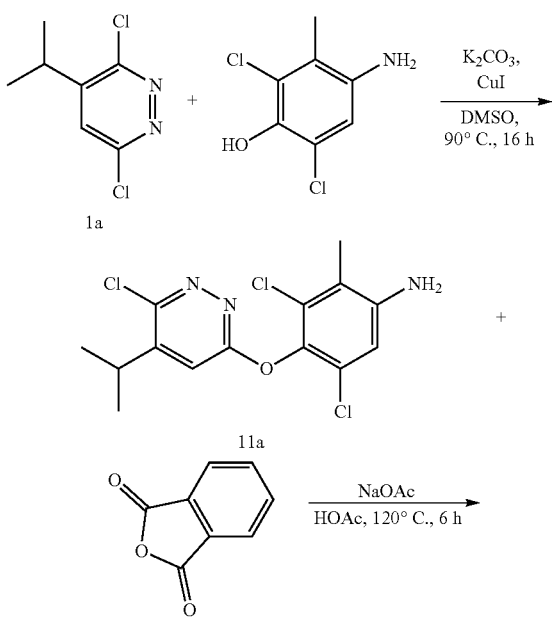

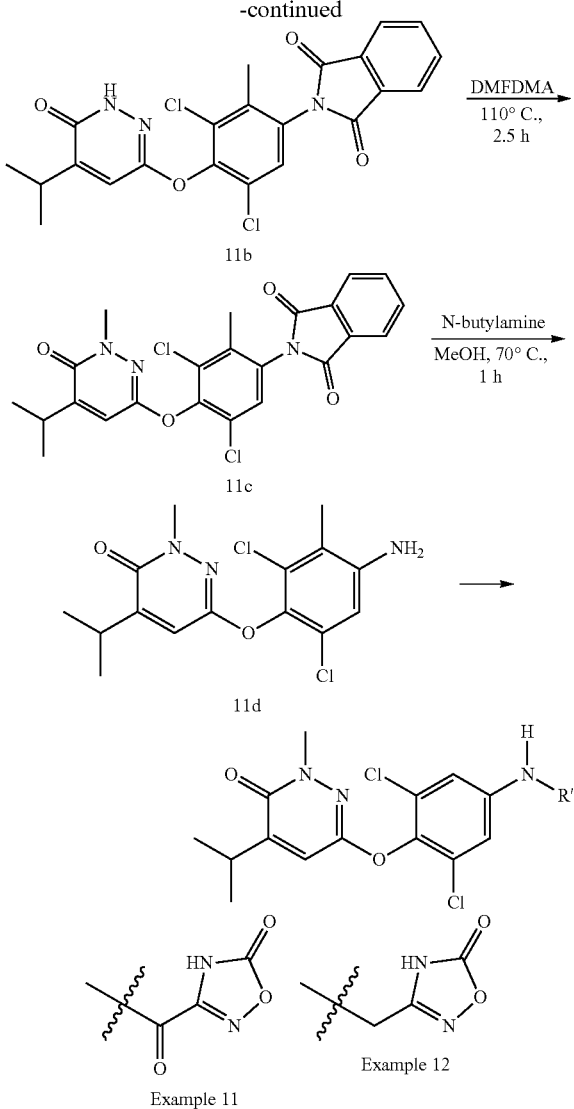

3,5-dichloro-4-((6-chloro-5-isopropylpyridazin-3-yl)oxy)-2-methylaniline (11a)

To a mixture of 4-amino-2,6-dichloro-3-methyl-phenol (0.2 g, 1.04 mmol) and 3,6-dichloro-4-isopropyl-pyridazine (1a) (198.97 mg, 1.04 mmol) in DMSO (5 mL) was added $K_2CO_3$ (575.75 mg, 4.17 mmol) and CuI (119.01 mg, 624.86 umol) at 25° C. Then the mixture was stirred at 90° C. for 16 hours. The mixture was added to $H_2O$ (25 mL) and extracted with ethyl acetate (20 mL*2). The combined organic phase was washed with brine (20 mL*2), dried with anhydrous $Na_2SO_4$, filtered and concentrated in vacuum. The mixture was washed by petroleum ether (5 mL), filtered. The filter cake was concentrated in vacuum to give 11a.

2-(3,5-dichloro-4-((5-isopropyl-6-oxo-1,6-dihydro-pyridazin-3-yl)oxy)-2-methylphenyl)isoindoline-1,3-dione (11b)

To a mixture of 3,5-dichloro-4-(6-chloro-5-isopropyl-pyridazin-3-yl)oxy-2-methyl-aniline (11a) (0.4 g, 1.15 mmol) and isobenzofuran-1,3-dione (170.92 mg, 1.15 mmol) in AcOH (10 mL) was added NaOAc (378.63 mg, 4.62 mmol) at 25° C. Then the mixture was stirred at 120° C. for 12 hours. LCMS showed the reaction was completed. The mixture was concentrated to get residue, to the residue was added to $H_2O$ (20 mL) and extracted with ethyl acetate (50 mL*2). The combined organic phase was washed with brine (50 mL*2), dried with anhydrous $Na_2SO_4$, filtered and concentrated in vacuum. The residue was washed by MTBE (5 mL) and filtered. The filter cake was concentrated to give 11b. MS mass calculated for $[M+1]^+$ ($C_{22}H_{17}Cl_2N_3O_4$) required m/z 458.1, LCMS found m/z 458.1.

2-(3,5-dichloro-4-((5-isopropyl-1-methyl-6-oxo-1,6-dihydropyridazin-3-yl)oxy)phenyl)isoindoline-1,3-dione (11c)

A mixture of 2-[3,5-dichloro-4-[(5-isopropyl-6-oxo-1H-pyridazin-3-yl)oxy]-2-methyl-phenyl]isoindoline-1,3-dione (11b) (0.37 g, 807.34 umol) in DMF-DMA (5 mL) was stirred at 105° C. for 4 hours. LCMS showed the reaction was completed. The mixture was added to $H_2O$ (20 mL) and extracted with ethyl acetate (20 mL*2). The combined organic phase was washed with brine (20 mL*2), dried with anhydrous $Na_2SO_4$, filtered and concentrated in vacuum to give 11c. The crude was used next step directly. MS mass calculated for $[M+1]^+$ ($C_{22}H_{17}Cl_2N_3O_4$) required m/z 472.1, LCMS found m/z 472.1.

6-(4-amino-2,6-dichloro-3-methylphenoxy)-4-isopropyl-2-methylpyridazin-3(2H)-one (11d)

To a solution of 2-[3,5-dichloro-4-(5-isopropyl-1-methyl-6-oxo-pyridazin-3-yl)oxy-2-methyl-phenyl]isoindoline-1,3-dione (11c) (440 mg, 931.57 umol) in MeOH (1 mL) were added butan-1-amine (2 M, 1.40 mL) at 70° C. The mixture was stirred at 70° C. for 1 hour. The mixture was concentrated in vacuum. The residue was purified by prep-TLC ($SiO_2$, petroleum ether/ethyl acetate=1:1) to give 11d. MS mass calculated for $[M+1]^+$ ($C_{22}H_{17}Cl_2N_3O_4$) required m/z 342.1, LCMS found m/z 342.1. $^1$H NMR (400 MHz, $CD_3OD$) δ 7.22 (s, 1H), 6.77 (s, 1H), 3.50 (s, 3H), 3.20-3.14 (m, 1H), 2.20 (s, 3H), 1.25 (d, J=6.8 Hz, 6H).

Example 11: N-(3,5-dichloro-4-((5-isopropyl-1-methyl-6-oxo-1,6-dihydropyridazin-3-yl)oxy)-2-methylphenyl)-5-oxo-4,5-dihydro-1,2,4-oxadiazole-3-carboxamide

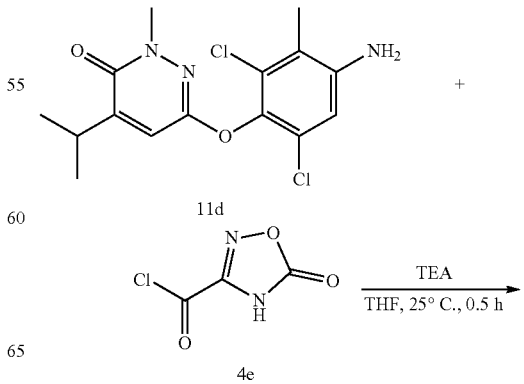

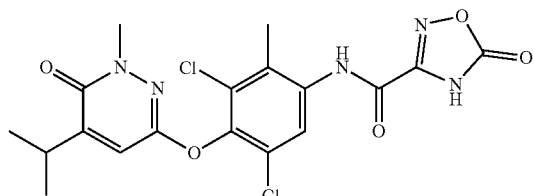

Example 11

N-(3,5-dichloro-4-((5-isopropyl-1-methyl-6-oxo-1,6-dihydropyridazin-3-yl)oxy)-2-methylphenyl)-5-oxo-4,5-dihydro-1,2,4-oxadiazole-3-carboxamide (Example 11)

To a solution of 6-(4-amino-2,6-dichloro-3-methylphenoxy)-4-isopropyl-2-methylpyridazin-3(2H)-one (11d) (20.85 mg, 60.94 umol) in THF (3 mL) was added TEA (18.50 mg, 182.82 umol) and 5-oxo-4,5-dihydro-1,2,4-oxadiazole-3-carbonyl chloride (4e) (13.57 mg, 91.41 umol). The mixture was stirred at 25° C. for 0.5 hours. TLC showed 11d was consumed. The reaction mixture was quenched by addition MeOH (1 mL) at 25° C., and then concentrated under reduced pressure to give a residue. The residue was purified by Prep-HPLC (column: Xtimate C18 150*25 mm*5 um; mobile phase: [water (10 mM $NH_4HCO_3$)-ACN]; B %: 20%-50%, 10 min) to give Example 11. MS mass calculated for $[M+1]^+$ ($C_{18}H_{17}Cl_2N_5O_5$) required m/z 454.1, LCMS found m/z 454.1; $^1$H NMR (400 MHz, $CD_3OD$) δ 7.77 (s, 1H), 7.31 (d, J=0.7 Hz, 1H), 3.49 (s, 3H), 3.23-3.11 (m, 1H), 2.38 (s, 3H), 1.27 (d, J=6.8 Hz, 6H).

Example 12: 3-(((3,5-dichloro-4-((5-isopropyl-1-methyl-6-oxo-1,6-dihydropyridazin-3-yl)oxy)-2-methylphenyl)amino)methyl)-1,2,4-oxadiazol-5(4H)-one

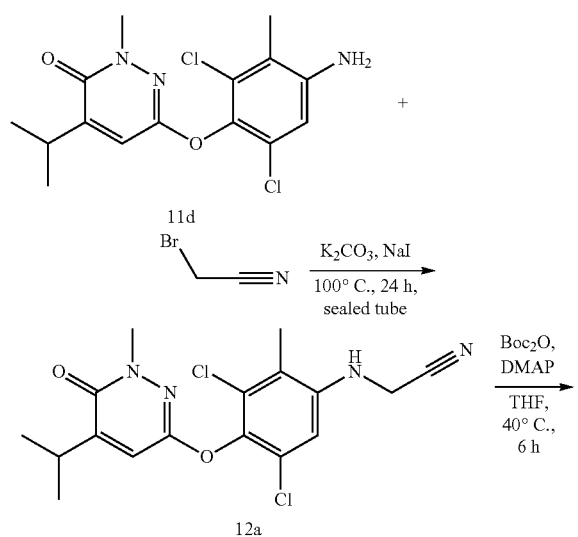

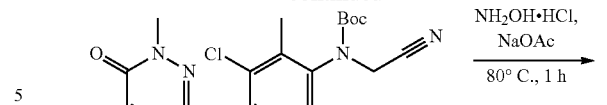

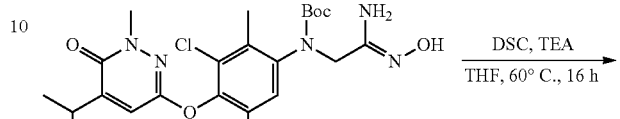

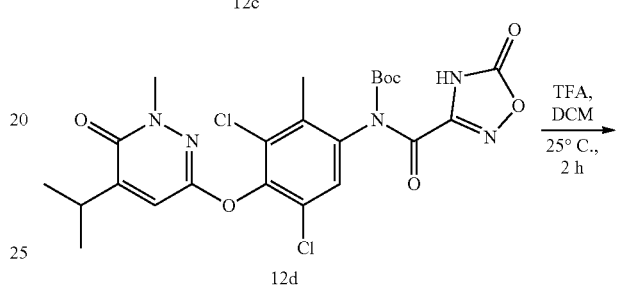

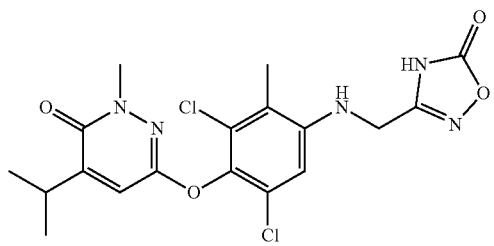

Example 12

2-[3,5-dichloro-4-(5-isopropyl-1-methyl-6-oxo-pyridazin-3-yl)oxy-2-methyl-anilino]acetonitrile (12a)

To a solution of 6-(4-amino-2,6-dichloro-3-methylphenoxy)-4-isopropyl-2-methylpyridazin-3(2H)-one (11d) (50 mg, 146.10 umol) in ACN (1 mL) was added 2-bromoacetonitrile (87.62 mg, 730.52 umol, 48.68 uL), NaI (43.80 mg, 292.21 umol) and $K_2CO_3$ (40.39 mg, 292.21 umol). The mixture was stirred at 100° C. for 16 hours. The suspension was filtered through a pad of Celite and the pad cake was washed with EtOAc (5 mL*3). The combined filtrates were concentrated to give a residue. The residue was purified by Prep-TLC ($SiO_2$, petroleum ether:ethyl acetate=1:1) to give (12a). $^1$HNMR (400 MHz, $CDCl_3$) δ 7.04 (s, 1H), 6.71 (s, 1H), 4.20 (d, J=6.6 Hz, 2H), 4.13 (q, J=7.2 Hz, 1H), 4.08-4.01 (m, 1H), 3.53 (s, 3H), 3.31-3.16 (m, 1H), 2.27 (s, 3H), 1.59 (br s, 4H), 1.38-1.15 (m, 8H).

tert-butyl N-(cyanomethyl)-N-[3,5-dichloro-4-(5-isopropyl-1-methyl-6-oxo-pyridazin-3-yl)oxy-2-methyl-phenyl]carbamate (12b)

To a solution of 2-[3,5-dichloro-4-(5-isopropyl-1-methyl-6-oxo-pyridazin-3-yl)oxy-2-methyl-anilino] acetonitrile (12a) (55 mg, 144.26 umol) in THF (1 mL) was added $Boc_2O$ (94.45 mg, 432.78 umol, 99.42 uL) and DMAP (17.62 mg, 144.26 umol). The mixture was stirred at 40° C.

for 1 hour. LCMS showed the starting material was consumed completely and desired MS was detected. The mixture was partitioned between ethyl acetate (10 mL) and H$_2$O (3 mL) twice. The combined organic phase was washed with brine (5 mL*3), dried with anhydrous Na$_2$SO$_4$, filtered and concentrated in vacuum to give a residue. The residue was purified by prep-TLC (SiO$_2$, petroleum ether:ethyl acetate=3:1) to give 12b. MS mass calculated for [M+1]$^+$ (C$_{22}$H$_{26}$Cl$_2$N$_4$O$_4$) required m/z 481.1, LCMS found m/z 481.1; $^1$H NMR (400 MHz, CDCl$_3$) δ 7.04 (d, J=1.0 Hz, 1H), 4.57-4.27 (m, 2H), 3.48 (br s, 3H), 3.28-3.16 (m, 1H), 2.29 (s, 3H), 1.66-1.47 (m, 10H), 1.38 (br s, 6H).

tert-butyl N-[(2Z)-2-amino-2-hydroxyimino-ethyl]-N-[3,5-dichloro-4-(5-isopropyl-1-methyl-6-oxo-pyridazin-3-yl)oxy-2-methyl-phenyl]carbamate (12c)

To a solution of tert-butyl N-(cyanomethyl)-N-[3,5-dichloro-4-(5-isopropyl-1-methyl-6-oxo-pyridazin-3-yl)oxy-2-methyl-phenyl]carbamate (12b) (40 mg, 83.10 umol) in DMF (1 mL) was added NH$_2$OH.HCl (46.19 mg, 664.77 umol) and NaOAc (54.53 mg, 664.77 umol). The mixture was stirred at 80° C. for 1 hour. The residue was partitioned between ethyl acetate (10 mL) and H$_2$O (3 mL) twice. The combined organic phase was washed with brine (5 mL*3), dried with anhydrous Na$_2$SO$_4$, filtered and concentrated in vacuum. The residue was purified by Prep-TLC (SiO$_2$, petroleum ether:ethyl acetate=1:1) to give 12c. MS mass calculated for [M+1]$^+$ (C$_{22}$H$_{29}$Cl$_2$N$_5$O$_5$) required m/z 514.2, LCMS found m/z 514.2; $^1$H NMR (400 MHz, CDCl$_3$) δ 7.16 (s, 1H), 7.05 (d, J=1.0 Hz, 1H), 5.27 (br s, 2H), 3.50 (s, 3H), 3.33-3.17 (m, 1H), 2.25 (s, 4H), 1.39 (s, 8H), 1.28-1.26 (m, 7H).

tert-butyl N-[3,5-dichloro-4-(5-isopropyl-1-methyl-6-oxo-pyridazin-3-yl)oxy-2-methyl-phenyl]-N-[(5-oxo-4H-1,2,4-oxadiazol-3-yl)methyl]carbamate (12d)

To a solution of tert-butyl N-[(2Z)-2-amino-2-hydroxyimino-ethyl]-N-[3,5-dichloro-4-(5-isopropyl-1-methyl-6-oxo-pyridazin-3-yl)oxy-2-methyl-phenyl]carbamate (12c) (40 mg, 77.76 umol) in THF (1 mL) was added DSC (25.90 mg, 101.09 umol) and TEA (15.74 mg, 155.52 umol, 21.65 uL). The mixture was stirred at 60° C. for 16 hours. LCMS showed the starting material was consumed completely and desired MS was detected. The mixture was partitioned between ethyl acetate (10 mL) and H$_2$O (3 mL). Twice. The combined organic phase was washed with brine (5 mL*3), dried with anhydrous Na$_2$SO$_4$, filtered and concentrated in vacuum to give a residue. The residue was purified by prep-TLC (SiO$_2$, DCM:MeOH=5:1) to give 12d. MS mass calculated for [M+1]$^+$ (C$_{22}$H$_{29}$Cl$_2$N$_5$O$_5$) required m/z 540.1, LCMS found m/z 540.1.

3-[[3,5-dichloro-4-(5-isopropyl-1-methyl-6-oxo-pyridazin-3-yl)oxy-2-methyl-anilino]methyl]-4H-1,2,4-oxadiazol-5-one (Example 12)

To a solution of tert-butyl N-[3,5-dichloro-4-(5-isopropyl-1-methyl-6-oxo-pyridazin-3-yl)oxy-2-methyl-phenyl]-N-[(5-oxo-4H-1,2,4-oxadiazol-3-yl)methyl]carbamate (12d) (30 mg, 55.51 umol) in EtOAc (1 mL) were added HCl/EtOAc (2 M, 27.76 uL) at 25° C. The mixture was stirred at 25° C. for 1 hour. The reaction mixture was concentrated under reduced pressure to give a residue. The residue was purified by Prep-HPLC (HCl condition) to give Example 12. MS mass calculated for [M+1]$^+$ (C$_{22}$H$_{29}$Cl$_2$N$_5$O$_5$) required m/z 440.1, LCMS found m/z 440.2. $^1$H NMR (400 MHz, CD$_3$OD) δ 7.24 (s, 1H), 6.72 (s, 1H), 4.37 (s, 2H), 3.48 (s, 3H), 3.23-3.11 (m, 1H), 2.29 (s, 3H), 1.26 (d, J=6.8 Hz, 6H).

Scheme C: 6-(4-amino-2,6-dichlorobenzyl)-4-isopropylpyridazin-3(2H)-one (Compound 13e)

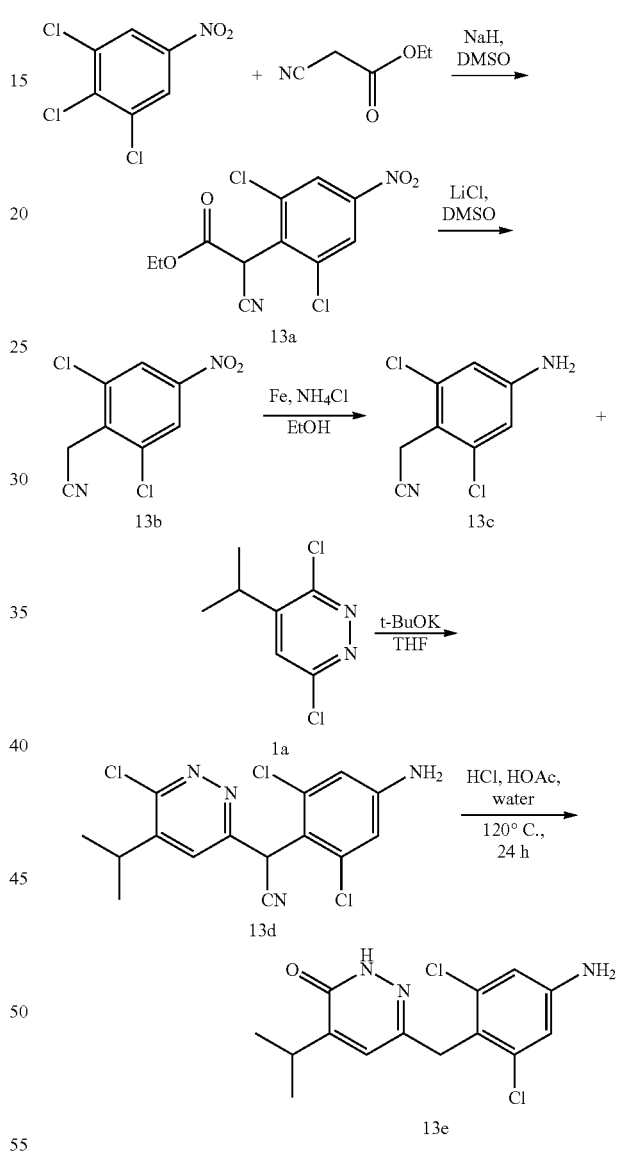

ethyl 2-cyano-2-(2,6-dichloro-4-nitrophenyl)acetate (13a)

To a suspension of NaH (1.41 g, 35.33 mmol, 60% purity) in DMSO (40 mL) was added ethyl 2-cyanoacetate (4.00 g, 35.33 mmol) drop wise at 0° C. and stirred at 15° C. for 30 minutes, then 1,2,3-trichloro-5-nitrobenzene (4 g, 17.66 mmol) was added, the resulting mixture was stirred at 15° C. for 16 hours. Then the mixture was quenched with water (100 mL) and adjusted to pH=1 with 1 M HCl. And the white precipitate was collected by filtration and dried over in vacuum. The solid was washed with petroleum ether (40 mL) and dried in vacuum to give 13a. ¹H NMR (400 MHz, CDCl₃) δ 8.32 (s, 2H), 5.72 (s, 1H), 4.38 (q, J 7.1 Hz, 2H), 1.37 (t, J 7.2 Hz, 3H).

2-(2,6-dichloro-4-nitrophenyl)acetonitrile (13b) A mixture of ethyl 2-cyano-2-(2,6-dichloro-4-nitrophenyl)acetate (13a)

(1.7 g, 5.61 mmol) and LiCl (285.33 mg, 6.73 mmol) in DMSO (6 mL), H₂O (2.5 mL) was heated to 165° C. for 1 hour. After cooling, the mixture was quenched with water (50 mL) and extracted with ethyl acetate (20 mL*2), the organic phases were washed with brine, dried over Na₂SO₄, filtered and concentrated to give 13b. ¹H NMR (400 MHz, CDCl₃) δ 8.21 (s, 2H), 4.03 (s, 2H).

2-(4-amino-2,6-dichlorophenyl)acetonitrile (13c)

A mixture of 2-(2,6-dichloro-4-nitrophenyl)acetonitrile (13b) (1 g, 4.33 mmol) and Fe (1.21 g, 21.64 mmol) in HOAc (10 mL) was heated to 15° C. for 1 hour. TLC showed new point, the mixture was filtered, the filtrate was added water (100 mL) and extracted with ethyl acetate (50 mL), the organic phase was neutralized with sat. NaHCO₃(20 mL*2), washed with brine (20 mL), dried over Na₂SO₄, filtered and concentrated to give 13c. ¹H NMR (400 MHz, CDCl₃) δ 6.67 (s, 2H), 3.88 (s, 4H).

2-(4-amino-2,6-dichlorophenyl)-2-(6-chloro-5-isopropylpyridazin-3-yl)acetonitrile (13d)

To a solution of 2-(4-amino-2,6-dichlorophenyl)acetonitrile (13c) (0.43 g, 2.14 mmol) and 3,6-dichloro-4-isopropylpyridazine (1a) (408.62 mg, 2.14 mmol) in THF (5 mL) was added t-BuOK (1 M, 4.28 mL) drop wise at 60° C., the resulting mixture was heated to 60° C. for 40 minutes. After cooling, the mixture was diluted with ethyl acetate (20 mL) and washed with brine (20 mL). The organic layer was separated, dried with Na₂SO₄, filtered and concentrated, the residue was purified by silica gel chromatography (petroleum ether:ethyl acetate=5:1) to give 13d. MS mass calculated for [M+1]⁺ (C₁₅H₁₃Cl₃N₄) required m/z 355.0, LCMS found m/z 0.355.1; ¹H NMR (400 MHz, CDCl₃) δ 7.60 (s, 1H), 6.69 (s, 2H), 6.33 (s, 1H), 3.99 (br s, 2H), 3.33 (td, J 6.8, 13.6 Hz, 1H), 1.32 (dd, J 4.0, 6.8 Hz, 6H).

6-(4-amino-2,6-dichlorobenzyl)-4-isopropylpyridazin-3(2H)-one (13e)

A solution of 2-(4-amino-2,6-dichlorophenyl)-2-(6-chloro-5-isopropylpyridazin-3-yl)acetonitrile (13d) (0.15 g, 421.76 umol) in HOAc (0.6 mL), H₂O (0.6 mL) and conc.HCl (2.4 mL) was heated to 120° C. for 32 hours. LCMS showed desired MS. After cooling, the mixture was adjusted to pH-7 with 4M NaOH at 0° C., the solid was filtered and dried to give 13e as off white solid, the solid was used for the next step directly. MS mass calculated for [M+1]⁺ (C₁₄H₁₅Cl₂N₃O) required m/z 311.0, LCMS found m/z 0.311.1.

Example 13: N-(3,5-dichloro-4-((5-isopropyl-6-oxo-1,6-dihydropyridazin-3-yl)methyl)phenyl)-5-oxo-4,5-dihydro-1,2,4-oxadiazole-3-carboxamide

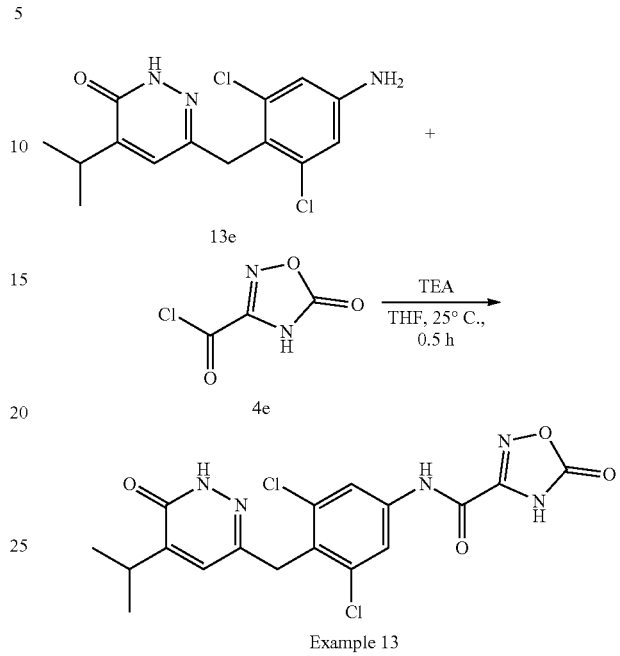

N-(3,5-dichloro-4-((5-isopropyl-6-oxo-1,6-dihydropyridazin-3-yl)oxy)phenyl)-5-oxo-4,5-dihydro-1,2,4-oxadiazole-3-carboxamide (Example 13)

To a solution of 6-(4-amino-2,6-dichlorobenzyl)-4-isopropylpyridazin-3(2H)-one (13e) (20 mg, 64.06 umol) in THF (3 mL) was added TEA (19.45 mg, 192.19 umol) and 5-oxo-4,5-dihydro-1,2,4-oxadiazole-3-carbonyl chloride (4e) (14.27 mg, 96.09 umol, 1.5 eq). The mixture was stirred at 25° C. for 0.5 hours. TLC showed 13e was consumed completely. The reaction mixture was quenched by addition MeOH (1 mL) at 25° C., and then concentrated under reduced pressure to give a residue. The residue was checked by HPLC and purified by Prep-HPLC (column: Waters Xbridge 150*25 5 u; mobile phase: [water (10 mM NH₄HCO₃)-ACN]; B %: 5%-35%, 10 min) to give Example 13. MS mass calculated for [M+1]⁺ (C₁₇H₁₅Cl₂N₅O₄) requires m/z 424.0, LCMS found m/z 424.0. ¹H NMR (400 MHz, CD₃OD) δ 7.87 (s, 2H), 7.23 (s, 1H), 4.30 (s, 2H), 3.16-3.04 (m, 1H), 1.20 (d, J=7.1 Hz, 6H).

Example 14: N-(3,5-dichloro-4-((5-isopropyl-1-methyl-6-oxo-1,6-dihydropyridazin-3-yl)methyl)phenyl)-5-oxo-4,5-dihydro-1,2,4-oxadiazole-3-carboxamide

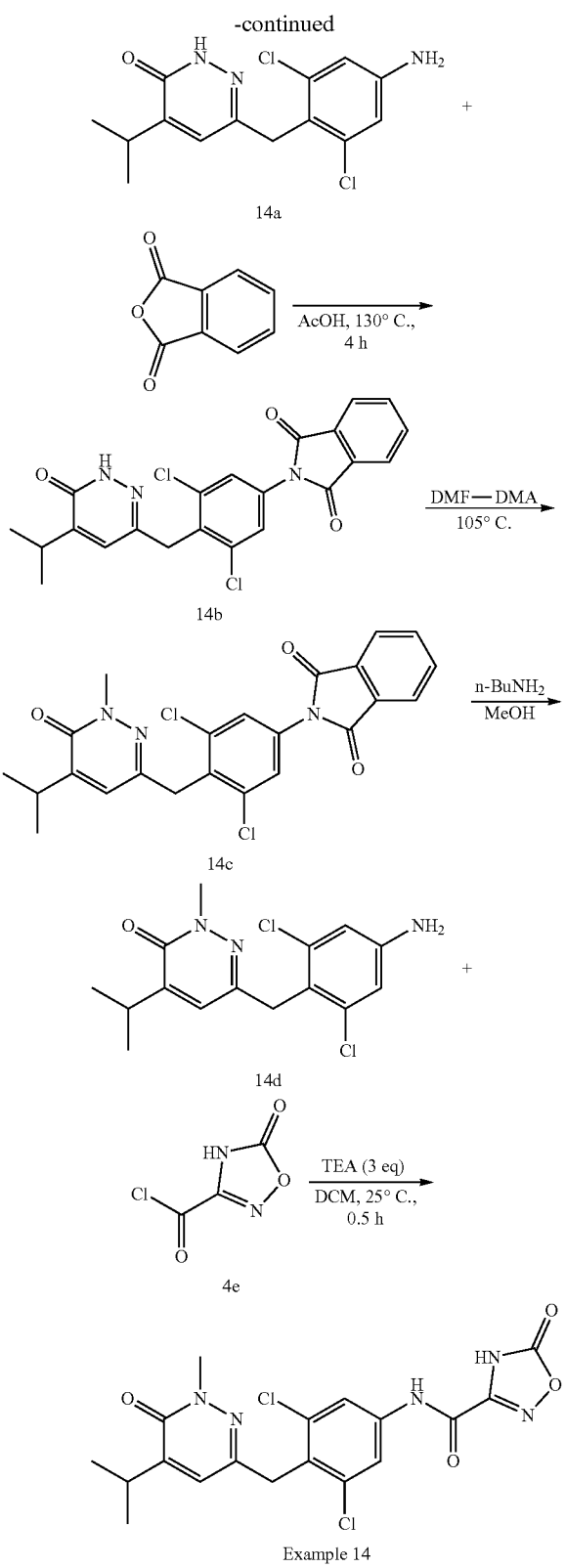

Example 14

6-(4-amino-2,6-dichlorobenzyl)-4-isopropylpyridazin-3(2H)-one (14a)

To a solution of 2-(4-amino-2,6-dichlorophenyl)-2-(6-chloro-5-isopropylpyridazin-3-yl) acetonitrile (13d) (1.5 g, 4.22 mmol) in con. HCl (16 mL) and HOAc (2 mL) was added H$_2$O (2 mL). The mixture was stirred at 120° C. for 72 hours. LCMS showed the desired mass. The mixture was adjusted to pH=7 by addition of 6 M aqueous sodium hydroxide solution. The suspension was stirred for 15 minutes. The resulting solid was filtered and washed with H$_2$O and petroleum ether. The residue was purified by column chromatography (petroleum ether:ethyl acetate=5:1 to 1:1) to give 14a. $^1$HNMR (400 MHz, DMSO-d6) δ 12.59 (s, 1H), 7.12-7.10 (m, 1H), 6.62 (s, 2H), 5.60 (s, 2H), 3.99 (s, 2H), 2.96 (td, J=6.9, 13.5 Hz, 1H), 1.11 (d, J=6.8 Hz, 6H).

2-(3,5-dichloro-4-((5-isopropyl-6-oxo-1,6-dihydropyridazin-3-yl)methyl)phenyl)isoindoline-1,3-dione (14b)

A solution of 6-(4-amino-2,6-dichlorobenzyl)-4-isopropylpyridazin-3(2H)-one (14a) (450 mg, 1.44 mmol) in AcOH (5 mL) was added isobenzofuran-1,3-dione (213.50 mg, 1.44 mmol). The mixture was stirred at 130° C. for 4 hours. LCMS showed desired mass. The reaction mixture was concentrated under reduced pressure to remove AcOH. This mixture was extracted with water (50 mL) and Ethyl acetate (50 mL), and then washed with NaHCO$_3$(20 mL*3), dried over Na$_2$SO$_4$, filtered and concentrated under reduced pressure to give 14b. The product was used in next step without further purification. MS mass calculated for [M+1]$^+$ (C$_{22}$H$_{17}$Cl$_2$N$_3$O$_3$) required m/z 442.1, LCMS found m/z 442.1.

2-(3,5-dichloro-4-((5-isopropyl-1-methyl-6-oxo-1,6-dihydropyridazin-3-yl)methyl)phenyl)isoindoline-1,3-dione (14c)

A mixture of 2-(3,5-dichloro-4-((5-isopropyl-6-oxo-1,6-dihydropyridazin-3-yl)methyl)phenyl)isoindoline-1,3-dione (14b) (600 mg, 1.36 mmol) and DMF-DMA (5 mL) was heated to 105° C. for 3 hours. LCMS showed desired mass. The reaction mixture was and concentrated under reduced pressure to give 14c. The product was used in next step without further purification. MS mass calculated for [M+1]$^+$ (C$_{23}$H$_{19}$Cl$_2$N$_3$O$_3$) required m/z 456.1, LCMS found m/z 456.1.

6-(4-amino-2,6-dichlorobenzyl)-4-isopropyl-2-methylpyridazin-3(2H)-one (14d)

A solution of 2-(3,5-dichloro-4-((5-isopropyl-1-methyl-6-oxo-1,6-dihydropyridazin-3-yl)methyl)phenyl)isoindoline-1,3-dione (14c) (600 mg, 1.31 mmol) in N-butylamine (981.11 mg, 6.57 mmol) and MeOH (3 mL) was heated to 70° C. for 3 hours. TLC showed reaction was completely. LCMS showed desired mass. The reaction mixture concentrated under reduced pressure. The residue was purified by column chromatography (petroleum ether:ethyl acetate=3:1 to 2:1) to give 14d. MS mass calculated for [M+1]$^+$ (C$_{18}$H$_{17}$Cl$_2$N$_5$O$_4$) required m/z 326.1, LCMS found m/z 326.0. $^1$H NMR (400 MHz, CD$_3$OD) δ 7.08-7.04 (m, 1H), 6.72-6.69 (m, 2H), 4.13 (s, 2H), 3.70 (s, 3H), 3.14-3.06 (m, 1H), 1.15 (d, J=6.8 Hz, 6H).

N-(3,5-dichloro-4-((5-isopropyl-1-methyl-6-oxo-1,6-dihydropyridazin-3-yl)methyl)phenyl)-5-oxo-4,5-dihydro-1,2,4-oxadiazole-3-carboxamide (Example 14)

A solution of 6-(4-amino-2,6-dichlorobenzyl)-4-isopropyl-2-methylpyridazin-3(2H)-one (14d) (19.43 mg, 59.78 umol) in DCM (2 mL) was added TEA (18.15 mg, 179.33 umol, 3eq) and 5-oxo-4,5-dihydro-1,2,4-oxadiazole-3-carbonyl chloride (4e) (8.88 mg, 59.78 umol). The mixture was degassed and purged with N₂ for 3 times stirred at 25° C. for 0.5 hours. The reaction mixture was concentrated under reduced pressure to give a residue. The residue was purified by Prep-HPLC (NH₄CO₃) to give Example 14. MS mass calculated for [M+1]⁺ (C₁₈H₁₇Cl₂N₅O₄) required m/z 438.1, LCMS found m/z 438.0; 1H NMR (400 MHz, CD₃OD) δ 7.89 (s, 2H), 7.18 (s, 1H), 4.30 (s, 2H), 3.69-3.63 (m, 3H), 3.13 (td, J=7.0, 13.8 Hz, 1H), 1.19 (d, J=6.8 Hz, 6H).

Example 15: 3-(((3,5-dichloro-4-((5-isopropyl-6-oxo-1,6-dihydropyridazin-3-yl)methyl)phenyl)amino)methyl)-1,2,4-oxadiazol-5(4H)-one

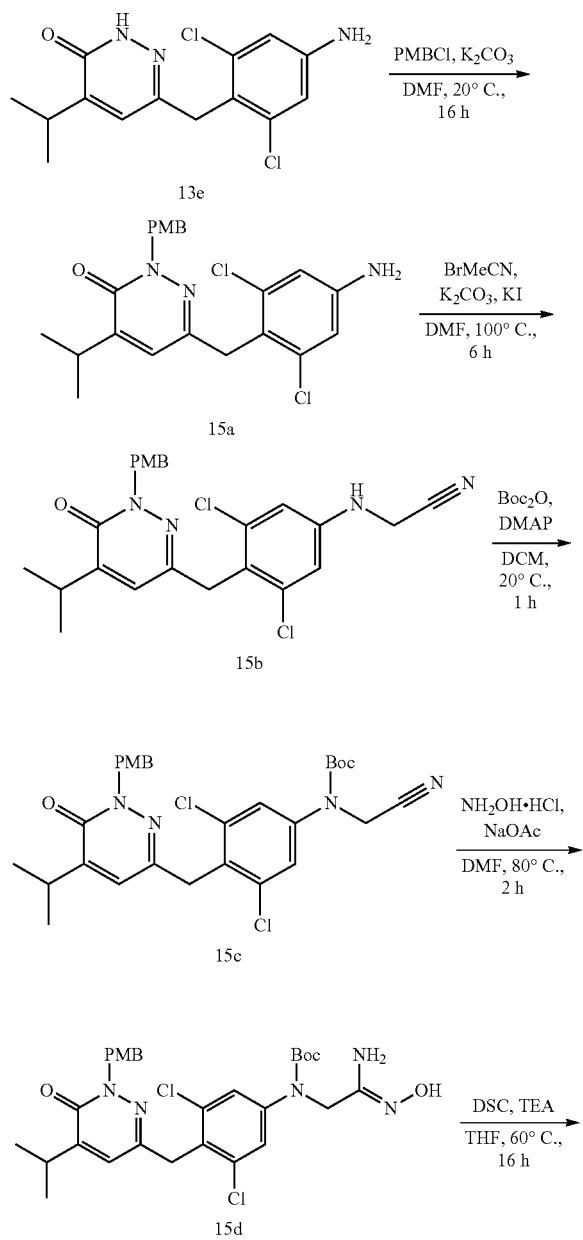

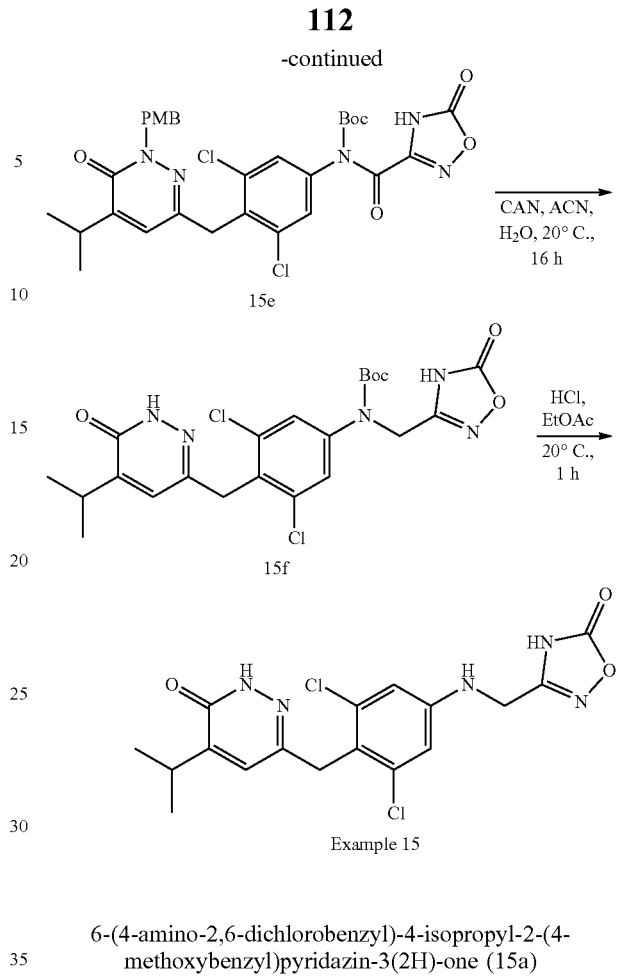

6-(4-amino-2,6-dichlorobenzyl)-4-isopropyl-2-(4-methoxybenzyl)pyridazin-3(2H)-one (15a)

To a solution of 6-(4-amino-2,6-dichlorobenzyl)-4-isopropylpyridazin-3(2H)-one (13e) (200 mg, 640.63 umol) in DMF (5 mL) was added PMB-Cl (120.39 mg, 768.75 umol), K₂CO₃ (106.25 mg, 768.75 umol). The mixture was stirred at 20° C. for 16 hours. The suspension was filtered through a pad of Celite and the pad cake was washed with EtOH (5 mL*3). The combined filtrates were concentrated to dryness to give a residue. The residue was purified by prep-TLC to give 15a. ¹H NMR (400 MHz, DMSO-d6) δ ppm 7.17 (d, J=8.6 Hz, 2H), 7.04 (s, 1H), 6.85-6.80 (m, 2H), 6.65 (s, 2H), 5.63 (s, 2H), 5.02 (s, 2H), 4.01 (s, 2H), 3.71 (s, 3H), 2.97 (td, J=6.8, 13.5 Hz, 1H), 1.07 (d, J=7.1 Hz, 6H).

2-((3,5-dichloro-4-((5-isopropyl-1-(4-methoxybenzyl)-6-oxo-1,6-dihydropyridazin-3-yl)methyl)phenyl)amino)acetonitrile (15b)

To a solution of 6-(4-amino-2,6-dichlorobenzyl)-4-isopropyl-2-(4-methoxybenzyl)pyridazin-3 (2H)-one (15a) (150 mg, 346.95 umol) and 2-bromoacetonitrile (416.16 mg, 3.47 mmol) in DMF (10 mL) was added K₂CO₃ (57.54 mg, 416.34 umol) and KI (28.80 mg, 173.47 umol). The mixture was stirred at 100° C. for 6 hours. The reaction mixture was quenched by addition water 5 mL, and then extracted with EtOAc (5 mL*3). The combined organic layers were washed with brine (5 mL), dried over anhydrous Na₂SO₄, filtered and concentrated under reduced pressure to give a residue. The residue was purified by prep-TLC (SiO₂, petroleum ether:ethyl acetate=1:1, according TLC) to give 15b. ¹H NMR (400 MHz, DMSO-d6) δ 7.15 (d, J=8.6 Hz, 2H), 7.12 (s, 1H), 6.87 (s, 2H), 6.83 (d, J=8.8 Hz, 2H), 6.76 (t, J=6.7

Hz, 1H), 5.00 (s, 2H), 4.37 (d, J=6.6 Hz, 2H), 4.08 (s, 2H), 3.71 (s, 3H), 2.99 (td, J=6.7, 13.7 Hz, 1H), 1.08 (d, J=6.8 Hz, 6H).

tert-butyl (cyanomethyl)(3,5-dichloro-4-((5-isopropyl-1-(4-methoxybenzyl)-6-oxo-1,6-dihydropyridazin-3-yl)methyl)phenyl)carbamate (15c)

To a solution of 2-((3,5-dichloro-4-((5-isopropyl-1-(4-methoxybenzyl)-6-oxo-1,6-dihydropyridazin-3-yl)methyl)phenyl)amino)acetonitrile (15 b) (133 mg, 282.15 umol) in THF (3 mL) was added DMAP (34.47 mg, 282.15 umol) and Boc$_2$O (184.74 mg, 846.45 umol). The mixture was stirred at 20° C. for 1 hour. The reaction was clean according to TLC. LCMS showed one main peak with desired MS. The reaction mixture was concentrated under reduced pressure to give a residue. The residue was purified by prep-TLC (SiO$_2$, petroleum ether:ethyl acetate=1:1, according TLC) to give 15c. MS mass calculated for [M+1]$^+$ (C$_{29}$H$_{32}$Cl$_2$N$_4$O$_4$) required m/z 571.2, LCMS found m/z 471.1/571.1; $^1$HNMR (400 MHz, CD$_3$C$_1$) $7.35-7.33 (m, 2H), 7.31 (s, 1H), 6.91 (s, 1H), 6.82 (d, J 8.8 Hz, 2H), 5.13 (s, 2H), 4.49 (s, 2H), 4.24 (s, 2H), 3.78 (s, 3H), 3.16 (quin, J=6.9 Hz, 1H), 1.51 (s, 9H), 1.15 (d, J=6.6 Hz, 6H).

(Z)-tert-butyl (2-amino-2-(hydroxyimino)ethyl)(3,5-dichloro-4-((5-isopropyl-1-(4-methoxybenzyl)-6-oxo-1,6-dihydropyridazin-3-yl)methyl)phenyl)carbamate (15d)

To a solution of tert-butyl (cyanomethyl)(3,5-dichloro-4-((5-isopropyl-1-(4-methoxybenzyl)-6-oxo-1,6-dihydropyridazin-3-yl)methyl)phenyl)carbamate (15c) (100 mg, 174.98 umol) in DMF (3 mL) was added NH$_2$OH.HCl (97.27 mg, 1.40 mmol) and NaOAc (114.83 mg, 1.40 mmol). The mixture was stirred at 80° C. for 6 hours. LCMS showed one main peak with desired MS. The suspension was filtered through a pad of Celite and the pad cake was washed with EtOAc (5 mL*3). The combined filtrates were washed with brine 10 mL, dried over anhydrous Na$_2$SO$_4$, filtered and concentrated under reduced pressure to give 15d was used into the next step without further purification as an off-white gum. MS mass calculated for [M+1]$^+$ (C$_{14}$H$_{15}$Cl$_2$N$_3$O$_2$) required m/z 604.2, LCMS found m/z 504.2/604.2; $^1$H NMR (400 MHz, DMSO-d6) $9.15 (s, 1H), 7.51 (s, 2H), 7.18 (s, 1H), 7.11 (d, J=8.6 Hz, 2H), 6.82 (d, J=8.6 Hz, 2H), 5.40 (s, 2H), 4.96 (s, 2H), 4.21 (s, 2H), 4.19 (s, 2H), 3.71 (s, 3H), 2.99 (td, J=6.8, 13.5 Hz, 1H), 1.38 (s, 9H), 1.09 (d, J=6.8 Hz, 6H).

tert-butyl (3,5-dichloro-4-((5-isopropyl-1-(4-methoxybenzyl)-6-oxo-1,6-dihydropyridazin-3-yl)methyl)phenyl)((5-oxo-4,5-dihydro-1,2,4-oxadiazol-3-yl)methyl)carbamate (15e)

To a solution of (Z)-tert-butyl (2-amino-2-(hydroxyimino)ethyl)(3,5-dichloro-4-((5-isopropyl-1-(4-methoxybenzyl)-6-oxo-1,6-dihydropyridazin-3-yl)methyl)phenyl) carbamate (15d) (40.00 mg, 66.17 umol) in THF (3 mL) was added TEA (13.39 mg, 132.34 umol) and DSC (22.04 mg, 86.02 umol) at 0° C. The mixture was stirred at 65° C. for 16 hours. LCMS showed one main peak with desired MS. The reaction mixture was concentrated under reduced pressure to give a residue. The residue was purified by Prep-TLC (dichloromethane:methanol=10:1) to give 15e. MS mass calculated for [M+1]$^+$ (C$_{30}$H$_{33}$Cl$_2$N$_5$O$_6$) required m/z 630.1, LCMS found m/z 630.1.

tert-butyl (3,5-dichloro-4-((5-isopropyl-6-oxo-1,6-dihydropyridazin-3-yl)methyl)phenyl)((5-oxo-4,5-dihydro-1,2,4-oxadiazol-3-yl)methyl)carbamate (15f)

To a solution of tert-butyl (3,5-dichloro-4-((5-isopropyl-1-(4-methoxybenzyl)-6-oxo-1,6-dihydropyridazin-3-yl) methyl)phenyl)((5-oxo-4,5-dihydro-1,2,4-oxadiazol-3-yl) methyl)carbamate (15e) (17 mg, 21.57 umol) in ACN (2 mL) and H$_2$O (0.5 mL) was added CAN (47.30 mg, 86.28 umol). The mixture was stirred at 20° C. for 4 hours. TLC showed 15e was remained ~10% and one new spot was formed. The reaction mixture was concentrated under reduced pressure to remove ACN. The residue was diluted with brine 5 mL and extracted with EtOAc 30 mL (10 mL*3). The combined organic layers were washed with brine 10 mL, dried over anhydrous Na$_2$SO$_4$, filtered and concentrated under reduced pressure to give 15f. MS mass calculated for [M+1]$^+$ (C$_{22}$H$_{25}$Cl$_2$N$_{50}$O$_5$) required m/z 510.1, LCMS found m/z 510.1.

3-(((3,5-dichloro-4-((5-isopropyl-6-oxo-1,6-dihydropyridazin-3-yl)methyl)phenyl)amino)methyl)-1,2,4-oxadiazol-5(4H)-one (Example 15)

A solution of tert-butyl (3,5-dichloro-4-((5-isopropyl-6-oxo-1,6-dihydropyridazin-3-yl)methyl)phenyl)((5-oxo-4,5-dihydro-1,2,4-oxadiazol-3-yl)methyl)carbamate (15f) (33 mg, 64.66 umol) in EtOAc (2 mL) and HCl/EtOAc (2 M, 161.65 uL) was stirred at 20° C. for 1 hour. TLC indicated starting material was consumed completely and one new spot was formed. LCMS detected the desired MS. The reaction mixture was concentrated under reduced pressure to remove EtOAc. The residue was purified by prep-HPLC (column: Luna C18 100*30 5 u; mobile phase: [water (0.04% HCl)-ACN]; B %: 25%-50%, 12 min) to give Example 15. MS mass calculated for [M+1]$^+$ (C$_{17}$H$_{17}$Cl$_2$N$_5$O$_3$) required m/z 410.0, LCMS found m/z 410.0. $^1$H NMR (400 MHz, CD$_3$OD) δ 7.12 (s, 1H), 6.76 (s, 2H), 4.28 (s, 2H), 4.17 (s, 2H), 3.08 (td, J=6.9, 13.6 Hz, 1H), 1.17 (d, J=6.8 Hz, 6H).

Example 16: 3-(((3,5-dichloro-4-((5-isopropyl-1-methyl-6-oxo-1,6-dihydropyridazin-3-yl)methyl) phenyl)amino)methyl)-1,2,4-oxadiazol-5(4H)-one

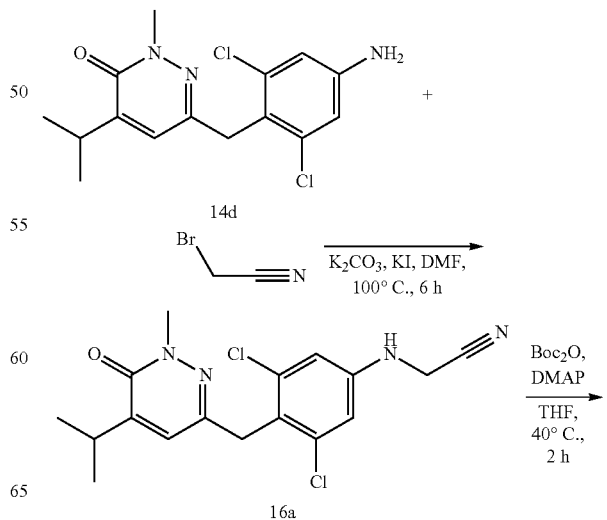

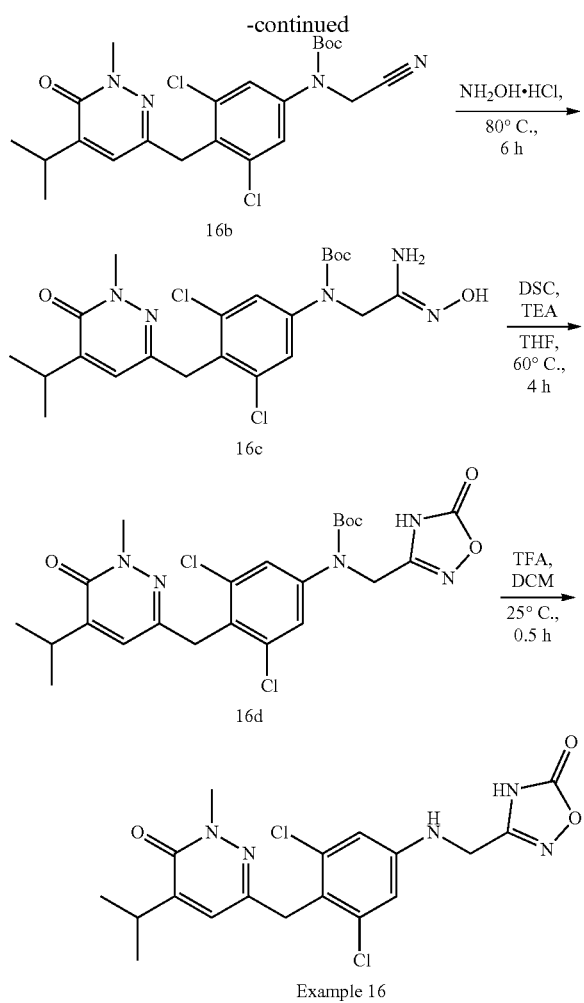

Example 16

2-((3,5-dichloro-4-((5-isopropyl-1-methyl-6-oxo-1,6-dihydropyridazin-3-yl)methyl)phenyl)amino)acetonitrile (16a)

To a solution of 6-(4-amino-2,6-dichlorobenzyl)-4-isopropyl-2-methylpyridazin-3(2H)-one (14d) (150 mg, 459.81 umol) and 2-bromoacetonitrile (551.53 mg, 4.60 mmol) in DMF (5 mL) was added KI (38.16 mg, 229.91 umol) and K$_2$CO$_3$ (76.26 mg, 551.77 umol). The mixture was stirred at 100° C. for 8 hours. LCMS showed desired mass. After cooling, the reaction mixture was partitioned between ethyl acetate (20 mL) and H$_2$O (20 mL). The organic phase was separated, washed with brine (10 mL), dried over Na$_2$SO$_4$, filtered and concentrated under reduced pressure to give a residue. The residue was purified by prep-TLC (petroleum ether:ethyl acetate=2:1) to give 16a. $^1$HNMR (400 MHz, DMSO-d6) δ 7.10 (s, 1H), 6.85 (s, 2H), 6.75 (t, J=6.7 Hz, 1H), 4.35 (d, J=6.6 Hz, 2H), 4.07 (s, 2H), 3.53 (s, 3H), 3.01 (td, J=7.0, 13.7 Hz, 1H), 1.10 (d, J=6.8 Hz, 6H).

tert-butyl (cyanomethyl)(3,5-dichloro-4-((5-isopropyl-1-methyl-6-oxo-1,6-dihydropyridazin-3-yl)methyl)phenyl)carbamate (16b)

A mixture of 2-((3,5-dichloro-4-((5-isopropyl-1-methyl-6-oxo-1,6-dihydropyridazin-3-yl)methyl)phenyl)amino)acetonitrile (16a) (20 mg, 54.76 umol), DMAP (6.69 mg, 54.76 umol) and Boc$_2$O (119.50 mg, 547.56 umol) in THF (2 mL) was stirred at 20° C. for 0.5 hours. The reaction mixture was concentrated under reduced pressure to give a residue. The residue was purified by prep-TLC (petroleum ether:ethyl acetate=2:1) to give 16b. $^1$H NMR (400 MHz, CD$_3$OD) δ 7.45 (s, 2H), 7.22-7.19 (m, 1H), 4.67-4.64 (m, 2H), 4.35-4.32 (m, 2H), 3.66-3.62 (m, 3H), 3.17-3.09 (m, 1H), 1.51-1.47 (m, 9H), 1.19 (d, J=7.0 Hz, 6H).

(Z)-tert-butyl (2-amino-2-(hydroxyimino)ethyl)(3,5-dichloro-4-((5-isopropyl-1-methyl-6-oxo-1,6-dihydropyridazin-3-yl)methyl)phenyl)carbamate (16c)

To a solution of tert-butyl (cyanomethyl)(3,5-dichloro-4-((5-isopropyl-1-methyl-6-oxo-1,6-dihydropyridazin-3-yl)methyl)phenyl)carbamate (16b) (50 mg, 107.44 umol) in DMF (2 mL) was added NH$_2$OH.HCl (37.33 mg, 537.20 umol) and NaOAc (44.07 mg, 537.20 umol). The mixture was stirred at 80° C. for 1 hour. LCMS showed desired mass. The reaction mixture was partitioned between ethyl acetate (20 mL) and H$_2$O (20 mL). The organic phase was separated, washed with brine (20 mL), dried over Na$_2$SO$_4$, filtered and concentrated under reduced pressure to give 16c without further purification. MS mass calculated for [M+1]$^+$ (C$_{22}$H$_{29}$Cl$_2$N$_5$O$_4$) required m/z 498.2, LCMS found m/z 498.2.

tert-butyl (3,5-dichloro-4-((5-isopropyl-1-methyl-6-oxo-1,6-dihydropyridazin-3-yl)methyl)phenyl)((5-oxo-4,5-dihydro-1,2,4-oxadiazol-3-yl)methyl)carbamate (16d)

To a solution of (Z)-tert-butyl (2-amino-2-(hydroxyimino)ethyl)(3,5-dichloro-4-((5-isopropyl-1-methyl-6-oxo-1,6-dihydropyridazin-3-yl)methyl)phenyl)carbamate (16c) (26 mg, 52.17 umol) in THF (2 mL) was added DSC (17.37 mg, 67.82 umol) and TEA (10.56 mg, 104.33 umol). The mixture was stirred at 60° C. for 16 hours. After cooling to room temperature, the reaction mixture was concentrated under reduced pressure. The residue was purified by prep-TLC (dichloromethane:methanol=10:1) to give 16d. MS mass calculated for [M+1]$^+$ (C$_{23}$H$_{27}$Cl$_2$N$_5$O$_5$) required m/z 524.1, LCMS found m/z 524.1.

3-(((3,5-dichloro-4-((5-isopropyl-1-methyl-6-oxo-1,6-dihydropyridazin-3-yl)methyl)phenyl)amino)methyl)-1,2,4-oxadiazol-5(4H)-one (Example 16)

To a solution of tert-butyl (3,5-dichloro-4-((5-isopropyl-1-methyl-6-oxo-1,6-dihydropyridazin-3-yl)methyl)phenyl)((5-oxo-4,5-dihydro-1,2,4-oxadiazol-3-yl)methyl)carbamate (16d) (24 mg, 45.77 umol) in EtOAc (1 mL) was added EtOAc/HCl (4 M, 11.44 uL). The mixture was stirred at 20° C. for 2 hours. LCMS showed desired mass. The reaction mixture was concentrated under reduced pressure to give a residue. The residue was purified by prep-HPLC (FA) to give Example 16. MS mass calculated for [M+1]$^+$ (C$_{18}$H$_{19}$Cl$_2$N$_5$O$_3$) required m/z 424.1, LCMS found m/z 424.1. $^1$H NMR (400 MHz, CD$_3$OD) δ 7.10-7.06 (m, 1H), 6.76 (s, 2H), 4.27 (s, 2H), 4.16 (s, 2H), 3.70-3.67 (m, 3H), 3.14-3.06 (m, 1H), 1.15 (d, J=6.8 Hz, 6H).

Example 17: N-(3,5-dichloro-4-(5-isopropyl-1-methyl-6-oxo-1,6-dihydropyridazine-3-carbonyl)phenyl)-5-oxo-4,5-dihydro-1,2,4-oxadiazole-3-carboxamide

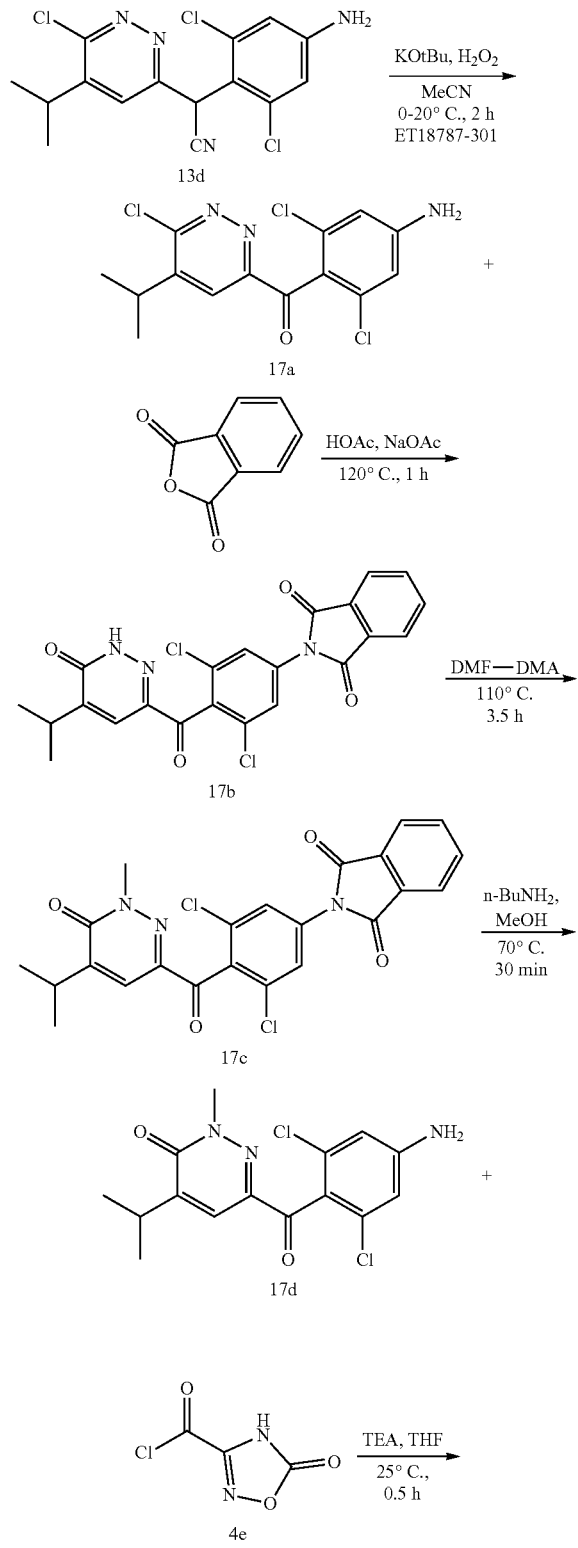

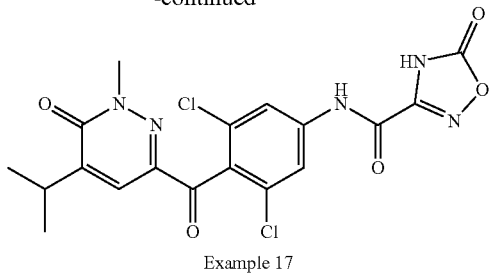

Example 17

(4-amino-2,6-dichlorophenyl)(6-chloro-5-isopropylpyridazin-3-yl)methanone (17a)

To a solution of 2-(4-amino-2,6-dichloro-phenyl)-2-(6-chloro-5-isopropyl-pyridazin-3-yl)acetonitrile (13d) (0.9 g, 2.53 mmol) in $CH_3CN$ (20 mL) was added t-BuOK (1 M, 2.40 mL) at 20° C. And the mixture was stirred at 20° C. for 0.5 hours. Then the mixture was cooled to 0° C. and $H_2O_2$ (573.85 mg, 5.06 mmol, 486.31 uL, 30% purity) was added in the mixture by dropwise. Then the mixture was stirred at 0° C. for 0.5 hours, and stirred at 20° C. for another 2 hours. Then saturated $Na_2SO_3$ solution (5 mL) was added in the mixture, and the mixture was stirred at 20° C. for 1 hour. Then the mixture was concentrated in vacuum to remove $CH_3CN$. The residue was extracted with EtOAc (10 mL*2). The combined organic layer was washed with brine (5 mL), dried over $Na_2SO_4$, filtered and concentrated in vacuum. The residue was purified by column silicagel chromatography (petroleum ether:ethyl acetate=30:1 to 5:1) to give 17a. MS mass calculated for $[M+1]^+$ ($C_{14}H_{12}Cl_3N_3O$) required m/z 344.0, LCMS found m/z 344.0/346.0; $^1$HNMR (400 MHz, DMSO-d6) δ 8.24 (s, 1H) 6.67 (s, 2H) 6.21 (s, 2H) 3.18-3.31 (m, 1H) 2.50 (br s, 5H) 1.27-1.39 (m, 6H).

2-(3,5-dichloro-4-(5-isopropyl-6-oxo-1,6-dihydropyridazine-3-carbonyl)phenyl)isoindoline-1,3-dione (17b)

To a solution of (4-amino-2,6-dichlorophenyl)(6-chloro-5-isopropylpyridazin-3-yl)methanone (17a) (260 mg, 797.11 umol) in HOAc (10 mL) was added NaOAc (326.94 mg, 3.99 mmol) and isobenzofuran-1,3-dione (129.87 mg, 876.82 umol). The mixture was stirred at 120° C. for 1 hour. LCMS showed the desired mass. The mixture was concentrated in vacuum, the residue was diluted in $H_2O$ (50 mL*2) and $NaHCO_3$(50 mL*2). Then the mixture was extracted with ethyl acetate (30 mL*2). The combined organic layer was concentrated in vacuum. The residue was purified by prep-TLC to give 17b. MS mass calculated for $[M+1]^+$ ($C_{22}H_{15}Cl_2N_3O_4$) required m/z 456.0, LCMS found m/z 456.0.

2-(3,5-dichloro-4-(5-isopropyl-1-methyl-6-oxo-1,6-dihydropyridazine-3-carbonyl)phenyl)isoindoline-1,3-dione (17c)

To a solution of 2-(3,5-dichloro-4-(5-isopropyl-6-oxo-1,6-dihydropyridazine-3-carbonyl)phenyl)isoindoline-1,3-dione (17b) (250 mg, 547.91 umol) in DMF-DMA (30 mL), the mixture was stirred at 110° C. for 3.5 hours. LCMS showed desired mass. The reaction mixture was partitioned between $H_2O$ 30 mL*2 and EtOAc 30 mL*2. The organic phase was concentrated under reduced pressure to give 17c.

The crude product was used into the next step without further purification. MS mass calculated for [M+1]+ ($C_{23}H_{17}Cl_2N_3O_4$) required m/z 470.1, LCMS found m/z 470.1.

6-(4-amino-2,6-dichlorobenzoyl)-4-isopropyl-2-methylpyridazin-3(2H)-one (17d)

To a solution of 2-(3,5-dichloro-4-(5-isopropyl-1-methyl-6-oxo-1,6-dihydropyridazine-3-carbonyl)phenyl)isoindoline-1,3-dione (17c) (200 mg, 425.26 umol) in MeOH (2 mL) was added N-butylamine (190.39 mg, 1.28 mmol, 204.72 uL). The mixture was stirred at 70° C. for 0.5 hours. LCMS showed desired mass. The mixture was concentrated under vacuum. The residue was purified by prep-TLC to give 17d. MS mass calculated for [M+1]+ ($C_{15}H_{15}Cl_2N_3O_2$) required m/z 340.1, LCMS found m/z 340.1; ¹HNMR (400 MHz, $CD_3OD$) δ 7.85 (d, J=0.9 Hz, 1H), 6.64 (s, 2H), 3.76-3.72 (m, 4H), 3.22-3.14 (m, 1H), 1.29-1.26 (m, 7H).

N-(3,5-dichloro-4-(5-isopropyl-1-methyl-6-oxo-1,6-dihydropyridazine-3-carbonyl)phenyl)-5-oxo-4,5-dihydro-1,2,4-oxadiazole-3-carboxamide (Example 17)

To a solution of 6-(4-amino-2,6-dichlorobenzoyl)-4-isopropyl-2-methylpyridazin-3(2H)-one (17d) (20 mg, 58.79 umol) in THF (5 mL) was added TEA (17.85 mg, 176.36 umol) and 5-oxo-4,5-dihydro-1,2,4-oxadiazole-3-carbonyl chloride (4e) (13.10 mg, 88.18 umol). The mixture was stirred at 25° C. for 0.5 hours. LCMS showed desired MS was detected. The reaction mixture was quenched by addition MeOH 1 mL at 25° C., and then concentrated under reduced pressure to give a residue. The residue was checked by HPLC and purified by Prep-HPLC (column: Waters Xbridge 150*25 5 u; mobile phase: [water (10 mM $NH_4HCO_3$)-ACN]; B %: 20%-40%, 10 min) to give Example 17. MS mass calculated for [M+1]+ ($C_{18}H_{15}Cl_2N_5O_5$) required m/z 452.0, LCMS found m/z 452.0; ¹H NMR (400 MHz, $CD_3OD$) δ 7.94 (br s, 2H), 7.93 (br d, J=2.9 Hz, 1H), 3.73 (s, 3H), 3.26-3.11 (m, 1H), 1.30 (br d, J=6.7 Hz, 6H).

Example 18: 3-(((3,5-dichloro-4-(5-isopropyl-1-methyl-6-oxo-1,6-dihydropyridazine-3-carbonyl)phenyl)amino)methyl)-1,2,4-oxadiazol-5(4H)-one

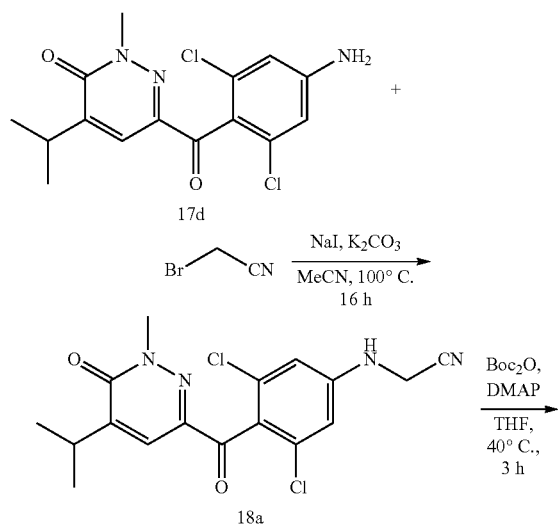

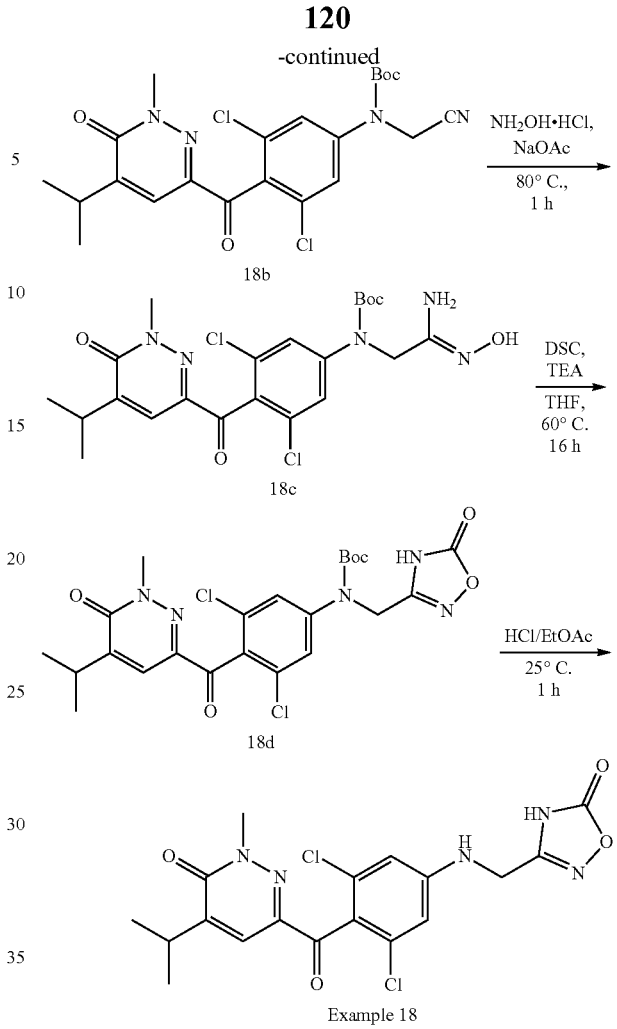

2-((3,5-dichloro-4-(5-isopropyl-1-methyl-6-oxo-1,6-dihydropyridazine-3-carbonyl)phenyl)amino)acetonitrile (18a)

To a solution of 6-(4-amino-2,6-dichlorobenzoyl)-4-isopropyl-2-methylpyridazin-3(2H)-one (72 mg, 211.64 umol) (17d) in MeCN (2 mL) was added 2-bromoacetonitrile (126.93 mg, 1.06 mmol, 70.52 uL), NaI (63.45 mg, 423.28 umol) and $K_2CO_3$ (58.50 mg, 423.28 umol). The mixture was stirred at 100° C. for 13 hours. The reaction mixture was extracted with ethyl acetate (20 mL*2) and $H_2O$ (20 mL*2). The combined organic layers were washed with brine (20 mL), dried over $Na_2SO_4$ filtered and concentrated under reduced pressure to give a residue. The residue was purified by prep-TLC (petroleum ether:ethyl acetate=1:1) to give 18a. MS mass calculated for [M+1]+ ($C_{17}H_{16}Cl_2N_4O_2$) required m/z 379.1, LCMS found m/z 379.2; ¹H NMR (400 MHz, $CDCl_3$) δ 7.84 (d, J=0.7 Hz, 1H), 6.68 (s, 2H), 4.16 (d, J=6.8 Hz, 2H), 3.77 (s, 3H), 3.27-3.19 (m, 1H), 1.28 (d, J=6.8 Hz, 6H).

tert-butyl (cyanomethyl)(3,5-dichloro-4-(5-isopropyl-1-methyl-6-oxo-1,6-dihydropyridazine-3-carbonyl)phenyl)carbamate (18b)

To a solution of 2-((3, 5-dichloro-4-(5-isopropyl-1-methyl-6-oxo-1,6-dihydropyridazine-3-carbonyl)phenyl)

amino)-acetonitrile (18a) (53 mg, 139.75 umol) in THF (3 mL) was added DMAP (17.07 mg, 139.75 umol) and Boc$_2$O (274.51 mg, 1.26 mmol, 288.95 uL). The mixture was stirred at 25° C. for 5 minutes. The mixture was partitioned between ethyl acetate (10 mL*2) and H$_2$O (10 mL*2). The combined organic phase was washed with brine (10 mL*2), dried with anhydrous Na$_2$SO$_4$, filtered and concentrated in vacuum to give a residue. The residue was purified by prep-TLC (petroleum ether:ethyl acetate=1:1) to give 18b. $^1$H NMR (400 MHz, CDCl$_3$) δ 7.87-7.84 (m, 1H), 7.35 (s, 2H), 4.52 (s, 2H), 3.75 (s, 3H), 3.28-3.19 (m, 1H), 1.54 (s, 9H), 1.29 (d, J=7.0 Hz, 6H).

(Z)-tert-butyl (2-amino-2-(hydroxyimino)ethyl)(3,5-dichloro-4-(5-isopropyl-1-methyl-6-oxo-1,6-dihydropyridazine-3-carbonyl)phenyl)carbamate (18c)

To a solution of tert-butyl (cyanomethyl)(3,5-dichloro-4-(5-isopropyl-1-methyl-6-oxo-1,6-dihydropyridazine-3-carbonyl)phenyl)carbamate (18b) (32 mg, 66.76 umol) in DMF (3 mL) was added NH$_2$OH.HCl (37.11 mg, 534.05 umol) and NaOAc (27.38 mg, 333.78 umol). The mixture was stirred at 80° C. for 1 hour. After cooling to room temperature, the reaction mixture was concentrated under reduced pressure to remove DMF. The residue was partitioned between ethyl acetate (10 mL) and H$_2$O (3 mL) twice. The combined organic phase was washed with brine (5 mL*3), dried with anhydrous Na$_2$SO$_4$, filtered and concentrated in vacuum to give 18c. The product was used directly for the next step without further purification.

tert-butyl (3,5-dichloro-4-(5-isopropyl-1-methyl-6-oxo-1,6-dihydropyridazine-3-carbonyl)phenyl)((5-oxo-4,5-dihydro-1,2,4-oxadiazol-3-yl)methyl)carbamate (18d)

To a solution of (Z)-tert-butyl (2-amino-2-(hydroxyimino)ethyl)(3,5-dichloro-4-(5-isopropyl-1-methyl-6-oxo-1,6-dihydropyridazine-3-carbonyl)phenyl)carbamate (32 mg, 62.45 umol) (18c) in THF (3 mL) was added DSC (20.80 mg, 81.19 umol) and TEA (12.64 mg, 124.91 umol, 17.39 uL). The mixture was stirred at 60° C. for 13 hours. LCMS showed the desired mass. The reaction mixture was extracted with ethyl acetates 20 mL*2 and H$_2$O 20 mL*2. The combined organic layers were washed with brine 20 mL, dried over Na$_2$SO$_4$, filtered and concentrated under reduced pressure to give 18d as a yellow solid. The crude product was used for the next step without further purification. MS mass calculated for [M+1]$^+$ (C$_{23}$H$_{25}$Cl$_2$N$_5$O$_6$) required m/z 538.1, LCMS found m/z 438.2/538.2.

3-(((3,5-dichloro-4-(5-isopropyl-1-methyl-6-oxo-1,6-dihydropyridazine-3-carbonyl)phenyl)amino)methyl)-1,2,4-oxadiazol-5(4H)-one (Example 18)

A solution of tert-butyl (3,5-dichloro-4-(5-isopropyl-1-methyl-6-oxo-1,6-dihydropyridazine-3-carbonyl)phenyl)((5-oxo-4,5-dihydro-1,2,4-oxadiazol-3-yl)methyl)carbamate (18d) (22 mg, 40.86 umol) in EtOAc/HCl (2 M, 2 mL). The mixture was stirred at 25° C. for 1 hour. LCMS showed desired mass. The mixture was concentrated in vacuum. The residue was purified by prep-HPLC (FA) to give Example 18. MS mass calculated for [M+1]$^+$ (C$_{18}$H$_{17}$Cl$_2$N$_5$O$_4$) required m/z 438.1, LCMS found m/z 438.2; $^1$H NMR (400 MHz, MeOD) δ 7.86 (s, 1H), 6.78-6.71 (m, 2H), 4.32 (s, 2H), 3.72 (s, 3H), 3.18 (td, J=6.8, 13.7 Hz, 1H), 1.27 (d, J=6.8 Hz, 6H).

Scheme D: 6-((4-amino-2,6-dichlorophenyl)thio)-4-isopropyl-2-methylpyridazin-3(2H)-one (19h)

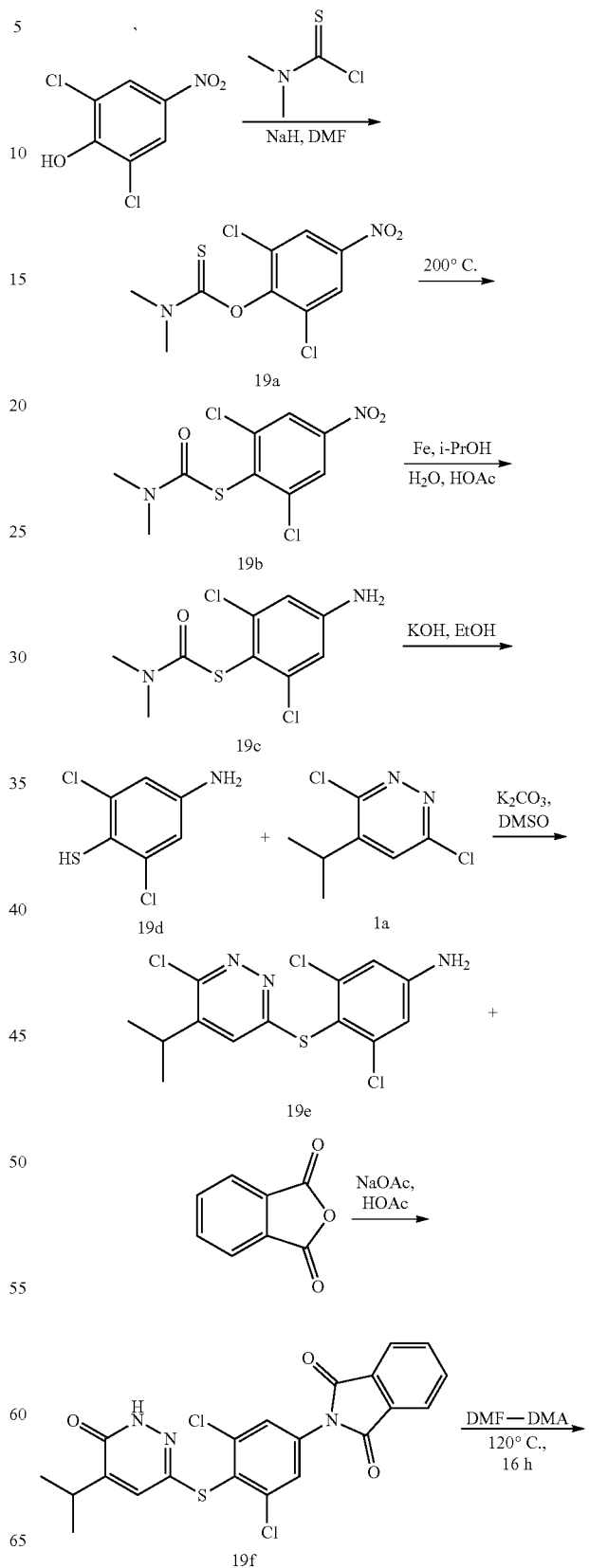

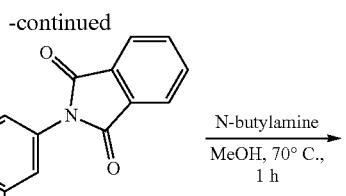

O-(2,6-dichloro-4-nitrophenyl) dimethylcarbamothioate (19a)

To a solution of 2,6-dichloro-4-nitrophenol (1 g, 4.81 mmol) in DMF (20 mL) was added NaH (288.44 mg, 7.21 mmol, 60% purity). Then the mixture was stirred at 20° C. for 1 hour. Then and N, N-dimethylcarbamothioyl chloride (950.81 mg, 7.69 mmol) was added in the mixture. The mixture was stirred at 20° C. for 16 hours. The mixture was extracted with EtOAc (20 mL*2). The combined organic layer was washed with brine (15 mL), dried over $Na_2SO_4$, filtered and concentrated in vacuum. The residue was purified by column silicagel chromatography (petroleum ether:ethyl acetate=20:1 to 5:1) to give 19a. $^1$HNMR (400 MHz, $CDCl_3$) δ 8.28 (s, 2H) 3.50 (s, 3H) 3.44 (s, 3H).

S-(2,6-dichloro-4-nitrophenyl) dimethylcarbamothioate (19b)

O-(2,6-dichloro-4-nitrophenyl) dimethylcarbamothioate (19a) (0.9 g, 3.05 mmol) was added in a flask and stirred at 200° C. for 4 hours. LCMS showed desired MS. The mixture was cooled to 20° C. to give 19b. The crude reaction product was used directly in next step. $^1$H NMR (400 MHz, DMSO-d6) δ 8.44 (s, 2H) 3.13 (br s, 3H) 2.95 (br s, 3H).

O-(2,6-dichloro-4-nitrophenyl) dimethylcarbamothioate (19c)

To a solution of S-(2,6-dichloro-4-nitrophenyl) dimethylcarbamothioate (19b) (0.8 g, 2.71 mmol) in AcOH (10 mL), 2-propanol (20 mL) and $H_2O$ (10 mL) was added Fe (1.06 g, 18.97 mmol). Then the mixture was stirred at 95° C. for 2 hours. The mixture was cooled to 20° C., and saturated $NaHCO_3$ solution was added in the mixture until pH=8-9 and filtered. Then the filtrate was concentrated in vacuum to remove most solvent. Then the residue was extracted with $H_2O$ (50 mL) and EtOAc (50 mL*2). The combined organic layer was dried over $Na_2SO_4$, filtered and concentrated in vacuum to give 19c. The product was used directly in next step. $^1$HNMR (400 MHz, $CDCl_3$) δ 6.73 (s, 2H) 3.98 (br s, 2H) 2.90-3.25 (m, 6H).

4-amino-2,6-dichlorobenzenethiol (19d)

To a solution of O-(2,6-dichloro-4-nitrophenyl) dimethylcarbamothioate (19c) (0.7 g, 2.64 mmol) in EtOH (20 mL) was added KOH (3 M, 20 mL). Then the mixture was refluxed at 100° C. for 16 hours. LCMS showed the reaction was completed. The mixture was cooled to 20° C., and HCl solution (1M) was added in the mixture until pH=2-3. The mixture was extracted with EtOAc (50 mL). The organic layer was dried over $Na_2SO_4$, filtered and concentrated in vacuum to give 19d. The product was used directly in next step. $^1$H NMR (400 MHz, $CDCl_3$) δ 7.27 (s, 2H) 6.70 (s, 2H) 4.23 (s, 1H) 3.70 (br s, 2H).

3,5-dichloro-4-((6-chloro-5-isopropylpyridazin-3-yl)thio)aniline (19e)

To a solution of 4-amino-2,6-dichlorobenzenethiol (19d) (520 mg, 2.68 mmol) and 3,6-dichloro-4-isopropylpyridazine (1a) (511.90 mg, 2.68 mmol) in DMSO (15 mL) was added $K_2CO_3$ (1.11 g, 8.04 mmol). Then the mixture was stirred at 95° C. for 16 hours. After cooling to room temperature, the mixture was was diluted with water (50 mL) and extracted with EtOAc (50 mL*2). The combined organic layer was washed with brine (30 mL), dried over $Na_2SO_4$, filtered and concentrated in vacuum. The residue was purified by Prep-TLC (petroleum ether:ethyl acetate=2:1) to give 19e. $^1$H NMR (400 MHz, $CDCl_3$) δ ppm 7.01 (s, 1H) 6.78 (s, 2H) 4.10 (br s, 2H) 3.14-3.27 (m, 1H) 1.23 (d, J=6.84 Hz, 6H).

2-(3,5-dichloro-4-((5-isopropyl-6-oxo-1,6-dihydropyridazin-3-yl)thio)phenyl)isoind-oline-1,3-dione (19f)

To a mixture of 3,5-dichloro-4-((6-chloro-5-isopropylpyridazin-3-yl)thio)aniline (19e) (1 g, 2.87 mmol) and isobenzofuran-1,3-dione (424.79 mg, 2.87 mmol) in HOAc (8 mL) was added NaOAc (1.18 g, 14.34 mmol). The mixture was stirred at 120° C. for 16 hours. The reaction mixture was concentrated under reduced pressure to remove AcOH. The solid was dissolved in water and the pH was adjusted to 9 with $NaHCO_3$(10 mL). Then the mixture was partitioned with ethyl acetate (30 mL) twice. The combined organic phase was washed with brine (10 mL*3), dried with anhydrous $Na_2SO_4$, filtered and concentrated in vacuum. The solid was stirred in ethyl acetate (10 mL) and petroleum ether (50 mL), then filtered and dried to give 19f. The product was used directly for the next step without further purification. $^1$H NMR (400 MHz, DMSO) δ 8.00-8.05 (m, 2H) 7.93-7.97 (m, 2H) 7.84 (s, 2H) 7.32 (d, J=0.86 Hz, 1H) 3.01 (quin, J=6.79 Hz, 1H) 1.14 (d, J=6.85 Hz, 6H).

2-(3,5-dichloro-4-((5-isopropyl-1-methyl-6-oxo-1,6-dihydropyridazin-3-yl)thio)-phenyl)isoindoline-1,3-dione (19g)

A solution of 2-(3,5-dichloro-4-((5-isopropyl-6-oxo-1,6-dihydropyridazin-3-yl)thio)phenyl)isoind-oline-1,3-dione (19f) (955 mg, 2.07 mmol) in DMF-DMA (8 mL) was stirred at 120° C. for 16 hr. The mixture was concentrated in vacuum to give a residue. The residue was partitioned between ethyl acetate (10 mL) and $H_2O$ (3 mL) twice. The combined organic phase was washed with brine (5 mL*3), dried with anhydrous $Na_2SO_4$, filtered and concentrated in vacuum to give 19g. The product was used directly for the next step without further purification. MS mass calculated for [M+1]$^+$ ($C_{22}H_{17}Cl_2N_3O_3S$) required m/z 474.0, LCMS found m/z 474.0.

6-((4-amino-2,6-dichlorophenyl)thio)-4-isopropyl-2-methylpyridazin-3(2H)-one (19h)

A mixture of 2-(3,5-dichloro-4-((5-isopropyl-1-methyl-6-oxo-1,6-dihydropyridazin-3-yl)thio)-phenyl)isoindoline-1,3-dione (19g) (980 mg, 2.07 mmol) and butan-1-amine (453.29 mg, 6.20 mmol, 612.55 uL in MeOH (2 mL) was stirred at 70° C. for 1 hour. The mixture was concentrated in vacuum to give a residue. The residue was purified by preparative TLC (petroleum ether:ethyl acetate=1:1) to give 19h. MS mass calculated for [M+1]$^+$ ($C_{14}H_{15}Cl_2N_3OS$) required m/z 344.0, LCMS found m/z 344.1; $^1$H NMR (400 MHz, CD$_3$OD) δ 6.85 (d, J=0.73 Hz, 1H) 6.80 (s, 2H) 3.64 (s, 3H) 3.09 (qd, J=7.01, 6.48 Hz, 1H) 1.12 (d, J=6.97 Hz, 6H).

Example 19: 3-(((3,5-dichloro-4-((5-isopropyl-1-methyl-6-oxo-1,6-dihydropyridazin-3-yl)sulfonyl)phenyl)amino)methyl)-1,2,4-oxadiazol-5(4H)-one

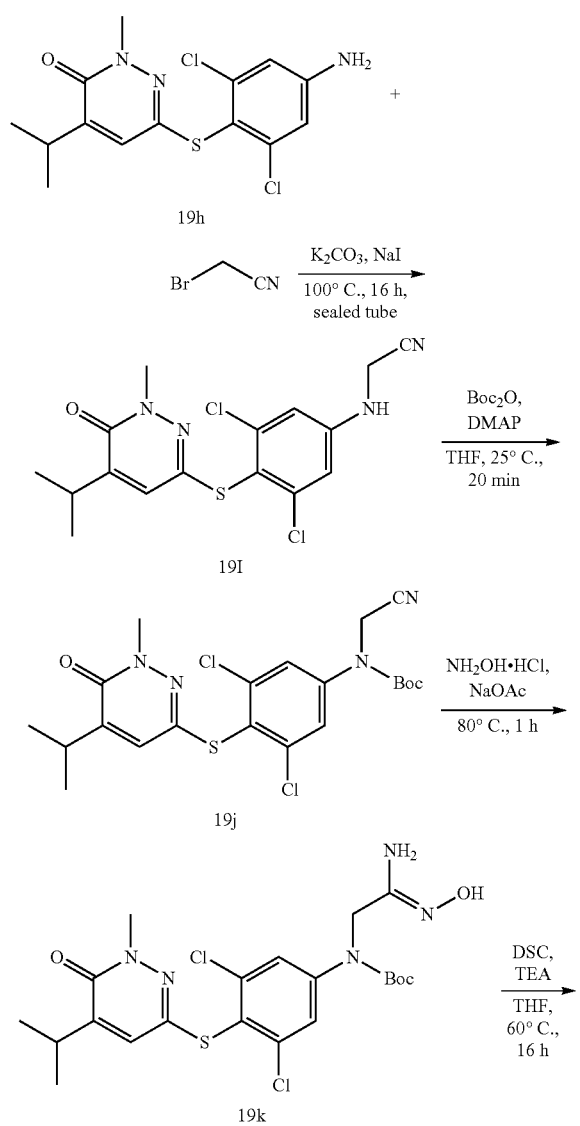

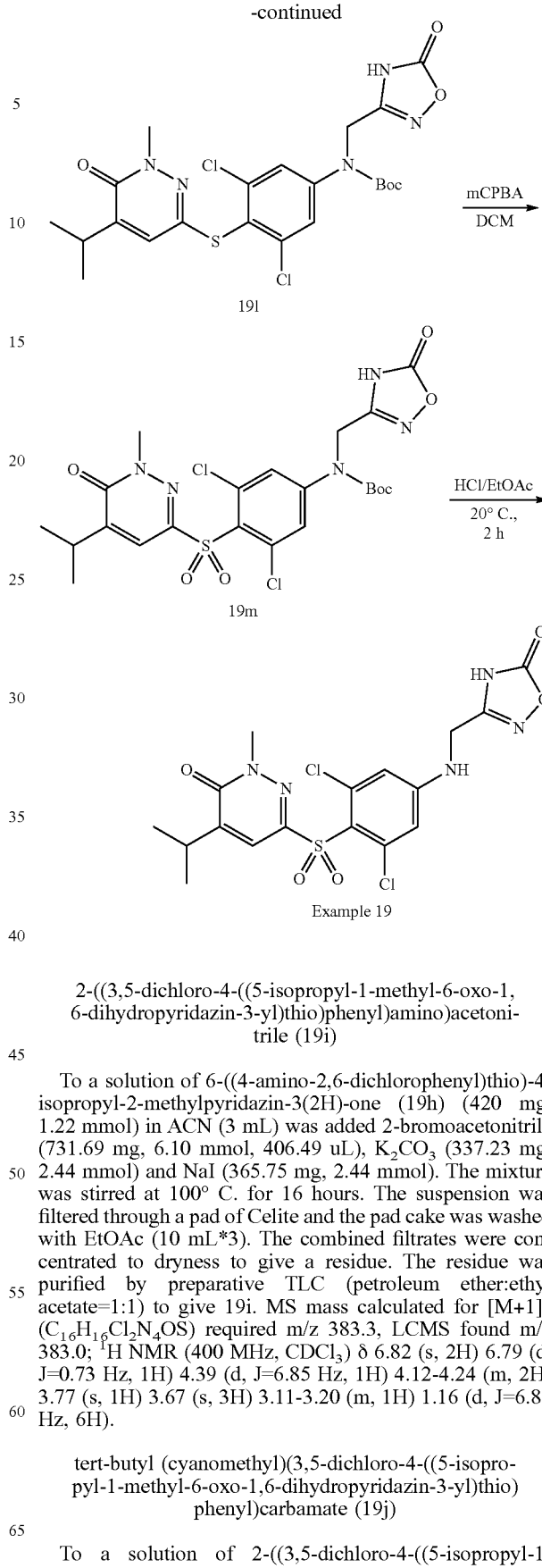

2-((3,5-dichloro-4-((5-isopropyl-1-methyl-6-oxo-1,6-dihydropyridazin-3-yl)thio)phenyl)amino)acetonitrile (19i)

To a solution of 6-((4-amino-2,6-dichlorophenyl)thio)-4-isopropyl-2-methylpyridazin-3(2H)-one (19h) (420 mg, 1.22 mmol) in ACN (3 mL) was added 2-bromoacetonitrile (731.69 mg, 6.10 mmol, 406.49 uL), K$_2$CO$_3$ (337.23 mg, 2.44 mmol) and NaI (365.75 mg, 2.44 mmol). The mixture was stirred at 100° C. for 16 hours. The suspension was filtered through a pad of Celite and the pad cake was washed with EtOAc (10 mL*3). The combined filtrates were concentrated to dryness to give a residue. The residue was purified by preparative TLC (petroleum ether:ethyl acetate=1:1) to give 19i. MS mass calculated for [M+1]$^+$ ($C_{16}H_{16}Cl_2N_4OS$) required m/z 383.3, LCMS found m/z 383.0; $^1$H NMR (400 MHz, CDCl$_3$) δ 6.82 (s, 2H) 6.79 (d, J=0.73 Hz, 1H) 4.39 (d, J=6.85 Hz, 1H) 4.12-4.24 (m, 2H) 3.77 (s, 1H) 3.67 (s, 3H) 3.11-3.20 (m, 1H) 1.16 (d, J=6.85 Hz, 6H).

tert-butyl (cyanomethyl)(3,5-dichloro-4-((5-isopropyl-1-methyl-6-oxo-1,6-dihydropyridazin-3-yl)thio)phenyl)carbamate (19j)

To a solution of 2-((3,5-dichloro-4-((5-isopropyl-1-methyl-6-oxo-1,6-dihydropyridazin-3-yl)thio)phenyl)

amino)acetonitrile (19i) (420 mg, 1.10 mmol) in THF (3 mL) was added DMAP (133.87 mg, 1.10 mmol) and Boc$_2$O (717.45 mg, 3.29 mmol) at 25° C. The mixture was stirred at 25° C. for 20 minutes. The mixture was partitioned between ethyl acetate 10 mL and H$_2$O 3 mL twice. The combined organic phase was washed with brine (5 mL*3), dried with anhydrous Na$_2$SO$_4$, filtered and concentrated in vacuum. The residue was purified by prep-TLC (SiO$_2$, petroleum ether:ethyl acetate=3:1) to give 19j. $^1$H NMR (400 MHz, CDCl$_3$) δ 7.46 (s, 2H) 6.84 (s, 1H) 4.53 (s, 2H) 3.64 (s, 3H) 3.18 (dt, J=13.66, 6.80 Hz, 1H) 1.53 (s, 9H) 1.18 (d, J=6.85 Hz, 6H).

(Z)-tert-butyl (2-amino-2-(hydroxyimino)ethyl)(3,5-dichloro-4-((5-isopropyl-1-methyl-6-oxo-1,6-dihydropyridazin-3-yl)thio)phenyl)carbamate (19k)

To a solution of tert-butyl (cyanomethyl)(3,5-dichloro-4-((5-isopropyl-1-methyl-6-oxo-1,6-dihydropyridazin-3-yl)thio)phenyl)carbamate (19j) (250 mg, 517.16 umol, 1 eq) in DMF (3 mL) was added NH$_2$OH.HCl (287.50 mg, 4.14 mmol, 8 eq) and NaOAc (339.38 mg, 4.14 mmol, 8 eq) at 25° C. The mixture was stirred at 80° C. for 1 hour. The reaction mixture was concentrated under reduced pressure to remove DMF. The residue was diluted with water (5 mL) and extracted with ethyl acetate (15 mL, twice). The combined organic phase was washed with brine (5 mL*3), dried with anhydrous Na$_2$SO$_4$, filtered and concentrated in vacuum to give a residue. The residue was purified by prep-TLC (SiO$_2$, petroleum ether:ethyl acetate=1:1) to give 19k.
$^1$H NMR (400 MHz, CDCl$_3$) δ 7.99 (s, 1H) 7.60 (s, 2H) 7.05 (d, J=0.66 Hz, 1H) 4.31 (s, 2H) 3.59 (s, 3H) 3.11 (dt, J=13.67, 6.84 Hz, 1H) 1.49 (s, 9H) 1.17 (d, J=7.06 Hz, 6H).

tert-butyl (3,5-dichloro-4-((5-isopropyl-1-methyl-6-oxo-1,6-dihydropyridazin-3-yl)thio)phenyl)((5-oxo-4,5-dihydro-1,2,4-oxadiazol-3-yl)methyl)carbamate (19l)

To a solution of (Z)-tert-butyl (2-amino-2-(hydroxyimino)ethyl)(3,5-dichloro-4-((5-isopropyl-1-methyl-6-oxo-1,6-dihydropyridazin-3-yl)thio)phenyl)carbamate (19k) (220 mg, 425.99 umol) in THF (4 mL) was added DSC (141.86 mg, 553.79 umol) and TEA (86.21 mg, 851.99 umol, 118.59 uL). The mixture was stirred at 60° C. for 16 hours. The mixture was concentrated in vacuum to give a residue. The residue was purified by prep-TLC (SiO$_2$, DCM:MeOH=10:1) to give 19l. MS mass calculated for [M+1]$^+$ (C$_{22}$H$_{25}$Cl$_2$N$_5$O$_5$S) required m/z 542.4, LCMS found m/z 542.1; $^1$H NMR (400 MHz, CD$_3$OD) δ 7.63 (s, 2H) 7.04 (d, J=0.73 Hz, 1H) 4.82 (s, 2H) 3.58 (s, 3H) 3.07-3.15 (m, 1H) 1.48 (s, 9H) 1.16 (d, J=6.85 Hz, 6H).

tert-butyl(3,5-dichloro-4-((5-isopropyl-1-methyl-6-oxo-1,6-dihydropyridazin-3-yl)sulfonyl)phenyl)((5-oxo-4,5-dihydro-1,2,4-oxadiazol-3-yl)methyl)carbamate (19m)

To a solution of tert-butyl (3,5-dichloro-4-((5-isopropyl-1-methyl-6-oxo-1,6-dihydropyridazin-3-yl)thio)phenyl)((5-oxo-4,5-dihydro-1,2,4-oxadiazol-3-yl)methyl)carbamate (19l) (20 mg, 36.87 umol) in DCM (2 mL) was added m-CPBA (37.43 mg, 184.35 umol, 85% purity). Then the mixture was stirred at 60° C. for 48 hours. The reaction mixture was quenched by addition Na$_2$SO$_3$ (23 mg) at 20° C. and was stirred for 30 minutes. Then the mixture was concentrated under reduced pressure to give 19m. MS mass calculated for [M+1]$^+$ (C$_{22}$H$_{25}$Cl$_2$N$_5$O$_7$S) required m/z 574.4, LCMS found m/z 574.1. The product was used directly for the next step without further purification.

3-(((3,5-dichloro-4-((5-isopropyl-1-methyl-6-oxo-1,6-dihydropyridazin-3-yl)sulfonyl)phenyl)amino)methyl)-1,2,4-oxadiazol-5(4H)-one (Example 19)

A solution of tert-butyl (3,5-dichloro-4-((5-isopropyl-1-methyl-6-oxo-1,6-dihydropyridazin-3-yl)sulfonyl)phenyl)((5-oxo-4,5-dihydro-1,2,4-oxadiazol-3-yl)methyl)carbamate (19m) (20 mg, 34.82 umol) in HCl/EtOAc (4 M, 2 mL) was stirred at 20° C. for 2 hours. The mixture was concentrated in vacuum to give a residue. The residue was purified by Prep-HPLC (column: Luna C18 100*30 5 u; mobile phase: [water (0.04% HCl)-ACN]; B %: 20%-50%, 11 min) to give Example 19. MS mass calculated for [M+1]$^+$ (C$_{17}$H$_{17}$Cl$_2$N$_5$O$_5$) requires m/z 474.3, LCMS found m/z 474.0; $^1$HNMR (400 MHz, CD$_3$OD) δ 7.74 (s, 1H) 6.83 (s, 2H) 4.38 (s, 2H) 3.72 (s, 3H) 3.13 (br d, J=1.71 Hz, 1H) 1.24 (d, J=6.85 Hz, 6H).

Example 20: N-(3,5-dichloro-4-((5-isopropyl-1-methyl-6-oxo-1,6-dihydropyridazin-3-yl)sulfonyl)phenyl)-5-oxo-4,5-dihydro-1,2,4-oxadiazole-3-carboxamide

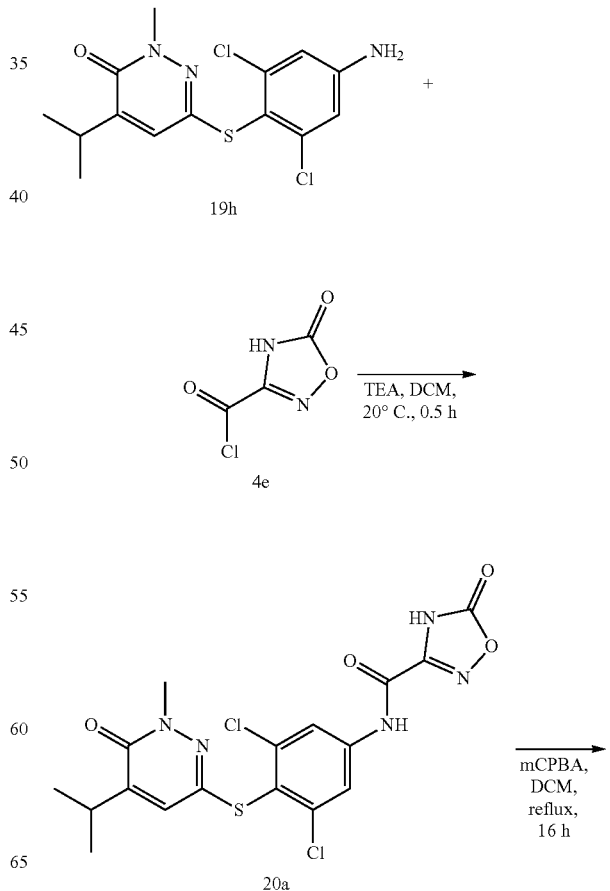

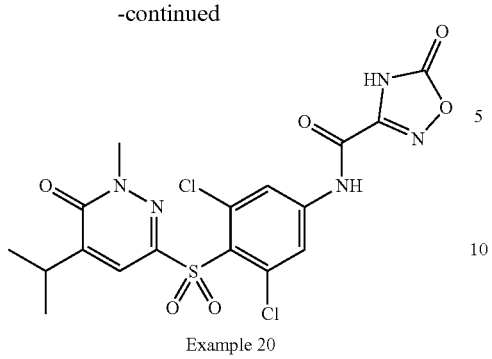

Example 20

N-(3,5-dichloro-4-((5-isopropyl-1-methyl-6-oxo-1,6-dihydropyridazin-3-yl)thio)ph-enyl)-5-oxo-4,5-dihydro-1,2,4-oxadiazole-3-carboxamide (20a)

To a mixture of 6-((4-amino-2,6-dichlorophenyl)thio)-4-isopropyl-2-methylpyridazin-3(2H)-one (19h) (20 mg, 58.10 umol) in DCM (5 mL) was add TEA (29.39 mg, 290.48 uml, 40.43 uL) and 5-oxo-4H-1,2,4-oxadiazole-3-carbonyl chloride (4e) (8.63 mg, 58.10 umol), the mixture was stirred at 25° C. for 0.2 hours. The reaction mixture was partitioned between H$_2$O (5 mL) and EtOAc (5 mL). The organic phase was separated, washed with brine (5 mL*3), dried over Na$_2$SO$_4$, filtered and concentrated under reduced pressure to give a residue. The crude product was purified by reversed-phase HPLC (0.1% FA condition) to give 20a. MS mass calculated for [M+1]$^+$ (C$_{17}$H$_{15}$Cl$_2$N$_5$O$_4$S) required m/z 456.0, LCMS found m/z 456.1; $^1$H NMR (400 MHz, CD$_3$OD) δ 7.94-8.14 (m, 2H) 7.07 (s, 1H) 3.52-3.64 (m, 3H) 3.05-3.18 (m, 1H) 1.17 (d, J=6.85 Hz, 6H).

N-(3,5-dichloro-4-((5-isopropyl-1-methyl-6-oxo-1,6-dihydropyridazin-3-yl)sulfonyl)-phenyl)-5-oxo-4,5-dihydro-1,2,4-oxadiazole-3-carboxamide (Example 20)

The mixture of N-(3,5-dichloro-4-((5-isopropyl-1-methyl-6-oxo-1,6-dihydropyridazin-3-yl)thio)ph-enyl)-5-oxo-4,5-dihydro-1,2,4-oxadiazole-3-carboxamide (20a) (8 mg, 17.53 umol) in DCM (1 mL) was added MCPBA (21.36 mg, 105.19 umol, 85% purity), the mixture was stirred at 50° C. for 16 hours. The reaction mixture was concentrated under reduced pressure to give a residue. The residue was purified by Prep-HPLC (aqueous acetonitrile w/TFA) to give Example 20. MS mass calculated for [M+1]$^+$ (C$_{17}$H$_{15}$Cl$_2$N$_5$O$_6$S) required m/z 488.0, LCMS found m/z 488.1; $^1$HNMR (400 MHz, DMSO) δ 11.40-11.66 (m, 1H) 8.09-8.13 (m, 2H) 7.72-7.75 (m, 1H) 3.62-3.65 (m, 3H) 3.08-3.11 (m, 1H) 1.16-1.21 (m, 6H).

Scheme E: 6-(4-amino-2,6-dichlorobenzyl)-4-cyclopropylpyridazin-3(2H)-one (21e)

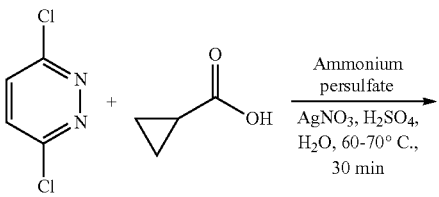

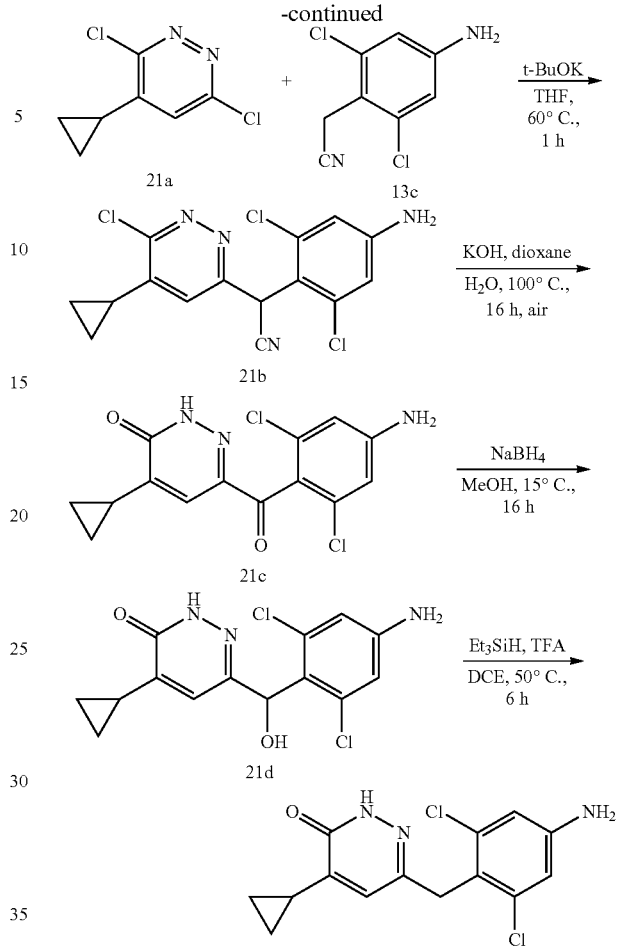

3,6-dichloro-4-cyclopropylpyridazine (21a)

H$_2$SO$_4$ (9.88 g, 100.69 mmol) was added to a solution of 3,6-dichloropyridazine (5 g, 33.56 mmol), cyclopropanecarboxylic acid (2.89 g, 33.56 mmol) and AgNO$_3$ (5.70 g, 33.56 mmol) in H$_2$O (100 mL) at 60° C., then ammonium persulfate (22.98 g, 100.69 mmol) in H$_2$O (100 mL) was added to the mixture at 70° C., the resulting mixture was stirred at 70° C. for 30 minutes The mixture was extracted with ethyl acetate (100 mL*2), the combined organic phase was washed with brine (100 mL), dried over Na$_2$SO$_4$, filtered and concentrated, the residue was purified by MPLC (silica gel, petroleum ether:ethyl acetate=5:1) to give 21a. $^1$HNMR (400 MHz, CD$_3$Cl) δ 6.94 (s, 1H), 2.27-2.14 (m, 1H), 1.37-1.23 (m, 2H), 0.91-0.77 (m, 2H).

2-(4-amino-2,6-dichlorophenyl)-2-(6-chloro-5-cyclopropylpyridazin-3-yl)acetonitrile (21b)

To a solution of 3,6-dichloro-4-cyclopropylpyridazine (21a) (0.4 g, 2.12 mmol) and 2-(4-amino-2,6-dichlorophenyl)acetonitrile (13c) (467.96 mg, 2.33 mmol) in THF (10 mL) was added t-BuOK (1 M, 4.23 mL) drop wise at 60° C., the resulting mixture was stirred at 60° C. for 40 minutes. After cooling, the mixture was diluted with ethyl acetate (20 mL), washed with brine (20 mL), the organic phase was dried over Na$_2$SO$_4$, filtered and concentrated, the residue was purified by silica gel chromatography (petroleum ether: ethyl acetate=2:1) to give 21b. ¹H NMR (400 MHz, DMSO-d₆) δ 7.00 (s, 1H), 6.71-6.68 (m, 2H), 6.46 (s, 1H), 6.02 (s, 2H), 2.22-2.14 (m, 1H), 1.25-1.19 (m, 2H), 0.88-0.75 (m, 2H).

6-(4-amino-2,6-dichlorobenzoyl)-4-cyclopropylpyridazin-3(2H)-one (21c)

To a solution of 2-(4-amino-2,6-dichlorophenyl)-2-(6-chloro-5-cyclopropylpyridazin-3-yl)acetonitrile (21b) (365 mg, 1.03 mmol) in dioxane (5 mL) and H₂O (10 mL) was added KOH (1.16 g, 20.64 mmol). The mixture was stirred at 100° C. for 16 hours under O2. LCMS showed one main peak with the desired MS. The reaction mixture was concentrated under reduced pressure to remove dioxane. The residue was diluted with aqueous HCl 2M to adjust the pH=5-7 and extracted with EtOAc (20 mL*4). The combined organic layers were washed with brine 20 mL, dried over anhydrous Na₂SO₄, filtered and concentrated under reduced pressure to give 21c. MS mass calculated for [M+1]⁺ (C₁₄H₁₁Cl₂N₃O₂) required m/z 324.0, LCMS found m/z 324.1.

6-((4-amino-2,6-dichlorophenyl)(hydroxy)methyl)-4-cyclopropylpyridazin-3(2H)-one (21d)

To a solution of 6-(4-amino-2,6-dichlorobenzoyl)-4-cyclopropylpyridazin-3(2H)-one (21c) (100 mg, 308.49 umol) in MeOH (5 mL) was added NaBH₄ (116.70 mg, 3.08 mmol) at 0° C. The mixture was stirred at 15° C. for 16 hours. LCMS detected the desired MS. The reaction mixture was concentrated under reduced pressure to remove MeOH. The residue was diluted with water (5 mL) and extracted with EtOAc (10 mL*3). The combined organic layers were washed with brine (5 mL), dried over anhydrous Na₂SO₄, filtered and concentrated under reduced pressure to give a residue. The residue was purified by prep-TLC (SiO₂, ethyl acetate:petroleum ether=2:1, TLC) to give 21d. MS mass calculated for [M+1]⁺ (C₁₄H₁₃Cl₂N₃O₂) required m/z 326.1, LCMS found m/z 326.1; ¹H NMR (400 MHz, DMSO-d6) (12.58 (s, 1H), 7.16 (s, 1H), 6.54 (s, 2H), 6.07-6.05 (m, 1H), 6.02-6.00 (m, 1H), 5.64 (s, 2H), 2.12-2.07 (m, 1H), 1.01 (br dd, J 2.8, 8.5 Hz, 2H), 0.81 (br t, J 6.0 Hz, 2H).

6-(4-amino-2,6-dichlorobenzyl)-4-cyclopropylpyridazin-3(2H)-one (21e)

To a solution of 6-((4-amino-2,6-dichlorophenyl)(hydroxy)methyl)-4-cyclopropylpyridazin-3(2H)-one (21d) (50 mg, 153.29 umol) in TFA (1 mL) and DCE (5 mL) was added Et₃SiH (89.12 mg, 766.46 umol). The mixture was stirred at 50° C. for 6 hours. LCMS showed one main peak the desired MS. The reaction mixture was diluted with saturated NaHCO₃(5 mL) and extracted with DCM (10 mL*2). The combined organic layers were washed with brine (5 mL), dried over anhydrous Na₂SO₄, filtered and concentrated under reduced pressure to give a residue. The residue was purified by prep-TLC (SiO₂, ethyl acetate: petroleum ether=2:1; TLC) to give 21e. MS mass calculated for [M+1]⁺ (C₁₄H₁₃Cl₂N₃O) required m/z 310.0, LCMS found m/z 310.1; 1H NMR (400 MHz, CDCl₃) δ 10.39 (br s, 2H), 6.68 (s, 2H), 6.64 (s, 1H), 4.10 (s, 2H), 2.19-2.14 (m, 1H), 1.12-1.06 (m, 2H), 0.85-0.79 (m, 2H).

Example 21: N-(3,5-dichloro-4-((5-cyclopropyl-6-oxo-1,6-dihydropyridazin-3-yl)methyl)phenyl)-5-oxo-4,5-dihydro-1,2,4-oxadiazole-3-carboxamide

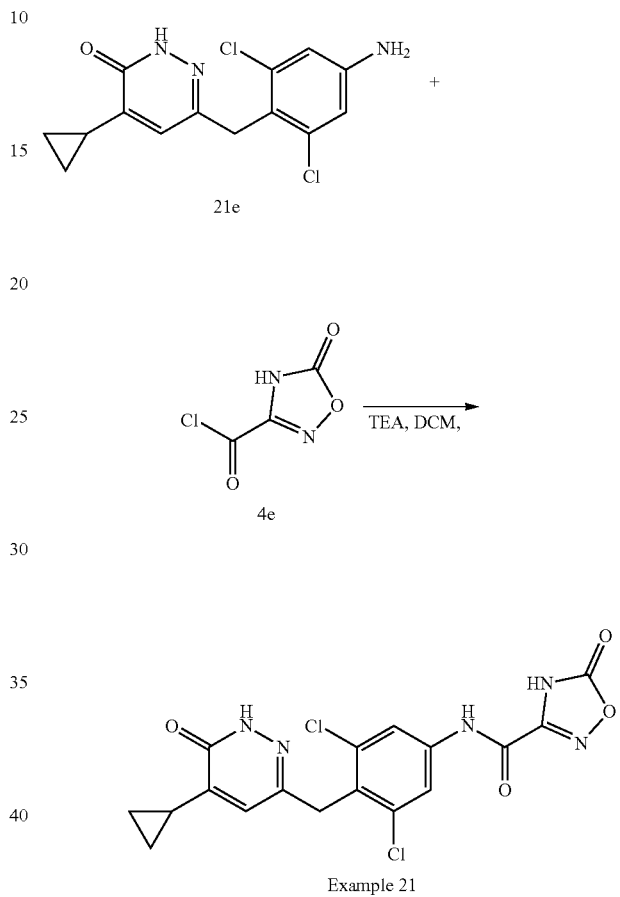

Example 21

N-(3,5-dichloro-4-((5-cyclopropyl-6-oxo-1,6-dihydropyridazin-3-yl)methyl)phenyl)-5-oxo-4,5-dihydro-1,2,4-oxadiazole-3-carboxamide (Example 21)

To a solution of 6-(4-amino-2,6-dichlorobenzyl)-4-cyclopropylpyridazin-3(2H)-one (21e) (16 mg, 51.58 umol) in DCM (2 mL) was added TEA (15.66 mg, 154.75 umol) and 5-oxo-4H-1,2,4-oxadiazole-3-carbonyl chloride (4e) (11.49 mg, 77.37 umol). The mixture was stirred at 25° C. for 0.5 hours. LCMS showed the desired MS. The reaction mixture was concentrated under reduced pressure to give a residue. The residue was purified by prep-HPLC (column: Xtimate C18 150*25 mm*5 um; mobile phase: [water (10 mM NH₄HCO₃)-ACN]; B %: 20%-40%, 10 min) to give Example 21. MS mass calculated for [M+1]⁺ (C₁₇H₁₃Cl₂N₅O₄) required m/z 422.0, LCMS found m/z 422.0; ¹H NMR (400 MHz, CD₃OD) δ 7.86 (s, 2H), 6.88 (s, 1H), 4.23 (s, 2H), 2.15-2.06 (m, 1H), 1.10-1.04 (m, 2H), 0.85-0.79 (m, 2H).

133

Example 22: N-(3,5-dichloro-4-((5-cyclopropyl-1-methyl-6-oxo-1,6-dihydropyridazin-3-yl)methyl)phenyl)-5-oxo-4,5-dihydro-1,2,4-oxadiazole-3-carboxamide

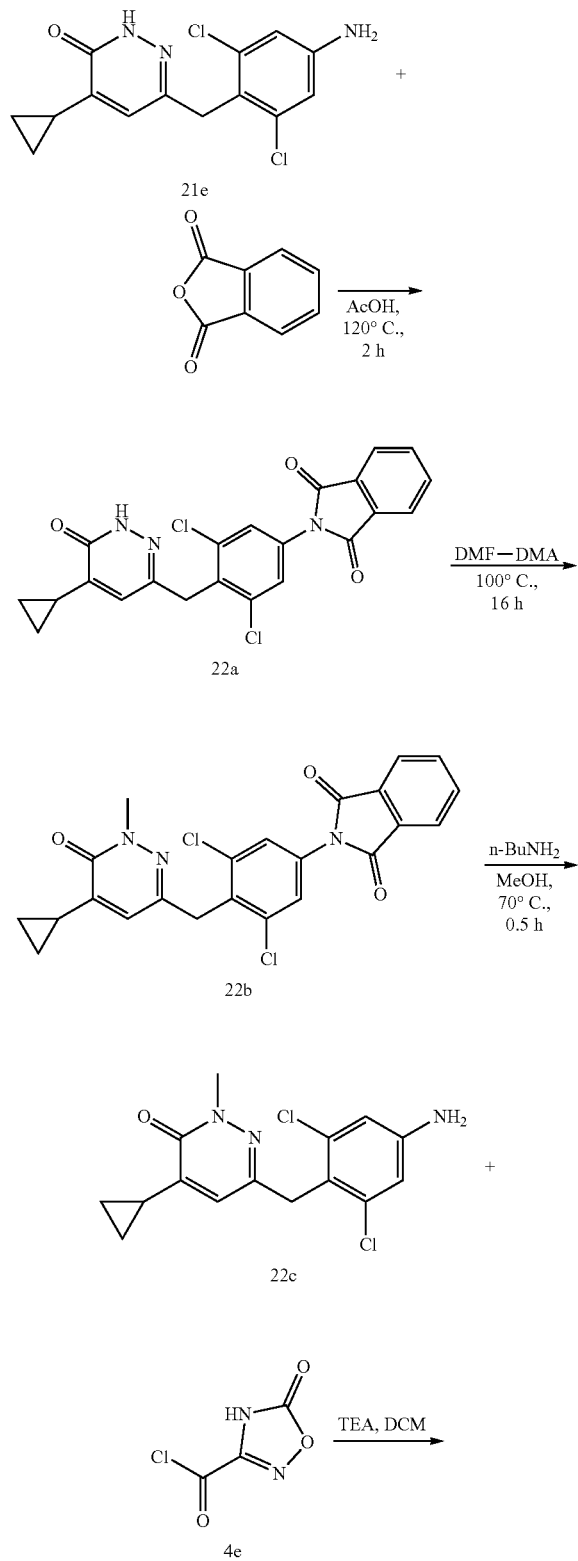

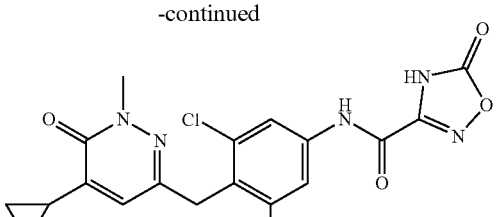

Example 22

2-(3,5-dichloro-4-((5-cyclopropyl-6-oxo-1,6-dihydropyridazin-3-yl)methyl)phenyl)isoindoline-1,3-dione (22a)

To a solution of 6-(4-amino-2,6-dichlorobenzyl)-4-cyclopropylpyridazin-3(2H)-one (21e) (44 mg, 141.85 umol) in AcOH (3 mL) was added isobenzofuran-1,3-dione (22.06 mg, 148.95 umol). The mixture was stirred at 120° C. for 2 hours. TLC showed one new spot was formed. The reaction mixture was concentrated under reduced pressure to remove AcOH. The residue was diluted with water 2 mL and added saturated aqueous NaHCO$_3$ to modified pH=9-10. The suspension was extracted with EtOAc 20 mL (5 mL*4), the combined organic layers were dried over anhydrous Na$_2$SO$_4$, filtered and concentrated under reduced pressure to give 22a was used into the next step without further purification as light yellow oil. MS mass calculated for [M+1]$^+$ (C$_{22}$H$_{15}$Cl$_2$N$_3$O$_3$) required m/z 440.1, LCMS found m/z 440.1.

2-(3,5-dichloro-4-((5-cyclopropyl-1-methyl-6-oxo-1,6-dihydropyridazin-3-yl)methyl)phenyl)isoindoline-1,3-dione (22b)

A solution of 2-(3,5-dichloro-4-((5-cyclopropyl-6-oxo-1,6-dihydropyridazin-3-yl)methyl)phenyl)isoindoline-1,3-dione (22a) (70 mg, 158.99 umol) in DMF-DMA (5 mL) was degassed and purged with N$_2$ for 3 times, and then the mixture was stirred at 100° C. for 3 hr under N$_2$ atmosphere. LCMS showed 22a was consumed completely and one main peak with the desired MS. The reaction mixture was concentrated under reduced pressure to remove DMF-DMA, and then the mixture was to give a residue. The residue was diluted with H$_2$O 5 mL and extracted with EtOAc 20 mL (5 mL*4). The combined organic layers were washed with brine 5 mL, dried over anhydrous Na$_2$SO$_4$, filtered and concentrated under reduced pressure to give 22b was used into the next step without further purification as a light yellow gum. MS mass calculated for [M+1]$^+$ (C$_{23}$H$_{17}$Cl$_2$N$_3$O$_3$) required m/z 454.1, LCMS found m/z 454.0.

6-(4-amino-2,6-dichlorobenzyl)-4-cyclopropyl-2-methylpyridazin-3(2H)-one (22c)

To a solution of 2-(3,5-dichloro-4-((5-cyclopropyl-1-methyl-6-oxo-1,6-dihydropyridazin-3-yl)methyl)phenyl)isoindoline-1,3-dione (22b) (100 mg, 154.08 umol) in MeOH (3 mL) was added N-butylamine (33.81 mg, 462.24 umol). The mixture was stirred at 70° C. for 0.5 hr. LCMS detected the desired MS. The reaction mixture was concentrated under reduced pressure to remove solvent. The residue was purified by prep-TLC (SiO$_2$, petroleum ether:ethyl acetate; TLC) to give 22c. MS mass calculated for [M+1]$^+$ (C$_{15}$H$_{15}$Cl$_2$N$_5$O) required m/z 324.1, LCMS found m/z 324.0; $^1$H NMR (400 MHz, CDCl$_3$) (6.70-6.65 (m, 2H), 6.48 (s, 1H), 4.07 (s, 2H), 3.79 (br s, 2H), 3.74 (s, 3H), 2.24-2.13 (m, 1H), 1.07-0.99 (m, 2H), 0.75-0.66 (m, 2H).

N-(3,5-dichloro-4-((5-cyclopropyl-1-methyl-6-oxo-1,6-dihydropyridazin-3-yl)methyl)phenyl)-5-oxo-4,5-dihydro-1,2,4-oxadiazole-3-carboxamide (Example 22)

To a solution of 6-(4-amino-2,6-dichlorobenzyl)-4-cyclopropyl-2-methylpyridazin-3(2H)-one (22c) (10 mg, 30.84 umol) in DCM (2 mL) was added TEA (9.36 mg, 92.53 umol, 12.88 uL) and 5-oxo-4H-1,2,4-oxadiazole-3-carbonyl chloride (4e) (6.87 mg, 46.27 umol). The mixture was stirred at 25° C. for 0.5 hours. LCMS showed the desired MS. The reaction mixture was concentrated under reduced pressure to give a residue. The residue was checked by HPLC and purified by prep-HPLC (column: Waters Xbridge 150*25 5 u; mobile phase: [water (10 mM NH$_4$HCO$_3$)-ACN]; B %: 5%-35%, 14 min) to give Example 22 as a white solid. MS mass calculated for [M+1]$^+$ (C$_{18}$H$_{15}$Cl$_2$N$_5$O$_4$) required m/z 436.0, LCMS found m/z 436.0; $^1$H NMR (400 MHz, CD$_3$OD) δ 7.87 (s, 2H), 6.85 (s, 1H), 4.24 (s, 2H), 3.65 (s, 3H), 2.20-2.09 (m, 1H), 1.11-1.04 (m, 2H), 0.83-0.75 (m, 2H).

Example 23: N-(3,5-dichloro-4-((5-isopropyl-6-oxo-1,6-dihydropyridazin-3-yl)methyl)phenyl)-5-oxo-4,5-dihydro-1,2,4-oxadiazole-3-carboxamide

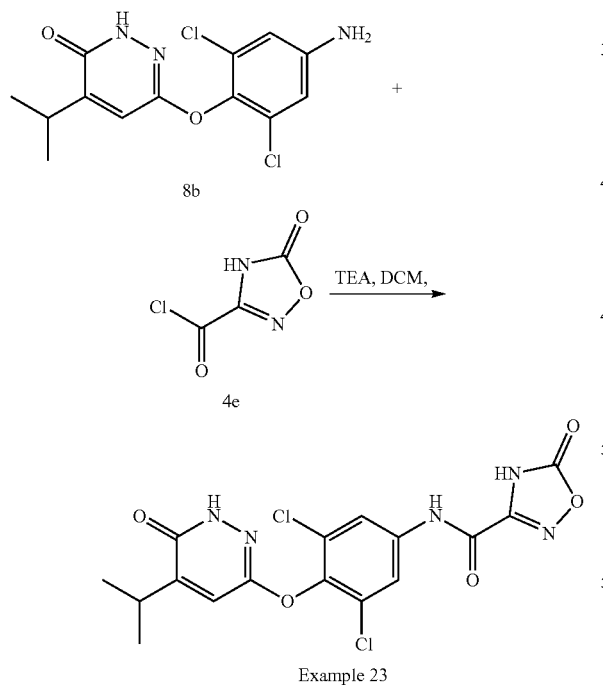

N-(3,5-dichloro-4-((5-isopropyl-6-oxo-1,6-dihydropyridazin-3-yl)oxy)phenyl)-5-oxo-4,5-dihydro-1,2,4-oxadiazole-3-carboxamide (Example 23)

To a solution of 3-(4-amino-2,6-dichloro-phenoxy)-5-isopropyl-1H-pyridazin-6-one(8b) (13.7 g, 43.61 mmol) in THF (140 mL) was added TEA (13.24 g, 130.82 mmol) and 5-oxo-4H-1,2,4-oxadiazole-3-carbonyl chloride (4e) (9.71 g, 65.41 mmol). The mixture was stirred at 20° C. for 0.5 hours. LCMS showed a peak with the desired MS. The reaction mixture was concentrated under reduced pressure to give a crude product. The crude product was triturated with EtOAc (100 mL) at 80° C. for 30 min, and then cooled to 20° C. The suspension was filtered and filter cake was washed with EtOAc (5 mL*3) and concentrated to dryness to give Example 23. MS mass calculated for [M+1]$^+$ (C$_{16}$H$_{13}$Cl$_2$N$_5$O$_5$) required m/z 426.0, LCMS found m/z 426.0; $^1$H NMR (400 MHz, CD$_3$OD) δ 7.92 (s, 2H), 7.33 (d, J=0.9 Hz, 1H), 3.21-3.13 (m, 1H), 1.29 (d, J=6.8 Hz, 6H).

Example 24: N-(6-chloro-7-((5-isopropyl-1-methyl-6-oxo-1,6-dihydropyridazin-3-yl)oxy)-2,3-dihydro-1H-inden-4-yl)-5-oxo-4,5-dihydro-1,2,4-oxadiazole-3-carboxamide

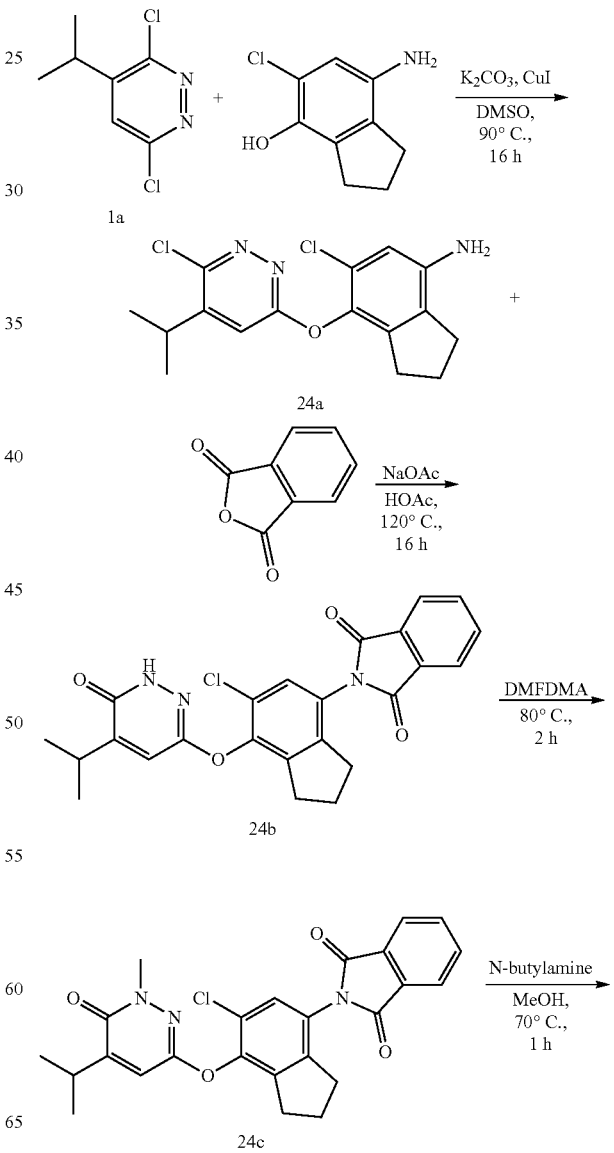

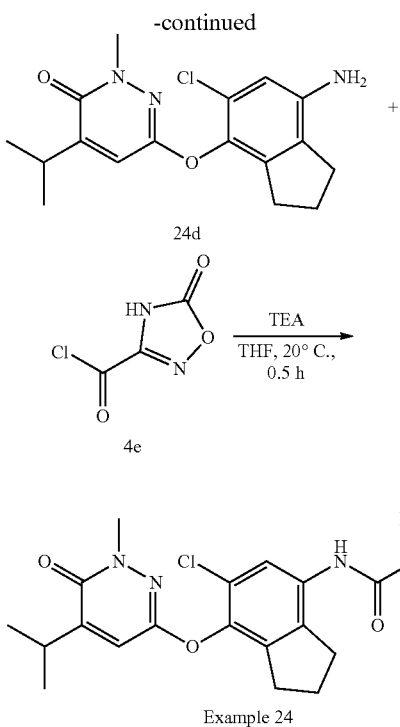

6-chloro-7-(6-chloro-5-isopropyl-pyridazin-3-yl)oxy-indan-4-amine (24a)

7-amino-5-chloro-indan-4-ol (0.39 g, 2.12 mmol), 3,6-dichloro-4-isopropyl-pyridazine (1a) (405.77 mg, 2.12 mmol), CuI (40.45 mg, 212.38 umol) and $K_2CO_3$ (440.28 mg, 3.19 mmol) in DMA (15 mL) was de-gassed with $N_2$ and then heated to 100° C. for 16 hours under $N_2$. LCMS showed the reaction was completed, and desired MS was detected. The mixture was filtered through a pad of celite, washed with ethyl acetate (20 mL*2). The combined organic phase was washed with brine (20 mL), dried over $Na_2SO_4$, filtered and concentrated. The residue was purified by silica gel chromatography (petroleum ether:ethyl acetate=3:1) to give 24a. MS mass calculated for [M+1]$^+$ ($C_{16}H_{17}Cl_2N_3O$) required m/z 338.1, LCMS found m/z 338.1. $^1$HNMR (400 MHz, DMSO-d6) δ 7.53 (s, 1H), 6.56 (s, 1H), 5.15 (br s, 2H), 3.14 (td, J=6.8, 13.6 Hz, 1H), 2.68 (br t, J=7.3 Hz, 2H), 2.60 (br t, J=7.4 Hz, 2H), 2.03-1.95 (m, 2H), 1.27 (d, J=6.7 Hz, 6H).

2-[6-chloro-7-[(5-isopropyl-6-oxo-1H-pyridazin-3-yl)oxy]indan-4-yl]isoindoline-1,3-dione (24b)

To a mixture of 6-chloro-7-(6-chloro-5-isopropyl-pyridazin-3-yl)oxy-indan-4-amine (24a) (120 mg, 354.79 umol) and isobenzofuran-1,3-dione (52.55 mg, 354.79 umol) in NaOAc (101.87 mg, 1.24 mmol) was added AcOH (1 mL). The mixture was stirred at 120° C. for 16 hours. The reaction mixture was concentrated under reduced pressure to remove AcOH. The solid was dissolved in water and the pH was adjusted to 9 with $NaHCO_3$(10 mL). Then the mixture was partitioned with Ethyl acetate (30 mL). Twice. The combined organic phase was washed with brine (10 mL*3), dried with anhydrous $Na_2SO_4$, filtered and concentrated in vacuum to give 24b. The product was used directly in next step without further purification. MS mass calculated for [M+1]$^+$ ($C_{24}H_{20}ClN_3O_4$) required m/z 450.1, LCMS found m/z 450.2.

2-[6-chloro-7-(5-isopropyl-1-methyl-6-oxo-pyridazin-3-yl)oxy-indan-4-yl]isoindoline-1,3-dione (24c)

A solution of 2-[6-chloro-7-[(5-isopropyl-6-oxo-1H-pyridazin-3-yl)oxy]indan-4-yl]isoindoline-1,3-dione (24b) (150 mg, 333.42 umol) in DMFDMA (2 mL) was stirred at 80° C. for 2 hours. The mixture was concentrated in vacuum. The residue was partitioned between ethyl acetate 10 mL and $H_2O$ 3 mL twice. The combined filtrate was washed with brine (20 mL), and the organic phase was concentrated to give 24c, the crude product was used for the next step directly. MS mass calculated for [M+1]$^+$ ($C_{25}H_{22}ClN_3O_4$) required m/z 464.1, LCMS found m/z 464.2.

6-(7-amino-5-chloro-indan-4-yl)oxy-4-isopropyl-2-methyl-pyridazin-3-one (24d)

A mixture of 2-[6-chloro-7-(5-isopropyl-1-methyl-6-oxo-pyridazin-3-yl)oxy-indan-4-yl]isoindoline-1,3-dione (24c) (100 mg, 215.56 umol) and N-butylamine (15.77 mg, 215.56 umol) in MeOH (2 mL) was stirred at 25° C. for 1 hour. The mixture was concentrated in vacuum. The residue was purified by prep-TLC ($SiO_2$, petroleum ether/ethyl acetate=1:1) to give 24d. MS mass calculated for [M+1]$^+$ ($C_{17}H_{20}ClN_3O_2$) required m/z 334.1, LCMS found m/z 334.1.

N-(6-chloro-7-((5-isopropyl-1-methyl-6-oxo-1,6-dihydropyridazin-3-yl)oxy)-2,3-dihydro-1H-inden-4-yl)-5-oxo-4,5-dihydro-1,2,4-oxadiazole-3-carboxamide (Example 24)

To a solution of 24d (10 mg, 29.96 umol, 1 eq) in THF (5 mL) was added TEA (9.09 mg, 89.87 umol, 12.51 uL) and 5-oxo-4H-1,2,4-oxadiazole-3-carbonyl chloride (4e) (6.67 mg, 44.94 umol). The mixture was stirred at 25° C. for 0.5 hours. The reaction mixture was quenched by addition MeOH (1 mL) at 25° C., and then concentrated under reduced pressure to give a residue. The residue was checked by HPLC and then was purified by Prep-HPLC (column: Luna C18 100*30 5 u; mobile phase: [water (0.04% HCl)-ACN]; B %: 35%-60%, 12 min) to give Example 24. MS mass calculated for [M+1]$^+$ ($C_{20}H_{20}ClN_5O_5$) required m/z 446.1, LCMS found m/z 446.2; $^1$H NMR (400 MHz, $CD_3OD$) δ 7.55 (s, 1H), 7.27 (s, 1H), 3.50 (s, 3H), 3.20-3.12 (m, 1H), 2.94 (br t, J=7.4 Hz, 2H), 2.87 (br t, J=7.3 Hz, 2H), 2.17-2.12 (m, 2H), 1.27 (d, J=6.8 Hz, 6H).

Example 25: N-(3,5-dichloro-4-((5-cyclopropyl-6-oxo-1,6-dihydropyridazin-3-yl)oxy)phenyl)-5-oxo-4,5-dihydro-1,2,4-oxadiazole-3-carboxamide

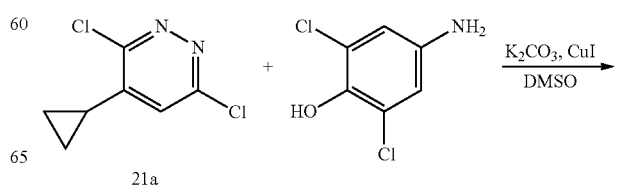

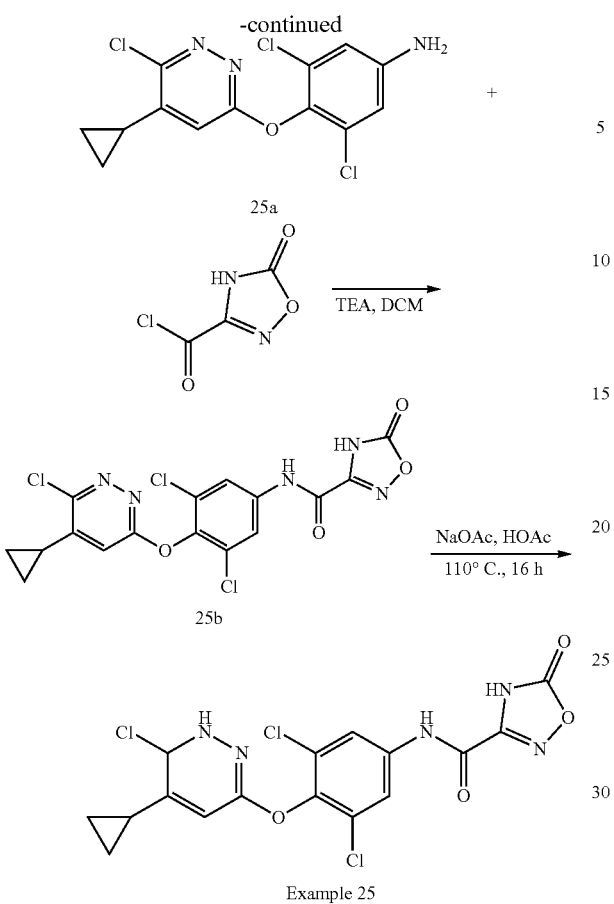

25a

25b

Example 25

3,5-dichloro-4-((6-chloro-5-cyclopropylpyridazin-3-yl)oxy)aniline (25a)

3,6-dichloro-4-cyclopropyl-pyridazine (1 g, 5.29 mmol) (21a), 4-amino-2,6-dichloro-phenol (941.67 mg, 5.29 mmol), $K_2CO_3$ (1.10 g, 7.93 mmol) and CuI (201.49 mg, 1.06 mmol) in DMA (5 mL) was de-gassed and then heated to 100° C. for 16 hours under $N_2$. Solids were filtered off and to the filtrate was added water (20 mL) and was extracted with ethyl acetate (15 mL*2). The combined organic layers were washed with brine (20 mL), dried over $Na_2SO_4$, filtered and concentrated. The residue was purified by silica gel chromatography (petroleum ether:ethyl acetate=5:1) to give 25a. MS mass calculated for $[M+1]^+$ ($C_{13}H_{10}Cl_3N_3O$) required m/z 330.0, LCMS found m/z 329.9/331.9;

N-(3,5-dichloro-4-((5-cyclopropyl-6-oxo-1,6-dihydropyridazin-3-yl)oxy)phenyl)-5-oxo-4,5-dihydro-1,2,4-oxadiazole-3-carboxamide (25b)

To a solution of 5-oxo-4,5-dihydro-1,2,4-oxadiazole-3-carboxylic acid (11.80 mg, 90.75 umo) in THF (2 mL) was added one drop DMF, then $(COCl)_2$ (11.52 mg, 90.75 umol, 7.94 uL, 1.5 eq) was added at 0° C., the mixture was stirred at 25° C. for 1 hour, the solution was added to a mixture of 3,5-dichloro-4-((6-chloro-5-cyclopropylpyridazin-3-yl)oxy) aniline (25a) (20 mg, 60.50 umol) and TEA (18.37 mg, 181.50 umol, 25.26 uL) in DCM (3 mL) at 25° C., the resulting mixture was stirred at 25° C. for 30 minutes. The mixture was concentrated, the residue was purified by prep-TLC (dichloromethane:methanol=10:1) to give 25b. MS mass calculated for $[M+1]^+$ ($C_{16}H_{10}Cl_3N_5O_4$) required m/z 442.0, LCMS found m/z 442.0.

N-(3,5-dichloro-4-((5-cyclopropyl-6-oxo-1,6-dihydropyridazin-3-yl)oxy)phenyl)-5-oxo-4,5-dihydro-1, 2,4-oxadiazole-3-carboxamide (Example 25)

A mixture of N-(3,5-dichloro-4-((6-chloro-5-cyclopropylpyridazin-3-yl)oxy)phenyl)-5-oxo-4,5-dihydro-1,2,4-oxadiazole-3-carboxamide (25b) (30 mg, 67.78 umol) and NaOAc (33.36 mg, 406.65 umol) in HOAc (3 mL) was heated to 110° C. for 16 hours. The mixture was concentrated. —The residue was purified by prep-HPLC (neutral) to give Example 25. MS mass calculated for $[M+1]^+$ ($C_{16}H_{11}Cl_2N_5O_5$) required m/z 424.2, LCMS found m/z 424.2; $^1$H NMR (400 MHz, MeOD) δ 7.92 (s, 2H), 7.03 (s, 1H), 2.28-2.18 (m, 1H), 1.23-1.14 (m, 2H), 1.04-0.94 (m, 2H).

Example 26: N-(3,5-dichloro-2-fluoro-4-((5-isopropyl-1-methyl-6-oxo-1,6-dihydropyridazin-3-yl)oxy) phenyl)-5-oxo-4,5-dihydro-1,2,4-oxadiazole-3-carboxamide

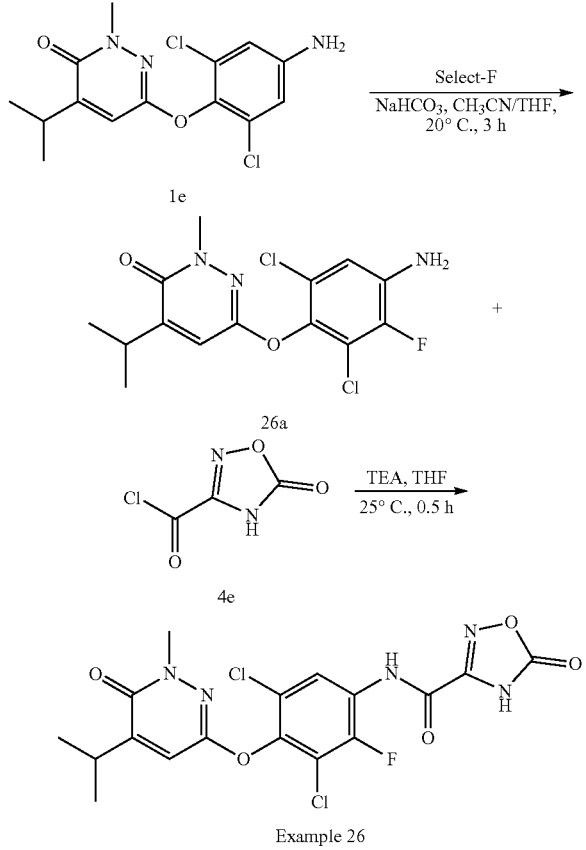

1e

26a

4e

Example 26

6-(4-amino-2,6-dichloro-3-fluorophenoxy)-4-isopropyl-2-methylpyridazin-3(2H)-one (26a)

To a suspension of 6-(4-amino-2,6-dichloro-phenoxy)-4-isopropyl-2-methyl-pyridazin-3-one (1e) (20 g, 60.94 mmol) in CH$_3$CN (200 mL) and THF (60 mL) under a nitrogen atmosphere was added NaHCO$_3$(15.36 g, 182.82 mmol). To the resulting solution was added Select F (21.59 g, 60.94 mmol) by portion wise addition over 30 min. The mixture was stirred at 20° C. for 16 hours. The reaction mixture was partitioned between H$_2$O 200 mL and EtOAc 300 mL. The organic phase was separated, washed with brine (100 mL), dried over Na$_2$SO$_4$, filtered and concentrated under reduced pressure to give a residue. The residue was purified by column chromatography (SiO$_2$, petroleum ether/ethyl acetate=4/1 to 1/1; TLC) to give 26a. MS mass calculated for [M+1]$^+$ (C$_{14}$H$_{14}$Cl$_2$FN$_3$O$_2$) required m/z 346.0, LCMS found m/z 346.0; $^1$HNMR (400 MHz, CDCl$_3$) δ 7.02 (s, 1H), 6.80 (d, J=8.8 Hz, 1H), 3.89 (br s, 2H), 3.53 (s, 3H), 3.24 (quind, J=6.8, 13.5 Hz, 1H), 1.26 (d, J=6.8 Hz, 6H).

N-(3,5-dichloro-2-fluoro-4-((5-isopropyl-1-methyl-6-oxo-1,6-dihydropyridazin-3-yl)oxy)phenyl)-5-oxo-4,5-dihydro-1,2,4-oxadiazole-3-carboxamide (Example 26)

To a solution of 6-(4-amino-2,6-dichloro-3-fluoro-phenoxy)-4-isopropyl-2-methyl-pyridazin-3-one (26a) (13 g, 37.55 mmol) in THF (130 mL) was added TEA (11.40 g, 112.66 mmol) and 5-oxo-4H-1,2,4-oxadiazole-3-carbonyl chloride (4e) (8.37 g, 56.33 mmol). The mixture was stirred at 20° C. for 0.5 hours. LCMS showed a peak with the desired MS. The mixture was diluted with 1M HCl to modified pH 6-7 and extracted with EtOAc 300 mL (100 mL*3). The combined organic layers were washed with brine 150 mL, dried over anhydrous Na$_2$SO$_4$, filtered to give a light yellow liquid The light yellow liquid was concentrated under reduced pressure to remove solvent and until the solid was dissolved out. The mixture was stirred at 20° C. for 1 hour and filtered to give Example 26. MS mass calculated for [M+1]$^+$ (C$_{17}$H$_{14}$Cl$_2$FN$_5$O$_5$) required m/z 458.0, LCMS found m/z 458.0; $^1$H NMR (400 MHz, CD$_3$OD) δ 8.30 (d, J=7.5 Hz, 1H), 7.35 (s, 1H), 3.51 (s, 3H), 3.24-3.12 (m, 1H), 1.28 (d, J=6.8 Hz, 6H).

Example 27: 3-(((3,5-dichloro-2-fluoro-4-((5-isopropyl-1-methyl-6-oxo-1,6-dihydropyridazin-3-yl)oxy)phenyl)amino)methyl)-1,2,4-oxadiazol-5(4H)-one

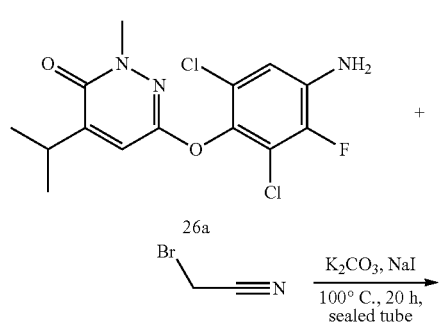

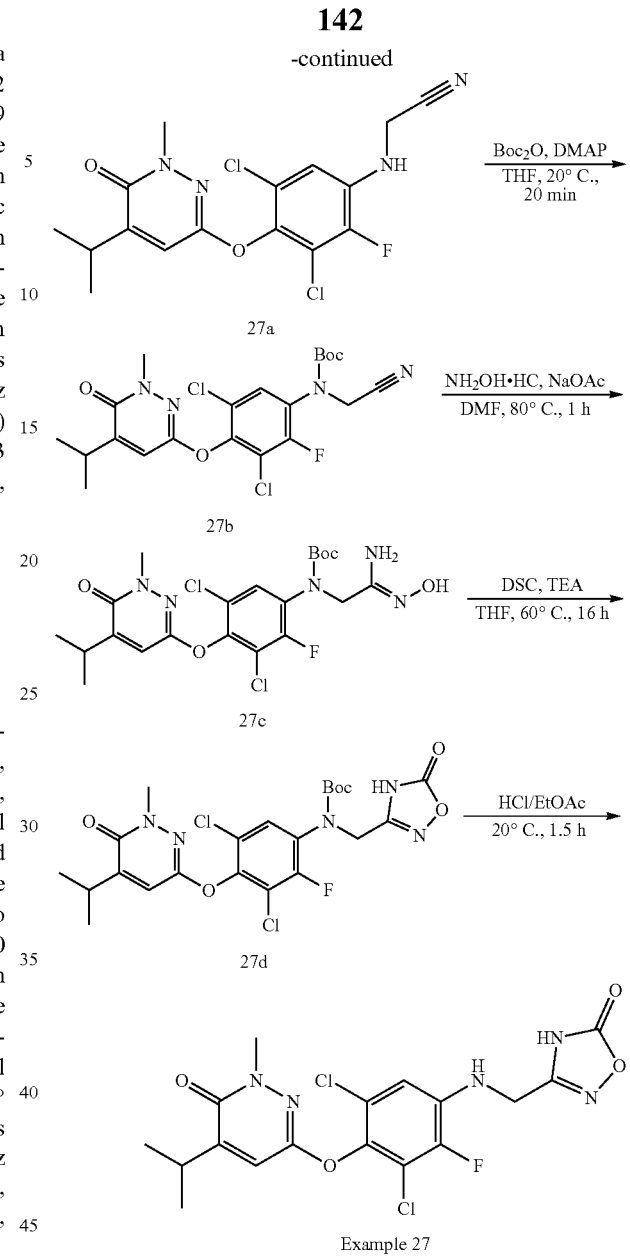

2-((3,5-dichloro-2-fluoro-4-((5-isopropyl-1-methyl-6-oxo-1,6-dihydropyridazin-3-yl)oxy)phenyl)amino)acetonitrile (27a)

To a solution of 6-(4-amino-2,6-dichloro-3-fluorophenoxy)-4-isopropyl-2-methylpyridazin-3(2H)-one (26a) (20 mg, 57.77 umol) in ACN (2 mL) was added 2-bromoacetonitrile (52.26 mg, 435.72 umol, 29.03 uL), K$_2$CO$_3$ (24.09 mg, 174.29 umol) and NaI (26.12 mg, 174.29 umol). The mixture was stirred at 100° C. for 20 hours. The suspension was filtered through a pad of Celite and the pad cake was washed with EtOAc (5 mL*3). The combined filtrates were concentrated to dryness to give a residue. The residue was purified by preparative TLC (petroleum ether:ethyl acetate=1:1) to give 27a. MS mass calculated for [M+1]$^+$ (C$_{16}$H$_{15}$Cl$_2$FN$_4$O$_2$) required m/z 385.2, LCMS found m/z 385.0; $^1$HNMR (400 MHz, CDCl$_3$) δ 7.04 (s, 1H) 6.81 (d, J=8.16 Hz, 1H) 4.38-4.50 (m, 1H) 4.21 (d, J=7.06 Hz, 2H) 3.54 (s, 3H) 3.24 (dt, J=13.62, 6.75 Hz, 1H) 1.26-1.28 (m, 6H).

tert-butyl (cyanomethyl)(3,5-dichloro-2-fluoro-4-((5-isopropyl-1-methyl-6-oxo-1,6-dihydropyridazin-3-yl)oxy)phenyl)carbamate (27b)

To a solution of 2-((3,5-dichloro-2-fluoro-4-((5-isopropyl-1-methyl-6-oxo-1,6-dihydropyridazin-3-yl)oxy)phenyl)amino)acetonitrile (27a) (20 mg, 51.92 umol) in THF (3 mL) was added DMAP (6.34 mg, 51.92 umol) and Boc$_2$O (33.99 mg, 155.76 umol, 35.78 uL) at 20° C. The mixture was stirred at 20° C. for 20 minutes. The mixture was concentrated in vacuum to give a residue. The residue was purified by prep-TLC (SiO$_2$, petroleum ether:ethyl acetate=2:1) to give 27b. MS mass calculated for [M+1]$^+$ (C$_{21}$H$_{23}$Cl$_2$FN$_4$O$_4$) required m/z 485.3, LCMS found m/z 485.2; $^1$H NMR (400 MHz, CDCl$_3$) δ 7.43 (br s, 1H) 7.07 (s, 1H) 4.52 (br s, 2H) 3.52 (s, 3H) 3.26 (dt, J 13.66, 6.92 Hz, 1H) 1.25-1.47 (m, 15H).

(Z)-tert-butyl (2-amino-2-(hydroxyimino)ethyl)(3,5-dichloro-2-fluoro-4-((5-isopropyl-1-methyl-6-oxo-1,6-dihydropyridazin-3-yl)oxy)phenyl)carbamate (27c)

To a solution of tert-butyl (cyanomethyl)(3,5-dichloro-2-fluoro-4-((5-isopropyl-1-methyl-6-oxo-1,6-dihydropyridazin-3-yl)oxy)phenyl)carbamate (27b) (20 mg, 41.21 umol) in DMF (2 mL) was added NH$_2$OH.HCl (22.91 mg, 329.67 umol) and NaOAc (27.04 mg, 329.67 umol) at 20° C. The mixture was stirred at 80° C. for 1 hour. The reaction mixture was concentrated under reduced pressure to remove DMF. The residue was partitioned between ethyl acetate 10 mL and H$_2$O 5 mL twice. The combined organic phase was washed with brine (5 mL*3), dried with anhydrous Na$_2$SO$_4$, filtered and concentrated in vacuum. The residue was purified by prep-TLC (SiO$_2$, petroleum ether:ethyl acetate=1:1) to give 27c. MS mass calculated for [M+1]$^+$ (C$_{21}$H$_{26}$Cl$_2$FN$_5$O$_5$) required m/z 518.4, LCMS found m/z 518.0.

tert-butyl (3,5-dichloro-2-fluoro-4-((5-isopropyl-1-methyl-6-oxo-1,6-dihydropyridazin-3-yl)oxy)phenyl)((5-oxo-4,5-dihydro-1,2,4-oxadiazol-3-yl)methyl)carbamate (27d)

To a solution of (Z)-tert-butyl (2-amino-2-(hydroxyimino)ethyl)(3,5-dichloro-2-fluoro-4-((5-isopropyl-1-methyl-6-oxo-1,6-dihydrop-yridazin-3-yl)oxy)phenyl)carbamate (27c) (20 mg, 38.58 umol) in THF (3 mL) was added DSC (12.85 mg, 50.16 umol) and TEA (7.81 mg, 77.17 umol, 10.74 uL). The mixture was stirred at 60° C. for 16 hours. The mixture was concentrated in vacuum to give a residue. The residue was purified by prep-TLC (SiO$_2$, DCM:MeOH=10:1, P1:R$_f$=0.3) to give 27d. MS mass calculated for [M+1]$^+$ (C$_{22}$H$_{24}$Cl$_2$FN$_5$O$_6$) required m/z 544.4, LCMS found m/z 544.0.

3-(((3,5-dichloro-2-fluoro-4-((5-isopropyl-1-methyl-6-oxo-1,6-dihydropyridazin-3-yl)oxy)phenyl)amino)methyl)-1,2,4-oxadiazol-5(4H)-one (Example 27)

A solution of tert-butyl (3,5-dichloro-2-fluoro-4-((5-isopropyl-1-methyl-6-oxo-1,6-dihydropyridazin-3-yl)oxy)phenyl)((5-oxo-4,5-dihydro-1,2,4-oxadiazol-3-yl)methyl)carbamate (27d) (8 mg, 14.70 umol) in HCl/EtOAc (2 mL) was stirred at 20° C. for 1.5 hours. The mixture was concentrated in vacuum to give a residue. The residue was purified by Prep-HPLC (column: Luna C18 100*30 5 u; mobile phase: [water (0.04% HCl)-ACN]; B %: 30%-60%, 12 min) to give Example 27. MS mass calculated for [M+1]$^+$ (C$_{17}$H$_{16}$Cl$_2$FN$_5$O$_4$) required m/z 444.2, LCMS found m/z 444.0; $^1$H NMR (400 MHz, CD$_3$OD) δ 7.27 (s, 1H) 6.91 (d, J=8.33 Hz, 1H) 4.38 (s, 2H) 3.49 (s, 3H) 3.13-3.21 (m, 1H) 1.26 (d, J=7.02 Hz, 6H).

Example 28: N-(4-((5-(tert-butyl)-6-oxo-1,6-dihydropyridazin-3-yl)oxy)-3,5-dichlorophenyl)-5-oxo-4,5-dihydro-1,2,4-oxadiazole-3-carboxamide

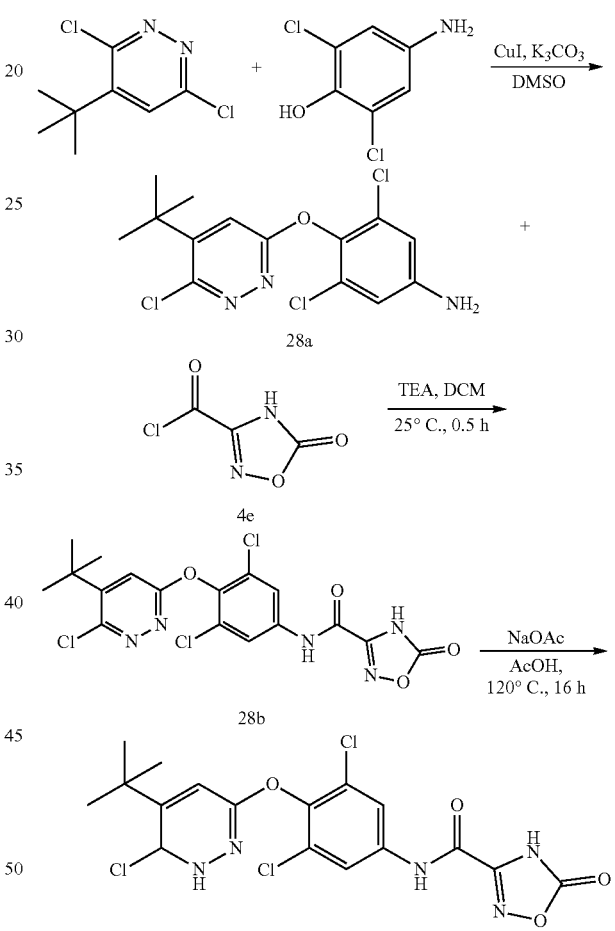

Example 28

4-((5-(tert-butyl)-6-chloropyridazin-3-yl)oxy)-3,5-dichloroaniline (28a)

To a solution of 4-(tert-butyl)-3,6-dichloropyridazine (200 mg, 0.975 mmol) in DMSO (5 mL) was added 4-amino-2,6-dichlorophenol (173.61 mg, 0.975 mmol), K$_2$CO$_3$ (404.34 mg, 2.93 mmol) and CuI (111.44 mg, 0.585 mmol), the mixture was stirred at 90° C. for 16 hours under N$_2$ atmosphere. The solvent was diluted with EtOAc (10 mL) and H$_2$O (10 mL), extracted with EA (10 mL*2), the organic layer was washed with brine (20 mL*2), dried over with Na$_2$SO$_4$, the organic layer was dried over with Na$_2$SO$_4$, concentrated in vacuo to get crude. The crude was purified with Prep-TLC (petroleum ether:ethyl acetate=5:1) to give 28a. MS mass calculated for [M+1]$^+$ (C$_{14}$H$_{14}$Cl$_3$N$_3$O) required m/z 346.6, LCMS found m/z 346.6; $^1$H NMR (400 MHz, CDCl$_3$) δ 1.51 (s, 9H), 6.67 (s, 2H), 7.24 (s, 1H).

N-(4-((5-(tert-butyl)-6-chloropyridazin-3-yl)oxy)-3,5-dichlorophenyl)-5-oxo-4,5-dihydro-1,2,4-oxadiazole-3-carboxamide (28b)

To a mixture of 4-((5-(tert-butyl)-6-chloropyridazin-3-yl)oxy)-3,5-dichloroaniline (28a) (100 mg, 288.48 mmol) in THF (2 mL), was added TEA (87.58 mg, 865.45 umol), 5-oxo-4,5-dihydro-1,2,4-oxadiazole-3-carbonyl chloride (4e) (64.26 mg, 432.73 umol) in DCM (2 mL) was added under N$_2$ atmosphere. The mixture was stirred at 20° C. under N$_2$ for 0.5 hours. The mixture was poured into H$_2$O (10 mE) and the resulting mixture was extracted with EtOAc (10 mL*3), the organic layer was washed with brine (20 mL*2), dried over with Na$_2$SO$_4$, filtrated, concentrated in vacuo to get crude 28c. The crude product was used for the next step without further purification. MS mass calculated for [M+1]$^+$ (C$_{17}$H$_{14}$Cl$_3$N$_5$O$_4$) required m/z 458.1, LCMS found m/z 458.1.

N-(4-((5-(tert-butyl)-6-oxo-1,6-dihydropyridazin-3-yl)oxy)-3,5-dichlorophenyl)-5-oxo-4,5-dihydro-1,2,4-oxadiazole-3-carboxamide (Example 28)

To a mixture of N-(4-((5-(tert-butyl)-6-chloropyridazin-3-yl)oxy)-3,5-dichlorophenyl)-5-oxo-4,5-dihydro-1,2,4-oxadiazole-3-carboxamide (140 mg, 305.2 umol) in HOAc (10 mL), was added NaOAc (125.19 mg, 1.53 mmol). Then the mixture was stirred at 120° C. for 16 hours. The solvent was removed in vacuo to get crude. The crude was purified with prep-HPLC (CH$_3$CN in H$_2$O, 40%). To get Example 28 (9.9 mg, 7.4% yield). MS mass calculated for [M+1]$^+$ (C$_{17}$H$_{15}$Cl$_2$N$_5$O$_5$) required m/z 440.2, LCMS found m/z 440.2; $^1$H NMR (400 MHz, CD$_3$OD) δ 1.44 (s, 9H), 7.32 (s, 1H), 7.92 (s, 2H).

Example 29 (P1 and P2): N-(3,5-dichloro-4-((5-(1-hydroxyethyl)-6-oxo-1,6-dihydropyridazin-3-yl)oxy)phenyl)-5-oxo-4,5-dihydro-1,2,4-oxadiazole-3-carboxamide

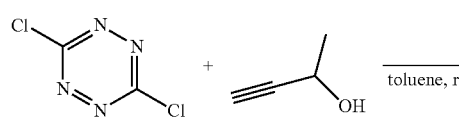

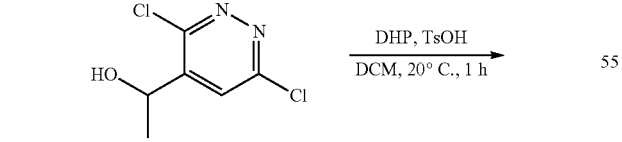

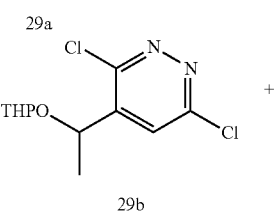

29b

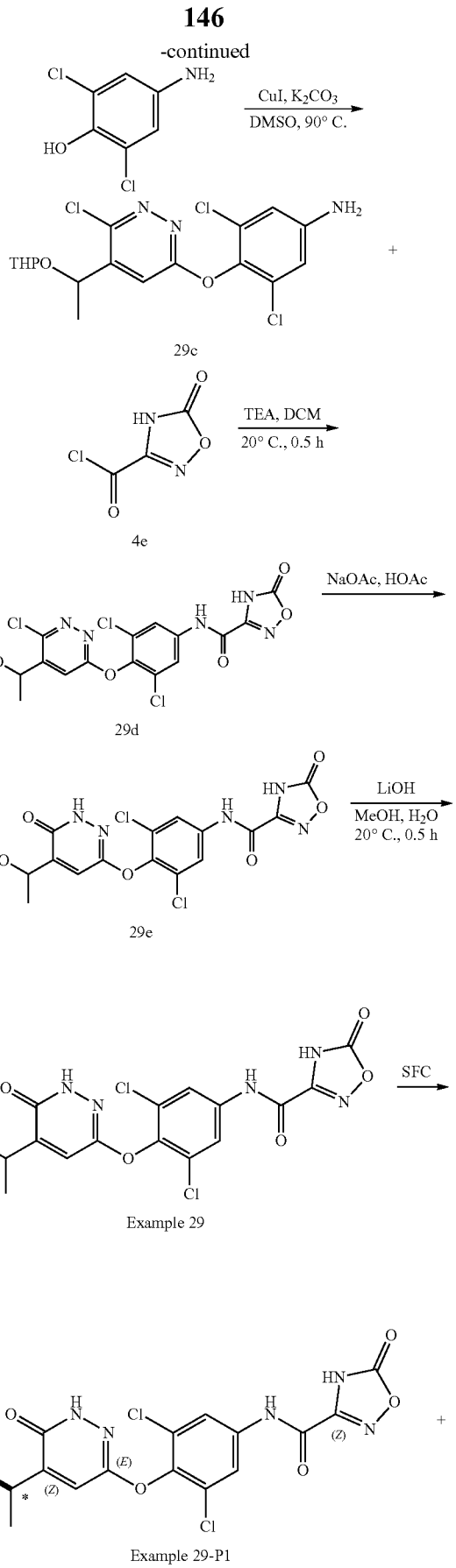

-continued

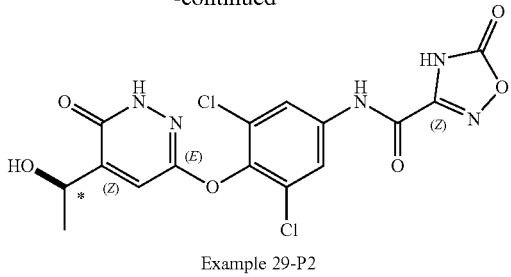

Example 29-P2

1-(3,6-dichloropyridazin-4-yl)ethanol (29a)

To a solution of 3,6-dichloro-1,2,4,5-tetrazine (500 mg, 3.31 mmol) in Tol. (3 mL) was added but-3-yn-2-ol (278.59 mg, 3.97 mmol). The mixture was stirred at 110° C. for 16 hours under sealed tube. The reaction mixture was concentrated under reduced pressure to give a residue. The residue was purified by prep-TLC (SiO$_2$, petroleum ether:ethyl acetate=1:1, TLC) to give 29a. $^1$H NMR (400 MHz, CDCl$_3$) δ 7.82 (d, J=1.0 Hz, 1H), 5.14 (dq, J=4.2, 6.3 Hz, 1H), 2.38 (d, J=3.4 Hz, 1H), 1.56 (d, J=6.4 Hz, 3H).

3,6-dichloro-4-(1-((tetrahydro-2H-pyran-2-yl)oxy)ethyl)pyridazine (29b)

To a solution of 1-(3,6-dichloropyridazin-4-yl)ethanol (29a) (300 mg, 1.55 mmol) and DHP (653.68 mg, 7.77 mmol, 710.52 uL) in DCM (10 mL) was added TsOH (13.38 mg, 77.71 umol). The mixture was stirred at 20° C. for 1 hour. The reaction mixture was concentrated under reduced pressure to give a residue. The residue was purified by prep-TLC (SiO$_2$, petroleum ether/ethyl acetate=5:1, according TLC) to give 29b. $^1$H NMR (400 MHz, CDCl$_3$) δ 7.77 (s, 1H), 7.63 (s, 1H), 5.10 (q, J=6.5 Hz, 1H), 4.98 (q, J=6.6 Hz, 1H), 4.81 (br d, J=4.6 Hz, 1H), 4.47 (br s, 1H), 3.99-3.90 (m, 1H), 3.67-3.53 (m, 2H), 3.47-3.40 (m, 1H), 1.95-1.55 (m, 12H), 1.53 (d, J=6.4 Hz, 3H), 1.46 (d, J=6.4 Hz, 3H).

3,5-dichloro-4-((6-chloro-5-(1-((tetrahydro-2H-pyran-2-yl)oxy)ethyl)pyridazin-3-yl)oxy)aniline (29c)

To a solution of 4-amino-2,6-dichloro-phenol (167.00 mg, 938.13 umol) and 3,6-dichloro-4-(1-((tetrahydro-2H-pyran-2-yl)oxy)ethyl)pyridazine (29b) (200 mg, 721.64 umol) in DMSO (5 mL) was added K$_2$CO$_3$ (299.21 mg, 2.16 mmol) and CuI (82.46 mg, 432.98 umol) was degassed and purged with N$_2$ for 3 times, and then the mixture was stirred at 90° C. for 2 hours under N$_2$ atmosphere. LCMS detected one main peak with desired MS. The reaction mixture was diluted with H$_2$O 5 mL and extracted with ethylacetate 30 mL (10 mL*3). The combined organic layers were washed with brine 10 mL, dried over anhydrous Na$_2$SO$_4$, filtered and concentrated under reduced pressure to give a residue. The residue was purified by prep-TLC (SiO$_2$, petroleum ether:ethyl acetate=1:1, TLC) to give 29c. $^1$H NMR (400 MHz, CDCl$_3$) δ 7.55 (s, 1H), 7.37 (s, 1H), 6.68 (s, 4H), 5.10 (q, J=6.6 Hz, 1H), 5.00 (q, J=6.4 Hz, 1H), 4.90-4.85 (m, 1H), 4.52 (t, J=3.6 Hz, 1H), 3.96 (ddd, J=3.8, 7.5, 11.2 Hz, 1H), 3.81 (br d, J=2.4 Hz, 4H), 3.65 (ddd, J=3.2, 8.0, 11.3 Hz, 1H), 3.61-3.54 (m, 1H), 3.47-3.40 (m, 1H), 1.96-1.60 (m, 12H), 1.55 (d, J=6.5 Hz, 3H), 1.49 (d, J=6.4 Hz, 3H).

N-(3,5-dichloro-4-((6-chloro-5-(1-((tetrahydro-2H-pyran-2-yl)oxy)ethyl)pyridazin-3-yl)oxy)phenyl)-5-oxo-4,5-dihydro-1,2,4-oxadiazole-3-carboxamide (29d)

To a solution of 3,5-dichloro-4-((6-chloro-5-(1-((tetrahydro-2H-pyran-2-yl)oxy)ethyl)pyridazin-3-yl)oxy)aniline (29c) (250 mg, 597.08 umol) in DCM (5 mL) was added TEA (181.26 mg, 1.79 mmol, 249.32 uL) and 5-oxo-4H-1,2,4-oxadiazole-3-carbonyl chloride (4e) (133.00 mg, 895.63 umol). The mixture was stirred at 25° C. for 0.5 hours. The reaction mixture was concentrated under reduced pressure to give a residue. The residue was purified by prep-TLC (SiO$_2$, DCM:MeOH=10:1, according TLC) to give 29d. MS mass calculated for [M+1]$^+$ (C$_{20}$H$_{18}$Cl$_3$N$_5$O$_6$) required m/z 530.0, LCMS found m/z 529.9.

1-(6-(2,6-dichloro-4-(5-oxo-4,5-dihydro-1,2,4-oxadiazole-3-carboxamido)phenoxy)-3-oxo-2,3-dihydropyridazin-4-yl)ethyl acetate (29e)

To a solution of N-(3,5-dichloro-4-((6-chloro-5-(1-((tetrahydro-2H-pyran-2-yl)oxy)ethyl)pyridazin-3-yl)oxy)phenyl)-5-oxo-4,5-dihydro-1,2,4-oxadiazole-3-carboxamide (29d) (60 mg, 90.44 umol) in AcOH (3 mL) was added NaOAc (37.09 mg, 452.19 umol). The mixture was stirred at 120° C. for 16 hours. The reaction mixture was concentrated under reduced pressure to remove AcOH and then to give 29e was used into the next step without further purification. MS mass calculated for [M+1]$^+$ (C$_{17}$H$_{13}$Cl$_2$N$_5$O$_7$) required m/z 470.0, LCMS found m/z 470.0.

N-(3,5-dichloro-4-((5-(1-hydroxyethyl)-6-oxo-1,6-dihydropyridazin-3-yl)oxy)phenyl)-5-oxo-4,5-dihydro-1,2,4-oxadiazole-3-carboxamide (Example 29)

To a solution of 1-(6-(2,6-dichloro-4-(5-oxo-4,5-dihydro-1,2,4-oxadiazole-3-carboxamido)phenoxy)-3-oxo-2,3-dihydropyridazin-4-yl)ethyl acetate (29 e) (105 mg, 223.30 umol) in MeOH (3 mL) and H$_2$O (0.5 mL) was added LiOH.H$_2$O (18.74 mg, 446.60 umol). The mixture was stirred at 25° C. for 1 hour. LCMS detected the desired MS. The reaction mixture was concentrated under reduced pressure to remove MeOH. The residue was diluted with 6 M HCl to modified pH=6-8 and extracted with EtOAc (5 mL*4), dried over anhydrous Na$_2$SO$_4$, filtered and concentrated under reduced pressure to give a residue. The residue was purified by prep-HPLC (column: Luna C18 100*30 5 u; mobile phase: [water (10 mM NH$_4$HCO$_3$)-ACN]; B %: 1%-40%, 12 min) to give Example 29 MS mass calculated for [M+1]$^+$ (C$_{15}$H$_{11}$Cl$_2$N$_5$O$_6$) required m/z 428.0, LCMS found m/z 428.0; $^1$H NMR (400 MHz, DMSO-d$_6$) δ 12.28 (s, 1H), 11.31 (s, 1H), 7.99 (s, 2H), 7.40 (d, J=1.1 Hz, 1H), 5.49 (br s, 1H), 4.70 (q, J=6.1 Hz, 1H), 1.33 (d, J=6.4 Hz, 3H).

(R)—N-(3,5-dichloro-4-((5-(1-hydroxyethyl)-6-oxo-1,6-dihydropyridazin-3-yl)oxy)phenyl)-5-oxo-4,5-dihydro-1,2,4-oxadiazole-3-carboxamide (Example 29-P1) and (S)—N-(3,5-dichloro-4-((5-(1-hydroxyethyl)-6-oxo-1,6-dihydropyridazin-3-yl)oxy)phenyl)-5-oxo-4,5-dihydro-1,2,4-oxadiazole-3-carboxamide (Example 29-P2)

The N-(3,5-dichloro-4-((5-(1-hydroxyethyl)-6-oxo-1,6-dihydropyridazin-3-yl)oxy)phenyl)-5-oxo-4,5-dihydro-1,2, 4-oxadiazole-3-carboxamide (Example 29) was checked and purified by Chiral SFC (column: DAICEL CHIRALPAK AD (250 mm*30 mm, 10 um); mobile phase: [0.1% NH3*H2O MeOH]; B %: 40%-40%, 10 min) to give Example 29-P1 and Example 29-P2.

Example 29-P1

MS mass calculated for [M+1]$^+$ ($C_{15}H_{11}Cl_2N_5O_6$) required m/z 428.0, LCMS found m/z 428.0; $^1$H NMR (400 MHz, DMSO-d6) c 12.26 (s, 1H), 10.71 (br s, 1H), 8.06 (s, 2H), 7.39 (d, J=1.3 Hz, 1H), 5.49 (br d, J=4.4 Hz, 1H), 4.74-4.66 (m, 1H), 1.33 (d, J=6.6 Hz, 3H).

Example 29-P2

MS mass calculated for [M+1]$^+$ ($C_{15}H_{11}Cl_2N_5O_6$) required m/z 428.0, LCMS found m/z 427.9; $^1$H NMR (400 MHz, DMSO-d6) δ 12.26 (s, 1H), 10.74 (br s, 1H), 8.05 (s, 2H), 7.39 (d, J=1.3 Hz, 1H), 5.49 (br d, J=4.4 Hz, 1H), 4.75-4.66 (m, 1H), 1.33 (d, J=6.4 Hz, 3H).

Example 30: N-(4-((5-isopropyl-6-oxo-1,6-dihydro-pyridazin-3-yl)methyl)-3,5-dimethylphenyl)-5-oxo-4,5-dihydro-1,2,4-oxadiazole-3-carboxamide

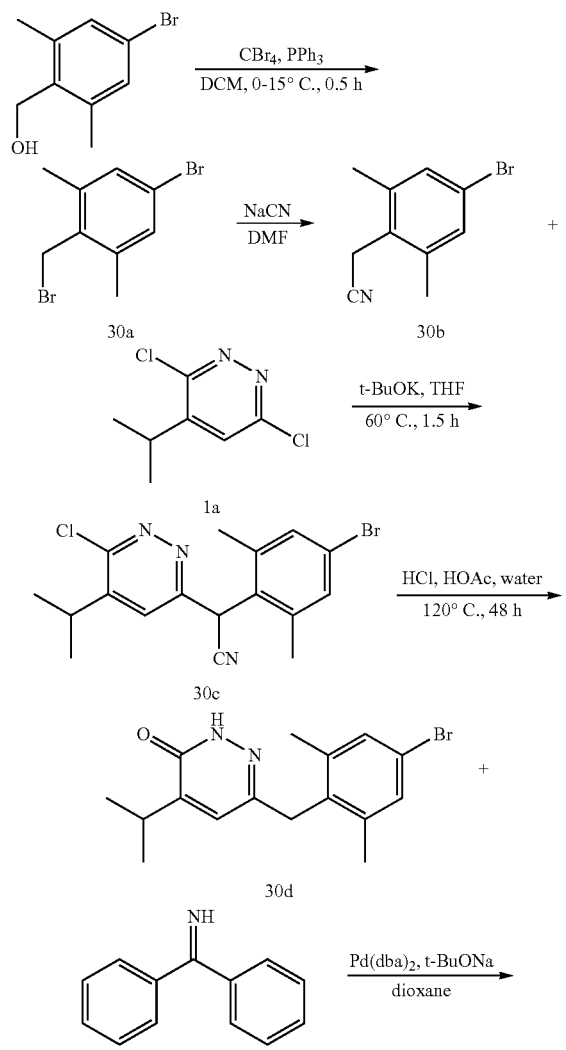

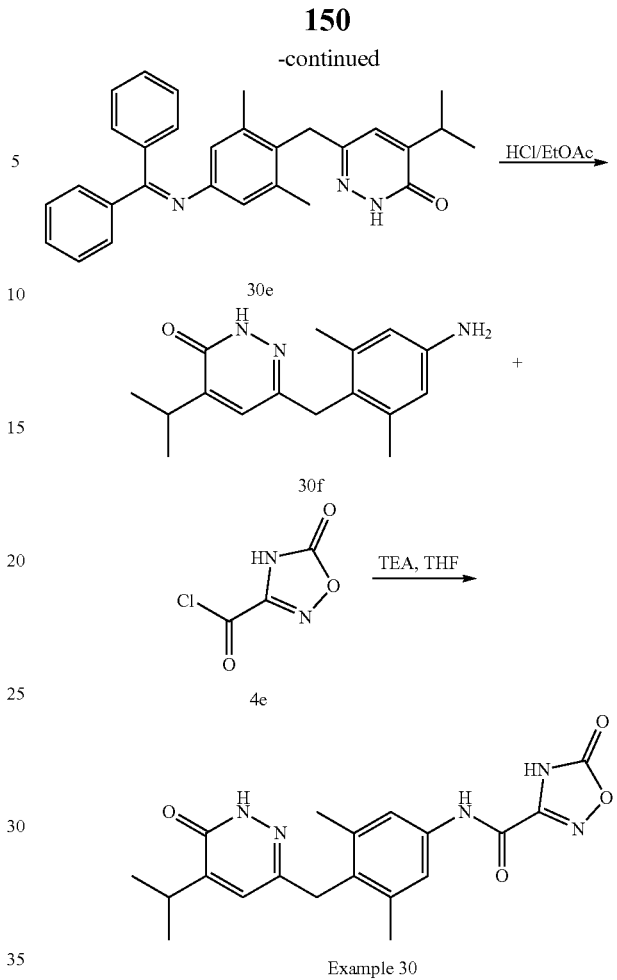

5-bromo-2-(bromomethyl)-1,3-dimethylbenzene (30a)

To a solution of (4-bromo-2,6-dimethylphenyl)methanol in DCM (30 mL) was added PPh$_3$ (1.83 g, 6.97 mmol). Then the mixture was cooled to 0-5° C. Then CBr$_4$ (2.31 g, 6.97 mmol) was added in the mixture by portions. Then the mixture was stirred at 15° C. for 0.5 hours under N$_2$. The mixture was concentrated in vacuum to give a residue. The residue was purified by column chromatography (SiO$_2$, petroleum ether/ethyl acetate=I/O to 10:1, TLC) to give 30a. $^1$H NMR (400 MHz, CDCl$_3$) δ 7.21 (s, 2H) 4.50 (s, 2H) 2.39 (s, 6H).

2-(4-bromo-2,6-dimethylphenyl)acetonitrile (30b)

To a solution of 5-bromo-2 (bromomethyl)-1,3-dimethylbenzene (30a) (1.26 g, 4.53 mmol) in DMF (30 mL) was added NaCN (244.35 mg, 4.99 mmol) at 15° C. Then the mixture was stirred at 15° C. for 16 hours. The mixture was partitioned between Ethyl acetate (50 mL) and NH$_4$Cl aqueous solution (20 mL) twice. The combined organic phase was washed with brine (20 mL*3), dried with anhydrous Na$_2$SO$_4$, filtered and concentrated in vacuum to give a residue. The residue was purified by column chromatography (SiO$_2$, petroleum ether:ethyl acetate=10:1 to 3:1, TLC) to give 30b. $^1$H NMR (400 MHz, CD$_3$OD) δ 7.28 (s, 2H) 3.79 (s, 2H) 2.38 (s, 6H).

2-(4-bromo-2,6-dimethylphenyl)-2-(6-chloro-5-isopropylpyridazin-3-yl)acetonitrile (30c)

To a solution of 2-(4-bromo-2,6-dimethylphenyl)acetonitrile (30b) (800 mg, 3.57 mmol) and 3,6-dichloro-4-isopropylpyridazine (1a) (682.05 mg, 3.57 mmol) in THF (10 mL) was was added t-BuOK (1 M, 7.14 mL, 2 eq) dropwise at 60° C., the resulting mixture was heated to 60° C. for 1 hour. The mixture was diluted with water (20 mL) and extracted with ethyl acetate (50 mL, 2×). The combined organic phase were washed with brine (10 mL*3), dried with anhydrous $Na_2SO_4$, filtered and concentrated. The residue was purified by column chromatography ($SiO_2$, petroleum ether:ethyl acetate=10:1 to 3:1, TLC) to give 30c. MS mass calculated for $[M+1]^+$ ($C_{17}H_{17}BrClN_3$) required m/z 378.0, LCMS found m/z 378.2; $^1$H NMR (400 MHz, $CD_3OD$) δ 7.34 (s, 3H) 7.21 (s, 1H) 6.28 (s, 1H) 3.01 (dt, J=13.54, 6.74 Hz, 1H) 2.89 (dt, J=13.72, 6.89 Hz, 1H) 2.27 (s, 6H) 1.27-1.30 (m, 6H).

6-(4-bromo-2,6-dimethylbenzyl)-4-isopropylpyridazin-3(2H)-one (30d)

A solution of 2-(4-bromo-2,6-dimethylphenyl)-2-(6-chloro-5-isopropylpyridazin-3-yl)acetonitrile (30c) (1 g, 2.78 mmol) in AcOH (10 mL), $H_2O$ (10 mL) and HCl (40 mL) was heated to 120° C. for 48 hours. LCMS showed the starting material was consumed and desired MS was detected. The mixture was adjusted to pH-7 with 3M NaOH at 15° C., the solid was filtered and dried to give 30d. The product was used directly for the next step without further purification. MS mass calculated for $[M+1]^+$ ($C_{16}H_{19}BrN_2O$) required m/z 335.1, LCMS found m/z 335.2; $^1$H NMR (400 MHz, DMSO) δ 12.56 (s, 1H) 7.24 (s, 2H) 7.11 (s, 1H) 3.90 (s, 2H) 2.97 (quin, J=6.82 Hz, 1H) 2.21 (s, 6H) 1.11 (d, J=6.85 Hz, 6H).

6-(4-(((diphenylmethylene)amino)-2,6-dimethylbenzyl)-4-isopropylpyridazin-3(2H)-one (30e)

To a solution of 6-(4-bromo-2,6-dimethylbenzyl)-4-isopropylpyridazin-3(2H)-one (30d) (100 mg, 298.30 umol) and benzophenone imine (54.06 mg, 298.30 umol, 50.06 uL) in dioxane (5 mL) was added t-BuONa (43.00 mg, 447.44 umol), $Pd_2(dba)_3$ (27.32 mg, 29.83 umol) and Xantphos (17.26 mg, 29.83 umol). The mixture was degassed and purged with $N_2$ for 3 times and stirred at 80° C. for 16 hours. The mixture was partitioned between DCM (20 mL) and sat. aq. $NH_4Cl$ solution (10 mL) and extracted with DCM a second time. The combined organic layers was washed with brine (10 mL*3), dried with anhydrous $Na_2SO_4$, filtered and concentrated in vacuum to give 30e. MS mass calculated for $[M+1]^+$ ($C_{29}H_{29}N_3O$) required m/z 436.2, LCMS found m/z 436.4. The residue was used directly for the next step without further purification.

6-(4-amino-2,6-dimethylbenzyl)-4-isopropylpyridazin-3(2H)-one (30f)

A solution of 6-(4-((diphenylmethylene)amino)-2,6-dimethylbenzyl)-4-isopropylpyridazin-3(2H)-one (30e) (100 mg, 229.59 umol) in HCl/EtOAc (5 mL) was stirred at 15° C. for 16 hr. LCMS showed desired MS was detected. The mixture was diluted with water 5 mL and added saturated aqueous of $NaHCO_3$ to modified pH=9-10. The suspension was extracted with EtOAc (15 mL*3), the combined organic layers were dried over anhydrous $Na_2SO_4$, filtered and concentrated under reduced pressure to give a residue. The residue was purified by prep-TLC ($SiO_2$, petroleum ether: ethyl acetate) to give 30f. MS mass calculated for $[M+1]^+$ ($C_{16}H_{21}N_3O$) required m/z 272.2, LCMS found m/z 272.3; $^1$H NMR (400 MHz, $CD_3OD$) δ 6.89 (s, 1H) 6.48 (s, 2H) 3.89 (s, 2H) 3.04 (dt, J=13.69, 6.72 Hz, 1H) 2.18 (s, 5H) 1.11 (d, J=6.97 Hz, 6H).

N-(4-((5-isopropyl-6-oxo-1,6-dihydropyridazin-3-yl)methyl)-3,5-dimethylphenyl)-5-oxo-4,5-dihydro-1,2,4-oxadiazole-3-carboxamide (Example 30)

To a mixture of 6-(4-amino-2,6-dimethylbenzyl)-4-isopropylpyridazin-3(2H)-one (30f) (10 mg, 36.85 umol) in THF (1 mL) was added TEA (14.92 mg, 147.41 umol, 20.52 uL) and 5-oxo-4H-1,2,4-oxadiazole-3-carbonyl chloride (4e) (10.95 mg, 73.70 umol) at 15° C. The mixture was stirred at 15° C. for 0.5 hours. The mixture was concentrated in vacuum to give a residue. The residue was purified by Prep-HPLC (column: Nano-micro Kromasil C18 100*30 mm 5 um; mobile phase: [water (0.225% FA)-ACN]; B %: 30%-50%, 12 min) to give Example 30. MS mass calculated for $[M+1]^+$ ($C_{19}H_{21}N_5O_4$) required m/z 384.2, LCMS found m/z 384.2; $^1$H NMR (400 MHz, $CD_3OD$) δ 7.41 (s, 2H) 7.02 (s, 1H) 4.86 (s, 19H) 4.02 (s, 2H) 3.07 (dt, J=13.72, 6.77 Hz, 1H) 2.30 (s, 6H) 1.15 (d, J=6.85 Hz, 6H).

Example 31: N-(4-((5-(bicyclo[1.1.1]pentan-1-yl)-6-oxo-1,6-dihydropyridazin-3-yl)oxy)-3,5-dichlorophenyl)-5-oxo-4,5-dihydro-1,2,4-oxadiazole-3-carboxamide

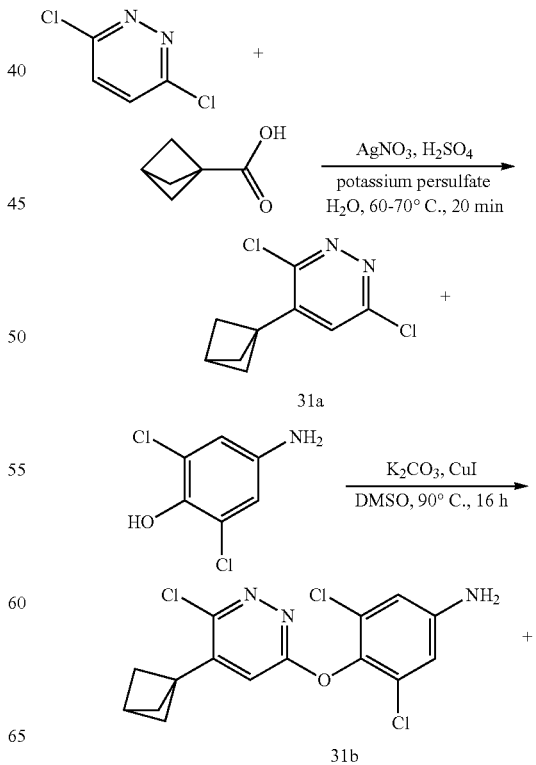

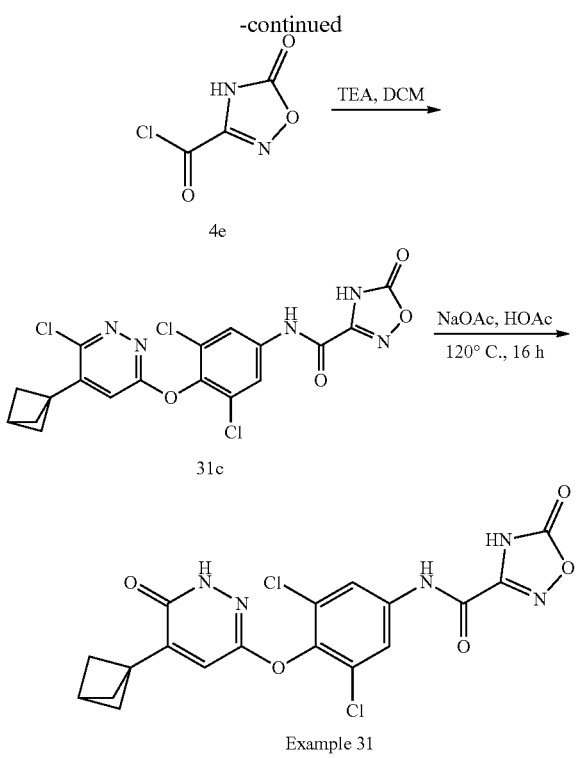

4-(bicyclo[1.1.1]pentan-1-yl)-3,6-dichloropyridazine (31a)

To a mixture of 3,6-dichloropyridazine (170 mg, 1.14 mmol) and bicyclo[1.1.1]pentane-1-carboxylic acid (134.35 mg, 1.20 mmol) in $H_2O$ (5 mL) was added $AgNO_3$ (193.84 mg, 1.14 mmol) and ammonium persulphate (286.44 mg, 1.26 mmol) and $H_2SO_4$ (335.75 mg, 3.42 mmol, 182.48 uL in $H_2O$ (2.5 mL) in one portion at 60° C. under $N_2$. The mixture was stirred at 70° C. for 20 minutes. After cooling the mixture was extracted with ethyl acetate (5 mL*2), the organic phases were washed with $NaHCO_3$(2 mL), brine (5 mL), then dried over $Na_2SO_4$, filtered and concentrated. The residue was purified by column chromatography ($SiO_2$, petroleum ether:ethyl acetate=5:1) to give 31a. $^1$H NMR (400 MHz, $CD_3OD$) δ 7.62 (s, 1H), 2.66 (s, 1H), 2.34 (s, 6H).

4-((5-(bicyclo[1.1.1]pentan-1-yl)-6-chloropyridazin-3-yl)oxy)-3,5-dichloroaniline (31b)

4-(bicyclo[1.1.1]pentan-1-yl)-3,6-dichloropyridazine (31a) (150 mg, 697.42 umol) and 4-amino-2,6-dichlorophenol (124.15 mg, 697.42 umo) in DMSO (9 mL) was added $K_2CO_3$ (385.55 mg, 2.79 mmol) and CuI (79.69 mg, 418.45 umol) in one portion at 25° C. under $N_2$. The mixture was stirred at 90° C. for 16 hours. The residue was partitioned between ethyl acetate (20 mL) and $H_2O$ (5 mL*2). The combined organic phase was washed with brine (5 mL*3), dried with anhydrous $Na_2SO_4$, filtered and concentrated in vacuum. The solid was purified by prep-TLC (petroleum ether:ethyl acetate=3:1) to give 31b. MS mass calculated for $[M+1]^+$ ($C_{15}H_{12}Cl_3N_3O$) required m/z 356.0, LCMS found m/z 355.9.

N-(4-((5-(bicyclo[1.1.1]pentan-1-yl)-6-chloropyridazin-3-yl)oxy)-3,5-dichlorophenyl-)-5-oxo-4,5-dihydro-1,2,4-oxadiazole-3-carboxamide (31c)

To a mixture of 4-((5-(bicyclo[1.1.1]pentan-1-yl)-6-chloropyridazin-3-yl)oxy)-3,5-dichloroaniline (31b) (30 mg, 84.12 umol) in DCM (5 mL) was added TEA (25.54 mg, 252.36 umol, 35.13 uL) and 5-oxo-4,5-dihydro-1,2,4-oxadiazole-3-carbonyl chloride (4e) (18.74 mg, 126.18 umol) in one portion at 0° C. under $N_2$, and the reaction was stirred at 0° C. for 30 minutes. The residue was diluted with water (5 mL) and extracted with DCM (10 mL, 2×). The combined organic layers were washed with brine (5 mL*3), dried with anhydrous $Na_2SO_4$, filtered and concentrated in vacuum. The solid was purified by prep-TLC (petroleum ether:ethyl acetate=1:1) to give 31c.

N-(4-((5-(bicyclo[1.1.1]pentan-1-yl)-6-oxo-1,6-dihydropyridazin-3-yl)oxy)-3,5-dichlorophenyl)-5-oxo-4,5-dihydro-1,2,4-oxadiazole-3-carboxamide (Example 31)

To a mixture of N-(4-((5-(bicyclo[1.1.1]pentan-1-yl)-6-chloropyridazin-3-yl)oxy)-3,5-dichlorophenyl-)-5-oxo-4,5-dihydro-1,2,4-oxadiazole-3-carboxamide (31c) (18 mg, 38.41 umol) in AcOH (3 mL) was added NaOAc (15.75 mg, 192.03 umol) in one portion. Then the mixture was stirred at 120° C. under $N_2$ for 16 hours. The mixture was concentrated. The residue was purified by prep-HPLC (column: Phenomenex Luna C18 100*30 mm*5 um; mobile phase: [water (0.225% FA)-ACN]; B %: 45%-75%, 10 min) to give Example 31. MS mass calculated for $[M+1]^+$ ($C_{18}H_{13}Cl_2N_5O_5$) required m/z 450.0, LCMS found m/z 450.0; $^1$H NMR (400 MHz, $CD_3OD$) δ 7.91 (s, 2H), 7.19 (s, 1H), 2.60 (s, 1H), 2.25 (s, 6H).

Example 32: N-(3,5-dichloro-4-((5-(1-hydroxypropyl)-6-oxo-1,6-dihydropyridazin-3-yl)oxy)phenyl)-5-oxo-4,5-dihydro-1,2,4-oxadiazole-3-carboxamide

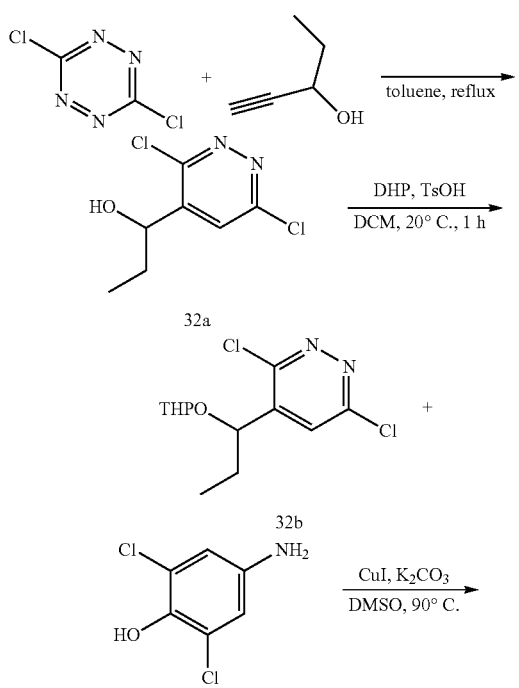

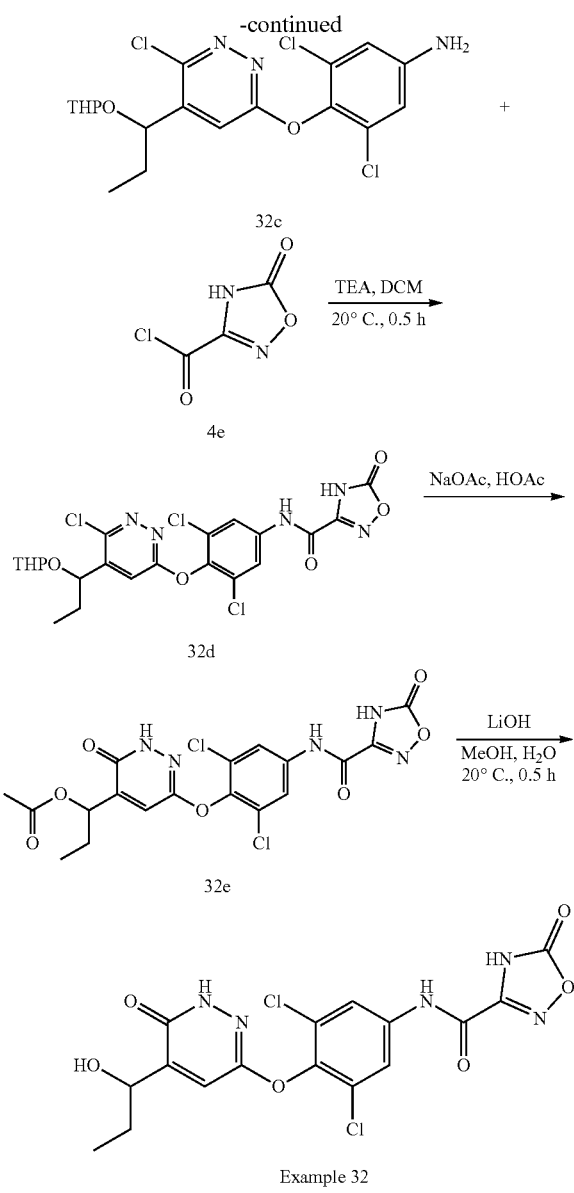

mmol, 309.10 uL) in DCM (5 mL) was added TsOH (5.82 mg, 33.81 umol). The mixture was stirred at 20° C. for 1 hour. LCMS showed desired MS. The reaction mixture was concentrated under reduced pressure to give a residue. The residue was purified by prep-TLC (SiO$_2$, petroleum ether/ethyl acetate=2:1, TLC) to give 32b. MS mass calculated for [M+1]$^+$ (C$_{12}$H$_{16}$Cl$_2$N$_2$O$_2$) required m/z 291.2, LCMS found m/z 291.1; $^1$H NMR (400 MHz, CDCl$_3$) δ 7.71 (s, 1H) 7.56 (s, 1H) 4.95-5.00 (m, 1H) 4.78 (dd, J=7.06, 3.97 Hz, 1H) 4.69 (dd, J=5.40, 2.09 Hz, 1H) 4.40 (t, J=3.42 Hz, 1H) 3.85-4.03 (m, 2H) 3.54-3.55 (m, 1H) 3.45-3.62 (m, 2H) 3.33-3.41 (m, 1H) 2.04-2.10 (m, 1H) 1.47-1.94 (m, 24H) 1.05 (t, J=7.39 Hz, 3H) 0.95 (t, J=7.39 Hz, 3H).

3,5-dichloro-4-((6-chloro-5-(1-((tetrahydro-2H-pyran-2-yl)oxy)propyl)pyridazin-3-yl)oxy)aniline (32c)

To a solution of 3,6-dichloro-4-(1-((tetrahydro-2H-pyran-2-yl)oxy)propyl)pyridazine (32b) (130 mg, 446.47 umol) and 4-amino-2,6-dichlorophenol (79.48 mg, 446.47 umol) in DMSO (5 mL) was added K$_2$CO$_3$ (246.83 mg, 1.79 mmol) and CuI (51.02 mg, 267.88 umol) was degassed and purged with N$_2$ for 3 times, and then the mixture was stirred at 90° C. for 16 hours under N$_2$ atmosphere. LCMS showed desired MS. The mixture was diluted in EtOAc (5 mL) and filtrated, and the filtration was partitioned between Ethyl acetate (5 mL) and H$_2$O 3 mL. The organic phase was separated, and the aqueous phase was extracted with EtOAc (5 mL). The combined organic phase was washed with brine (10 mL*2), dried with anhydrous Na$_2$SO$_4$, filtered and concentrated in vacuum. The residue was purified by Prep-TLC (petroleum ether:ethyl acetate=2:1) to give 32c. MS mass calculated for [M+1]$^+$ (C$_{18}$H$_{20}$Cl$_3$N$_3$O$_3$) required m/z 432.7, LCMS found m/z 432.1; $^1$H NMR (400 MHz, CDCl$_3$) δ 7.48 (s, 1H) 7.29 (s, 1H) 6.68 (s, 2H) 4.97 (dd, J=7.46, 3.79 Hz, 1H) 4.76-4.83 (m, 1H) 4.46 (t, J=3.30 Hz, 1H) 3.93-4.02 (m, 1H) 3.80 (br s, 2H) 3.54-3.62 (m, 1H) 3.33-3.41 (m, 1H) 1.85-1.99 (m, 2H) 1.66-1.83 (m, 4H) 1.06 (t, J=7.34 Hz, 2H) 0.96 (t, J=7.34 Hz, 2H).

N-(3,5-dichloro-4-((6-chloro-5-(1-((tetrahydro-2H-pyran-2-yl)oxy)propyl)pyridazin-3-yl)oxy)phenyl)-5-oxo-4,5-dihydro-1,2,4-oxadiazole-3-carboxamide (32d)

To a solution of 3,5-dichloro-4-((6-chloro-5-(1-((tetrahydro-2H-pyran-2-yl)oxy)propyl)pyridazin-3-yl)oxy)aniline (32c) (110 mg, 254.20 umol) in DCM (5 mL) was added TEA (77.17 mg, 762.60 umol, 106.15 uL) and 5-oxo-4H-1,2,4-oxadiazole-3-carbonyl chloride (56.63 mg, 381.30 umol). The mixture was stirred at 20° C. for 0.5 hours. LCMS showed desired MS. The reaction mixture was concentrated under reduced pressure to give a residue. The residue was purified by prep-TLC (SiO$_2$, petroleum ether: ethyl acetate=1:1) to give 32d. MS mass calculated for [M+1]$^+$ (C$_{21}$H$_{20}$Cl$_3$N$_5$O$_6$) required m/z 544.8, LCMS found m/z 544.6; $^1$H NMR (400 MHz, CD$_3$OD) δ 7.97 (s, 2H) 7.64 (s, 1H) 4.83 (dd, J=8.05, 3.20 Hz, 1H) 3.92 (s, 1H) 1.87-1.97 (m, 2H) 1.59-1.69 (m, 1H) 1.06 (t, J=7.28 Hz, 3H).

1-(6-(2,6-dichloro-4-(5-oxo-4,5-dihydro-1,2,4-oxadiazole-3-carboxamido)phenoxy)-3-oxo-2,3-dihydropyridazin-4-yl)propyl acetate (32e)

To a solution of N-(3,5-dichloro-4-((6-chloro-5-(1-((tetrahydro-2H-pyran-2-yl)oxy)propyl) pyridazin-3-yl)oxy)

1-(3,6-dichloropyridazin-4-yl)propan-1-ol (32a)

To a solution of 3,6-dichloro-1,2,4,5-tetrazine (1 g, 6.62 mmol) in Tol. (10 mL) was added pent-1-yn-3-ol (1.11 g, 13.25 mmol, 1.14 mL) at 20° C. The mixture was stirred at 110° C. for 16 hours under sealed tube. LCMS showed desired MS. The reaction mixture was concentrated under reduced pressure to give a residue. The residue was purified by prep-TLC (SiO$_2$, petroleum ether:ethyl acetate=1:1) to give 32a. MS mass calculated for [M+1]$^+$ (C$_7$H$_8$Cl$_2$N$_2$O) required m/z 207.1, LCMS found m/z 207.0; $^1$H NMR (400 MHz, CDCl$_3$) δ 7.79 (s, 1H) 4.94 (dt, J=7.73, 3.77 Hz, 1H) 2.72 (d, J=4.03 Hz, 1H) 1.94 (dqd, J=14.52, 7.39, 7.39, 3.55 Hz, 1H) 1.60-1.72 (m, 1H) 1.06 (t, J=7.34 Hz, 3H).

3,6-dichloro-4-(1-((tetrahydro-2H-pyran-2-yl)oxy) propyl)pyridazine (32b)

To a solution of 1-(3,6-dichloropyridazin-4-yl)propan-1-ol (32a) (140 mg, 676.14 umol) and DHP (284.37 mg, 3.38 phenyl)-5-oxo-4,5-dihydro-1,2,4-oxadiazole-3-carboxamide (32d) (130 mg, 238.63 umol, 1 eq) in HOAc (5 mL) was added NaOAc (97.88 mg, 1.19 mmol). The mixture was stirred at 120° C. for 16 hours. The reaction mixture was concentrated under reduced pressure to remove AcOH to give 32e. MS mass calculated for [M+1]$^+$ ($C_{18}H_{15}Cl_2N_5O_7$) required m/z 484.2, LCMS found m/z 484.1. The crude product was used into the next step without further purification.

N-(3,5-dichloro-4-((5-(1-hydroxypropyl)-6-oxo-1,6-dihydropyridazin-3-yl)oxy)phenyl)-5-oxo-4,5-dihydro-1,2,4-oxadiazole-3-carboxamide (Example 32)

To a solution of 1-(6-(2, 6-dichloro-4-(5-oxo-4,5-dihydro-1,2,4-oxadiazole-3-carboxamido) phenoxy)-3-oxo-2,3-dihydropyridazin-4-yl)propyl acetate (32e) (115 mg, 237.48 umol) in MeOH (3 mL) and H$_2$O (0.5 mL) was added LiOH.H$_2$O (1 M, 474.97 uL). The mixture was stirred at 25° C. for 1 hour. The reaction mixture was concentrated under reduced pressure to remove AcOH. The residue was diluted with water 5 mL. The suspension was extracted with EtOAc (30 mL*3), the combined organic layers were dried over anhydrous Na$_2$SO$_4$, filtered and concentrated under reduced pressure to give a residue. The residue was purified by Prep-HPLC (column: Phenomenex Luna C18 100*30 mm*5 um; mobile phase: [water (0.225% FA)-ACN]; B %: 30%-60%, 10 min) to give Example 32. MS mass calculated for [M+1]$^+$ ($C_{16}H_{13}Cl_2N_5O_6$) required m/z 442.2, LCMS found m/z 442.0; $^1$H NMR (400 MHz, CD$_3$OD) δ 7.92 (s, 2H) 7.47 (s, 1H) 4.85 (s, 29H) 4.74 (br d, J=4.77 Hz, 1H) 1.88-2.02 (m, 1H) 1.51-1.64 (m, 1H) 1.02 (t, J=7.40 Hz, 3H).

Example 32 P1 and P2: N-(3,5-dichloro-4-((5-(1-hydroxypropyl)-6-oxo-1,6-dihydropyridazin-3-yl)oxy)phenyl)-5-oxo-4,5-dihydro-1,2,4-oxadiazole-3-carboxamide

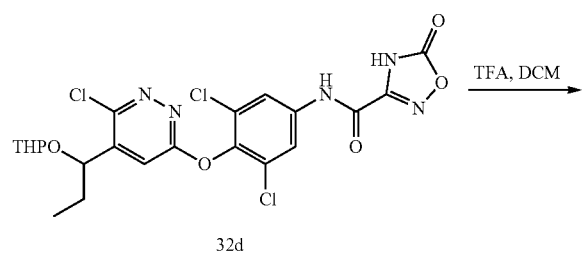

32d

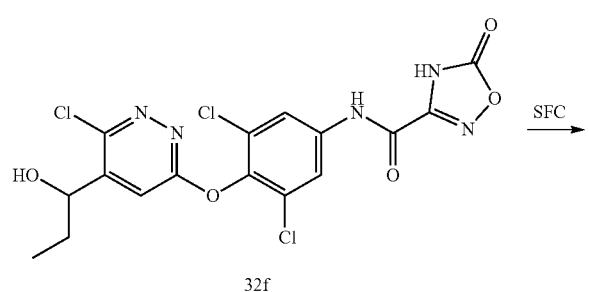

32f

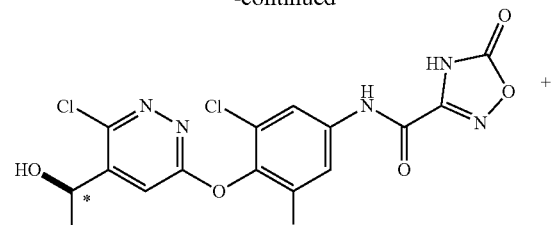

32d-P1

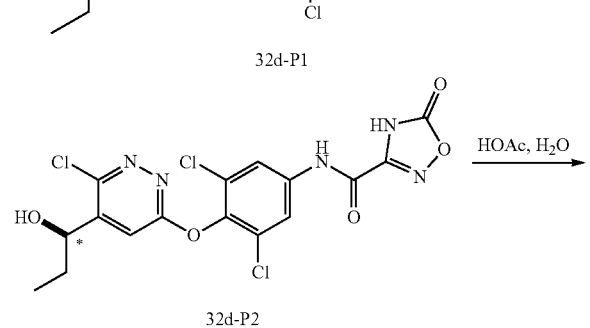

32d-P2

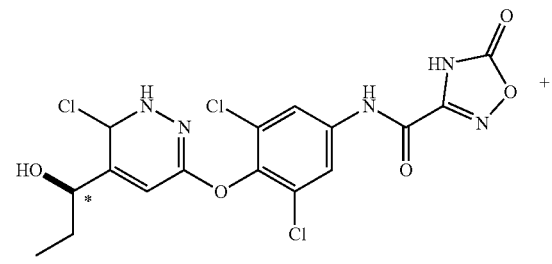

Example 32-P1

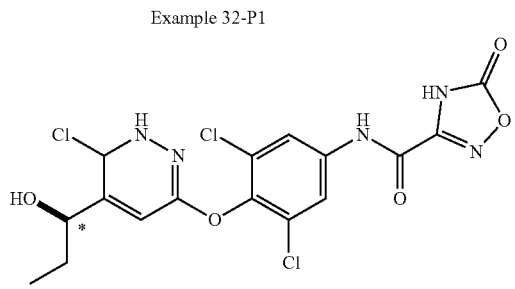

Example 32-P2

N-(3,5-dichloro-4-((6-chloro-5-(1-hydroxypropyl)pyridazin-3-yl)oxy)phenyl)-5-oxo-4,5-dihydro-1,2,4-oxadiazole-3-carboxamide (32f)

A solution of N-(3,5-dichloro-4-((6-chloro-5-(1-((tetrahydro-2H-pyran-2-yl)oxy)propyl)pyridazin-3-yl)oxy)phenyl)-5-oxo-4,5-dihydro-1,2,4-oxadiazole-3-carboxamide (32d) (160 mg, 293.70 umol) in TFA (1 mL) and DCM (3 mL) was stirred at 20° C. for 2 hours. The reaction mixture was concentrated under reduced pressure to give a residue. The residue was purified by Prep-HPLC (column: Phenomenex Luna C18 100*30 mm*5 um; mobile phase: [water (0.2% FA)-ACN]; B %: 35%-65%, 10 min) to give 32f. MS mass calculated for [M+1]$^+$ ($C_{16}H_{12}Cl_3N_5O_5$) required m/z 460.0, LCMS found m/z 460.1.

Sfc Separation.

N-(3,5-dichloro-4-((6-chloro-5-(1-hydroxypropyl)pyridazin-3-yl)oxy)phenyl)-5-oxo-4,5-dihydro-1,2,4-oxadiazole-3-carboxamide (32f) (95 mg, 206.23 umol) was separated by SFC (column: DAICEL CHIRALCEL OJ (250

(R)—N-(3,5-dichloro-4-((5-(1-hydroxypropyl)-6-oxo-1,6-dihydropyridazin-3-yl)oxy)phenyl)-5-oxo-4,5-dihydro-1,2,4-oxadiazole-3-carboxamide (Example 32-P1)

A solution of (R)—N-(3,5-dichloro-4-((6-chloro-5-(1-hydroxypropyl)pyridazin-3-yl)oxy)phenyl)-5-oxo-4,5-dihydro-1,2,4-oxadiazole-3-carboxamide (32f-P1) (10.00 mg, 21.71 umol) in HOAc (2 mL) and $H_2O$ (0.1 mL) was stirred at 120° C. for 16 hours. The reaction mixture was concentrated under reduced pressure to give a residue. The residue was purified by Prep-HPLC (column: Phenomenex Luna C18 200*40 mm*10 um; mobile phase: [water (0.225% FA)-ACN]; B %: 20%-50%, 12 min) to give Example 32-P1. MS mass calculated for $[M+1]^+$ ($C_{16}H_{13}Cl_2N_5O_6$) required m/z 442.0, LCMS found m/z 442.0; $^1H$ NMR (400 MHz, $CD_3OD$) δ 7.92 (s, 2H) 7.47 (d, J=0.98 Hz, 1H) 4.87 (s, 40H) 4.73 (br d, J=4.03 Hz, 1H) 1.90-1.98 (m, 1H) 1.58 (dt, J=14.15, 7.29 Hz, 1H) 1.02 (t, J=7.40 Hz, 3H).

(S)—N-(3,5-dichloro-4-((5-(1-hydroxypropyl)-6-oxo-1,6-dihydropyridazin-3-yl)oxy)phenyl)-5-oxo-4,5-dihydro-1,2,4-oxadiazole-3-carboxamide (Example 32-P2)

A solution of (S)—N-(3,5-dichloro-4-((6-chloro-5-(1-hydroxypropyl)pyridazin-3-yl)oxy)phenyl)-5-oxo-4,5-dihydro-1,2,4-oxadiazole-3-carboxamide (32f-P2) (10.00 mg, 21.71 umol) in HOAc (2 mL) and $H_2O$ (0.1 mL) was stirred at 120° C. for 16 hr. The reaction mixture was concentrated under reduced pressure to give a residue. The residue was purified by Prep-HPLC (column: Phenomenex Luna C18 100*30 mm*5 um; mobile phase: [water (0.2% FA)-ACN]; B %: 20%-50%, 10 min to give Example 32-P2. MS mass calculated for $[M+1]^+$ ($C_{16}H_{13}Cl_2N_5O_6$) required m/z 442.0, LCMS found m/z 442.0; $^1H$ NMR (400 MHz, $CD_3OD$) δ 7.91 (s, 2H) 7.47 (d, J=1.10 Hz, 1H) 4.87 (s, 19H) 4.73 (dd, J=7.09, 3.06 Hz, 1H) 1.95 (ddd, J=13.91, 7.43, 3.48 Hz, 1H) 1.52-1.63 (m, 1H) 1.02 (t, J=7.34 Hz, 3H).

Example 33: N-(3,5-dichloro-4-((5-(2-hydroxypropan-2-yl)-6-oxo-1,6-dihydropyridazin-3-yl)oxy)phenyl)-5-oxo-4,5-dihydro-1,2,4-oxadiazole-3-carboxamide

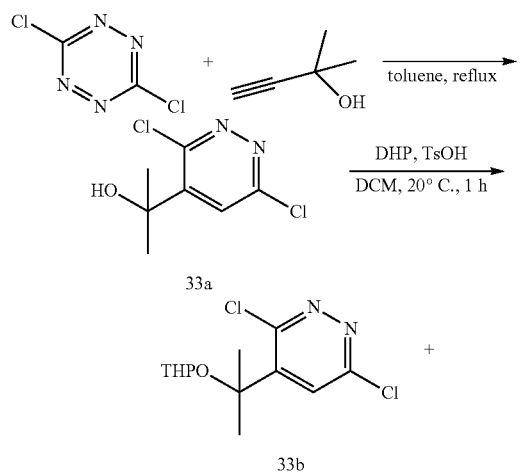

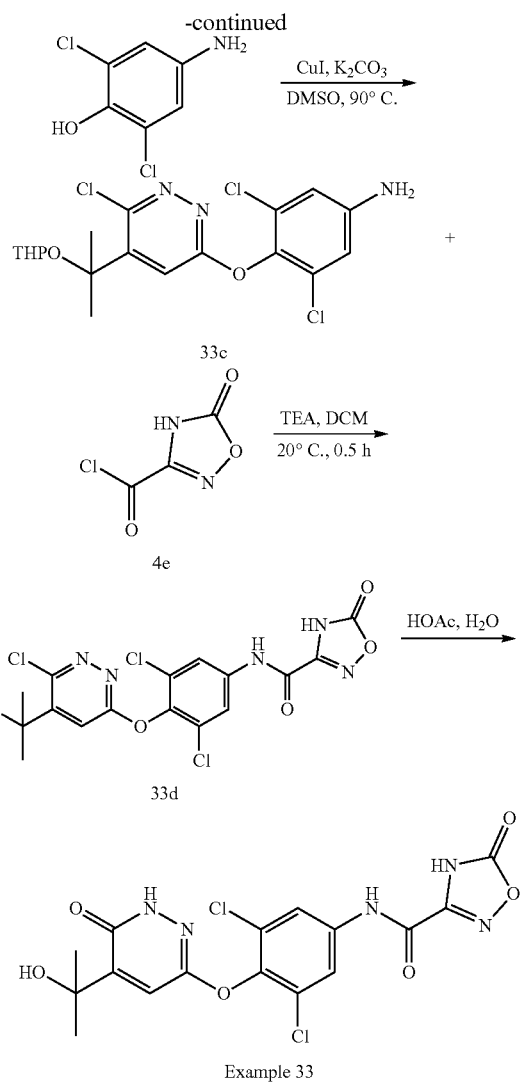

Example 33

2-(3,6-dichloropyridazin-4-yl)propan-2-ol (33a)

To a solution of 3,6-dichloro-1,2,4,5-tetrazine (500 mg, 3.31 mmol) in Tol. (5 mL) was added 2-methylbut-3-yn-2-ol at 20° C. The mixture was stirred at 115° C. for 16 hours under sealed tube. LCMS showed desired MS. The reaction mixture was concentrated under reduced pressure to give a residue. The residue was purified by column chromatography ($SiO_2$, petroleum ether:ethyl acetate=10:1 to 4:1, TLC) to give 33a. MS mass calculated for $[M+1]^+$ ($C_7HCl_2N_2O$) required m/z 207.0, LCMS found m/z 207.0; $^1H$ NMR (400 MHz, $CDCl_3$) δ 7.98 (s, 1H) 2.17 (s, 1H) 1.77 (s, 6H).

3,6-dichloro-4-(2-((tetrahydro-2H-pyran-2-yl)oxy)propan-2-yl)pyridazine (33b)

To a solution of 2-(3,6-dichloropyridazin-4-yl)propan-2-ol (33a) (70 mg, 338.07 umol) in DCM (5 mL) was added DHP (142.19 mg, 1.69 mmol, 154.56 uL) and PPTS (16.99 mg, 67.61 umol). The mixture was stirred at 20° C. for 16 hours. The mixture was diluted with water (5 mL) and extracted with ethyl acetate (15 mL, 2×). The combined organic layers were washed with brine (10 mL*3), dried with anhydrous Na$_2$SO$_4$, filtered and concentrated in vacuum to give a residue. The residue was purified by prep-TLC (SiO$_2$, petroleum ether:ethyl acetate=5:1, TLC) to give 33b. MS mass calculated for [M+1]$^+$ (C$_{12}$H$_{16}$Cl$_2$N$_2$O$_2$) required m/z 291.1, LCMS found m/z 291.1; $^1$H NMR (400 MHz, CDCl$_3$) δ 7.85 (s, 1H) 4.84 (dd, J=5.62, 2.81 Hz, 1H) 4.01-4.08 (m, 1H) 3.88-3.95 (m, 1H) 3.57 (dt, J=11.13, 5.44 Hz, 1H) 3.47 (dt, J=11.37, 5.69 Hz, 1H) 1.83-1.96 (m, 2H) 1.78 (s, 3H) 1.75 (s, 3H) 1.56-1.73 (m, 6H).

3,5-dichloro-4-((6-chloro-5-(2-((tetrahydro-2H-pyran-2-yl)oxy)propan-2-yl)pyridazin-3-yl)oxy)aniline (33c)

To a solution of 3,6-dichloro-4-(2-((tetrahydro-2H-pyran-2-yl)oxy)propan-2-yl)pyridazine (33b) (40 mg, 137.38 umol) and 4-amino-2,6-dichlorophenol (24.45 mg, 137.38 umol) in DMSO (4 mL) was added K$_2$CO$_3$ (75.94 mg, 549.50 umol) and CuI (15.70 mg, 82.43 umol) was degassed and purged with N$_2$ for 3 times, and then the mixture was stirred at 90° C. for 16 hours under N$_2$ atmosphere LCMS showed desired MS. The mixture was diluted in EtOAc (5 mL) and filtered. The filtrate was partitioned between ethyl acetate (5 mL) and H$_2$O (3 mL). The organic phase was separated, and the aqueous phase was extracted with EtOAc (5 mL). The combined organic phase was washed with brine (10 mL*2), dried with anhydrous Na$_2$SO$_4$, filtered and concentrated in vacuum. The mixture was purified by Prep-TLC (petroleum ether:ethyl acetate=3:1) to give 33c. MS mass calculated for [M+1]$^+$ (C$_{18}$H$_{20}$Cl$_3$N$_3$O$_3$) required m/z 432.1, LCMS found m/z 432.1.

N-(3,5-dichloro-4-((6-chloro-5-(2-((tetrahydro-2H-pyran-2-yl)oxy)propan-2-yl)pyridazin-3-yl)oxy)phenyl)-5-oxo-4,5-dihydro-1,2,4-oxadiazole-3-carboxamide (33d)

To a solution of 3,5-dichloro-4-((6-chloro-5-(2-((tetrahydro-2H-pyran-2-yl)oxy)propan-2-yl)pyridazin-3-yl)oxy)aniline (33c) (25 mg, 57.77 umol) in DCM (1.5 mL) was added TEA (17.54 mg, 173.32 umol, 24.12 uL and 5-oxo-4,5-dihydro-1,2,4-oxadiazole-3-carbonyl chloride (4e) (12.87 mg, 86.66 umol). The mixture was stirred at 20° C. for 0.5 hours. LCMS showed desired MS. The reaction mixture was concentrated under reduced pressure to give a residue. The residue was purified by prep-TLC (SiO$_2$, petroleum ether:ethyl acetate) to give 33d. MS mass calculated for [M+1]$^+$ (C$_{21}$H$_{20}$Cl$_3$N$_5$O$_6$) required m/z 544.0, LCMS found m/z 544.1; $^1$H NMR (400 MHz, CD$_3$OD) δ 7.98 (s, 2H) 7.76 (s, 1H) 4.36-4.41 (m, 6H) 3.93 (s, 3H) 3.83-3.89 (m, 1H) 3.62-3.65 (m, 2H) 3.59 (t, J=6.60 Hz, 5H) 3.48 (dt, J=7.73, 6.22 Hz, 9H) 1.92 (dt, J=6.14, 3.10 Hz, 4H) 1.78-1.88 (m, 16H) 1.66-1.75 (m, 9H).

N-(3,5-dichloro-4-((5-(2-hydroxypropan-2-yl)-6-oxo-1,6-dihydropyridazin-3-yl)oxy)phenyl)-5-oxo-4,5-dihydro-1,2,4-oxadiazole-3-carboxamide (Example 33)

A solution of N-(3,5-dichloro-4-((6-chloro-5-(2-((tetrahydro-2H-pyran-2-yl)oxy)propan-2-yl)pyridazin-3-yl)oxy)phenyl)-5-oxo-4,5-dihydro-1,2,4-oxadiazole-3-carboxamide (33d) (25 mg, 45.89 umol) in HOAc (2 mL) and H$_2$O (0.1 mL) was stirred at 120° C. for 16 hours. The reaction mixture was concentrated under reduced pressure to give a residue. The residue was purified by Prep-HPLC (column: Phenomenex Luna C18 200*40 mm*10 um; mobile phase: [water (0.225% FA)-ACN]; B %: 20%-55%, 12 min) to give Example 33. MS mass calculated for [M+1]$^+$ (C$_{16}$H$_{13}$Cl$_2$N$_5$O$_6$) required m/z 442.0, LCMS found m/z 441.9; 1H NMR (400 MHz, CD$_3$OD) δ 7.91 (s, 2H) 7.58 (s, 1H) 4.85 (br s, 126H) 1.62 (s, 6H).

Example 34: N-(3,5-dichloro-2-fluoro-4-((5-isopropyl-6-oxo-1,6-dihydropyridazin-3-yl)oxy)phenyl)-5-oxo-4,5-dihydro-1,2,4-oxadiazole-3-carboxamide

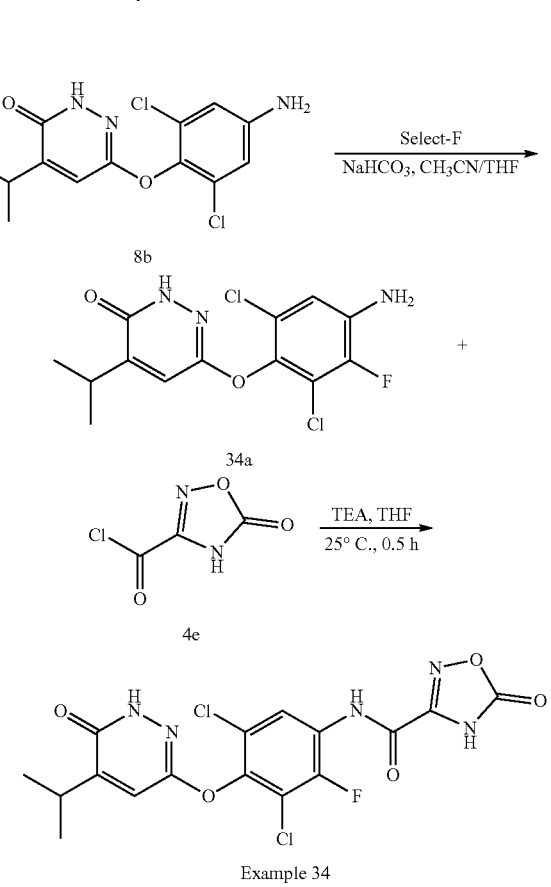

Example 34

6-(4-amino-2,6-dichloro-3-fluorophenoxy)-4-isopropylpyridazin-3(2H)-one (34a)

To a solution of 6-(4-amino-2,6-dichlorophenoxy)-4-isopropylpyridazin-3(2H)-one (8b) (300 mg, 954.91 umol) in CH$_3$CN (10 mL) and THF (10 mL) was added NaHCO$_3$ (240.66 mg, 2.86 mmol, 111.41 uL). Then Select F (372.11 mg, 1.05 mmol) was added to the mixture in portions at 20° C. Then the mixture was stirred at 20° C. for 2 hours. The mixture was diluted with EtOAc (30 mL) and H$_2$O (30 mL). The organic layer was washed with brine (10 mL), dried in vacuum. The residue was purified by Prep-TLC (petroleum ether:ethyl acetate=1:1) to give 34a. $^1$H NMR (400 MHz, CD$_3$OD) δ 7.29 (d, J=0.86 Hz, 1H) 6.89 (d, J=8.44 Hz, 1H) 3.10-3.23 (m, 1H) 1.25-1.33 (m, 6H).

N-(3,5-dichloro-2-fluoro-4-((5-isopropyl-6-oxo-1,6-dihydropyridazin-3-yl)oxy)phenyl)-5-oxo-4,5-dihydro-1,2,4-oxadiazole-3-carboxamide (Example 34)

To a solution of 6-(4-amino-2,6-dichloro-3-fluorophenoxy)-4-isopropylpyridazin-3(2H)-one (34a) (100 mg, 301.06 umol) in DCM (4 mL) was added TEA (91.39 mg, 903.19 umol, 125.71 uL) and 5-oxo-4H-1,2,4-oxadiazole-3-carbonyl chloride (4e) (67.06 mg, 451.59 umol). The mixture was stirred at 20° C. for 0.5 hours. LCMS showed desired MS. The reaction mixture was concentrated under reduced pressure to give a residue. The residue was purified by prep-TLC (SiO$_2$, petroleum ether:ethyl acetate) to give the desired material. The desired compound was re-purified by Prep-HPLC (column: Phenomenex Luna C18 200*40 mm*10 um; mobile phase: [water (0.225% FA)-ACN]; B %: 20%-60%, 12 min) to give Example 34. MS mass calculated for [M+1]$^+$ (C$_{16}$H$_{12}$Cl$_2$FN$_5$O$_5$) required m/z 444.0, LCMS found m/z 443.9; $^1$H NMR (400 MHz, CD$_3$OD) δ 7.97 (br d, J=6.72 Hz, 1H) 7.37 (s, 1H) 4.87 (br s, 13H) 3.12-3.22 (m, 1H) 1.28 (br d, J=6.60 Hz, 6H).

Scheme F: 4-((5-(1-(((tert-butyldimethylsilyl)oxy)
propan-2-yl)-6-chloropyridazin-3-yl)oxy)-3,5-di-
chloroaniline (Compound 35c)

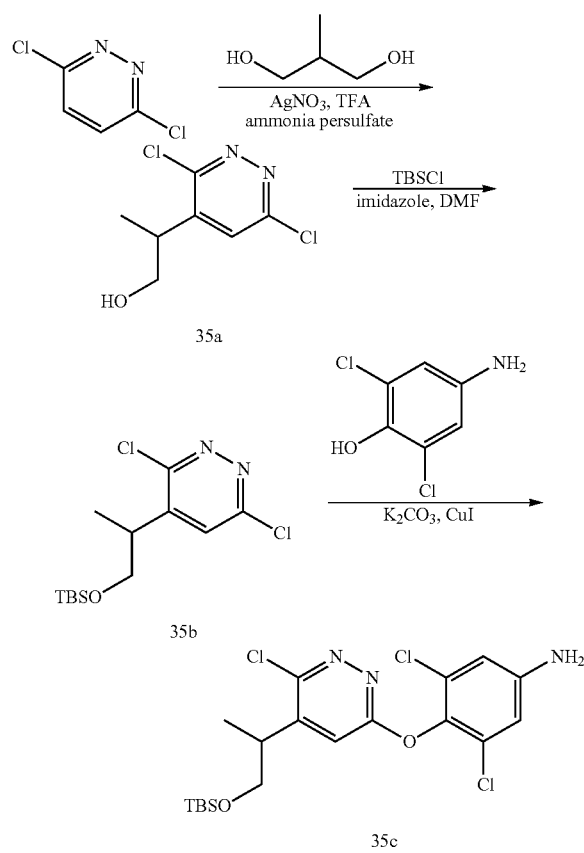

2-(3,6-dichloropyridazin-4-yl)propan-1-ol (35a)

To H$_2$O (25 mL) was added TFA (4.97 g, 43.63 mmol, 3.23 mL) at 50° C., then 2-methylpropane-1,3-diol (6.65 g, 73.8 mmol, 6.59 mL) was added in the mixture, followed by addition of 3,6-dichloropyridazine (5 g, 33.6 mmol) and AgNO$_3$ (7.70 g, 45.3 mmol). Then a solution of ammonia hydrogen thiosulfate (15.3 g, 67.1 mmol, 14.6 mL) in H$_2$O (15 mL) was added in the mixture in portions at 50° C., and the resulting mixture was stirred at 50° C. for 0.5 hours. The reaction mixture was partitioned between H$_2$O (45 mL) and EtOAc (50 mL). The organic phase was separated, washed with H$_2$O (50 mL*3), dried over Na$_2$SO$_4$, filtered and concentrated under reduced pressure to give a residue. The residue was purified by column chromatography (SiO$_2$, petroleum ether/ethyl acetate) to give 35a. MS mass calculated for [M+1]$^+$ (C$_7$H$_8$Cl$_2$N$_2$O) requires m/z 207.0, LCMS found m/z 207.0; $^1$H NMR (400 MHz, CDCl$_3$) δ 7.52 (s, 1H), 3.93-3.84 (m, 2H), 3.45-3.30 (m, 1H), 1.35 (d, J=7.2 Hz, 3H).

4-(1-((tert-butyldimethylsilyl)oxy)propan-2-yl)-3,6-
dichloropyridazine (35b)

To a solution of 2-(3,6-dichloropyridazin-4-yl)propan-1-ol (35a) (3.4 g, 16.4 mmol) and tert-butyl-chloro-dimethyl-silane (2.47 g, 16.4 mmol, 2.01 mL) in DMF (25 mL) was added imidazole (1.34 g, 19.7 mmol). The mixture was stirred at 25° C. for 1 hr under N$_2$ atmosphere. The reaction mixture was diluted with water (100 mL) and extracted with EtOAc (100 mL*3). The combined organic phase was washed with brine (50 mL*2), dried with anhydrous Na$_2$SO$_4$, filtered and concentrated in vacuum to give 35b. The product was used directly in the next step without further purification. MS mass calculated for [M+1]$^+$ (C$_{13}$H$_{22}$Cl$_2$N$_2$OSi) requires m/z 321.1, LCMS found m/z 321.0; $^1$H NMR (400 MHz, CDCl$_3$) δ 7.48 (s, 1H), 3.77 (d, J=4.4 Hz, 2H), 3.38-3.29 (m, 1H), 1.32 (d, J=6.8 Hz, 3H), 0.88-0.79 (m, 9H), 0.04-0.02 (m, 3H), 0.02-0.08 (m, 3H).

4-((5-(1-(((tert-butyldimethylsilyl)oxy)propan-2-yl)-
6-chloropyridazin-3-yl)oxy)-3,5-dichloroaniline
(35c)

To a solution of 4-(1-((tert-butyldimethylsilyl)oxy)pro-pan-2-yl)-3,6-dichloropyridazine (35b) (1 g, 3.11 mmol) in DMSO (15 mL) was added 4-amino-2,6-dichlorophenol (752.84 mg, 3.11 mmol), K$_2$CO$_3$ (1.29 g, 9.34 mmol) and CuI (355.63 mg, 1.87 mmol). The mixture was stirred at 90° C. under N$_2$ atmosphere for 5 hours. The suspension was filtered through a pad of Celite and the pad cake was washed with EtOAc (50 mL). The reaction mixture was quenched by addition H$_2$O (30 mL), and then extracted with ethyl acetate (50 mE) and extracted with EtOAc (50 mL*5). The combined organic layers were washed with brine (50 mL*2), dried over Na$_2$SO$_4$, filtered and concentrated under reduced pressure. The residue was purified by column chromatography (SiO$_2$, petroleum ether:ethyl acetate) to give 35c. MS mass calculated for [M+1]$^+$ (C$_{19}$H$_{26}$Cl$_3$N$_3$O$_2$Si) requires m/z 462.1, LCMS found m/z 462.1.

Example 35: N-(3,5-dichloro-4-((5-(1-hydroxypro-
pan-2-yl)-1-methyl-6-oxo-1,6-dihydropyridazin-3-
yl)oxy)phenyl)-5-oxo-4,5-dihydro-1,2,4-oxadiazole-
3-carboxamide

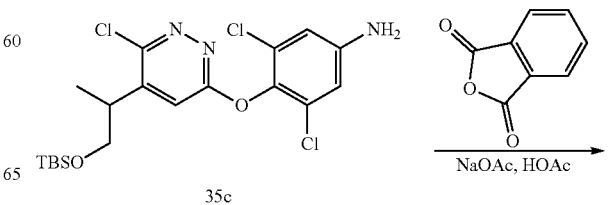

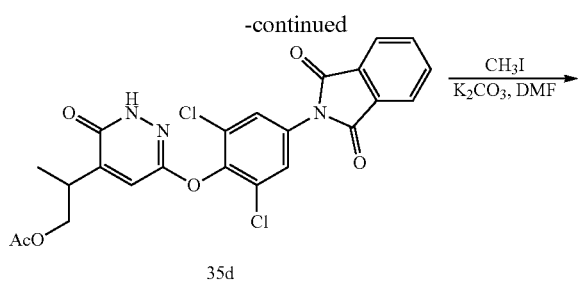

35d

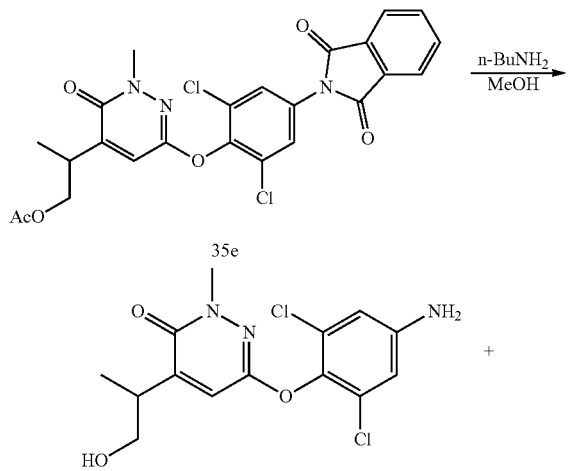

35e

35f

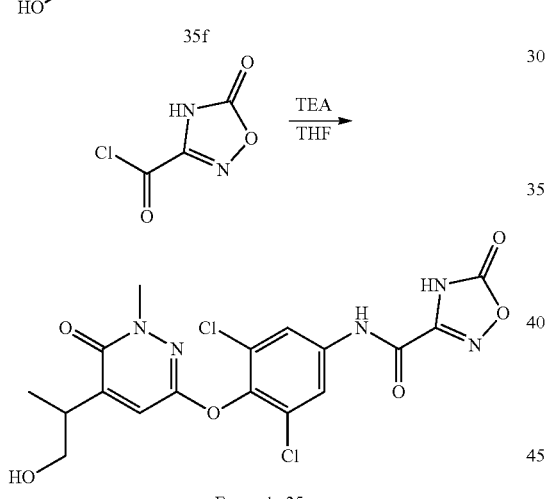

Example 35

2-(6-(2,6-dichloro-4-(1,3-dioxoisoindolin-2-yl)phenoxy)-3-oxo-2,3-dihydropyridazin-4-yl)propyl acetate (35d)

To a solution of 4-((5-(1-((tert-butyldimethylsilyl)oxy)propan-2-yl)-6-chloropyridazin-3-yl)oxy)-3,5-dichloroaniline (35c) (510 mg, 1.10 mmol) in HOAc (8 mL) was added isobenzofuran-1, 3-dione (244.8 mg, 1.65 mmol) and NaOAc (271.2 mg, 3.31 mmol). The mixture was stirred at 120° C. for 16 hours. The reaction mixture was concentrated under reduced pressure to remove HOAc. The residue was diluted with H₂O (30 mL) and extracted with EtOAc (30 mL*3). The combined organic layers were washed with brine (30 mL), dried over Na₂SO₄, filtered and concentrated under reduced pressure to give a residue. The residue was purified by column chromatography (SiO₂, petroleum ether: ethyl acetate) to give 35d. MS mass calculated for [M+1]⁺ ($C_{23}H_{17}Cl_2N_3O_6$) requires m/z 502.0, LCMS found m/z 502.1.

2-(6-(2,6-dichloro-4-(1,3-dioxoisoindolin-2-yl)phenoxy)-2-methyl-3-oxo-2,3-dihydropyridazin-4-yl) propyl acetate (35e)

To a solution of 2-(6-(2,6-dichloro-4-(1,3-dioxoisoindolin-2-yl)phenoxy)-3-oxo-2,3-dihydropyridazin-4-yl)propyl acetate (35d) (230 mg, 457.9 umol) in DMF (3 mL) was added K₂CO₃ (107.6 mg, 778.4 umol) and MeI (130.0 mg, 915.8 umol, 57.0 uL). The mixture was stirred at 25° C. for 3 hours. The reaction mixture was quenched by addition H₂O (15 mL) at 25° C., and then extracted with EtOAc (15 mL*3). The combined organic layers were washed with brine (30 mL), dried over Na₂SO₄, filtered and concentrated under reduced pressure to give 35e. The mixture was used into the next step without further purification. MS mass calculated for [M+1]⁺ ($C_{24}H_{19}Cl_2N_3O_6$) requires m/z 516.1, LCMS found m/z 516.1.

6-(4-amino-2,6-dichlorophenoxy)-4-(1-hydroxypropan-2-yl)-2-methylpyridazin-3(2H)-one (35f)

To a solution of 2-(6-(2,6-dichloro-4-(1,3-dioxoisoindolin-2-yl)phenoxy)-2-methyl-3-oxo-2,3-dihydropyridazin-4-yl)propyl acetate (35e) (223 mg, 431.89 umol) in MeOH (5 mL) was added butan-1-amine (1.11 g, 15.2 mmol, 1.5 mL). The mixture was stirred at 70° C. for 1 hr. The reaction mixture was concentrated under reduced pressure to remove MeOH. The residue was purified by prep-TLC (SiO₂, petroleum ether:ethyl acetate) to give 35f. MS mass calculated for [M+1]⁺ ($C_{14}H_{15}Cl_2N_3O_3$) requires m/z 344.0, LCMS found m/z 344.0.

N-(3,5-dichloro-4-((5-(1-hydroxypropan-2-yl)-1-methyl-6-oxo-1,6-dihydropyridazin-3-yl)oxy)phenyl)-5-oxo-4,5-dihydro-1,2,4-oxadiazole-3-carboxamide (Example 35)

To a solution of 6-(4-amino-2,6-dichlorophenoxy)-4-(1-hydroxypropan-2-yl)-2-methylpyridazin-3(2H)-one (35f) (50 mg, 145.3 umol) in THF (3 mL) was added TEA (44.1 mg, 435.8 umol, 60.7 uL) and 5-oxo-4H-1,2,4-oxadiazole-3-carbonyl chloride (32.4 mg, 217.9 umol). The mixture was stirred at 25° C. for 5 minutes. TLC and LCMS showed 35f was consumed completely and desired mass+Ac was detected. The reaction mixture was quenched by addition of MeOH (5 mL) at 25° C. Then the pH was adjusted to 10-12 with LiOH·H₂O, and the resulting mixture was stirred at 25° C. for 1 hour. LCMS showed the desired MS was found in the major peak. Then the mixture was concentrated in vacuum, and the residue was purified by prep-HPLC (column: Waters Xbridge Prep OBD C18 150*40 mm*10 um; mobile phase: [water (10 mM NH₄HCO₃)-MeCN]) to give Example 35. MS mass calculated for [M+1]⁺ ($C_{17}H_{15}Cl_2N_5O_6$) requires m/z 456.0, LCMS found m/z 456.1; ¹H NMR (400 MHz, CD₃OD) δ 7.93 (s, 2H), 7.34 (s, 1H), 3.80 (dd, J=6.0, 10.6 Hz, 1H), 3.73-3.66 (m, 1H), 3.51 (s, 3H), 3.29-3.23 (m, 1H), 1.29 (d, J=7.0 Hz, 3H).

Example 36: N-(3,5-dichloro-4-((5-(1-hydroxypropan-2-yl)-6-oxo-1,6-dihydropyridazin-3-yl)oxy)phenyl)-5-oxo-4,5-dihydro-1,2,4-oxadiazole-3-carboxamide

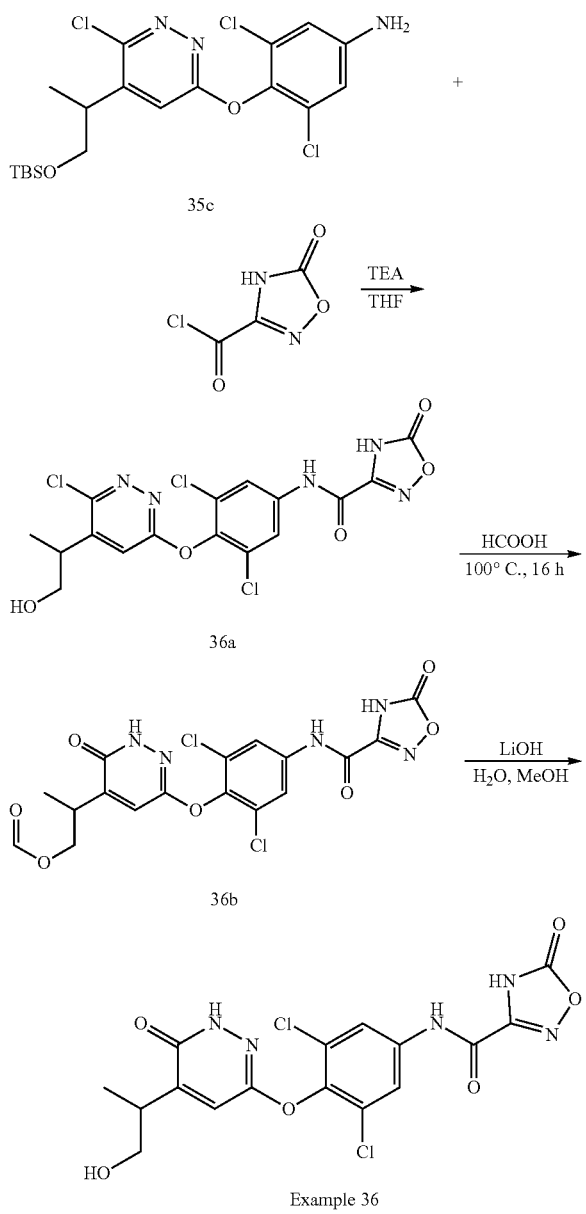

N-(3,5-dichloro-4-((6-chloro-5-(1-hydroxypropan-2-yl)pyridazin-3-yl)oxy)phenyl)-5-oxo-4,5-dihydro-1,2,4-oxadiazole-3-carboxamide (36a)

To a solution of 4-((5-(1-((tert-butyldimethylsilyl)oxy)propan-2-yl)-6-chloropyridazin-3-yl)oxy)-3,5-dichloroaniline (35c) (50 mg, 108.0 umol) in THF (2 mL) was added TEA (32.8 mg, 324.0 umol, 45.1 uL) and 5-oxo-4H-1,2,4-oxadiazole-3-carbonyl chloride (24.1 mg, 162.0 umol). The mixture was stirred at 25° C. for 5 minutes. The reaction mixture was quenched by addition of MeOH (25 mL) at 25° C., and the reaction mixture was concentrated under reduced pressure to give a residue. The residue was purified by prep-TLC (SiO$_2$, petroleum ether:ethyl acetate) to give 36a. MS mass calculated for [M+1]$^+$ (C$_{16}$H$_{12}$Cl$_3$N$_5$O$_5$) requires m/z 460.0, LCMS found m/z 460.0.

2-(6-(2,6-dichloro-4-(5-oxo-4,5-dihydro-1,2,4-oxadiazole-3-carboxamido)phenoxy)-3-oxo-2,3-dihydropyridazin-4-yl)propyl formate (36b)

To a solution of N-(3,5-dichloro-4-((6-chloro-5-(1-hydroxypropan-2-yl)pyridazin-3-yl)oxy)phenyl)-5-oxo-4,5-dihydro-1,2,4-oxadiazole-3-carboxamide (36a) (40 mg, 86.8 umol) in HCOOH (5 mL) was stirred at 100° C. for 16 hours. The reaction mixture was concentrated under reduced pressure to remove HCOOH. The residue was purified by prep-TLC (SiO$_2$, ethyl acetate:petroleum ether) to give 36b. MS mass calculated for [M+1]$^+$ (C$_{17}$H$_{13}$Cl$_2$N$_5$O$_7$) requires m/z 470.0, LCMS found m/z 470.0.

N-(3,5-dichloro-4-((5-(1-hydroxypropan-2-yl)-6-oxo-1,6-dihydropyridazin-3-yl)oxy)phenyl)-5-oxo-4,5-dihydro-1,2,4-oxadiazole-3-carboxamide (Example 36)

To a solution of 2-(6-(2,6-dichloro-4-(5-oxo-4,5-dihydro-1,2,4-oxadiazole-3-carboxamido)phenoxy)-3-oxo-2,3-dihydropyridazin-4-yl)propyl formate (36b) (35 mg, 74.4 umol) in MeOH (4 mL) was added LiOH·H$_2$O (3.8 mg, 89.3 umol) in H$_2$O (1 mL). The mixture was stirred at 25° C. for 1 hour. The reaction mixture was concentrated under reduced pressure to remove MeOH. The residue was purified by prep-HPLC (column: Waters Xbridge BEH C18 100*30 mm*10 um; mobile phase: [water (10 mM NH$_4$HCO$_3$)-MeCN]) to give Example 36. MS mass calculated for [M+1]$^+$ (C$_{16}$H$_{13}$Cl$_2$N$_5$O$_6$) requires m/z 442.0, LCMS found m/z 442.1, $^1$H NMR (400 MHz, CD$_3$OD) δ 7.91 (s, 1H), 7.36 (s, 1H), 3.84-3.78 (m, 1H), 3.73-3.67 (m, 1H), 3.26-3.20 (m, 1H), 1.30 (d, J=7.0 Hz, 3H).

Example 37: N-(3,5-dichloro-4-((5-(2-hydroxypropan-2-yl)-1-methyl-6-oxo-1,6-dihydropyridazin-3-yl)oxy)phenyl)-5-oxo-4,5-dihydro-1,2,4-oxadiazole-3-carboxamide

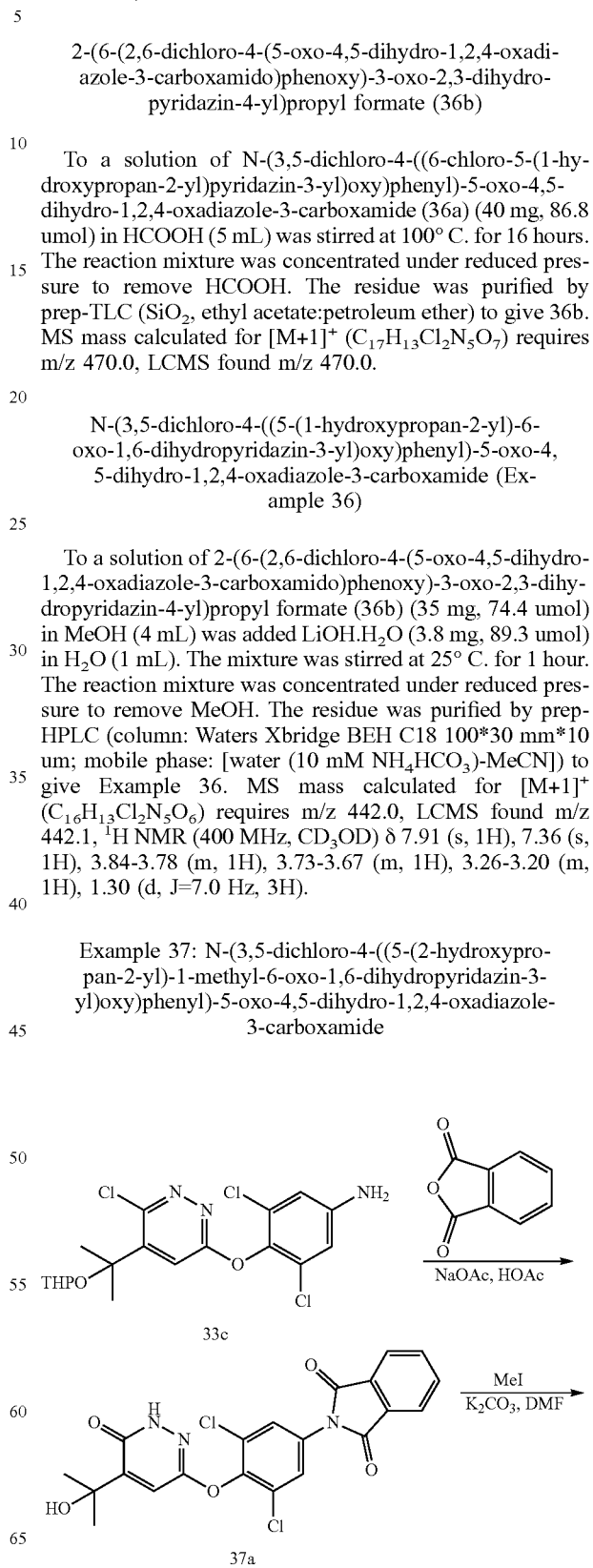

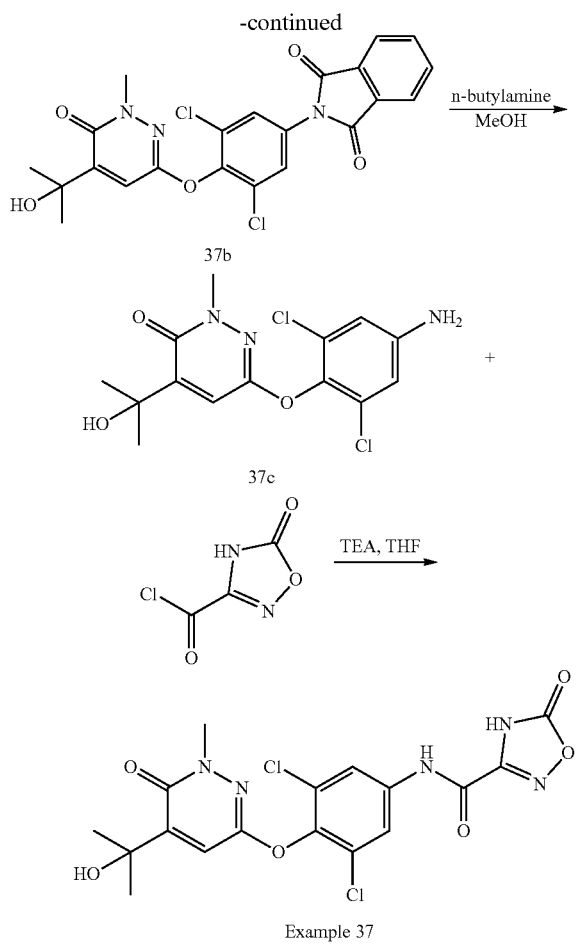

Example 37

2-(3,5-dichloro-4-((5-(2-hydroxypropan-2-yl)-6-oxo-1,6-dihydropyridazin-3-yl)oxy)phenyl)isoindoline-1,3-dione (37a)

To a mixture of 3,5-dichloro-4-((6-chloro-5-(2-((tetrahydro-2H-pyran-2-yl)oxy)propan-2-yl)pyridazin-3-yl)oxy)aniline (33c) (100 mg, 231.1 umol) and isobenzofuran-1,3-dione (37.7 mg, 254.2 umol) in HOAc (2 mL) was added NaOAc (94.8 mg, 1.16 mmol) under $N_2$. The mixture was stirred at 120° C. for 16 hours. The residue was poured into water (5 mL). The aqueous phase was extracted with ethyl acetate (10 mL*3). The combined organic phase was washed with brine (10 mL*2), dried with anhydrous $Na_2SO_4$, filtered and concentrated in vacuum. The residue was purified by prep-TLC ($SiO_2$, petroleum ether/ethyl acetate) to give 37a. MS mass calculated for $[M+1]^+$ ($C_{21}H_{15}Cl_2N_3O_5$) requires m/z 460.0, MS mass found m/z 460.0; $^1$H NMR (400 MHz, $CDCl_3$) δ 9.91 (br s, 2H), 8.11-7.93 (m, 2H), 7.92-7.74 (m, 3H), 7.61 (d, J=1.6 Hz, 3H), 7.30-7.28 (m, 1H), 2.16-2.00 (m, 3H), 1.90-1.84 (m, 2H), 1.68 (br d, J=6.0 Hz, 1H), 1.67-1.65 (m, 1H), 1.67-1.65 (m, 1H), 1.66 (s, 1H).

2-(3,5-dichloro-4-((5-(2-hydroxypropan-2-yl)-1-methyl-6-oxo-1,6-dihydropyridazin-3-yl)oxy)phenyl)isoindoline-1,3-dione (37b)

To a mixture of 2-(3,5-dichloro-4-((5-(2-hydroxypropan-2-yl)-6-oxo-1,6-dihydropyridazin-3-yl)oxy)phenyl)isoindoline-1,3-dione (37a) (50 mg, 108.6 umol) in DMF (3 mL) was added $K_2CO_3$ (30.0 mg, 217.3 umol) and MeI (30.8 mg, 217.3 umol, 13.53 uL) under $N_2$. The mixture was stirred at 20° C. for 1 hour. The reaction was poured into water (5 mL). The aqueous phase was extracted with EtOAc (15 mL*2). The combined organic phase was washed with brine (10 mL*2), dried with anhydrous $Na_2SO_4$, filtered and concentrated in vacuum. The residue was purified by prep-TLC ($SiO_2$, petroleum ether:ethyl acetate) to give 37b. MS mass calculated for $[M+1]^+$ ($C_{22}H_{17}Cl_2N_3O_5$) requires m/z 474.1, MS mass found m/z 474.1.

6-(4-amino-2,6-dichlorophenoxy)-4-(2-hydroxypropan-2-yl)-2-methylpyridazin-3(2H)-one (37c)

To a mixture of 2-(3,5-dichloro-4-((5-(2-hydroxypropan-2-yl)-1-methyl-6-oxo-1,6-dihydropyridazin-3-yl)oxy)phenyl)isoindoline-1,3-dione (37b) (30 mg, 63.3 umol) in MeOH (1.5 mL) was added n-butylamine (11.6 mg, 158.1 umol, 15.63 uL) under $N_2$. The mixture was stirred at 70° C. for 1.5 hours. The reaction mixture was concentrated under reduced pressure to give a residue. The residue was purified by prep-TLC ($SiO_2$, petroleum ether:ethyl acetate) and the obtained crude product was re-purified by prep-HPLC (column: Waters Xbridge BEH C18 100*30 mm*10 um; mobile phase: [water (10 mM $NH_4HCO_3$)-MeCN]) to give 37c. $^1$H NMR (400 MHz, $CDCl_3$) δ 7.20-7.08 (m, 1H), 6.75-6.62 (m, 2H), 5.68-5.51 (m, 1H), 3.85-3.71 (m, 2H), 3.63-3.50 (m, 3H), 1.62 (s, 6H).

N-(3,5-dichloro-4-((5-(2-hydroxypropan-2-yl)-1-methyl-6-oxo-1,6-dihydropyridazin-3-yl)oxy)phenyl)-5-oxo-4,5-dihydro-1,2,4-oxadiazole-3-carboxamide (Example 37)

To a mixture of 6-(4-amino-2,6-dichlorophenoxy)-4-(2-hydroxypropan-2-yl)-2-methylpyridazin-3(2H)-one (37c) (10 mg, 29.05 umol) in THF (2 mL) was added TEA (8.82 mg, 87.12 umol, 12.1 uL) and 5-oxo-4,5-dihydro-1,2,4-oxadiazole-3-carbonyl chloride (12.9 mg, 87.2 umol) under $N_2$. The mixture was stirred at 20° C. for 2 hours. The reaction mixture was concentrated under reduced pressure to give a residue. The residue was purified by prep-HPLC (column: Welch Ultimate AQ-C18 150*30 mm*5 um; mobile phase: [water (0.1% TFA)-MeCN]) to give Example 37. MS mass calculated for $[M+1]^+$ ($C_{17}H_{15}Cl_2N_5O_6$) requires m/z 456.0, MS mass found m/z 456.0; $^1$H NMR (400 MHz, $CD_3OD$) δ 7.96-7.88 (m, 2H), 7.60-7.52 (m, 1H), 4.46-4.37 (m, 1H), 3.68-3.59 (m, 1H), 3.53-3.47 (m, 1H), 3.50-3.47 (m, 1H), 3.49 (s, 1H), 1.94-1.84 (m, 1H), 1.66-1.54 (m, 6H).

Biological Example: Biological Screening

Example B1: Time-Resolved Fluorescence Resonance Energy Transfer (TR-FRET) Assay for Thyroid Hormone Receptor Agonist Screening LanthaScreen™ TR-FRET Thyroid Receptor alpha Coactivator Assay kit (ThermoFisher) and LanthaScreen™ TR-FRET Thyroid Receptor beta Coactivator Assay kit (ThermoFisher) were used for agonist compound screening. Compounds in DMSO were diluted using ECHO Liquid Handler (Labcyte Inc.) into 384 plates in 10-point 3-fold series in duplicate (5 micro M final top concentration). Buffer C (ThermoFisher) was added to each well before the 4× mixture of fluorescein-SCR2-2 coactivator (200 nM final concentration), Terbium-labeled anti-GST antibody (2 nM final concentration), and TR alpha-LBD (0.4 nM final concentration) or TR beta-LBD (1.0 nM final concentration) was added. After 2 hour incubation at room temperature in dark, the TR-FRET signal was measured on an EnVision plate reader (PerkinElmer) with excitation at 340 nm and dual emission readout at 495 and 520 nm with the delay time of 100 micro second and the integration time of 200 micro second. The ratio of emission signal at 520 and at 495 was used to calculate $EC_{50}$ using GraphPad Prism (GraphPad Software). In every batch of compound screening, T3 (L-3, 3',5-Triiodothyronine sodium salt, >95%) (Calbiochem) was used as reference compound. The $EC_{50}$ of T3 measured were within 3-fold of the reference value provided by the assay kit manufacturer (ThermoFisher Scientific). The Z' factors measured in every batch of screening using T3 as high percent effect (HPE) control and 0.5% DMSO as zero percent effect (ZPE) control were in the range of 0.5 to 0.8. Compounds' THR-beta selectivity values are derived from T3-selectivity normalized data. Data obtained using the TR-FRET assay for certain compounds disclosed herein are listed in Table 2.

TABLE 2

| Example | $EC_{50}$ THRβ-FRET [nM]$^a$ | $EC_{50}$ THRα-FRET [nM]$^a$ | THRβ-Selectivity |
|---|---|---|---|
| 1 | 7.6 | 49.5 | 17.2 |
| 2 | >5000 | >5000 | n.a. |
| 3-P1 | 276.6 | 75.9 | 1.0 |
| 3-P2 | 732.1 | 817.4 | 4.2 |
| 4 | 27.1 | 313.8 | 31.7 |
| 5 | 74.2 | 469.3 | 27.8 |
| 6 | 58.1 | 78.0 | 3.6 |
| 7 | 60.9 | 472.6 | 13.1 |
| 8 | 896.1 | 2298 | 7 |
| 9 | 290.2 | 125.5 | 0.7 |
| 11 | 115.8 | 192.4 | 4.8 |
| 12 | 71.2 | 151.8 | 6.2 |
| 13 | 53.6 | 1632 | 86.5 |
| 14 | 46.6 | 548.7 | 48 |
| 15 | 31.5 | 102 | 11.7 |
| 16 | 44.2 | 82.4 | 6.7 |
| 17 | 2112 | >5000 | >7.2 |
| 18 | 271.2 | 550 | 6.1 |
| 19 | >5000 | 1926 | n.a. |
| 20 | >5000 | >5000 | n.a. |
| 21 | 180 | >5000 | >113 |
| 22 | 180.8 | 897.7 | 19.5 |
| 23 | 87.3 | 1323 | 67.3 |
| 24 | 188.2 | 2049 | 39.5 |
| 25 | 230.6 | 2419 | 42.1 |
| 26 | 58.1 | 699.1 | 44.6 |
| 27 | 26.8 | 143.8 | 21.5 |
| 28 | 286.1 | 4265 | 67 |
| 29 | 234.9 | 4339 | 88.9 |
| 29P1 | 2642 | >5000 | >10.4 |
| 29P2 | 91.3 | 1761 | 80.8 |
| 30 | 821.4 | 3109 | 14.3 |
| 31 | 600.5 | >5000 | >34.8 |
| 32 | 86.4 | 1546 | 77.9 |
| 32P1 | 450.5 | 4231 | 27.9 |
| 32P2 | 43.3 | 1154 | 81 |
| 33 | 212.2 | >5000 | >84.3 |
| 34 | 165.9 | 577 | 10.9 |
| 35 | 761.8 | 2601 | 15.8 |
| 36 | 468.5 | >5000 | >15.7 |
| 37 | 34.5 | 212.4 | 15.5 | n.a. denotes not applicable;
$^a$all compounds were run in duplicate multiple times, and the average data is reported All publications, including patents, patent applications, and scientific articles, mentioned in this specification are herein incorporated by reference in their entirety for all purposes to the same extent as if each individual publication, including patent, patent application, or scientific article, were specifically and individually indicated to be incorporated by reference.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

The invention claimed is:

1. A compound of formula (I):

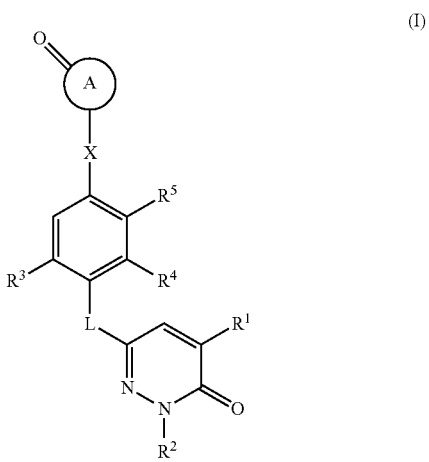

or a pharmaceutically acceptable salt thereof, wherein:

ring A together with the carbonyl (keto) group within the ring form a 5 membered heterocycle containing 1-3 ring heteroatoms selected from the group consisting of N, O, and S, wherein the heterocycle is optionally substituted with 1-2 $C_1$-$C_3$ alkyl or $C_3$-$C_4$ cycloalkyl groups, and wherein the carbonyl (keto) group is not adjacent to the atom attached to X;

$R^1$ is $C_1$-$C_4$ alkyl optionally substituted with 1-5 halo or hydroxyl groups, $C_3$-$C_5$ cycloalkyl, $CON(R^{10})_2$, or $NR^{10}COR^{10}$;

$R^2$ is H or $C_1$-$C_3$ alkyl;

L is O, $CH_2$, S, SO, $SO_2$, CO, CHF, $CF_2$, $C(R^{11})CN$, $CHR^{11}$, or $C(R^{11})R^{11}$;

$R^3$ and $R^4$ are independently Cl, Br, methyl, or ethyl;

$R^5$ is H, halo, $C_1$-$C_4$ alkyl, or $C_3$-$C_4$ cycloalkyl;

or $R^5$ together with $R^4$ and the intervening atoms form a 5-7 membered cycloalkyl or a 5-7 membered heterocycle containing 1-2 ring heteroatoms;

X is absent, O, $NR^{12}$, $C(O)NR^{12}$, $NR^{12}C(O)$, $CR^{12}R^{12}$, $OCR^{12}R^{12}$, $CR^{12}R^{12}O$, $NR^{12}CR^{12}R^{12}$, $CR^{12}R^{12}NR^{12}$, $SO_2NR^{12}$, or $NR^{12}SO_2$;

each $R^{10}$ is independently $C_1$-$C_3$ alkyl or H;

each $R^{11}$ is independently $C_1$-$C_2$ alkyl optionally substituted with 1-5 halo, or two $R^{11}$ groups together with the carbon atom to which they are attached form a cyclopropyl or cyclobutyl ring; and each $R^{12}$ is independently H or methyl.

2. The compound of claim 1, or a pharmaceutically acceptable salt thereof, which is of formula (IIA) or (IIB):

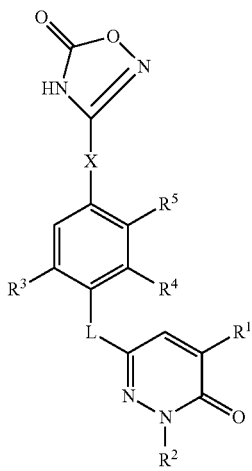

(IIA)

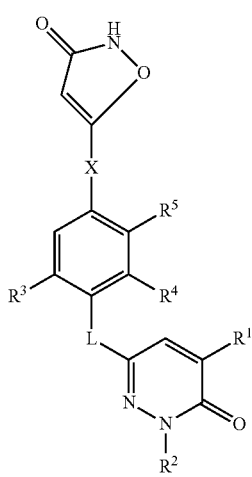

(IIB)

wherein $R^1$, $R^2$, $R^3$, $R^4$, $R^5$, X, and L are as defined in claim 1.

3. The compound of claim 1, or a pharmaceutically acceptable salt thereof, which is of formula (VD):

(VD)

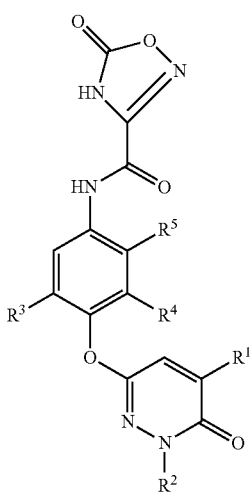

wherein $R^1$, $R^2$, $R^3$, $R^4$, and $R^5$ are as defined in claim 1.

4. The compound of claim 1, or a pharmaceutically acceptable salt thereof, wherein:

$R^1$ is $C_1$-$C_4$ alkyl optionally substituted with 1-2 halo or hydroxyl groups, or $C_3$-$C_5$ cycloalkyl.

5. The compound of claim 4, or a pharmaceutically acceptable salt thereof, wherein:

$R^1$ is isopropyl, t-butyl, HO—CH($CH_3$)—, HO—CH($CH_2CH_3$)—, HO—C($CH_3$)$_2$—, HO—$CH_2$CH($CH_3$)—, cyclopropyl, or

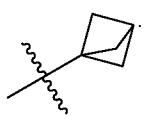

6. The compound of claim 1, or a pharmaceutically acceptable salt thereof, wherein:

$R^2$ is H or —$CH_3$.

7. The compound of claim 1, or a pharmaceutically acceptable salt thereof, wherein:

$R^3$ is chloro or —$CH_3$.

8. The compound of claim 1, or a pharmaceutically acceptable salt thereof, wherein:

$R^4$ is chloro or —$CH_3$;

or $R^5$ together with $R^4$ and the intervening atoms form a 5-6 membered cycloalkyl.

9. The compound of claim 8, or a pharmaceutically acceptable salt thereof, wherein:

$R^5$ together with $R^4$ and the intervening atoms form cyclopentyl.

10. The compound of claim 1, or a pharmaceutically acceptable salt thereof, wherein:

$R^5$ is H or fluoro.

11. The compound of claim 1, or a pharmaceutically acceptable salt thereof, wherein:

X is a bond.

12. The compound of claim 1, or a pharmaceutically acceptable salt thereof, wherein:

X is $NR^{12}C(O)$, $OCR^{12}R^{12}$, or $NR^{12}CR^{12}R^{12}$; and each $R^{12}$ is independently H or methyl.

13. The compound of claim 12, or a pharmaceutically acceptable salt thereof, wherein:

X is —$OCH_2$—, —$NHCH_2$—, —NHC(O)—, —N($CH_3$)$CH_2$—, or —N(H)CH($CH_3$)—.

14. The compound of claim 1, or a pharmaceutically acceptable salt thereof, wherein:

L is O, $CH_2$, $SO_2$, CO, $CHR^{11}$, or $C(R^{11})R^{11}$; and each $R^{11}$ is independently methyl or ethyl.

15. The compound of claim 14, or a pharmaceutically acceptable salt thereof, wherein:

L is O, $CH_2$, $SO_2$, or CO.

16. A compound of formula (I-a):

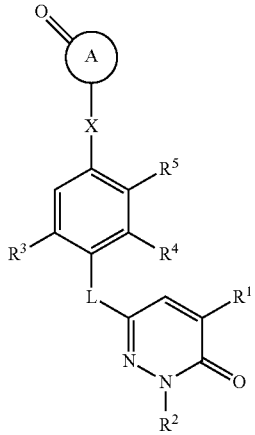

or a tautomer or an N-oxide thereof, or an isotopomer of each thereof, or a prodrug of each of the above, or a stereoisomer of the aforesaid, or a pharmaceutically acceptable salt of each of the foregoing, or a solvate of each of the preceding, wherein:

ring A together with the carbonyl (keto) group within the ring form a 5 membered heterocycle containing 1-3 ring heteroatoms selected from the group consisting of N, O, and S, wherein the heterocycle is optionally substituted with 1-2 $C_1$-$C_3$ alkyl or $C_3$-$C_4$ cycloalkyl, and wherein the carbonyl (keto) group is not adjacent to the atom attached to X;

$R^1$ is $C_1$-$C_4$ alkyl; $C_1$-$C_4$ alkyl optionally substituted with 1-5 halo; $C_3$-$C_5$ cycloalkyl, $CON(R^{10})_2$, or $NR^{10}COR^{10}$, wherein each $R^{10}$ is independently $C_1$-$C_3$ alkyl or H;

$R^2$ is H or $C_1$-$C_3$ alkyl;

L is O, $CH_2$, S, SO, $SO_2$, CO, CHF, $CF_2$, $C(R^{11})CN$, $CHR^{11}$, or $C(R^{11})R^{11}$, wherein each $R^{11}$ is $C_1$-$C_2$ alkyl optionally substituted with 1-5 halo, or the 2 $R^{11}$ groups together with the carbon atom they are attached to form a cyclopropyl or cyclobutyl ring;

each of $R^3$ and $R^4$ is independently $C_1$, Br, methyl, or ethyl;

$R^5$ is H, halo, $C_1$-$C_4$ alkyl, or $C_3$-$C_4$ cycloalkyl, or $R^5$ together with $R^4$ and the intervening atoms form a 5-7 membered cycloalkyl or a 5-7 membered heterocycle containing 1-2 ring heteroatoms;

X is absent, or is O, $NR^{12}$, $C(O)NR^{12}$, $NR^{12}C(O)$, $CR^{12}R^{12}$, $OCR^{12}R^{12}$, $CR^{12}R^{12}O$, $NR^{12}CR^{12}R^{12}$, $CR^{12}R^{12}NR^{12}$, $SO_2NR^{12}$, or $NR^{12}SO_2$, wherein each $R^{12}$ is independently H or methyl.

17. A compound selected from the the group consisting of

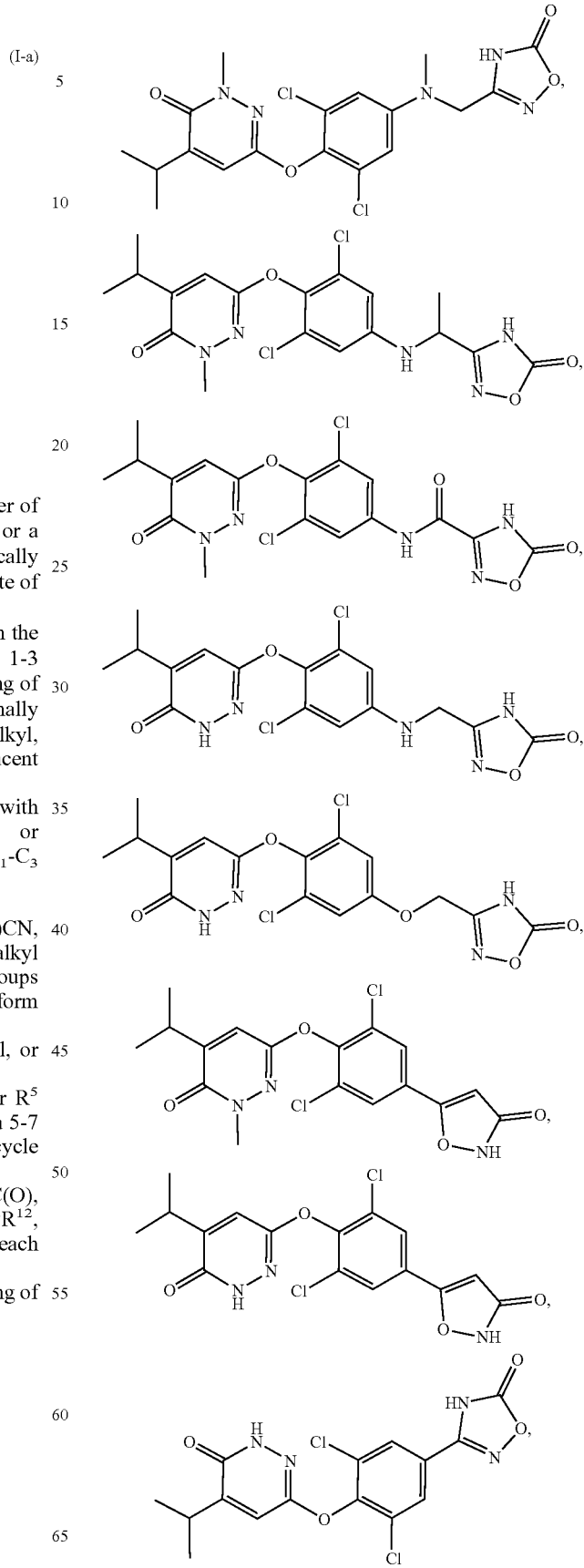

177
-continued
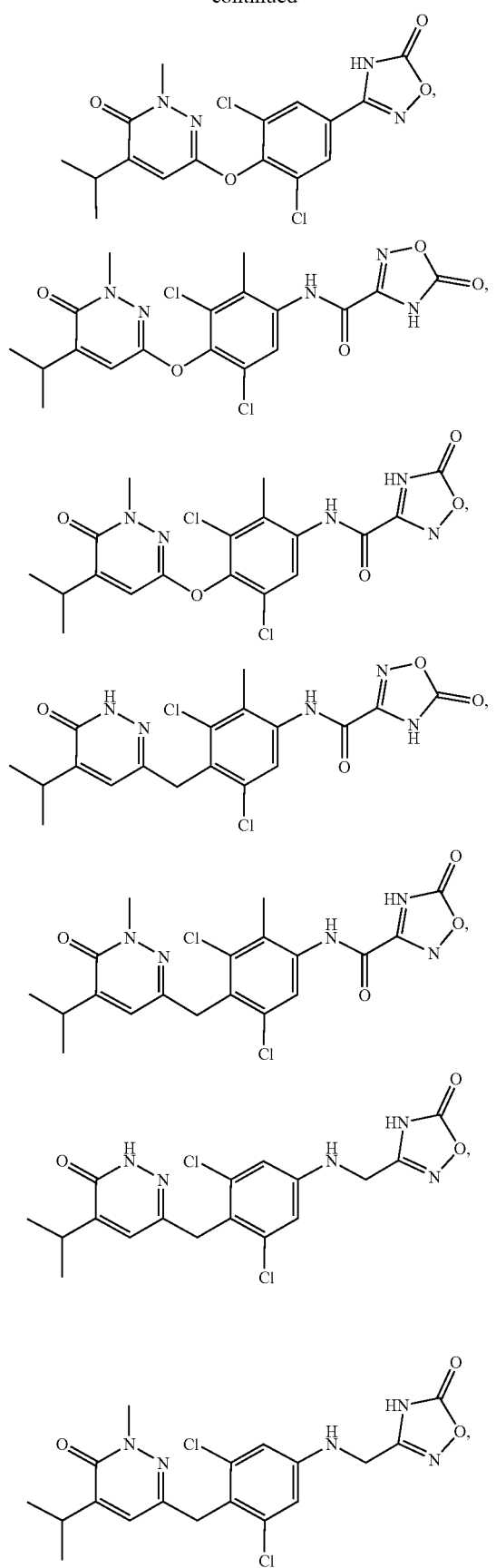
178
-continued
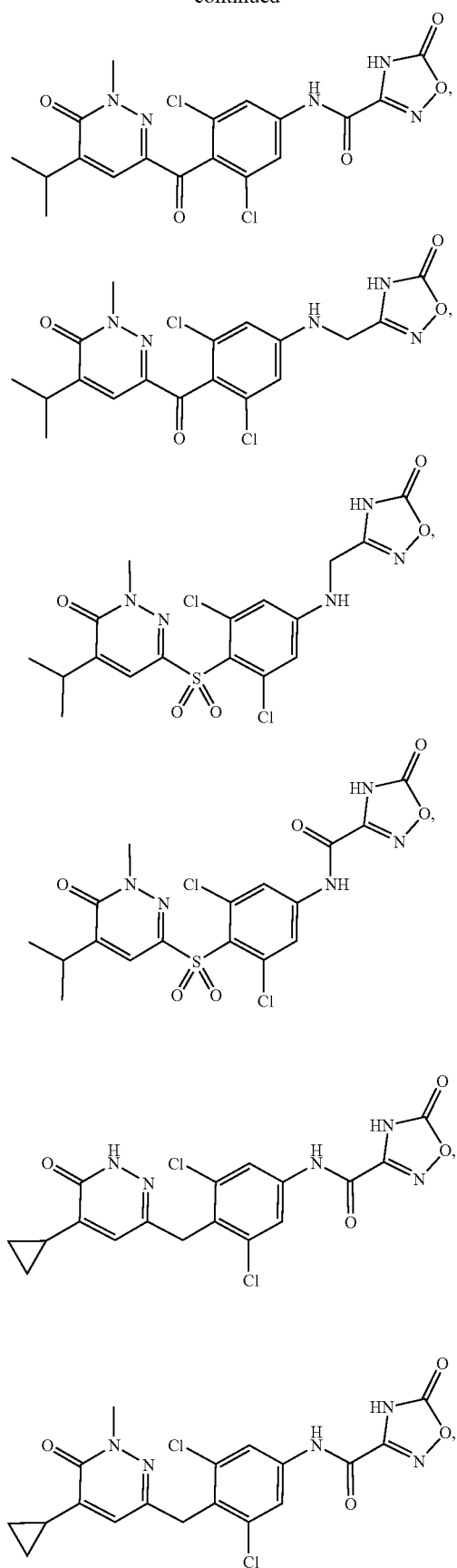

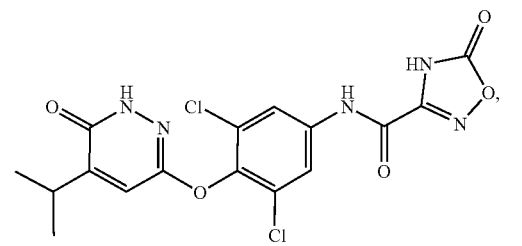
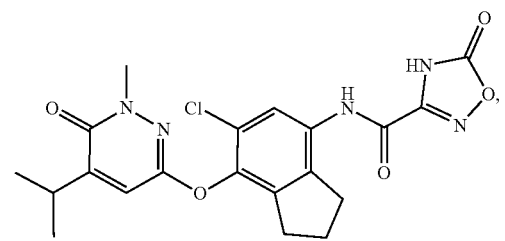
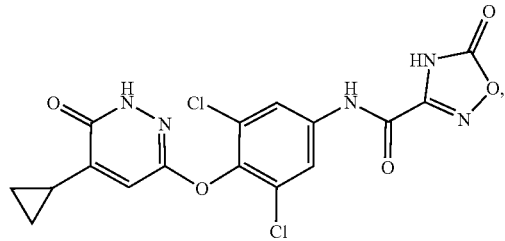
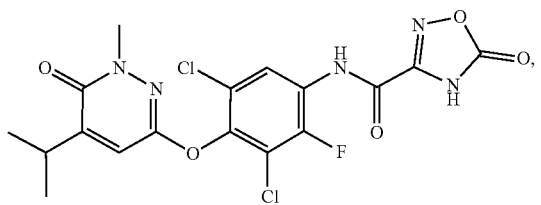
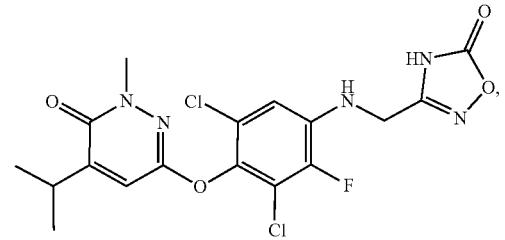
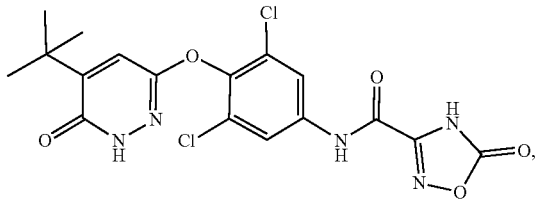
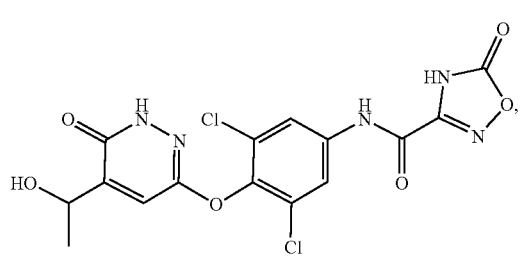
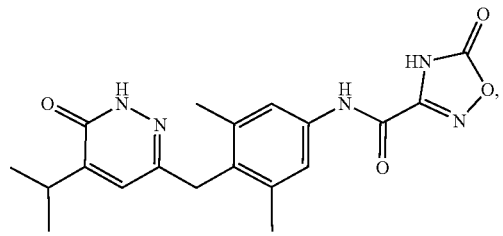
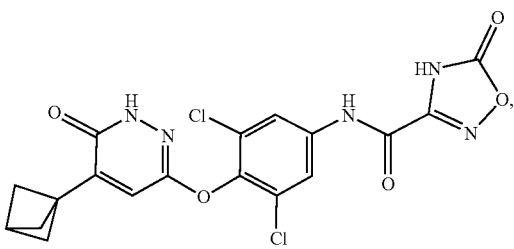
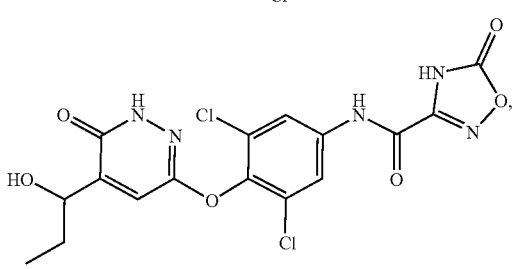
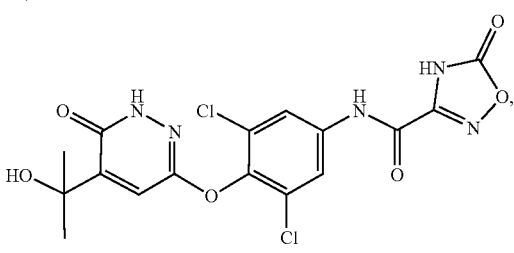
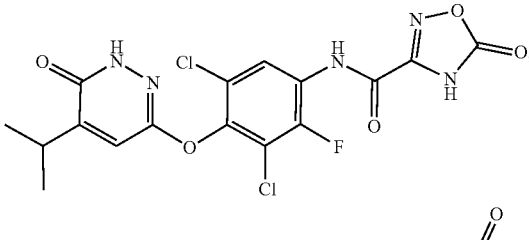
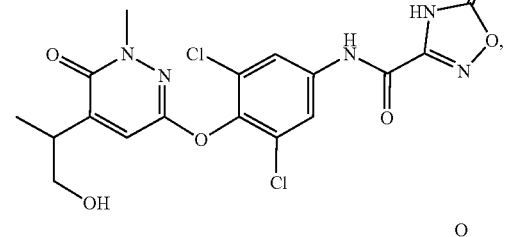
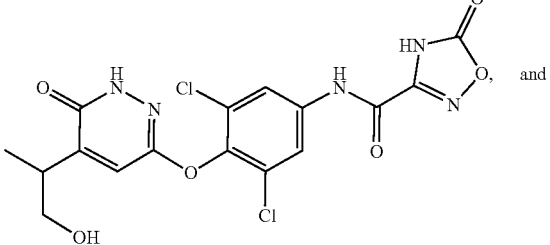 and

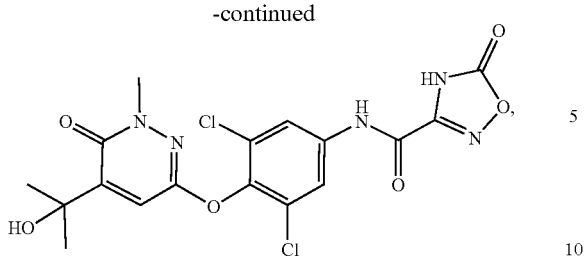

18. A pharmaceutical composition comprising the compound of claim 1, or a pharmaceutically acceptable salt thereof, and at least one pharmaceutically acceptable excipient.

19. A method of agonizing thyroid hormone receptor beta (THR beta) comprising contacting an effective amount of the compound of claim 1, or a pharmaceutically acceptable salt thereof, with the THR beta.

20. A method of treating a disorder which is mediated by THR beta in a patient in need thereof, comprising administering to the patient a therapeutically effective amount of the compound of claim 1, or a pharmaceutically acceptable salt thereof.

21. The method of claim 20, wherein the disorder is non-alcoholic steatohepatitis (NASH).

* * * * *